United States Patent
Dotsenko et al.

(10) Patent No.: US 11,147,884 B2
(45) Date of Patent: Oct. 19, 2021

(54) INHIBITORS OF NHE-MEDIATED ANTIPORT

(71) Applicant: Ardelyx, Inc., Fremont, CA (US)

(72) Inventors: Irina Dotsenko, Fremont, CA (US); Dean Dragoli, Fremont, CA (US); Jason Lewis, Fremont, CA (US)

(73) Assignee: ARDELYX, INC., Fremont, CA (US)

( * ) Notice: Subject to any disclaimer, the term of this patent is extended or adjusted under 35 U.S.C. 154(b) by 0 days.

(21) Appl. No.: 16/476,835

(22) PCT Filed: Jan. 9, 2018

(86) PCT No.: PCT/US2018/013027
§ 371 (c)(1),
(2) Date: Jul. 9, 2019

(87) PCT Pub. No.: WO2018/129557
PCT Pub. Date: Jul. 12, 2018

(65) Prior Publication Data
US 2019/0374649 A1    Dec. 12, 2019

Related U.S. Application Data

(60) Provisional application No. 62/444,338, filed on Jan. 9, 2017.

(51) Int. Cl.
| | | |
|---|---|---|
| A61K 47/55 | (2017.01) | |
| A61P 3/12 | (2006.01) | |
| A61P 1/10 | (2006.01) | |
| A61P 9/12 | (2006.01) | |
| C07D 401/12 | (2006.01) | |
| C07D 401/14 | (2006.01) | |

(52) U.S. Cl.
CPC .......... *A61K 47/55* (2017.08); *A61P 3/12* (2018.01); *C07D 401/12* (2013.01); *C07D 401/14* (2013.01)

(58) Field of Classification Search
CPC ... A61K 47/55; A61P 3/12; A61P 1/10; A61P 9/12; C07D 401/12; C07D 401/14
See application file for complete search history.

(56) References Cited

U.S. PATENT DOCUMENTS

| | | |
|---|---|---|
| 3,926,891 A | 12/1975 | Gross et al. |
| 3,935,099 A | 1/1976 | Weaver et al. |
| 3,997,484 A | 12/1976 | Weaver et al. |
| 4,076,663 A | 2/1978 | Masuda et al. |
| 4,090,013 A | 5/1978 | Ganslaw et al. |
| 4,093,776 A | 6/1978 | Aoki et al. |
| 4,190,562 A | 2/1980 | Westerman |
| 4,286,082 A | 8/1981 | Tsubakimoto et al. |
| 4,340,706 A | 7/1982 | Obayashi et al. |
| 4,446,261 A | 5/1984 | Yamasaki et al. |
| 4,459,396 A | 7/1984 | Yamasaki et al. |
| 4,470,975 A | 9/1984 | Berger et al. |
| 4,683,274 A | 7/1987 | Nakamura |
| 4,708,997 A | 11/1987 | Stanley et al. |
| 4,766,004 A | 8/1988 | Moskowitz |
| 4,806,532 A | 2/1989 | Dousa |
| 4,857,610 A | 8/1989 | Chmelir et al. |
| 4,985,518 A | 1/1991 | Alexander et al. |
| 4,999,200 A | 3/1991 | Casillan |

(Continued)

FOREIGN PATENT DOCUMENTS

| | | |
|---|---|---|
| EP | 505322 B1 | 9/1992 |
| EP | 507672 B1 | 10/1992 |

(Continued)

OTHER PUBLICATIONS

Ueda, H , et al., "Kyotorphin (tyrosine-arginine) synthetase in rat brain synaptosomes", J Biol Chem 262, 8165 (1987).
Van , et al., "Dietary phosphate restriction ameliorates endothelial dysfunction in adenine-induced kidney disease rats", J Clin Biochem Nutr 51, 27-32 (2012).
Van Den Mooter, G , et al., "Colon Drug Delivery", Expert Opin Drug Deliv (1), 111-125 (2006).
Vigne , et al., "The Amiloride-sensitive Na+/H' Exchange System in SkeleMtalu scle Cells in Cultur", J Biol Chem 57, 9394 (1982).
Wahba, I , et al., "Obesity and Obesity-Initiated Metabolic Syndrome: Mechanistic Links to Chronic Kidney Disease", Clinical Journal of American Society of Nephrology 2, 550-562 (2007).

(Continued)

*Primary Examiner* — John M Mauro
(74) *Attorney, Agent, or Firm* — Viksnins Harris Padys Malen LLP

(57) ABSTRACT

The present disclosure is directed to compounds (I') and to their use in methods for the treatment of disorders associated with fluid retention or salt overload, such as heart failure (in particular, congestive heart failure), chronic kidney disease, end-stage renal disease, liver disease, and peroxisome proliferator-activated receptor (PPAR) gamma agonist-induced fluid retention. The present disclosure is also directed to compounds (I') and their use in methods for the treatment of hypertension. The present disclosure is also directed to compounds (I') and to their use in methods for the treatment of gastrointestinal tract disorders, including the treatment or reduction of pain associated with gastrointestinal tract disorders.

(I)

(I')

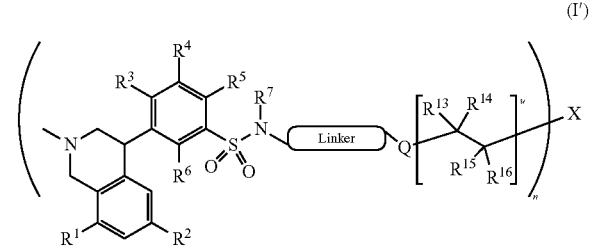

13 Claims, 1 Drawing Sheet

(56) References Cited

U.S. PATENT DOCUMENTS

| | | |
|---|---|---|
| 5,126,150 A | 6/1992 | Piatt et al. |
| 5,130,474 A | 7/1992 | Makovec et al. |
| 5,140,102 A | 8/1992 | Currie |
| 5,145,906 A | 9/1992 | Chambers et al. |
| 5,273,983 A | 12/1993 | Christinaki et al. |
| 5,364,842 A | 11/1994 | Justice et al. |
| 5,445,831 A | 8/1995 | Leis et al. |
| 5,489,670 A | 2/1996 | Currie et al. |
| 5,510,353 A | 4/1996 | Giger et al. |
| 5,587,454 A | 12/1996 | Justice et al. |
| 5,629,377 A | 5/1997 | Burgert et al. |
| 5,650,222 A | 7/1997 | Desmarais et al. |
| 5,763,499 A | 6/1998 | Desmarais |
| 5,795,864 A | 8/1998 | Amstutz et al. |
| 5,824,645 A | 10/1998 | Justice et al. |
| 5,824,691 A | 10/1998 | Kuno et al. |
| 5,859,186 A | 1/1999 | Justice et al. |
| 5,866,610 A | 2/1999 | Lang et al. |
| 5,891,849 A | 4/1999 | Amstutz et al. |
| 5,900,436 A | 5/1999 | Ramakrishna et al. |
| 5,969,097 A | 10/1999 | Wiegand et al. |
| 5,994,305 A | 11/1999 | Justice et al. |
| 6,005,010 A | 12/1999 | Schwark et al. |
| 6,054,429 A | 4/2000 | Bowersox et al. |
| 6,087,091 A | 7/2000 | Justice et al. |
| 6,107,356 A | 8/2000 | Desmarais |
| 6,136,786 A | 10/2000 | Justice et al. |
| 6,166,002 A | 12/2000 | Weichert et al. |
| 6,277,862 B1 | 8/2001 | Giardina et al. |
| 6,287,609 B1 | 9/2001 | Marlett et al. |
| 6,319,518 B1 | 11/2001 | Lee et al. |
| 6,333,354 B1 | 12/2001 | Schudt |
| 6,355,823 B1 | 3/2002 | Peerce |
| 6,399,824 B1 | 6/2002 | Hofmeister et al. |
| 6,413,494 B1 | 7/2002 | Lee et al. |
| 6,414,016 B1 | 7/2002 | Ueno |
| 6,451,781 B1 | 9/2002 | Kleemann et al. |
| 6,504,057 B2 | 1/2003 | Schwark et al. |
| 6,624,150 B2 | 9/2003 | Yerxa et al. |
| 6,703,405 B2 | 3/2004 | Hofmeister et al. |
| 6,734,188 B1 | 5/2004 | Rhodes et al. |
| 6,736,705 B2 | 5/2004 | Benning et al. |
| 6,737,423 B2 | 5/2004 | Heinelt et al. |
| 6,787,528 B2 | 9/2004 | Peerce |
| 6,887,870 B1 | 5/2005 | Ahmad et al. |
| 6,908,609 B2 | 6/2005 | Simon et al. |
| 6,911,453 B2 | 6/2005 | Hofmeister et al. |
| 7,014,862 B2 | 3/2006 | Myatt et al. |
| 7,026,303 B2 | 4/2006 | Cimiluca et al. |
| 7,041,786 B2 | 5/2006 | Shailubhai et al. |
| 7,109,184 B2 | 9/2006 | Jozefiak et al. |
| 7,119,120 B2 | 10/2006 | Jozefiak et al. |
| 7,241,775 B2 | 7/2007 | Hofmeister et al. |
| 7,309,690 B2 | 12/2007 | Dardenne et al. |
| 7,326,705 B2 | 2/2008 | Ahmad et al. |
| 7,666,898 B2 | 2/2010 | Chang et al. |
| 7,772,262 B2 | 8/2010 | Kleemann |
| 7,790,742 B2 | 9/2010 | Lang et al. |
| 8,134,015 B2 | 3/2012 | Eto et al. |
| 9,408,840 B2 | 8/2016 | Bell et al. |
| 10,272,079 B2 | 4/2019 | Carreras et al. |
| 10,385,024 B2 * | 8/2019 | Bell .................. A61K 31/496 |
| 10,543,207 B2 * | 1/2020 | Charmot ............ C07D 217/14 |
| 2001/0006972 A1 | 7/2001 | Williams |
| 2003/0109417 A1 | 6/2003 | Nimmo et al. |
| 2003/0171580 A1 | 9/2003 | Hofmeister et al. |
| 2003/0216449 A1 | 11/2003 | Weinstock et al. |
| 2004/0039001 A1 | 2/2004 | Gericke et al. |
| 2004/0044211 A1 | 3/2004 | Hofmeister et al. |
| 2004/0113396 A1 | 6/2004 | Tsai |
| 2004/0224965 A1 | 11/2004 | Gericke et al. |
| 2005/0009863 A1 | 1/2005 | Hofmeister et al. |
| 2005/0020612 A1 | 1/2005 | Gericke |
| 2005/0054705 A1 | 3/2005 | Heinelt et al. |
| 2005/0113396 A1 | 5/2005 | Gericke et al. |
| 2005/0176746 A1 | 8/2005 | Weber et al. |
| 2005/0244367 A1 | 11/2005 | Hui et al. |
| 2007/0135383 A1 | 6/2007 | Chang et al. |
| 2007/0135385 A1 | 6/2007 | Chang et al. |
| 2007/0225323 A1 | 9/2007 | Lang et al. |
| 2007/0270414 A1 | 11/2007 | Kleemann |
| 2008/0058328 A1 | 3/2008 | Heinelt et al. |
| 2008/0194621 A1 | 8/2008 | Lang |
| 2008/0227685 A1 | 9/2008 | Currie et al. |
| 2008/0234317 A1 | 9/2008 | Kleemann et al. |
| 2012/0040025 A9 | 2/2012 | Currie et al. |
| 2012/0263670 A1 | 10/2012 | Charmot et al. |
| 2013/0274285 A1 | 10/2013 | Bell et al. |
| 2017/0340623 A1 | 11/2017 | Charmot et al. |
| 2019/0275028 A1 | 9/2019 | Carreras et al. |

FOREIGN PATENT DOCUMENTS

| | | |
|---|---|---|
| EP | 625162 B1 | 11/1994 |
| EP | 0744397 A2 | 11/1996 |
| EP | 835126 B1 | 4/1998 |
| EP | 873753 A1 | 10/1998 |
| EP | 1321142 A1 | 6/2003 |
| EP | 1336409 A1 | 8/2003 |
| EP | 0876347 B1 | 3/2005 |
| EP | 1485391 B1 | 8/2006 |
| EP | 1465638 B1 | 5/2007 |
| EP | 1196396 B1 | 3/2008 |
| JP | 2007131532 A | 5/2007 |
| WO | 1993013128 A1 | 7/1993 |
| WO | 1994026709 A1 | 11/1994 |
| WO | 1995028418 A2 | 10/1995 |
| WO | 1997001351 A1 | 1/1997 |
| WO | 1997019927 A1 | 6/1997 |
| WO | 1997021680 A1 | 6/1997 |
| WO | 1997024113 A1 | 7/1997 |
| WO | 1998011090 A2 | 3/1998 |
| WO | 2001005398 A1 | 1/2001 |
| WO | 2001017954 A1 | 3/2001 |
| WO | 2001019849 A1 | 3/2001 |
| WO | 2001021582 A1 | 3/2001 |
| WO | 2001052844 A1 | 7/2001 |
| WO | 2001064212 A1 | 9/2001 |
| WO | 2001072742 A1 | 10/2001 |
| WO | 2001082924 A1 | 11/2001 |
| WO | 2001087294 A1 | 11/2001 |
| WO | 2002020496 A1 | 3/2002 |
| WO | 2002024637 A1 | 3/2002 |
| WO | 2002028353 A2 | 4/2002 |
| WO | 2002094187 A2 | 11/2002 |
| WO | 2000048134 A1 | 6/2003 |
| WO | 2003048129 A1 | 6/2003 |
| WO | 2003048134 A1 | 6/2003 |
| WO | 2003051866 A1 | 6/2003 |
| WO | 2003053432 A1 | 7/2003 |
| WO | 2003055490 A1 | 7/2003 |
| WO | 2003057225 A2 | 7/2003 |
| WO | 2003080630 A2 | 10/2003 |
| WO | 2004085382 A1 | 10/2004 |
| WO | 2004085404 A1 | 10/2004 |
| WO | 2004085448 A2 | 10/2004 |
| WO | 2006001931 A2 | 1/2006 |
| WO | 2006032372 A1 | 3/2006 |
| WO | 2008002971 A2 | 1/2008 |
| WO | 2008106429 A2 | 9/2008 |
| WO | 2008137318 A1 | 11/2008 |
| WO | 2010025856 A1 | 3/2010 |
| WO | 2010078449 A2 | 7/2010 |
| WO | 2012006473 A1 | 1/2012 |
| WO | 2012006475 A1 | 1/2012 |
| WO | 2012006477 A1 | 1/2012 |
| WO | 2012054110 A2 | 4/2012 |
| WO | 2014029983 A1 | 2/2014 |

(56) References Cited

FOREIGN PATENT DOCUMENTS

| | | |
|---|---|---|
| WO | 2014029984 A1 | 2/2014 |
| WO | 2014169094 A2 | 10/2014 |

OTHER PUBLICATIONS

Weinman, E., et al., "Fibroblast Growth Factor-23-mediated Inhibition of Renal Phosphate Transport in Mice Requires Sodium-Hydrogen Exchanger Regulatory Factor-1 (NHERF-1) and Synergizes with Parathyroid Hormone", Journal of Biological Chemistry 286 (43), 37216-37221 (2011).
Weinman, E, et al., "The role of NHERF-1 in the regulation of renal proximal tubule sodium—hydrogen exchanger 3 and sodium-dependent phosphate cotransporter 2a", J Physiol 567.1, 27-32 (2005).
Wenzl, et al., "Determinants of decreased fecal consistency in patients with diarrhea", Gastroenterology 108 (6), 1729-1738 (1995).
Wiley, et al., "Peptidomimetics derived from natural products", Medical Research Reviews 13 (3), 327-384 (1993).
Yang, T, et al., "Renal and Vascular Mechanisms of Thiazolidinedoine-Induced Fluid Retention", PPAR Reserach, article ID 943614, 8 pages (2008).
Zachos, et al., "Molecular Physiology of Intestinal N+/H+ Exchange", Annu Rev Physiol 67, 411-443 (2005).
Zammit, P, et al., "Effects on fluid and Na+ flux of varying luminal hydraulic resistance in rat colon in vivo", J Physiol 477 (Pt 3), 539-548 (1994).
Achinger, et al., "Left Ventricular Hypertrophy: Is Hyperphosphatemia among Dialysis Patients a Risk Factor?", J Am Soc Nephrol 17 (12 Suppl 3), S255-S261 (2006).
Ahmad, S, et al., "Aminoimidazoles as bioisosteres of acylguanidines: novel, potent, selective and orally bioavailable inhibitors of the sodium hydrogen exchanger isoform-1", Bioorganic & Med Chem Lett 14 (1), 177-180 (2004).
Ahmed, et al., "A propensity-matched study of the effects of chronic diuretic therapy on mortality and hospitalization in older adults with heart failure", Int J Cardiol 125(2), 246-253 (2008).
Akbar, A, et al., "Review article: visceral hypersensitivity in irritable bowel syndrome: molecular mechanisms and therapeutic agents", Aliment Pharmaco Ther 30, 423-435 (2009).
Altun, B, et al., "Salt and Blood Pressure: Time to Challenge", Cardiology 105(1), 9-16 (2006).
Barreto, F, et al., "Pharmacotherapy of chronic kidney disease and mineral bone disorder", Exp Op Pharmacother 12, 2627-2640 (2011).
Basit, A, "Advances in Colonic Drug Delivery", Drugs 65(14), 1991-2007 (2005).
Beubler, E, et al., "5-HT receptor antagonists and heat-stable *Escherichia coli* enterotoxin-induced effects in the rat", Eur J Pharm 219, 445 (1992).
Bleakman, D, et al., "Hypertonic fluid absorption from rabbit descending colon in vitro", Am J Physiol 258(3), Pt 1, G377-G390 (1990).
Bouras, E, et al., "Prucalopride accelerates gastrointestinal and colonic transit in patients with constipation without a rectal evacuation disorder", Gastroenterology 120, 354-360 (2001).
Brandt, et al., "An Evidence-Based Approach to the Management of Chronic Constipation in North America", Am J Gastroenterol 100 (Suppl 1), S1-S21 (2005).
Bueno, et al., "Serotonergic and non-serotonergic targets in the pharmacotherapy of visceral hypersensitivity", Neurogastroenterol Motility 19 (Suppl 1), 89-119 (2007).
Bundgard, H, "Design of Prodrugs: Bioreversible derivatives for various functional groups and chemical entites", Design of Prodrugs, Elsevier, Amsterdam, 7-24 (1985).
Burton, D, et al., "Colonic Transit Scintigraphy Labeled Activated Charcoal Compared with Ion Exchange Pellets", J Nucl Med 38, 1807-1810 (1997).

Camilleri, M, et al., "Effect of renzapride on transit in constipation-predominant irritable bowel syndrome", Clin Gastroenterol Hepatol 2, 895-904 (2004).
Camilleri, M, et al., "Towards a relatively inexpensive, noninvasive, accurate test for colonic motility disorders", Gastroenterology 103, 36-42 (1992).
Campbell, C, et al., "Characterisation of SB-221420-A, a neuronal Ca and Na channel antagonist in experimental models of stroke", European Journal of Pharmacology 401(3), 419-428 (2000).
Campbell, R, et al., "Type 2 diabetes: Where we are today: An overview of disease burden, current treatments, and treatment strategies", Journal of American Pharmacists Assoc 49(5), S3-S9 (2009).
Chang, et al., "Current gut-directed therapies for irritable bowel syndrome", Curr Treat Options Gastroenterol 9(4), 314-323 (2006).
Chen, J, et al., "Synthesis and characterization of superporous hydrogel composites", Journal of Controlled Release 65, 73-82 (2000).
Cheng, et al., "Macroporous poly(N-isopropylacrylamide) hydrogels with fast response rates and improved protein release properties", Journal of Biomedical Materials Research—Part A, 67(1), 96-103 (2003).
Chiba, S, et al., "A Pd(II)-Catalyzed Ring-Expansion Reaction of Cyclic 2-Azidoalcohol Derivatives: Synthesis of Azaheterocycles", J Am Chem Soc 131 (36), 12886-12887 (2009).
Choi, N, "Kidney and Phosphate Metabolism", Electrolyte & Blood Pressure 6, 77-85 (2008).
Chou, et al., "Obstructive Sleep Apnea: a stand-along risk for chronic kidney diseases", Nephrol Dial Transplant 26 (7), 2244-2250 (2011).
Chourasia, M, et al., "Pharmaceutical Approaches to Colon Targeted Drug Delivery Systems", J Pharm Sci 6 (1), 33-66 (2003).
Chourasia, M, et al., "Polysaccharides for Colon Targeted Drug Delivery", Drug Deliv 11 (2), 129-148 (2004).
Coulie, B, et al., "Recombinant human neurotrophic factors accelerate colonic transit and relieve constipation in humans", Gastroenterology 119, 41-50 (2000).
Cremonini, F, et al., "Performance characteristics of scintigraphic transit measurements for studies of experimental therapies", Aliment Pharmacol Ther 16, 1781-1790 (2002).
Cruz, et al., "Incidence and Predictors of Development of Acute Renal Failure Related to Treatment of Congestive Heart Failure with Ace Inhibitors", Nephron Clin Pract 105 (2), c77-c83 (2007).
Davenport, A, et al., "Blood Pressure Control and Symptomatic Intradialytic Hypotension in Diabetic Haemodialysis Patients: A Cross-Sectional Survey", Nephron Clin Pract 109 (2), c65-c71 (2008).
Di Marco, et al., "High phosphate directly affects endothelial function by downregulating annexin II", Kidney International 83, 213-222 (2013).
Eherer, A, et al., "Effect of psyllium, calcium polycarbophil, and wheat bran on secretory diarrhea induced by phenolphthalein", Gastroenterology 104 (4), 1007-1012 (1993).
Ertl, P, et al., "Fast calculation of molecular polar surface area as a sum of fragment-based contributions and its application to the prediction of drug transport properties", J Med Chem 43(20), 3714-3717 (2000).
Eutamen, "Guanylate cyclase C-mediated antinociceptive effects of linaclotide in rodent models of visceral pain", Neurogastroenterol Motil 22(3), 312 (2010).
Fischer, M, et al., "The gel-forming polysaccharide of psyllium husk (Plantago ovata Forsk)", Carbohydrate Research 339, 2009-2012 (2004).
Geibel, J, "Secretion and Absorption by Colonic Crypts", Annu Rev Physiol 67, 471-490 (2005).
Gershon, et al., "The Serotonin Signaling System: From Basic Understanding to Drug Development for Functional GI Disorders", Gastroenterology 132 (1), 397-414 (2007).
Giachelli, "The emerging role of phosphate in vascular calcification", Kidney Int 75, 890-897 (2009).

(56) References Cited

OTHER PUBLICATIONS

Giral, H, et al., "NHE3 Regulatory Factor 1 (NHERF1) Modulates Intestinal Sodium-dependent Phosphate Transporter (NaPi-2b) Expression in Apical Microvilli", Journal of Biological Chemistry 287(42), 35047-35056 (2012).
Griffin, et al., "Multivalent Drug Design. Synthesis and in Vitro Analysis of an Array of Vancomycin Dimers", J Am Chem Soc 125, 6517-6531 (2003).
Guerin, et al., "Impact of Aortic Stiffness Attenuation on Survival of Patients in End-Stage Renal Failure", Circulation 103, 987-992 (2001).
Hammerle, et al., "Updates on treatment of irritable bowel syndrome", World J Gastroenterol 14 (17), 2639-2649 (2008).
Horkay, F, "Effect of cross-links on the swelling equation of state: polyacrylamide hydrogels", Macromolecules 22, 2007-2009 (1989).
Jacobsen, E, et al., "Highly enantioselective epoxidation catalysts derived from 1,2-diaminocyclohexane", J Am Chem Soc 113, 7063-7064 (1991).
Jain, A, et al., "Perspectives of Biodegradable Natural Polysaccharides for Site-Specific Drug Delivery to the Colon", J Pharm Sci 10 (1), 86-128 (2007).
Jain, S, et al., "Target-specific drug release to the colon", Expert Opin Drug Deliv 5 (5), 483-498 (2008).
Johanson, et al., "Chronic constipation: a survey of the patient perspective", Aliment Pharmacol Ther 25 (5), 599-608 (2007).
Kashani, et al., "Fluid retention in cirrhosis: pathophysiology and management", QJM 101 (2), 71-85 (2008).
Katopodis, K, "Inorganic Phosphorus Homeostasis during the First Hour of Dialysis", Renal Failure 33, 562-567 (2011).
Kiela, P, et al., "Apical NA+/H+ exchangers in the mammalian gastrointestinal tract", J Physiol Pharmacol 57(Supp 7), 51-79 (2006).
Kirkpantur, et al., "Serum fibroblast growth factor-23 (FGF-23) levels are independently associated with left ventricular mass and myocardial performance index in maintenance haemodialysis patients", Nephrol Dial Transplant 26, 1346-1354 (2011).
Kumar, P, et al., "Colon Targeted Drug Delivery Systems—An Overview", Curr Drug Deliv 5 (3), 186-198 (2008).
Kunzelmann, et al., "Electrolyte Transport in the Mammalian Colon: Mechanisms and Implications for Disease", Physiol Rev 82 (1), 245-289 (2002).
Ledoussal, C, et al., "Renal salt wasting in mice lacking NHE3 Na+/H+ exchanger but not in mice lacking NHE2", Am J Physiol Renal Physiol 281, F718-F727 (2001).
Lewis, et al., "Stool form scale as a useful guide to intestinal transit time", Scand J Gastroenterol 32, 920-924 (1997).
Li, X, "Biodegradable Polymeric Prodrugs of Antihypertensive Agents", Department of Pharmaceutics Dissertation, 1-241 (1991).
Li, et al., "Lysophosphatidic acid inhibits cholera toxin-induced secretory diarrhea through CFTR-dependent protein interactions", J Exp Med 202, 975-986 (2005).
Linz, et al., "Antihypertensive and Laxative Effects by Pharmacological Inhibition of Sodium-Proton-Exchanger Subtype 3—Mediated Sodium Absorption in the Gut", Hypertension 60, 1560-1567 (2012).
Lipinski, "Drug-like properties and the causes of poor solubility and poor permeability", J Pharm & Toxicol Methods 44, 235-249 (2000).
Lipinski, et al., "Experimental and computational approaches to estimate solubility and permeability in drug discovery and development settings", Advanced Drug Delivery Reviews 46, 3-26 (2001).
Lopes, A, et al., "Phosphate Binder Use and Mortality Among Hemodialysis Patients in the DOPPS: Evaluation of Possible Confounding by Nutritional Status", Am J Kidney Dis 60(1), 90-101 (2012).
Lopez, et al., "Calcimimetic R-568 decreases extraosseous calcifications in uremic rats treated with calcitriol", J Am Soc Nephrol 17, 795-804 (2006).
Luks, et al., "Chronic Kidney Disease at High Altitude", J Am Soc Nephrol 19, 2262-2271 (2008).
Mahon, M, et al., "Na+/H+ Exchanger-Regulatory Factor 1 Mediates Inhibition of Phosphate Transport by Parathyroid Hormone and Second Messengers by Acting at Multiple Sites in Opossum Kidney Cells", Molecular Endocrinology 17(11), 2355-2364 (2003).
Mammen, et al., "Effective Inhibitors of Hemagglutination by Influenza Virus Synthesized from Polymers Having Active Ester Groups. Insight into Mechanism of Inhibition", Journal of Medicinal Chemistry 38, 4179-4190 (1995).
Marlett, J, et al., "The active fraction of psyllium seed husk", Proceedings of Nutrition Socity 62, 207-209 (2003).
Masereel, B, et al., "An overview of inhibitors of Na+/H+ exchanger", European J of Med Chem 38, 547-554 (2003).
McKie, A, et al., "Mechanical aspects of rabbit fecal dehydration", Am J Physiol 258 (3), Pt 1, G391-G394 (1990).
McPhee, W, "Poly(N-isopropylacrylamide) Latices Prepared with Sodium Dodecyl Sulfate", Journal of Colloid and Interface Science 156, 24-30 (1993).
Medline Plus, entry for Chronic Kidney Disease, retried from www.nlm.nih.gov/medlineplus/ency/article/000471.htm, on Aug. 6, 2015, 1-8.
Medline Plus, entry for End-stage Kidney Diseases, retrieved from www.nlm.nih.gov/medlineplus/ency/article/000500.htm, Aug. 6, 2015, 1-6.
Medline Plus, for Irritable Bowel Syndrome, retrieved from medlineplus/irritablebowelsyndrome.html>on Aug. 6, 2015, 1-6.
Merck Manual, "Hyperphosphatemia", www.merckmanuals.com/professional/endocrine-and-metabolic-disorders/electrolyte-disorders/hyperphosphatemia, 4 pages (Last full review/revision Mar. 2018).
Miyamoto, K, et al., "Sodium-dependent phosphate cotransporters: Lessons from gene knockout and mutation studies", J Pharm Sci 100, 3719-3730 (2011).
Mohrmann, et al., "Sodium-dependent transport of Pi by an established intestinal epithelial cell line (CaCo-2)", Am J Phys 250 (3), G323-G330 (1986).
Molony, D, et al., "Derangements in Phosphate Metabolism in Chronic Kidney Diseases/Endstage Renal Disease: Therapeutic Considerations", Adv Chron Kidney Disease 18(2), 120-131 (2011).
Musso, D, et al., "Indanylidenes. 2. Design and Synthesis of (E)-2-(4-Chloro-6-fluoro-1-indanylidene)-N-methylacetamide, a Potent Antiinflammatory and Analgesic Agent without Centrally Acting Muscle Relaxant Activity", J Med Chem 46 (3), 409-416 (2003).
Neves, et al., "Adverse effects of hyperphosphatemia on myocardial hypertrophy, renal function, and bone in rats with renal failure", Kidney Int 66, 2237-2244 (2004).
Ogden, C, et al., "Prevalence of Overweight and Obesity in the United States, 1999-2004", JAMA 295, 1549-1555 (2006).
Oh, K, et al., "Swelling behavior of submicron gel particles", Journal of Applied Polymer Science 69, 109-114 (1998).
Ohnishi, et al., "Dietary and genetic evidence for phosphate toxicity accelerating mammalian aging", FASEB J 24, 362-371 (2010).
Pappagallo, "Incidence, Prevalence, and Management of Opioid Bowel Dysfunction", Am J Surg 182 (5A Suppl), 11S-18S (2001).
Paradiso, et al., "Na+-H+ exchange in gastric glands as measured with a cytoplasmic-trapped, fluorescent pH indicator", PNAS USA 81(23), 7436-7440 (1984).
Patent Cooperation Treaty, International Searching Authority, Search Report and Written Opinion for PCT/US2018/013027, 15 pages, Mar. 8, 2018.
Patil, S, et al., "Mucoadhesive Microspheres: A Promising Tool in Drug Delivery", Curr Drug Deliv 5(4), 312-318 (2008).
Pelton, R, et al., "Temperature-sensitive aqueous microgels", Advanceds in Colloid and Interface Science 8, 1-33 (2000).
Posserud, I, et al., "Altered Rectal Perception in Irritable Bowel Syndrome Is Associated With Symptom Severity", Gastroenterolgy 133, 1113-1123 (2007).
Prather, C, et al., "Tegaserod accelerates orocecal transit in patients with constipation-predominant irritable bowel syndrome", Gastroenterology 118, 463-468 (2000).

(56) References Cited

OTHER PUBLICATIONS

Rao, et al., "Evaluation of gastrointestinal transit in clinical practice: position paper of the American and European Neurogastroenterology and Motility Societies", Neurogastroenterol Motil 2, 8-23 (2011).
Sarkar, et al., "Interdialytic weight gain: implications in hemodialysis patients", Semin Dial 19, 429-433 (2006).
Schocken, D, et al., "A Scientific Statement From the American Heart Association Councils on Epidemiology and Prevention, Clinical Cardiology, Cardiovascular Nursing, and High Blood Pressure Research; Quality of Care and Outcomes Research Interdisciplinary Working Group; . . . ", Circulation 117 (19), 2544-2565 (2008).
Selvaraj, et al., "Tool development for Prediction of pIC50 values from the IC50 values—A pIC50 value calculator", Current Trends in Biotechnology and Pharmacy 5, 1104-1109 (2011).
Shareef, M, et al., "Colonic drug delivery: an updated review", AAPS Pharm Sci (2), E17 (2003).
Shuto, et al., "Dietary Phosphorus Acutely Impairs Endothelial Function", J Am Soc Nephrol 20 (7), 1504-1512 (2009).
Silva, A, "Advances in Prodrug Design", Mini-Reviews in Medicinal Chemistry 5, 893-914 (2005).
Sinha, V, et al., "Colonic Drug Delivery: Prodrug Approach", Pharm Res 18 (5), 557-564 (2001).
Spencer, A, et al., "Intestinal Inhibition of the Na+/H+ Exchanger 3 Prevents Cardiorenal Damage in Rats and Inhibits Na+ Uptake in Humans", Science Translational Medicine 6(227), 227ra36, 10 pages, (2014).
Spherix Global Insights Report, "RealWorld Dynamix—Exploring the Patient Journey", Dialysis Market, 2018, CKD, Non-dialysis Market 2017 (Slides 1-5).
STN Medline, AN 2011625687, 1 page (2011).
Townsend, R, et al., "Metabolic Syndrome, Components, and Cardiovascular Disease Prevalence in Chronic Kidney Disease: Findings from the Chronic Renal Insufficiency Cohort (CRIC) Study", American Journal of Nephrology 33, 477-484 (2011).

* cited by examiner

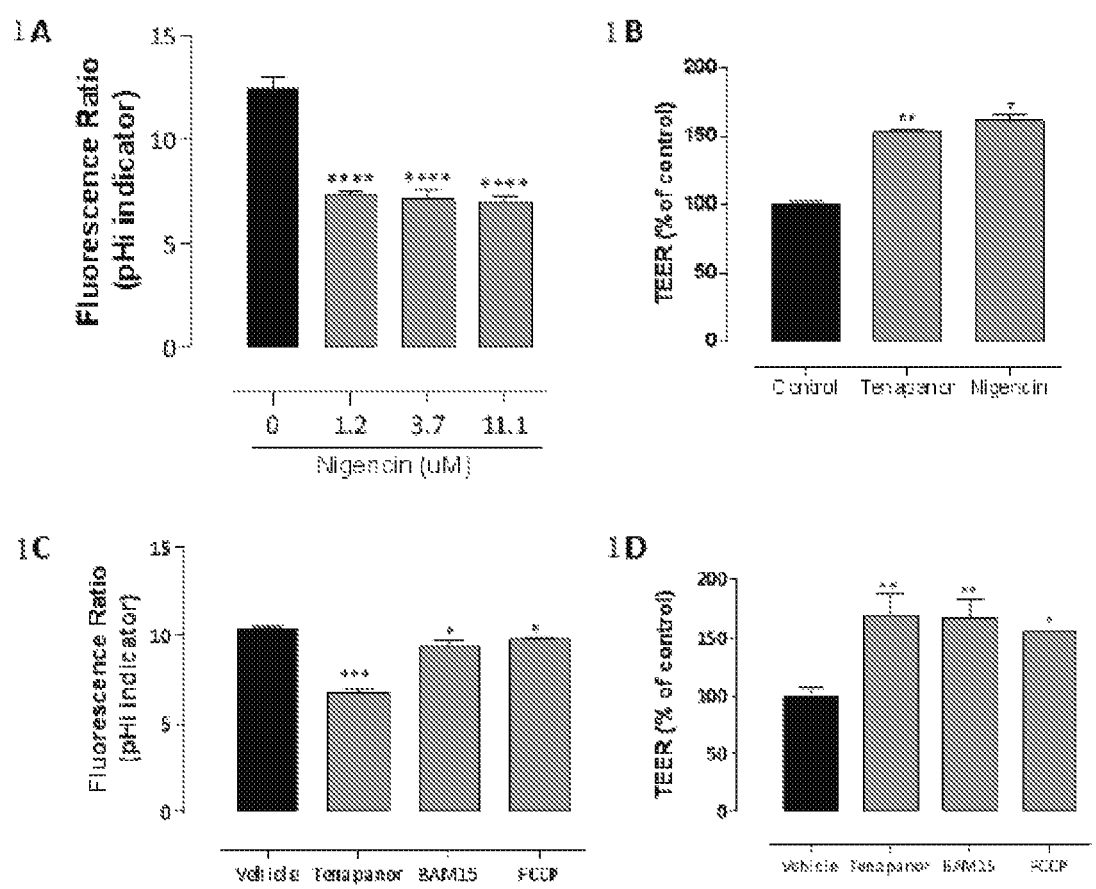

INHIBITORS OF NHE-MEDIATED ANTIPORT

This application claims priority to and benefit of U.S. provisional patent application No. 62/444,338, filed 9 Jan. 2017, which is herein incorporated by reference in its entirety.

FIELD OF INVENTION

The present disclosure is directed to tetrahydroisoquinoline derivatives that are substantially active in the gastrointestinal tract to inhibit NHE-mediated antiport of sodium ions and hydrogen ions, and the use of such compounds in the treatment of disorders associated with fluid retention or salt overload and in the treatment of gastrointestinal tract disorders, including the treatment or reduction of pain associated with a gastrointestinal tract disorder.

BACKGROUND OF THE INVENTION

Disorders Associated with Fluid Retention and Salt Overload

According to the American Heart Association, more than 5 million Americans have suffered from heart failure, and an estimated 550,000 cases of congestive heart failure (CHF) occur each year (Schocken, D. D. et al., *Prevention of heart failure: a scientific statement from the American Heart Association Councils on Epidemiology and Prevention. Clinical Cardiology Cardiovascular Nursing, and High Blood Pressure Research*; Quality of Care and Outcomes Research Interdisciplinary Working Group; and Functional Genomics and Translational Biology Interdisciplinary Working Group: Circulation, v. 117, no. 19, p. 2544-2565 (2008)). The clinical syndrome of congestive heart failure occurs when cardiac dysfunction prevents adequate perfusion of peripheral tissues. The most common form of heart failure leading to CHF is systolic heart failure, caused by contractile failure of the myocardium. A main cause of CHF is due to ischemic coronary artery disease, with or without infarction. Long standing hypertension, particularly when it is poorly controlled, may lead to CHF.

In patients with CHF, neurohumoral compensatory mechanisms (i.e., the sympathetic nervous system and the renin-angiotensin system) are activated in an effort to maintain normal circulation. The renin-angiotensin system is activated in response to decreased cardiac output, causing increased levels of plasma renin, angiotensin II, and aldosterone. As blood volume increases in the heart, cardiac output increases proportionally, to a point where the heart is unable to dilate further. In the failing heart, contractility is reduced, so the heart operates at higher volumes and higher filling pressures to maintain output. Filling pressures may eventually increase to a level that causes transudation of fluid into the lungs and congestive symptoms (e.g., edema, shortness of breath). All of these symptoms are related to fluid volume and salt retention, and this chronic fluid and salt overload further contribute to disease progression.

Compliance with the medication regimen and with dietary sodium restrictions is a critical component of self-management for patients with heart failure and may lengthen life, reduce hospitalizations and improve quality of life. Physicians often recommend keeping salt intake below 2.3 g per day and no more than 2 g per day for people with heart failure. Most people eat considerably more than this, so it is likely that a person with congestive heart failure will need to find ways to reduce dietary salt.

A number of drug therapies currently exist for patients suffering from CHF. For example, diuretics may be used or administered to relieve congestion by decreasing volume and, consequently, filling pressures to below those that cause pulmonary edema. By counteracting the volume increase, diuretics reduce cardiac output; however, fatigue and dizziness may replace CHF symptoms. Among the classes or types of diuretics currently being used is thiazides. Thiazides inhibit NaCl transport in the kidney, thereby preventing reabsorption of Na in the cortical diluting segment at the ending portion of the loop of Henle and the proximal portion of the distal convoluted tubule. However, these drugs are not effective when the glomerular filtration rate (GFR) is less than 30 ml/min. Additionally, thiazides, as well as other diuretics, may cause hypokalemia. Also among the classes or types of diuretics currently being used is loop diuretics (e.g., furosemide). These are the most potent diuretics and are particularly effective in treating pulmonary edema. Loop diuretics inhibit the NaKCl transport system, thus preventing reabsorption of Na in the loop of Henle.

Patients that have persistent edema despite receiving high doses of diuretics may be or become diuretic-resistant. Diuretic resistance may be caused by poor availability of the drug. In patients with renal failure, which has a high occurrence in the CHF population, endogenous acids compete with loop diuretics such as furosemide for the organic acid secretory pathway in the tubular lumen of the nephron. Higher doses, or continuous infusion, are therefore needed to achieve entrance of an adequate amount of drug into the nephron. However, recent meta-analysis has raised awareness about the long-term risk of chronic use of diuretics in the treatment of CHF. For instance, in a recent study (Ahmed et al., *Int J Cardiol.* 2008 Apr. 10; 125(2): 246-253) it was shown that chronic diuretic use was associated with significantly increased mortality and hospitalization in ambulatory older adults with heart failure receiving angiotensin converting enzyme inhibitor and diuretics.

Angiotensin-converting enzyme ("ACE") inhibitors are an example of another drug therapy that may be used to treat congestive heart failure. ACE inhibitors cause vasodilatation by blocking the renin-angiotensin-aldosterone system. Abnormally low cardiac output may cause the renal system to respond by releasing renin, which then converts angiotensinogen into angiotensin I. ACE converts angiotensin I into angiotensin II. Angiotensin II stimulates the thirst centers in the hypothalamus and causes vasoconstriction, thus increasing blood pressure and venous return. Angiotensin II also causes aldosterone to be released, causing reabsorption of Na and concomitant passive reabsorption of fluid, which in turn causes the blood volume to increase. ACE inhibitors block this compensatory system and improve cardiac performance by decreasing systemic and pulmonary vascular resistance. ACE inhibitors have shown survival benefit and conventionally have been a treatment of choice for CHF. However, since ACE inhibitors lower aldosterone, the K-secreting hormone, one of the side-effects of their use is hyperkalemia. In addition, ACE inhibitors have been show to lead to acute renal failure in certain categories of CHF patients. (See, e.g., C. S. Cruz et al., "Incidence and Predictors of Development of Acute Renal Failure Related to the Treatment of Congestive Heart Failure with ACE Inhibitors, Nephron Clin. Pract., v. 105, no. 2, pp c77-c83 (2007)).

Patients with end stage renal disease ("ESRD"). i.e., stage 5 chronic kidney failure, must undergo hemodialysis three times per week. The quasi-absence of renal function and ability to eliminate salt and fluid results in large fluctuations in body weight as fluid and salt build up in the body (sodium/volume overload). The fluid overload is characterized as interdialytic weight gain. High fluid overload is also worsened by heart dysfunction, specifically CHF. Dialysis is used to remove uremic toxins and also adjust salt and fluid homeostasis. However, symptomatic intradialytic hypotension (SIH) may occur when patients are over-dialyzed. SIH is exhibited in about 15% to 25% of the ESRD population (Davenport, A., C. Cox, and R. Thuraisingham, *Blood pressure control and symptomatic intradialytic hypotension in diabetic haemodialysis patients: a cross-sectional survey*; Nephron Clin. Pract., v. 109, no. 2, p. c65-c71 (2008)). Like in hypertensive and CHF patients, dietary restrictions of salt and fluid are highly recommended but poorly followed because of the poor palatability of low-salt food The cause of primary or "essential" hypertension is elusive. However, several observations point to the kidney as a primary factor. The strongest data for excess salt intake and elevated blood pressure come from INTERSALT, a cross-sectional study of greater than 10,000 participants. For individuals, a significant, positive, independent linear relation between 24-hour sodium excretion and systolic blood pressure was found. Higher individual 24-hour urinary sodium excretions were found to be associated with higher systolic/diastolic blood pressure on average, by 6-3/3-0 mm Hg. Primary hypertension is a typical example of a complex, multifactorial, and polygenic trait. All these monogenic hypertensive syndromes are virtually confined to mutated genes involving gain of function of various components of the renin-angiotensin-aldosterone system, resulting in excessive renal sodium retention. In a broad sense, these syndromes are characterized by increased renal sodium reabsorption arising through either primary defects in sodium transport systems or stimulation of mineralocorticoid receptor activity (Altun, B., and M. Arici, 2006, *Salt and blood pressure: time to challenge*; Cardiology, v. 105, no. 1, p. 9-16 (2006)). A much larger number of controlled studies have been performed on hypertensive subjects during the last three decades to determine whether sodium reduction will reduce established high blood pressure. Meta-analyses of these studies have clearly shown a large decrease in blood pressure in hypertensive patients.

In end stage liver disease (ESLD), accumulation of fluid as ascites, edema or pleural effusion due to cirrhosis is common and results from a derangement in the extracellular fluid volume regulatory mechanisms. Fluid retention is the most frequent complication of ESLD and occurs in about 50% of patients within 10 years of the diagnosis of cirrhosis. This complication significantly impairs the quality of life of cirrhotic patients and is also associated with poor prognosis. The one-year and five-year survival rate is 85% and 56%, respectively (Kashani et al., *Fluid retention in cirrhosis: pathophysiology and management*; QJM, v. 101, no. 2, p. 71-85 (2008)). The most acceptable theories postulate that the initial event in ascites formation in the cirrhotic patient is sinusoidal hypertension. Portal hypertension due to an increase in sinusoidal pressure activates vasodilatory mechanisms. In advanced stages of cirrhosis, arteriolar vasodilation causes underfilling of systemic arterial vascular space. This event, through a decrease in effective blood volume, leads to a drop in arterial pressure. Consequently, baroreceptor-mediated activation of renin-angiotensin aldosterone system, sympathetic nervous system and non-osmotic release of antidiuretic hormone occur to restore the normal blood homeostasis. These events cause further retention of renal sodium and fluid. Splanchnic vasodilation increases splanchnic lymph production, exceeding the lymph transportation system capacity, and leads to lymph leakage into the peritoneal cavity. Persistent renal sodium and fluid retention, alongside increased splanchnic vascular permeability in addition to lymph leakage into the peritoneal cavity, play a major role in a sustained ascites formation.

Thiazolidinediones (TZD's), such as rosiglitazone, are peroxisome proliferator-activated receptor (PPAR) gamma agonist agents used for the treatment of type-2 diabetes and are widely prescribed. Unfortunately, fluid retention has emerged as the most common and serious side-effect of TZD's and has become the most frequent cause of discontinuation of therapy. The incidence of TZD-induced fluid retention ranges from 7% in monotherapy and to as high as 15% when combined with insulin (Yan, T., Soodvilai, S., *PPAR Research* volume 2008, article ID 943614). The mechanisms for such side-effects are not fully understood but may be related in Na and fluid re-absorption in the kidney. However, TZD-induced fluid retention is resistant to loop diuretics or thiazide diuretics, and combination of peroxisome proliferator-activated receptor (PPAR) alpha with PPAR gamma agonists, which were proposed to reduce such fluid overload, are associated with major adverse cardiovascular events.

In view of the foregoing, it is recognized that salt and fluid accumulation contribute to the morbidity and mortality of many diseases, including heart failure (in particular, congestive heart failure), chronic kidney disease, end-stage renal disease, liver disease and the like. It is also accepted that salt and fluid accumulation are risk factors for hypertension. Accordingly, there is a clear need for a medicament that, when administered to a patient in need, would result in a reduction in sodium retention, fluid retention, or both. Such a medicament would also not involve or otherwise impair renal mechanisms of fluid/Na homeostasis.

One option to consider for treating excessive fluid overload is to induce diarrhea. Diarrhea may be triggered by several agents including, for example, laxatives such as sorbitol, polyethyleneglycol, bisacodyl and phenolphthaleine. Sorbitol and polyethyleneglycol triggers osmotic diarrhea with low levels of secreted electrolytes; thus, their utility in removing sodium salt from the GI tract is limited. The mechanism of action of phenolphthalein is not clearly established, but is thought to be caused by inhibition of the Na/K ATPase and the Cl/HCO$_3$ anion exchanger and stimulation of electrogenic anion secretion (see, e.g., Eherer, A. J., C. A. Santa Ana, J. Porter, and J. S. Fordtran, 1993. Gastroenterology, v. 104, no. 4, p. 1007-1012). However, some laxatives, such as phenolphthalein, are not viable options for the chronic treatment of fluid overload, due to the potential risk of carcinogenicity in humans. Furthermore, laxatives may not be used chronically, as they have been shown to be an irritant and cause mucosal damage. Accordingly, it should also be recognized that the induction of chronic diarrhea as part of an effort to control salt and fluid overload would be an undesired treatment modality for most patients. Any medicament utilizing the GI tract for this purpose would therefore need to control diarrhea in order to be of practical benefit.

One approach for the treatment of mild diarrhea is the administration of a fluid-absorbing polymer, such as the natural plant fiber psyllium. Polymeric materials, and more specifically hydrogel polymers, may also be used for the removal of fluid from the gastrointestinal (GI) tract. The use of such polymers is described in, for example, U.S. Pat. Nos. 4,470,975 and 6,908,609, the entire contents of which are incorporated herein by reference for all relevant and consistent purposes. However, for such polymers to effectively remove significant quantities of fluid, they must desirably resist the static and osmotic pressure range existing in the GI tract. Many mammals, including humans, make a soft feces with a water content of about 70%, and do so by transporting fluid against the high hydraulic resistance imposed by the fecal mass. Several studies show that the pressure required to dehydrate feces from about 80% to about 60% is between about 500 kPa and about 1000 kPa (i.e., about 5 to about 10 atm). (See, e.g., McKie, A. T., W. Powrie, and R. J. Naftalin, 1990, Am J Physiol, v. 258, no. 3 Pt 1, p. G391-G394; Bleakman, D., and R. J. Naftalin, 1990, Am J Physiol, v. 258, no. 3 Pt 1, p. G377-G390; Zammit, P. S., M. Mendizabal, and R. J. Naftalin, 1994, J Physiol, v. 477 (Pt 3), p. 539-548.) However, the static pressure measured intraluminally is usually between about 6 kPa and about 15 kPa. The rather high pressure needed to dehydrate feces is essentially due to an osmotic process and not a mechanical process produced by muscular forces. The osmotic pressure arises from the active transport of salt across the colonic mucosa that ultimately produces a hypertonic fluid absorption. The osmotic gradient produced drives fluid from the lumen to the serosal side of the mucosa. Fluid-absorbing polymers, such as those described in for example U.S. Pat. Nos. 4,470,975 and 6,908,609, may not be able to sustain such pressure. Such polymers may collapse in a normal colon where the salt absorption process is intact, hence removing a modest quantity of fluid and thereby salt.

Synthetic polymers that bind sodium have also been described. For example, ion-exchange polymeric resins, such as Dowex-type cation exchange resins, have been known since about the 1950's. However, with the exception of Kayexalate™ (or Kionex™), which is a polystyrene sulfonate salt approved for the treatment of hyperkalemia, cation exchange resins have very limited use as drugs, due at least in part to their limited capacity and poor cation binding selectivity. Additionally, during the ion-exchange process, the resins may release a stochiometric amount of exogenous cations (e.g., H, K, Ca), which may in turn potentially cause acidosis (H), hyperkalemia (K) or contribute to vascular calcification (Ca). Such resins may also cause constipation.

Gastrointestinal Tract Disorders

Constipation is characterized by infrequent and difficult passage of stool and becomes chronic when a patient suffers specified symptoms for over 12 non-consecutive weeks within a 12-month period. Chronic constipation is idiopathic if it is not caused by other diseases or by use of medications. An evidence-based approach to the management of chronic constipation in North America (Brandt et al., 2005. Am. J. Gastroenterol. 100(Suppl. 1):S5-S21) revealed that prevalence is approximately 15% of the general population. Constipation is reported more commonly in women, the elderly, non-whites, and individuals from lower socioeconomic groups.

Irritable bowel syndrome (IBS) is a common GI disorder associated with alterations in motility, secretion and visceral sensation. A range of clinical symptoms characterizes this disorder, including stool frequency and form, abdominal pain and bloating. The recognition of clinical symptoms of IBS are yet to be defined, but it is now common to refer to diarrhea-predominant IBS (D-IBS) and constipation-predominant IBS (C-IBS), wherein D-IBS is defined as continuous passage of loose or watery stools and C-IBS as a group of functional disorders which present as difficult, infrequent or seemingly incomplete defecation. The pathophysiology of IBS is not fully understood, and a number of mechanisms have been suggested. Visceral hypersensitivity is often considered to play a major etiologic role and has been proposed to be a biological marker even useful to discriminate IBS from other causes of abdominal pain. In a recent clinical study (Posserud, I. et al, *Gastroenterology*, 2007; 133:1113-1123) IBS patients were submitted to a visceral sensitivity test (Balloon distention) and compared with healthy subjects. It revealed that 61% of the IBS patients had an altered visceral perception as measured by pain and discomfort threshold. Other reviews have documented the role of visceral hypersensitivity in abdominal pain symptomatic of various gastrointestinal tract disorders (Akbar, A, et al, *Aliment. Pharmaco. Ther.,* 2009, 30, 423-435: Bueno et al., *Neurogastroenterol Motility* (2007) 19 (suppl. 1), 89-119). Colonic and rectal distention have been widely used as a tool to assess visceral sensitivity in animal and human studies. The type of stress used to induce visceral sensitivity varies upon the models (see for instance Eutamen, H *Neurogastroenterol Motil.* 2009 Aug. 25. [Epub ahead of print]), however stress such as Partial restraint stress (PRS) is a relatively mild, non-ulcerogenic model that is considered more representative of the IBS setting.

Constipation is commonly found in the geriatric population, particularly patients with osteoporosis who have to take calcium supplements. Calcium supplements have shown to be beneficial in ostoporotic patients to restore bone density but compliance is poor because of calcium-induced constipation effects.

Opioid-induced constipation (OIC) (also referred to as opioid-induced bowel dysfunction or opioid bowel dysfunction (OBD)) is a common adverse effect associated with opioid therapy. OIC is commonly described as constipation; however, it is a constellation of adverse gastrointestinal (GI) effects, which also includes abdominal cramping, bloating, and gastroesophageal reflux. Patients with cancer may have disease-related constipation, which is usually worsened by opioid therapy. However, OIC is not limited to cancer patients. A recent survey of patients taking opioid therapy for pain of non-cancer origin found that approximately 40% of patients experienced constipation related to opioid therapy (<3 complete bowel movements per week) compared with 7.6% in a control group. Of subjects who required laxative therapy, only 46% of opioid-treated patients (control subjects, 84%) reported achieving the desired treatment results >50% of the time (Pappagallo, 2001, Am. J. Surg. 182(5A Suppl.): 11S-18S).

Some patients suffering from chronic idiopathic constipation can be successfully treated with lifestyle modification, dietary changes and increased fluid and fiber intake, and these treatments are generally tried first. For patients who fail to respond to these approaches, physicians typically recommend laxatives, most of which are available over-the-counter. Use of laxatives provided over-the-counter is judged inefficient by about half of the patients (Johanson and Kralstein, 2007, Aliment. Pharmacol. Ther. 25(5):599-608). Other therapeutic options currently prescribed or in clinical development for the treatment of IBS and chronic constipation including OIC are described in, for example: Chang et al., 2006, Curr. Teat. Options Gastroenterol. 9(4):314-323; Gershon and Tack. 2007, Gastroenterology 132(1):397-414: and, Hammerle and Surawicz, 2008, World J. Gastroenterol. 14(17):2639-2649. Such treatments include but are not limited to serotonin receptor ligands, chloride channel activators, opioid receptor antagonists, guanylate-cyclase receptor agonists and nucleotide P2Y(2) receptor agonists. Many of these treatment options are inadequate, as they may be habit forming, ineffective in some patients, may cause long term adverse effects, or otherwise are less than optimal.

Na+/H+ Exchanger (NHE) Inhibitors

A major function of the GI tract is to maintain water Na homeostasis by absorbing virtually all water and Na to which the GI tract is exposed. The epithelial layer covering the apical surface of the mammalian colon is a typical electrolyte-transporting epithelium, which is able to move large quantities of salt and water in both directions across the mucosa. For example, each day the GI tract processes about 9 liters of fluid and about 800 meq of Na. (See, e.g., Zachos et al., *Molecular physiology of intestinal Na+/H+ exchange*; Annu. Rev. Physiol., v. 67, p. 411-443 (2005).) Only about 1.5 liters of this fluid and about 150 meq of this sodium originates from ingestion; rather, the majority of the fluid (e.g., about 7.5 liters) and sodium (about 650 meq) is secreted via the GI organs as part of digestion. The GI tract therefore represents a viable target for modulating systemic sodium and fluid levels.

Many reviews have been published on the physiology and secretory and/or absorption mechanisms of the GI tract (see, e.g., Kunzelmann et al., *Electrolyte transport in the mammalian colon: mechanisms and implications for disease*; Physiol. Rev., v. 82, no. 1, p. 245-289 (2002); Geibel, J. P.; *Secretion and absorption by colonic crypts*; Annu. Rev. Physiol, v. 67, p. 471-490 (2005); Zachos et al., supra; Kiela, P. R. et al., *Apical NA+/H+ exchangers in the mammalian gastrointestinal tract*; J. Physiol. Pharmacol., v. 57 Suppl. 7, p. 51-79 (2006)). The two main mechanisms of Na absorption are electroneutral and electrogenic transport. Electroneutral transport is essentially due to the $Na^+/H^+$ antiport NHE (e.g., NHE-3) and is responsible for the bulk of Na absorption. Electrogenic transport is provided by the epithelium sodium channel ("ENaC"). Electroneutral transport is located primarily in the ileal segment and proximal colon and electrogenic transport is located in the distal colon.

Plasma membrane NHEs contribute to maintenance of intracellular pH and volume, transcellular absorption of NaCl and $NaHCO_3$, and fluid balance carried out by epithelial cells, especially in the kidney, intestine, gallbladder, and salivary glands, as well as regulation of systemic pH. There exists a body of literature devoted to the role and clinical intervention on systemic NHEs to treat disorders related to ischemia and reperfusion for cardioprotection or renal protection. Nine isoforms of NHEs have been identified (Kiela, P. R., et al.; *Apical NA+/H+ exchangers in the mammalian gastrointestinal tract*; J. Physiol. Pharmacol., v. 57 Suppl 7, p. 51-79 (2006)), of which NHE-2, NHE-3 and NHE-8 are expressed on the apical side of the GI tract, with NHE-3 providing a larger contribution to transport. Another, yet to be identified, Cl-dependant NHE has been identified in the crypt of rat cells. In addition, much research has been devoted to identifying inhibitors of NHEs. The primary targets of such research have been NHE-1 and NHE-3. Small molecule NHE inhibitors are, for example, described in: U.S. Pat. Nos. 5,866,610; 6,399,824; 6,911,453; 6,703,405; 6,005,010; 6,736,705; 6,887,870; 6,737,423; 7,326,705; 5,824,691 (WO 94/026709); U.S. Pat. No. 6,399,824 (WO 02/024637): U.S. Pat. Pub. Nos. 2004/0039001 (WO 02/020496); 2005/0020612 (WO 03/055490); 2004/0113396 (WO 03/051866); 2005/0020612; 2005/0054705; 2008/0194621; 2007/0225323; 2004/0039001; 2004/0224965; 2005/0113396; 2007/0135383; 2007/0135385; 2005/0244367; 2007/0270414; International Publication Nos. WO 01/072742: WO 01/021582 (CA2387529); WO 97/024113 (CA02241531) and European Pat. No. EP0744397 (CA2177007): all of which are incorporated herein by reference in their entirety for all relevant and consistent purposes.

However, such research failed to develop or recognize the value or importance of NHE inhibitors that are not absorbed (i.e., not systemic) and target the gastrointestinal tract, as disclosed recently in WO 2010/078449. Such inhibitors can be utilized in the treatment of disorders associated with fluid retention and salt overload and in the treatment of GI tract disorders, including the treatment or reduction of pain associated with a gastrointestinal tract disorder. Such inhibitors are particular advantageous because they can be delivered with reduced fear of systemic on-target or off-target effects (e.g., little or no risk of renal involvement or other systemic effects.

Accordingly, while progress has been made in the foregoing fields, there remains a need in the art for novel compounds for use in the disorders associated with fluid retention and salt overload and in the treatment of gastrointestinal tract disorders, including the treatment or reduction of pain associated with a gastrointestinal tract disorder. The present invention fulfills this need and provides further related advantages.

SUMMARY OF THE INVENTION

In brief, the present invention is directed to compounds that are substantially active in the gastrointestinal tract to inhibit NHE-mediated antiport of sodium ions and hydrogen ions, and the use of such compounds in the treatment of disorders associated with fluid retention and salt overload and in the treatment of gastrointestinal tract disorders, including the treatment or reduction of pain associated with a gastrointestinal tract disorder.

In one aspect of the invention are provided compounds of Formula I'

(I)

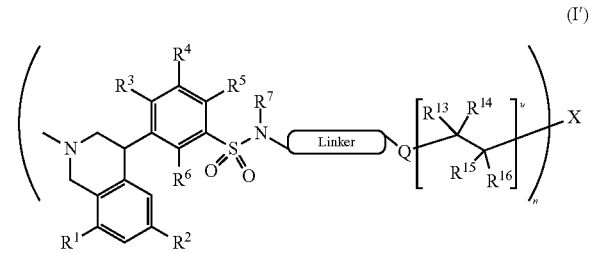

(I')

and pharmaceutically acceptable salts, prodrugs, solvates, hydrates, isomers, or tautomers thereof, wherein:

Linker is —$R^{13}$—$(CHR^{13})_p$—[Y—$(CH_2)_r]_s$—Z—$R^{13}$—$(CH_2)_t$—Z—;

Q is a bond or —NHC(O)NH—;

Z is independently, at each occurrence, a bond, C(O), or —C(O)NH—;

Y is independently, at each occurrence, O, S, NH, N($C_1$-$C_3$alkyl), or —C(O)NH—;

X is a bond, NH, O, $CR^{11}R^{12}$, $CR^{11}$, C, or —NHC(O)NH—;

n is an integer from 2 to 4;

r and p are independently, at each occurrence, integers from 0 to 8;

s is an integer from 0 to 4:

t is an integer from 0 to 4;

u is an integer from 0 to 2;

$R^1$ and $R^2$ are independently halogen, OH, CN, $C_1$-$C_6$alkyl, $C_1$-$C_6$alkoxy, $C_1$-$C_6$haloalkyl, $C_1$-$C_6$haloalkoxy, or —C(O)NR$^9$R$^{10}$;

$R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —NR$^9$S(O)$_2$R$^{10}$, —S(O)R$^9$, —S(O)NR$^9$R$^{10}$, —NR$^8$S(O)R$^9$;

$R^7$ is independently, at each occurrence, H, $C_1$-$C_6$alkyl, or $C_1$-$C_6$haloalkyl;

$R^8$ is independently, at each occurrence, a bond, H, $C_1$-$C_6$alkyl, $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more R$^{17}$; or $R^7$ and $R^8$ together with the atoms to which they are attached may combine to form independently, at each occurrence, heterocyclyl or heteroaryl containing 1-5 heteroatoms selected from the group consisting of N, S, P and O, wherein each heterocyclyl or heteroaryl is optionally substituted with one or more R$^{17}$;

$R^9$ and $R^{10}$ are independently H, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, or heteroaryl containing 1-5 heteroatoms selected from the group consisting of N, S, P and O;

$R^{11}$ and $R^{12}$ are independently H, $C_1$-$C_6$alkyl, OH, NH$_2$, CN, or NO$_2$;

$R^{13}$, $R^{14}$, $R^{15}$, and $R^{16}$ are independently, at each occurrence, H, OH, NH$_2$, or $C_1$-$C_3$ alkyl, wherein the alkyl is optionally substituted with one or more R$^{17}$; and $R^{17}$ is independently, at each occurrence, H, OH, NH$_2$, oxo, $C_1$-$C_6$alkyl, $C_1$-$C_6$haloalkyl, or $C_1$-$C_6$alkoxy;

provided that:

(1) when X is a bond, O, or CR$^{11}$R$^{12}$, n is 2;

(2) when n is 3, X is CR$^{11}$ or NH;

(3) when n is 4 X is C;

(4) only one of Q or X is —NHC(O)NH— at the time:

(5) when R$^1$ and R$^2$ are chloro, Q is —NHC(O)NH—, and R$^3$, R$^4$, R$^5$, and R$^6$ are H, Linker is not

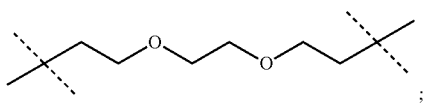

(6) when R$^1$ and R$^2$ are chloro, Q is —NHC(O)NH—, and R$^3$, R$^4$, R$^5$, and R$^6$ are H, Linker is not

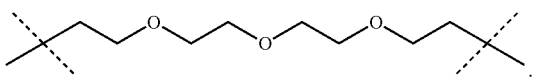

In another aspect of the invention, are provided compounds of Formula (I):

(I)

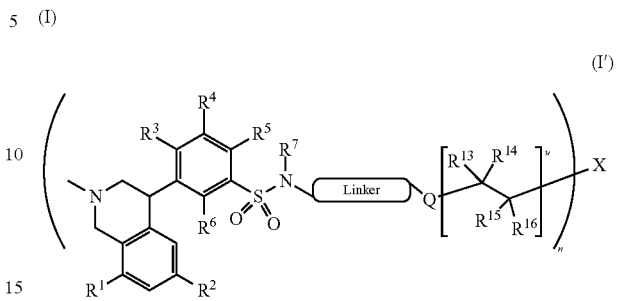

(I')

and pharmaceutically acceptable salts, prodrugs, solvates, hydrates, isomers, and tautomers thereof, wherein:

Linker is —(CHR$^8$)$_p$—[Y—(CH$_2$)$_r$]$_s$—Z—R$^8$—(CH)$_t$—Z—;

Q is a bond or —NHC(O)NH—;

Z is independently, at each occurrence, a bond, C(O), or —C(O)NH—;

Y is independently, at each occurrence, O, S, NH, N(C$_1$-C$_3$alkyl), or —C(O)NH—;

X is a bond, N, O, CR$^{11}$R$^{12}$, CR$^{11}$, C, or —NHC(O)NH—;

n is an integer from 2 to 4;

r and p are independently, at each occurrence, integers from 0 to 8;

s is an integer from 0 to 4;

t is an integer from 0 to 4;

u is an integer from 0 to 2:

$R^1$ and $R^2$ are independently halogen, OH, CN, $C_1$-$C_6$alkyl, $C_1$-$C_6$alkoxy, $C_1$-$C_6$haloalkyl, $C_1$-$C_6$haloalkoxy, or —C(O)NR$^9$R$^{10}$;

$R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —NR$^9$S(O)$_2$R$^{10}$, —S(O)R$^9$, —S(O)NR$^9$R$^{10}$, —NR$^8$(O)R$^9$;

$R^7$ is independently, at each occurrence, H, $C_1$-$C_6$alkyl, or $C_1$-$C_6$haloalkyl;

$R^8$ is independently, at each occurrence, a bond, H, $C_1$-$C_6$alkyl, $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more R$^{17}$; or $R^7$ and $R^8$ together with the atoms to which they are attached may combine to form independently, at each occurrence, heterocyclyl or heteroaryl containing 1-5 heteroatoms selected from the group consisting of N, S, P and O, wherein each heterocyclyl or heteroaryl is optionally substituted with one or more R$^{17}$;

$R^9$ and $R^{10}$ are independently H, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, or heteroaryl containing 1-5 heteroatoms selected from the group consisting of N, S, P and O;

$R^{11}$ and $R^{12}$ are independently H, $C_1$-$C_6$alkyl, OH, NH$_2$, CN, or NO$_2$;

$R^{13}$, $R^{14}$, $R^{15}$, and $R^{16}$ are independently, at each occurrence, H, OH, $NH_2$, or $C_1$-$C_3$ alkyl, wherein the alkyl is optionally substituted with one or more $R^{17}$; and $R^{17}$ is independently, at each occurrence, H, OH, $NH_2$, oxo, $C_1$-$C_6$alkyl, $C_1$-$C_6$haloalkyl, or $C_1$-$C_6$alkoxy;

provided that:
(1) when X is a bond, O, or $CR^{11}R^{12}$, n is 2;
(2) when n is 3, X is $CR^{11}$ or N;
(3) when n is 4 X is C;
(4) only one of Q or X is —NHC(O)NH— at the time:
(5) when $R^1$ and $R^2$ are chloro, Q is —NHC(O)NH—, and $R^3$, $R^4$, $R^5$, and $R^6$ are H, Linker is not

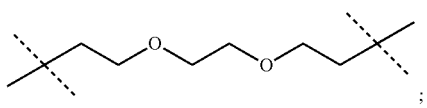

or
(6) when $R^1$ and $R^2$ are chloro, Q is —NHC(O)NH—, and $R^3$, $R^4$, $R^5$, and $R^6$ are H, Linker is not

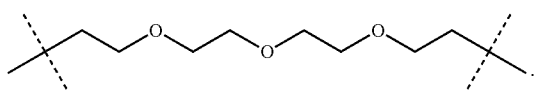

In another aspect pharmaceutical compositions are provided comprising a compound as set forth above, or a stereoisomer, pharmaceutically acceptable salt or prodrug thereof, and a pharmaceutically acceptable carrier, diluent or excipient. The pharmaceutical composition can be effective for treating a disease or disorder associated with fluid retention or salt overload. The pharmaceutical compositions can comprise the compounds of the present invention for use in treating diseases described herein. The compositions can contain at least one compound of the invention and a pharmaceutically acceptable carrier.

Another aspect of the invention relates a method for inhibiting NHE-mediated antiport of sodium and hydrogen ions. The method comprises administering to a mammal in need thereof a pharmaceutically effective amount of a compound or pharmaceutical composition described herein.

In another aspect, a method for treating a disorder associated with fluid retention or salt overload is provided. The method comprises administering to a mammal in need thereof a pharmaceutically effective amount of a compound or pharmaceutical composition as set forth above. The present invention further provides compounds that can inhibit NHE-mediated antiport of sodium and hydrogen ions. The efficacy-safety profile of the compounds of the current invention can be improved relative to other known NHE-3 inhibitors. Additionally, the present technology also has the advantage of being able to be used for a number of different types of diseases, including, but not limited to, heart failure (such as congestive heart failure), chronic kidney disease, end-stage renal disease, hypertension, essential hypertension, primary hypertension, salt-sensitive hypertension, liver disease, and peroxisome proliferator-activated receptor (PPAR) gamma agonist-induced fluid retention is provided, gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, a functional gastrointestinal tract disorder, Parkinson's disease, multiple sclerosis, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, gastric ulcers, infectious diarrhea, cancer (colorectal), "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type 1 diabetes. Celiac's Secondary PTH, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome). Schizophrenia, autism spectrum disorders, hepatic encephlopathy, small intestitinal bacterial overgrowth, and chronic alcoholism, secondary hyperparathyroidism (PTH), celiac disease, hyperphosphatemia and the like. Additional features and advantages of the present technology will be apparent to one of skill in the art upon reading the Detailed Description of the Invention, below.

BRIEF DESCRIPTION OF THE FIGURES

FIGS. 1A-1D: Depicts NHE3-independent changes in intracellular pH (pHi) modulate trans-epithelial electrical resistance in intestinal ileum monolayer cultures. Changes in pHi and trans-epithelial electrical resistance (TEER) with (A, B) nigericin and (C, D) BAM15 (3 μM) and FCCP (3 μM) compared with the known NHE3 inhibitor tenapanor and vehicle (DMSO) control in monolayer cultures. *P<0.05, P<0.01, *P<0.001, ****P<0.0001 vs DMSO.

DETAILED DESCRIPTION OF THE INVENTION

A first aspect of the present invention relates to compounds of Formula:

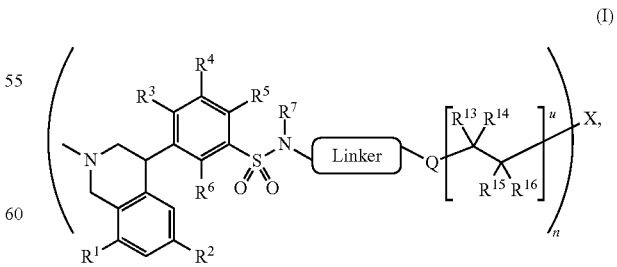

(I)

and pharmaceutically acceptable salts, prodrugs, solvates, hydrates, isomers, or tautomers thereof, wherein $R^1$, $R^2$, $R^3$, $R^4$, $R^5$, $R^6$, $R^7$, $R^{13}$, $R^{14}$, $R^{15}$, $R^{16}$, n, u, X, Q, and Linker are described as herein.

The details of the invention are set forth in the accompanying description below. Although methods and materials similar or equivalent to those described herein can be used in the practice or testing of the present invention, illustrative methods and materials are now described.

Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

Unless the context requires otherwise, throughout the present specification and claims, the word "comprise" and variations thereof, such as, "comprises" and "comprising" are to be construed in an open, inclusive sense, that is as "including, but not limited to".

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.
"Cyano" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups: a nitrogen atom in groups such as amines, amides, alkylamines, dialkylamines, arylamines, alkylarylamines, diarylamines, N-oxides, imides, and enamines: a silicon atom in groups such as trialkylsilyl groups, dialkylarylsilyl groups, alkyldiarylsilyl groups, and triarylsilyl groups: and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)N\ R_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$, —$(CH_2CH_2O)_{2-10}R_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bonded to a halogen atom, a hydroxyl group, or any other substituent described herein. Thus the term "optionally substituted" means that a given chemical moiety has the potential to contain other functional groups, but does not necessarily have any further functional groups.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propanyl, n-butynyl, iso-butynyl, pentynyl, or hexynyl. An alkynyl group can be unsubstituted or substituted.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

The terms "heterocyclyl" or "heterocycloalkyl" or "heterocycle" refer to monocyclic or polycyclic 3 to 24-membered rings containing carbon and heteroatoms taken from oxygen, phosphorous, nitrogen, or sulfur and wherein there is not delocalized π electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring can also be fused or bridged, e.g., can be a bicyclic ring.

As used herein, the term "halo" or "halogen" means a fluoro, chloro, bromo, or iodo group.

The term "carbonyl" refers to a functional group composing a carbon atom double-bonded to an oxygen atom. It can be abbreviated herein as "oxo", as C(O), or as C=O.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —$OC_2$-$C_6$alkenyl, —$OC_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —$NH_2$, —NH($C_1$-$C_6$alkyl), —N($C_1$-$C_6$alkyl)$_2$, —S(O)$_2$-$C_1$-$C_6$alkyl, —S(O)NH$C_1$-$C_6$alkyl, and —S(O)N($C_1$-$C_6$alkyl)$_2$. The substituents can themselves be optionally substituted. Furthermore, when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical or a polycyclic aromatic radical of 5 to 24 ring atoms, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1□$^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo1[5,4-d]thiazolyl, imidazo[2,1-b][1,3,4]thiadiazolyl, thieno[2,3-b]pyrrolyl, 3H-indolyl, and derivatives thereof. Furthermore, when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R) or (S) or, as (D) or (L) for amino acids. The present invention is meant to include all such possible isomers, as well as their racemic and optically pure forms. Optically active (+) and (−), (R) and (S), or (D) and (L) isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable.

The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

In accordance with the present disclosure, the compounds described herein are designed to be substantially active or localized in the gastrointestinal lumen of a human or animal subject. The term "gastrointestinal lumen" is used interchangeably herein with the term "lumen," to refer to the space or cavity within a gastrointestinal tract (GI tract, which can also be referred to as the gut), delimited by the apical membrane of GI epithelial cells of the subject. In some embodiments, the compounds are not absorbed through the layer of epithelial cells of the GI tract (also known as the GI epithelium). "Gastrointestinal mucosa" refers to the layer(s) of cells separating the gastrointestinal lumen from the rest of the body and includes gastric and intestinal mucosa, such as the mucosa of the small intestine. A "gastrointestinal epithelial cell" or a "gut epithelial cell" as used herein refers to any epithelial cell on the surface of the gastrointestinal mucosa that faces the lumen of the gastrointestinal tract, including, for example, an epithelial cell of the stomach, an intestinal epithelial cell, a colonic epithelial cell, and the like.

A "subject" is a human, but can also be an animal in need of treatment with a compound of the disclosure, e.g., companion animals (e.g., dogs, cats, and the like), farm animals (e.g., cows, pigs, horses and the like) and laboratory animals (e.g., rats, mice, guinea pigs and the like).

"Substantially systemically non-bioavailable" and/or "substantially impermeable" as used herein (as well as variations thereof) generally refer to situations in which a statistically significant amount, and in some embodiments essentially all of the compound of the present disclosure (which includes the NHE-inhibitor small molecule), remains in the gastrointestinal lumen. For example, in accordance with one or more embodiments of the present disclosure, at least about 70%, about 80%, about 90/%, about 95%, about 98%, about 99%, or even about 99.5%, of the compound remains in the gastrointestinal lumen. In such cases, localization to the gastrointestinal lumen refers to reducing net movement across a gastrointestinal layer of epithelial cells, for example, by way of both transcellular and paracellular transport, as well as by active and/or passive transport. The compound in such embodiments is hindered from net permeation of a layer of gastrointestinal epithelial cells in transcellular transport, for example, through an apical membrane of an epithelial cell of the small intestine. The compound in these embodiments is also hindered from net permeation through the "tight junctions" in paracellular transport between gastrointestinal epithelial cells lining the lumen.

In this regard it is to be noted that, in one particular embodiment, the compound is essentially not absorbed at all by the GI tract or gastrointestinal lumen. As used herein, the terms "substantially impermeable" or "substantially systemically non-bioavailable" refers to embodiments wherein no detectable amount of absorption or permeation or systemic exposure of the compound is detected, using means generally known in the art.

In this regard it is to be further noted, however, that in alternative embodiments "substantially impermeable" or "substantially systemically non-bioavailable" provides or allows for some limited absorption in the GI tract, and more particularly the gut epithelium, to occur (e.g., some detectable amount of absorption, such as for example at least about 0.1%, 0.5%, 1% or more and less than about 30%, 20%, 10%, 5%, etc., the range of absorption being for example between about 1% and 30%, or 5% and 20%, etc.; stated another way, "substantially impermeable" or "substantially systemically non-bioavailable" refers to compounds that exhibit some detectable permeability to an epithelium layer of cells in the GI tract of less than about 20% of the administered compound (e.g., less than about 15%, about 10%, or even about 5%, and for example greater than about 0.5%, or 1%), but then are cleared by the liver (i.e., hepatic extraction) and/or the kidney (i.e., renal excretion).

In accordance with the present disclosure, and as further detailed herein below, it has been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of various disorders that may be associated with or caused by fluid retention and/or salt overload, and/or disorders such as heart failure (in particular, congestive heart failure), chronic kidney disease, end-stage renal disease, liver disease, and/or peroxisome proliferator-activated receptor (PPAR) gamma agonist-induced fluid retention. More specifically, it has been found that the inhibition of the NHE-mediated antiport of sodium ions and hydrogen ions in the GI tract increases the fecal excretion of sodium, effectively reducing systemic levels of sodium and fluid. This, in turn, improves the clinical status of a patient suffering from, for example, CHF, ESRD/CKD and/or liver disease. It has further been found that such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE-inhibiting compound.

Additionally, and also as further detailed herein below, it has further been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of hypertension, that may be associated with or caused by fluid retention and/or salt overload. More specifically, it has been found that the inhibition of the NHE-mediated antiport of sodium ions and hydrogen ions in the GI tract increases the fecal excretion of sodium, effectively reducing systemic levels of sodium and fluid. This, in turn, improves the clinical status of a patient suffering from hypertension. Such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE-inhibiting compound.

Additionally, and also as further detailed herein below, it has further been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of various gastrointestinal tract disorders, including the treatment or reduction of pain associated with gastrointestinal tract disorders, and more particularly to the restoration of appropriate fluid secretion in the gut and the improvement of pathological conditions encountered in constipation states. Applicants have further recognized that by blocking sodium ion re-absorption, the compounds of the present disclosure restore fluid homeostasis in the GI tract, particularly in situations wherein fluid secretion/absorption is altered in such a way that it results in a high degree of feces dehydration, low gut motility, and/or a slow transit-time producing constipation states and GI discomfort generally. It has further been found that such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE-inhibiting compound. Due to the presence of NHEs in other organs or tissues in the body, the method of the present disclosure employs the use of compounds and compositions that are desirably highly selective or localized, thus acting substantially in the gastrointestinal tract without exposure to other tissues or organs. In this way, any systemic effects can be minimized (whether they are on-target or off-target). Accordingly, it is to be noted that, as used herein, and as further detailed elsewhere herein, "substantially active in the gastrointestinal tract" generally refers to compounds that are substantially systemically non-bioavailable and/or substantially impermeable to the layer of epithelial cells, and more specifically epithelium of the GI tract. It is to be further noted that, as used herein, and as further detailed elsewhere herein, "substantially impermeable" more particularly encompasses compounds that are impermeable to the layer of epithelial cells, and more specifically the gastrointestinal epithelium (or epithelial layer). "Gastrointestinal epithelium" refers to the membranous tissue covering the internal surface of the gastrointestinal tract. Accordingly, by being substantially impermeable, a compound has very limited ability to be transferred across the gastrointestinal epithelium, and thus contact other internal organs (e.g., the brain, heart, liver, etc.). The typical mechanism by which a compound can be transferred across the gastrointestinal epithelium is by either transcellular transit (a substance travels through the cell, mediated by either passive or active transport passing through both the apical and basolateral membranes) and/or by paracellular transit, where a substance travels between cells of an epithelium, usually through highly restrictive structures known as "tight junctions". Without wishing to be bound to any particular theory, it is believed that the NHE-inhibiting compounds (e.g., NHE-3, -2 and/or -8 inhibitors) of the present disclosure are believed to act via a distinct and unique mechanism, to decrease paracellular permeability of the intestine. NHE3 is expressed at high levels on the apical surface of the gastrointestinal tract and couples luminal Na absorption to the secretion of intracellular protons. Inhibition of NHE3, by the NHE-inhibiting compounds (e.g., NHE-3, -2 and/or -8 inhibitors) of the present disclosure, results in accumulation of intracellular protons. The intracellular proton retention accompanying NHE3 inhibition modulates the tight junction between cells to decrease paracellular permeability which can be measured by an increase in transepithelial electrical resistance. Since increased paracellular and/or transcellular permeability of the intestine is observed in many diseases including, but not limited to a gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, multiple sclerosis-induced constipation, parkinson's disease-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, gastric ulcers, infectious diarrhea, cancer (colorectal), "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type I diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestinal bacterial overgrowth, and chronic alcoholism, and the like it is anticipated that NHE inhibition could provide therapeutic benefit in these diseases by decreasing paracellular and/or transcellular permeability in the intestine.

Thus in some embodiments, the present disclosure provides methods of decreasing paracellular permeability of the intestine. In some embodiments, the method of decreasing paracellular permeability of the intestine comprises administration of an NHE3 inhibitor. In some embodiments, the inhibition of NHE3 results in an accumulation of intracellular protons. In some embodiments, the decrease in paracellular permeability is due to an increase in intracellular protons independent of and without NHE3 inhibition. In other words, an increase in intracellular protons without NHE3 inhibition results in a decrease in paracellular permeability. Thus methods of decreasing paracellular permeability comprising increasing intracellular protons is provided. In some embodiments, methods of treating diseases associated with paracellular permeability are provided comprising administering an agent that increases intracellular protons at tight junctions thereby decreasing paracellular permeability and thus treating the disease. Non limiting examples of such diseases include, Crohn's disease, ulcerative colitis and related diseases referred to as inflammatory bowel syndrome, colonic pseudo-obstruction, gastric ulcers, infectious diarrhea, cancer (colorectal), "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type 1 diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestinal bacterial overgrowth, and chronic alcoholism, and the like.

In some embodiments, the present disclosure provides methods of modulating transcellular permeability of the intestine. In some embodiments, the method of modulating transcellular permeability of the intestine comprises administration of an NHE3 inhibitor. In some embodiments, the inhibition of NHE3 results in a substance travelling through the cell, mediated by either passive or active transport passing through both the apical and basolateral membranes. Thus methods of modulating transcellular permeability comprising mediating either passive or active transport of a substance passing through both the apical and basolateral membranes is provided. In some embodiments, methods of treating diseases associated with transcellular permeability are provided comprising administering an agent that mediates either passive or active transport of a substance passing through both the apical and basolateral membranes of a cell, thereby modulating transcellular permeability and thus treating the disease. Non limiting examples of such diseases include a gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, multiple sclerosis-induced constipation, parkinson's disease-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction.

The compounds of the present disclosure may therefore not be absorbed, and are thus essentially not systemically bioavailable at all (e.g., impermeable to the gastrointestinal epithelium at all), or they show no detectable concentration of the compound in serum. Alternatively, the compounds may: (i) exhibit some detectable permeability to the layer of epithelial cells, and more particularly the epithelium of the GI tract, of less than about 20% of the administered compound (e.g., less than about 15%, about 10%, or even about 5%, and for example greater than about 0.5%, or 1%), but then are rapidly cleared in the liver (i.e., hepatic extraction) via first-pass metabolism; and/or (ii) exhibit some detectable permeability to the layer of epithelial cells, and more particularly the epithelium of the GI tract, of less than about 20% of the administered compound (e.g., less than about 15%, about 10%, or even about 5%, and for example greater than about 0.5%, or 1%), but then are rapidly cleared in the kidney (i.e., renal excretion).

Compounds may also be cleared from circulation unchanged into the bile by biliary excretion. The compounds of the present disclosure may therefore not exhibit detectable concentrations in the bile. Alternatively, the compounds may exhibit some detectable concentration in the bile and more particularly the epithelium of the biliary tract and gallbladder of 10 µM, less than 1 µM, less than 0.1 µM, less than 0.01 µM or less than about 0.001 µM.

In this regard it is to be still further noted that, as used herein, "substantially systemically non-bioavailable" generally refers to the inability to detect a compound in the systemic circulation of an animal or human following an oral dose of the compound. For a compound to be bioavailable, it must be transferred across the gastrointestinal epithelium (that is, substantially permeable as defined above), be transported via the portal circulation to the liver, avoid substantial metabolism in the liver, and then be transferred into systemic circulation.

Without being held to any particular theory, the NHE-inhibiting compounds (e.g., NHE-3, -2 and/or -8 inhibitors) of the present disclosure are believed to act via a distinct and unique mechanism, causing the retention of fluid and ions in the GI tract (and stimulating fecal excretion) rather than stimulating increased secretion of said fluid and ions. For example, lubiprostone (Amitiza® Sucampo/Takeda) is a bicyclic fatty acid prostaglandin E1 analog that activates the Type 2 Chloride Channel (ClC-2) and increases chloride-rich fluid secretion from the serosal to the mucosal side of the GI tract (see, e.g., Pharmacological Reviews for Amitiza®, NDA package). Linaclotide (MD-1100 acetate, MicrobiaForest Labs) is a 14 amino acid peptide analogue of an endogenous hormone, guanylin, and indirectly activates the Cystic Fibrosis Transmembrane Conductance Regulator (CFTR) thereby inducing fluid and electrolyte secretion into the GI (see, e.g., Li et al., J. Exp. Med., vol. 202 (2005), pp. 975-986). The substantially impermeable NHE-inhibiting compounds of the present disclosure act to inhibit the reuptake of salt and fluid rather than promote secretion. Since the GI tract processes about 9 liters of fluid and about 800 meq of Na each day, it is anticipated that NHE inhibition could permit the removal of substantial quantities of systemic fluid and sodium to resorb edema and resolve CHF symptoms.

I. NHE-Inhibiting Compounds

In one aspect, the compounds of the present disclosure are generally represented by Formula (I):

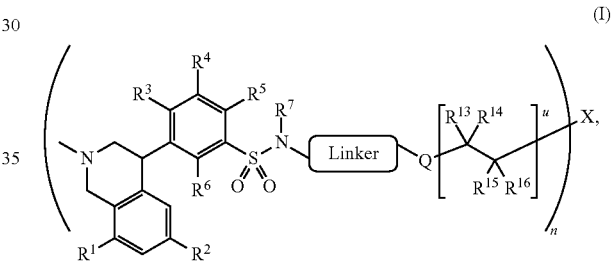

and pharmaceutically acceptable salts, prodrugs, solvates, hydrates, isomers, or tautomers thereof, wherein: $R^1$, $R^2$, $R^3$, $R^4$, $R^5$, $R^6$, $R^7$, $R^{13}$, $R^{14}$, $R^{15}$, $R^{16}$, n, u, X, Q, and Linker are described as herein. In an embodiment, these NHE-inhibiting compounds (i.e., a compound of Formula (I)) possess overall physicochemical properties that render them substantially impermeable or substantially systemically non-bioavailable.

It is to be noted that, in the many structures illustrated herein, all of the various linkages or bonds will not be shown in every instance. However, this should not be viewed in a limiting sense. Rather, it is to be understood that the NHE-inhibiting molecule is bound or interconnected in some way (e.g., by a bond or Linker) such that the resulting NHE-inhibiting compound is suitable for use (i.e., substantially impermeable or substantially systemically non-bioavailable in the GI tract).

In yet other embodiments, the polyvalent NHE-inhibiting compound may be in oligomeric or polymeric form. It is to be noted that the repeat unit in each Formula (I) generally encompasses repeating units of various polymeric embodiments, including linear, branched and dendritic structures, which may optionally be produced by methods referred to herein. In each polymeric, or more general polyvalent, embodiment, it is to be noted that each repeat unit may be the same or different, and may or may not be linked through the "X" moiety by a Linker, which in turn may be the same or different when present. In this regard it is to be noted that as used herein, "polyvalent" refers to a molecule that has multiple (e.g., 2, 4, 6, 8, 10 or more) NHE-inhibiting molecule.

In one embodiment of the invention, the Linker may be represented by, but not limited to,

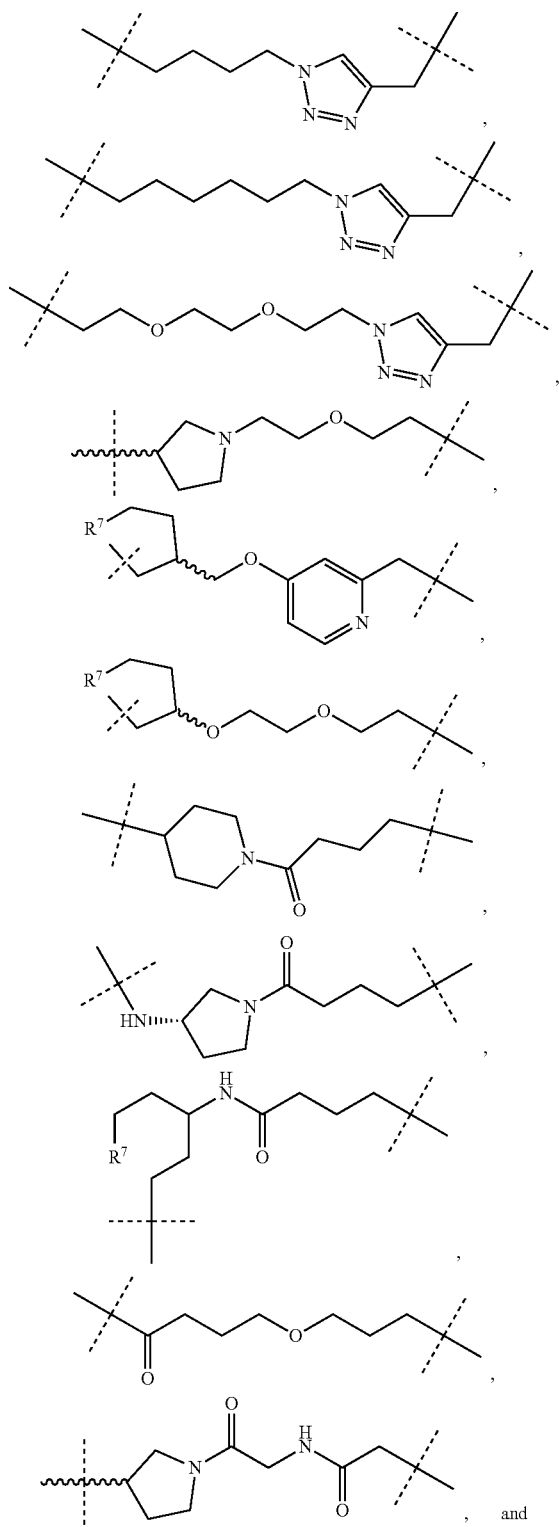

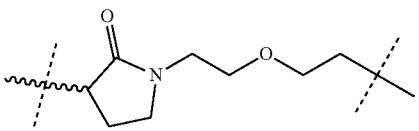

In another embodiment, the Linker may represent, without limitation, by

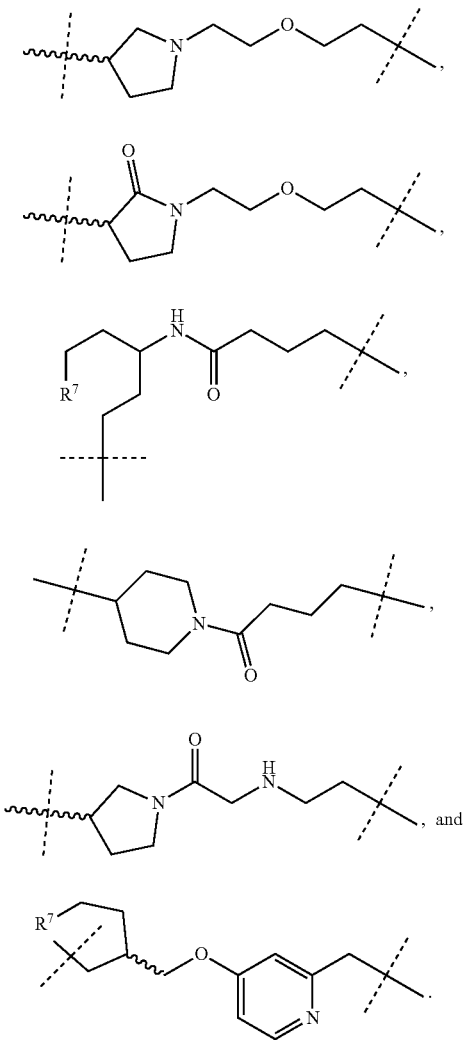

In some embodiments, of the invention, $R^1$ and $R^2$ are $C_1$-$C_6$alkyl, CN, or halogen. In some embodiments, $R^1$ and $R^2$ are $C_1$-$C_6$alkyl. In other embodiments, $R^1$ and $R^2$ are methyl. In other embodiments, $R^1$ is $C_1$-$C_6$alkyl and $R^2$ is halogen. In other embodiments, $R^1$ is methyl and $R^2$ is halogen. In other embodiments, $R^1$ is CN and $R^2$ is halogen.

Yet in other embodiments of the compounds of Formula I, $R^3$, $R^4$, $R^5$, and $R^6$ are H, halogen, or $C_1$-$C_6$alkyl. In other embodiments, $R^3$, $R^4$, $R^5$, and $R^6$ are H. In other embodiments, $R^3$ is methyl or fluoro and $R^4$, $R^5$, and $R^6$ are H. In embodiments, $R^5$ is methyl and $R^3$, $R^4$, and $R^6$ are H.

In some embodiments of the compounds of Formula I, Q is —NHC(O)NH—. In another embodiment of the compounds of Formula I, Q is —NHC(O)NH—. In a particular embodiment, Q is —NHC(O)NH— and the Linker is -heterocyclyl-(CHR³)$_p$—[Y—(CH$_2$)$_r$]$_s$—. In a particular embodiment, Q is —NHC(O)NH—, the Linker is -heterocyclyl-(CHR¹³)$_p$—[Y—(CH$_2$)$_r$]$_s$— and u is 0. In a particular embodiment, Q is —NHC(O)NH—, the Linker is -heterocyclyl-(CHR¹³)$_p$—[Y—(CH$_2$)$_r$]$_s$—, u is 0 and n is 2. In a particular embodiment, Q is —NHC(O)NH—, the Linker is -heterocyclyl-(CHR¹³)$_p$—[Y—(CH$_2$)$_r$]$_s$—, u is 0, n is 2 and X is —(CHR¹³)$_p$— or C$_3$-C$_6$cycloalkyl. In some embodiments, Q is a bond. In some embodiments, Q is a bond and X is —NHC(O)NH—.

In one embodiment of the compounds of Formula I, R¹³, R¹⁴, R¹⁵, and R¹⁶ are all H. In one embodiment of the compounds of Formula I, R¹³ and R¹⁶ are H. In one embodiment of the compounds of Formula I, R¹⁴ and R¹⁵ are OH. In yet another embodiment of the compounds of Formula I, R¹³ and R¹⁵ are H and R¹⁴ and R¹⁶ are OH.

In one embodiment of the compounds of Formula I, Y is O, r is 2, and s is 1. In another embodiment, Y is O, r is 2, and s is 2. In some embodiments, s is 0. In some embodiments, Z is C(O).

In some embodiments of the compounds of Formula I, R¹¹ is H, C$_1$-C$_6$ alkyl, heterocyclyl or heteroaryl. In some embodiments of the compounds of Formula I, the heterocyclyl or heteroaryl of R⁸ is optionally substituted with one or more R¹⁷. In some embodiments, R⁸ is heterocyclyl optionally substituted with one or more R¹⁷. In some embodiments, R¹⁷ is oxo. In some embodiments of the compounds of Formula I, n is 2. In other embodiments of the compounds of Formula I, n is 3 or 4.

In one embodiment of the invention, the compounds of Formula I have the Formula Ia:

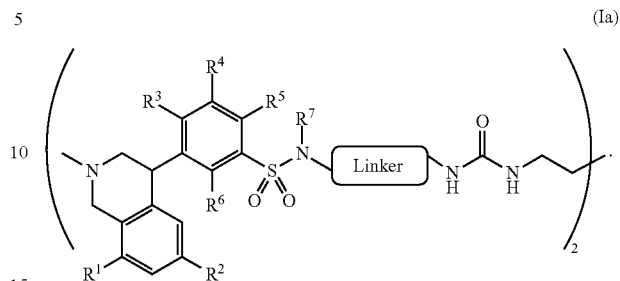

(Ia)

In one embodiment of the invention, the compounds of Formula I have the Formula Ib:

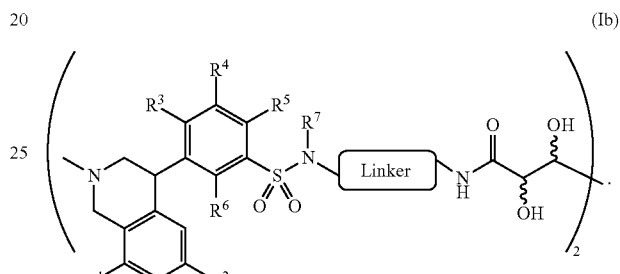

(Ib)

In one embodiment of the invention, the compounds of Formula I have the Formula Ic:

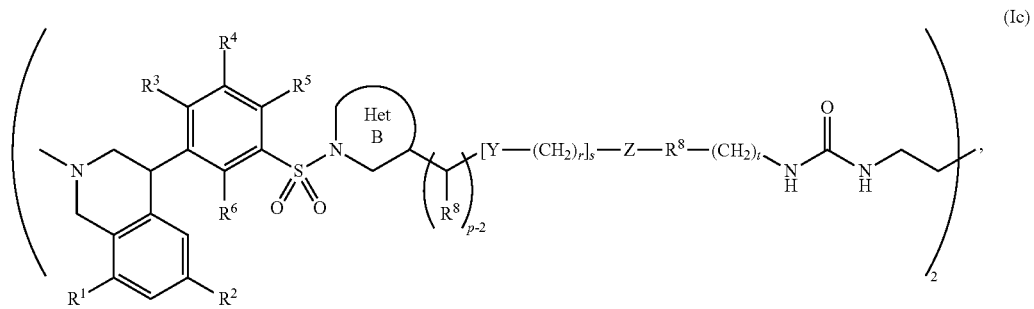

(Ic)

wherein Het B represents a heterocyclyl or heteroaryl containing 1-5 heteroatoms selected from the group consisting of N, S, P and O, wherein each heterocyclyl or heteroaryl is optionally substituted with one or more R¹⁷.

In one embodiment of the invention, the compounds of Formula I have the Formula Id:

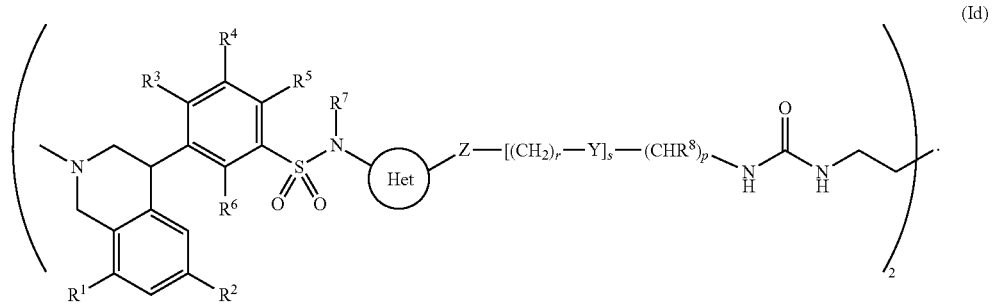

(Id)

wherein Het represents R⁸ which is $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more $R^{17}$.

In one embodiment of the invention, the compounds of Formula I have the Formula Ie:

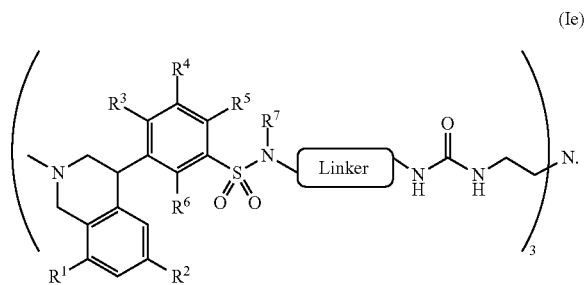

(Ie)

In one embodiment of the invention, the compounds of Formula I have the Formula Ig:

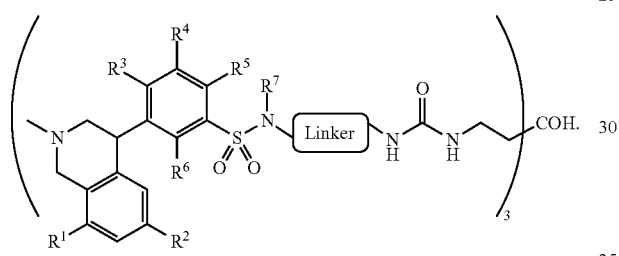

(If)

In one embodiment of the invention, the compounds of Formula I have the Formula Ig:

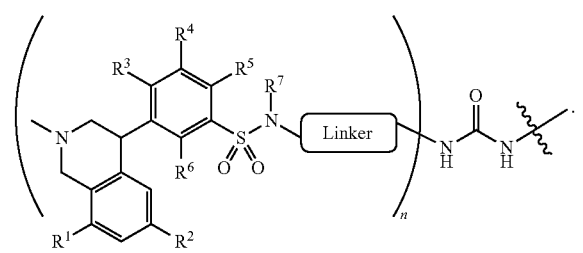

(Ig)

In other embodiments, compounds of Formula I include, but are not limited to,

N,N'-(10,17-Dioxo-3,6,21,24-tetraoxa-9,11,16,18-tetraazahexacosane-1,26-diyl)bis[3-(6-chloro-2,8-dimethyl-1,2,3,4-tetrahydroisoquinolin-4-yl)benzenesulfonamide];

N,N'-(10,17-Dioxo-3,6,21,24-tetraoxa-9,11,16,18-tetraazahexacosane-1,26-diyl)bis[3-(6-chloro-8-cyano-2-methyl-1,2,3,4-tetrahydroisoquinolin-4-yl)benzenesulfonamide];

N,N'-(10,17-Dioxo-3,6,21,24-tetraoxa-9,11,16,18-tetraazahexacosane-1,26-diyl)bis[3-(6,8-dichloro-2-methyl-1,2,3,4-tetrahydroisoquinolin-4-yl)-4-methylbenzenesulfonamide];

N,N'-(10,17-Dioxo-3,6,21,24-tetraoxa-9,11,16,18-tetraazahexacosane-1,26-diyl)bis[3-(6-chloro-2,8-dimethyl-1,2,3,4-tetrahydroisoquinolin-4-yl)-4-methylbenenesulfonamide];

N,N'-(10,17-Dioxo-3,6,21,24-tetraoxa-9,11,16,18-tetraazahexacosane-1,26-diyl)bis[3-(6-chloro-8-cyano-2-methyl-1,2,3,4-tetrahydroisoquinolin-4-yl)-4-methylbenzenesulfonamide];

N,N'-(10,17-Dioxo-3,6,21,24-tetraoxa-9,11,16,18-tetraazahexacosane-1,26-diyl)bis[5-(6,8-dichloro-2-methyl-1,2,3,4-tetrahydroisoquinolin-4-yl)-2-methylbenzenesulfonamide];

N,N'-(10,17-Dioxo-3,6,21,24-tetraoxa-9,11,16,18-tetraazahexacosane-1,26-diyl)bis[5-(6-chloro-2,8-dimethyl-1,2,3,4-tetrahydroisoquinolin-4-yl)-2-methylbenzenesulfonamide];

N,N'-(10,17-Dioxo-3,6,21,24-tetraoxa-9,11,16,18-tetraazahexacosane-1,26-diyl)bis(5-(6-chloro-8-cyano-2-methyl-1,2,3,4-tetrahydroisoquinolin-4-yl)-2-methylbenzenesulfonamide);

N,N'-(10,17-Dioxo-3,6,21,24-tetraoxa-9,11,16,18-tetraazahexacosane-1,26-diyl)bis[3-(6,8-dichloro-2-methyl-1,2,3,4-tetrahydroisoquinolin-4-yl)-4-fluorobenzenesulfonamide]; N,N'-(10,17-Dioxo-3,6,21,24-tetraoxa-9,11,16,18-tetraazahexacosane-1,26-diyl)bis[3-(6-chloro-2,8-dimethyl-1,2,3,4-tetrahydroisoquinolin-4-yl)-4-fluorobenzenesulfonamide;

N,N'-(10,17-Dioxo-3,6,21,24-tetraoxa-9,11,16,18-tetraazahexacosane-1,26-diyl)bis[3-(6-chloro-8-cyano-2-methyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6,8-dichloro-2-methyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6-chloro-2,8-dimethyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6-chloro-8-cyano-2-methyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)benzenesulfonamide;]

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6,8-dichloro-2-methyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6-chloro-2,8-dimethyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6-chloro-8-cyano-2-methyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-fluorobenzenesulfonamide];

N,N'-[(7,14-Dioxo-3,18-dioxa-6,8,13,15-tetraazaicosane-1,20-diyl)bis(piperidine-1,4-diyl)]bis[3-(6-chloro-2,8-dimethyl-1,2,3,4-tetrahydroisoquinolin-4-yl)benzenesulfonamide];

N,N'-[(7,14-Dioxo-3,18-dioxa-6,8,13,15-tetraazaicosane-1,20-diyl)bis(piperidine-1,4-diyl)]bis[3-(6-chloro-8-cyano-2-methyl-1,2,3,4-tetrahydroisoquinolin-4-yl)benzenesulfonamide];

1,1'-[(3R,3'R)-(7,14-Dioxo-3,18-dioxa-6,8,13,15-tetraazaicosane-1,20-diyl)bis(pyrrolidine-1,3-diyl)]bis[N-([3-(6-chloro-2,8-dimethyl-1,2,3,4-tetrahydroisoquinolin-4-yl)phenyl]sulfonyl)formamide];

1,1'-[(3R,3'R)-(7,14-Dioxo-3,18-dioxa-6,8,13,15-tetraazaicosane-1,20-diyl)bis(pyrrolidine-1,3-diyl)]bis[N-([3-(6-chloro-8-cyano-2-methyl-1,2,3,4-tetrahydroisoquinolin-4-yl)phenyl]sulfonyl)formamide];

1,1'-(5,12-Dioxo-4,6,11,13-tetraazahexadecane-1,16-diyl)bis[N-([3-(6,8-dichloro-2-methyl-1,2,3,4-tetrahydroisoquinolin-4-yl)phenyl]sulfonyl)piperidine-4-carboxamide];

1,1'-(5,12-Dioxo-4,6,11,13-tetraazahexadecane-1,16-diyl)bis[N-([3-(6,8-dichloro-2-methyl-1,2,3,4-tetrahydroisoquinolin-4-yl)phenyl]sulfonyl)piperidine-3-carboxamide];

$N^1,N^{18}$-Bis([3-(6,8-Dichloro-2-dimethyl-1,2,3,4-tetrahydroisoquinolin-4-yl)phenyl]sulfonyl)-6,13-dioxo-5,7,12,14-tetraazaoctadecanediamide;

N,N'-[(3S,3'S)-(6,13-Dioxo-5,7,12,14-tetraazaoctadecanedioyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3S,3'S)-(6,13-Dioxo-5,7,12,14-tetraazaoctadecanedioyl)bis(pyrrolidine-1,3-diyl)]bis[3-(6-chloro-8-cyano-2-methyl-1,2,3,4-tetrahydroisoquinolin-4-yl)benzenesulfonamide];

1-[2-(2-[(1-[(3-[(S)-6,8-Dichloro-2-methyl-1,2,3,4-tetrahydroisoquinolin-4-yl]phenyl)sulfonyl]piperidin-4-yl)oxy]ethoxy)ethyl]-3-[4-(3-[2-(2-[(1-(3-[(S)-6,8-dichloro-2-methyl-1,2,3,4-tetrahydroisoquinolin-4-yl]phenyl)sulfonyl]piperidin-4-yl)oxy]ethoxy)ethyl]ureido)butyl]urea;

1-(2-(2-(((R)-1-((3-((S)-6,8-dichloro-2-methyl-1,2,3,4-tetrahydroisoquinolin-4-yl)phenyl)sulfonyl)pyrrolidin-3-yl)oxy)ethoxy)ethyl)-3-(4-(3-(2-(2-(((R)-1-((3-((S)-6,8-dichloro-2-methyl-1,2,3,4-tetrahydroisoquinolin-4-yl)phenyl)sulfonyl)pyrrolidin-3-yl)oxy)ethoxy)ethyl)ureido)butyl)urea;

1-(2-[2-([(S)-[(3-[(S)-6,8-dichloro-2-methyl-1,2,3,4-tetrahydroisoquinolin-4-yl]phenyl)sulfonyl]pyrrolidin-3-yl]oxy)ethoxy]ethyl)-3-(4-[3-(2-[2-([(S)-1-[(3-[(S)-6,8-dichloro-2-methyl-1,2,3,4-tetrahydroisoquinolin-4-yl]phenyl)sulfonyl]pyrrolidin-3-yl]oxy)ethoxy]ethyl)ureido]butyl)urea;

3-[(S)-6,8-Dichloro-2-methyl-1,2,3,4-tetrahydroisoquinolin-4-yl]-N-[(3R,28R)-28-[(3-[(S)-6,8-dichloro-2-methyl-1,2,3,4-tetrahydroisoquinolin-4-yl]phenyl)sulfonamido]-2,29-dimethyl-12,19-dioxo-5,8,23,26-tetraoxa-11,13,18,20-tetraazatriacontan-3-yl]benzenesulfonamide;

N,N'-(10-Oxo-3,6,14,17-tetraoxa-9,11-diazanonadecane-1,19-diyl)bis[3-(6,8-dichloro-2-methyl-1,2,3,4-tetrahydroisoquinolin-4-yl)benzenesulfonamide];

N,N'-[(3S,3'S)-(7-Oxo-3,11-dioxa-6,8-diazatridecane-1,13-diyl)bis[pyrrolidine-1,3-diyl]))bis(3-(6,8-dichloro-2-methyl-1,2,3,4-tetrahydroisoquinolin-4-yl)benzenesulfonamide];

$N^1,N^{18}$-Bis(1-[(3-[(S)-6,8-dichloro-2-methyl-1,2,3,4-tetrahydroisoquinolin-4-yl]phenyl)sulfonyl]piperidin-4-yl)-6,13-dioxo-5,7,12,14-tetraazaoctadecanediamide;

$N^1,N^{18}$-Bis(1-[(3-[(S)-6-chloro-8-cyano-2-methyl-1,2,3,4-tetrahydroisoquinolin-4-yl]phenyl)sulfonyl]piperidin-4-yl)-6,13-dioxo-5,7,12,14-tetraazaoctadecanediamide; or $N^1,N^{18}$-Bis(1-[(3-[(S)-6-chloro-2,8-dimethyl-1,2,3,4-tetrahydroisoquinolin-4-yl]phenyl)sulfonyl]piperidin-4-yl)-6,13-dioxo-5,7,12,14-tetraazaoctadecanediamide.

In some embodiments, Y is O, S, NH, N($C_1$-$C_3$alkyl), or —C(O)NH—. In some embodiments, Y is O. In some embodiments, Y is S. In some embodiments, Y is NH. In some embodiments, Y is N($C_1$-$C_3$alkyl). In some embodiments, Y is —C(O)NH—. In some embodiments. Y is O, S, NH, or N($C_1$-$C_3$alkyl). In some embodiments, Y is O, S, or NH. In some embodiments, Y is O or S.

In some embodiments, Q is a bond or —NHC(O)NH—. In some embodiments, Q is a bond, NH, —C(O)NH—, —NHC(O)NH—, or —NHC(O)N(CH$_3$)—. In some embodiments, Q is a bond. In some embodiments, Q is —NHC(O)NH—.

In another embodiment, $R^1$ is halogen, OH, CN, $C_1$-$C_6$alkyl, $C_1$-$C_6$alkoxy, $C_1$-$C_6$haloalkyl, $C_1$-$C_6$haloalkoxy, or —C(O)NR$^9$R$^{10}$. In one embodiment, $R^1$ is halogen, OH, CN, $C_1$-$C_6$alkyl, $C_1$-$C_6$alkoxy, $C_1$-$C_6$haloalkyl, or $C_1$-$C_6$haloalkoxy. In one embodiment, $R^1$ is halogen, OH, CN, $C_1$-$C_6$alkyl, $C_1$-$C_6$alkoxy, or $C_1$-$C_6$haloalkyl. In one embodiment, $R^1$ is halogen, OH, CN, $C_1$-$C_6$alkyl, or $C_1$-$C_6$alkoxy. In one embodiment, $R^1$ is halogen, OH, CN, or $C_1$-$C_6$alkyl. $R^1$ is halogen, OH, or CN. In one embodiment, $R^1$ is halogen or OH. In one embodiment, $R^1$ is halogen. $R^1$ is OH. In one embodiment, $R^1$ is CN. In one embodiment, $R^1$ is $C_1$-$C_6$alkyl. In one embodiment, $R^1$ is $C_1$-$C_6$alkoxy. In one embodiment, $R^1$ is $C_1$-$C_6$haloalkyl. In one embodiment, $R^1$ is $C_1$-$C_6$haloalkoxy. In one embodiment, $R^1$ is —C(O)NR$^9$R$^{10}$.

In another embodiment, $R^2$ is halogen, OH, CN, $C_1$-$C_6$alkyl, $C_1$-$C_6$alkoxy, $C_1$-$C_6$haloalkyl, $C_1$-$C_6$haloalkoxy, or —C(O)NR$^9$R$^{10}$. In one embodiment, $R^2$ is halogen, OH, CN, $C_1$-$C_6$alkyl, $C_1$-$C_6$alkoxy, $C_1$-$C_6$haloalkyl, or $C_1$-$C_6$haloalkoxy. In one embodiment, $R^2$ is halogen, OH, CN, $C_1$-$C_6$alkyl, $C_1$-$C_6$alkoxy, or $C_1$-$C_6$haloalkyl. In one embodiment, $R^2$ is halogen, OH, CN, $C_1$-$C_6$alkyl, or $C_1$-$C_6$alkoxy. In one embodiment, $R^2$ is halogen. OH, CN, or $C_1$-$C_6$alkyl. $R^2$ is halogen, OH, or CN. In one embodiment, $R^2$ is halogen or OH. In one embodiment, $R^2$ is halogen. $R^2$ is OH. In one embodiment, $R^1$ is CN. In one embodiment. $R^2$ is $C_1$-$C_6$alkyl. In one embodiment, $R^2$ is $C_1$-$C_6$alkoxy. In one embodiment, $R^2$ is $C_1$-$C_6$haloalkyl. In one embodiment, $R^4$ is $C_1$-$C_6$haloalkoxy. In one embodiment, $R^2$ is —C(O)NR$^9$R$^{10}$.

In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —NR$^9$S(O)$_2$R$^{10}$, —S(O)R$^9$, —S(O)NR$^9$R$^{10}$, —NR$^8$S(O)R$^9$. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —NR$^9$S(O)$_2$R$^{10}$, —S(O)R$^9$, —S(O)NR$^9$R$^{10}$. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$, —C(O)OR$^9$, —NR$^9$S(O)$_2$. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R)$_2$—, —S(O)$_2$R$^9$, —C(O)R$^9$, —C(O)OR$^9$. In one embodiment, $R^3$, $R^5$, $R^6$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—, —S(O)$_2$R$^9$, —C(O)R$^9$. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—. —S(O)$_2$R$^9$. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$, —S(O)$_2$N(R$^9$)$_2$—. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$, —NR$^9$R$^{10}$. In one embodiment, $R^5$, $R^6$, $R^7$, and $R^8$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$, —OR$^9$, —NHR$^9$. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl. $C_3$-$C_8$cycloalkyl, heterocyclyl, aryl, heteroaryl containing 1-5 heteroatoms selected from the group consisting of N, S, P and O, —SR$^9$, —OR$^9$. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —SR$^9$. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, or heteroaryl containing 1-5 heteroatoms selected from the group consisting of N, S, P and O. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, or aryl. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, or heterocyclyl. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, $C_2$-$C_6$alkynyl, or $C_3$-$C_8$cycloalkyl. In one embodiment, $R^3$, $R^4$, $R^5$, and $R^6$ are independently H, halogen, OH, CN, —NO$_2$, $C_1$-$C_6$alkyl, $C_2$-$C_6$alkenyl, $C_4$-$C_8$cycloalkenyl, or $C_2$-$C_6$alkynyl. In one embodiment, $R^3$, $R^4$, $R^5$, and $R^6$ are independently H, halogen, OH, CN, —NO$_2$, $C_1$-$C_6$alkyl, $C_2$-$C_6$alkenyl, or $C_4$-$C_8$cycloalkenyl. In one embodiment, $R^3$, $R^4$, $R^5$, and $R^6$ are independently H, halogen, OH, CN, —NO$_2$, $C_1$-$C_6$alkyl, or $C_2$-$C_6$alkenyl. In one embodiment, $R^3$, $R^4$, $R^5$, and $R^6$ are independently H, halogen, OH, CN, —NO$_2$, or $C_1$-$C_6$alkyl. In one embodiment, $R^3$, $R^4$, $R^5$, and $R^6$ are independently H, halogen, OH, CN, or —NO$_2$. In one embodiment, $R^3$, $R^4$, $R^5$, and $R^6$ are independently H, halogen, OH, or CN. In one embodiment, $R^3$, $R^4$, $R^5$, and $R^6$ are independently H, halogen, or OH. In one embodiment, $R^3$, $R^4$, $R^5$, and $R^6$ are independently H or halogen.

In one embodiment, $R^{13}$, $R^{14}$, $R^{15}$, and $R^{16}$ are independently, at each occurrence, H, OH, $NH_2$, or $C_1$-$C_3$ alkyl. In a further embodiment. $R^{13}$, $R^{14}$, $R^{15}$, and $R^{16}$ are independently, at each occurrence, H, OH, or $NH_2$. In a further embodiment, $R^{13}$, $R^{14}$, $R^{15}$, and $R^{16}$ are independently, at each occurrence, H or OH. In a further embodiment, $R^{13}$, $R^{14}$, $R^{15}$, and $R^{16}$ are independently, at each occurrence, H, OH, $NH_2$, or $C_1$-$C_3$ alkyl, wherein the alkyl is optionally substituted with one or more $R^{17}$.

In one embodiment, X is a bond, H, N, O, $CR^{11}R^{12}$, $CR^{11}$, C, or —NHC(O)NH—. In one embodiment, X is a bond, H, N, O, $CR^{11}R^{12}$, $CR^{11}$, or C. In one embodiment, X is a bond. H, N, O, $CR^{11}R^{12}$, or $CR^{11}$. In one embodiment, X is a bond, H, N, O, or $CR^{11}R^{12}$. In one embodiment, X is a bond, H, N, or O. In one embodiment, X is a bond, H, or N. In one embodiment, X is a bond or H. In one embodiment, X is a bond. In another embodiment X is H and n is 1. In another embodiment, X is N when n is 3. In another embodiment, X is O and n is 2. In another embodiment, X is $CR^{11}R^{12}$ and n is 2. In another embodiment, X is $CR^{11}$ and n is 3. In another embodiment, X is C and n is 4. In another embodiment, X is —NHC(O)NH—.

In some embodiments, $R^7$ is H, $C_1$-$C_6$alkyl, or $C_1$-$C_6$haloalkyl. In some embodiments, $R^7$ is H or $C_1$-$C_6$alkyl. In some embodiments, $R^7$ is H. In some embodiments, $R^7$ is $C_1$-$C_6$alkyl. In some embodiments, $R^7$ is $C_1$-$C_6$haloalkyl.

In some embodiments, $R^8$ is independently, at each occurrence, a bond, H, $C_1$-$C_6$alkyl, $C_4$-$C_8$cycloalkenyl, $C_3$-$C_8$cycloalkyl, heterocyclyl, aryl, or heteroaryl. In some embodiments, $R^8$ is independently, at each occurrence, a bond, H, $C_1$-$C_6$alkyl, $C_4$-$C_8$cycloalkenyl, $C_3$-$C_8$cycloalkyl, heterocyclyl, or aryl. In some embodiments, $R^8$ is independently, at each occurrence, a bond, H, $C_1$-$C_6$alkyl, $C_4$-$C_8$cycloalkenyl, $C_3$-$C_8$cycloalkyl, or heterocyclyl. In some embodiments, $R^8$ is independently, at each occurrence, a bond, H, $C_1$-$C_6$alkyl, $C_4$-$C_8$cycloalkenyl, or $C_3$-$C_8$cycloalkyl. In some embodiments, $R^8$ is independently, at each occurrence, a bond, H, $C_1$-$C_6$alkyl, $C_4$- or $C_8$cycloalkenyl. In some embodiments, $R^8$ is independently, at each occurrence, a bond, H, or $C_1$-$C_6$alkyl. In some embodiments, $R^8$ is independently, at each occurrence, a bond or H.

In some embodiments, $R^8$ is independently, at each occurrence, a bond, H, $C_1$-$C_6$alkyl, $C_4$-$C_8$cycloalkenyl, $C_3$-$C_8$cycloalkyl, heterocyclyl, aryl, or heteroaryl, wherein each alkyl, cycloalkenyl, cycloalkyl, heterocyclyl, aryl, or heteroaryl is optionally substituted with one or more $R^{17}$. In some embodiments, $R^8$ is independently, at each occurrence, a bond, H, $C_1$-$C_6$alkyl, $C_4$-$C_8$cycloalkenyl, $C_3$-$C_8$cycloalkyl, heterocyclyl, or aryl, wherein each alkyl, cycloalkenyl, cycloalkyl, heterocyclyl, or aryl, is optionally substituted with one or more $R^{17}$. In some embodiments, $R^8$ is independently, at each occurrence, a bond, H, $C_1$-$C_6$alkyl, $C_4$-$C_8$cycloalkenyl, $C_3$-$C_8$cycloalkyl, or heterocyclyl, wherein each alkyl, cycloalkenyl, cycloalkyl, or heterocyclyl, is optionally substituted with one or more $R^{17}$. In some embodiments, $R^8$ is independently, at each occurrence, a bond, H, $C_1$-$C_6$alkyl, $C_4$-$C_8$cycloalkenyl, or $C_3$-$C_8$cycloalkyl, wherein each alkyl, cycloalkenyl or cycloalkyl is optionally substituted with one or more $R^{17}$. In some embodiments, $R^8$ is independently, at each occurrence, a bond, H, $C_1$-$C_6$alkyl, $C_4$- or $C_8$cycloalkenyl. In some embodiments, Re is independently, at each occurrence, a bond, H, or $C_1$-$C_6$alkyl, wherein each alkyl is optionally substituted with one or more $R^{17}$.

In other embodiments, $R^7$ and $R^8$ together with the atoms to which they are attached may combine to form independently, at each occurrence, heterocyclyl or heteroaryl. In other embodiments, $R^7$ and $R^8$ together with the atoms to which they are attached may combine to form independently, at each occurrence, heterocyclyl. In some embodiments, $R^7$ and $R^8$ together with the atoms to which they are attached may combine to form independently, at each occurrence, heteroaryl.

In other embodiments, $R^7$ and $R^8$ together with the atoms to which they are attached may combine to form independently, at each occurrence, heterocyclyl or heteroaryl, wherein each heterocyclyl or heteroaryl is optionally substituted with one or more $R^{17}$. In other embodiments, $R^7$ and $R^8$ together with the atoms to which they are attached may combine to form independently, at each occurrence, heterocyclyl, wherein each heterocyclyl is optionally substituted with one or more $R^{17}$. In some embodiments, $R^{13}$ and $R^{14}$ together with the atoms to which they are attached may combine to form independently, at each occurrence, heteroaryl, wherein each heteroaryl is optionally substituted with one or more $R^{17}$.

In some embodiments, u is 0, 1, or 2. In some embodiments, u is 0 or 1. In some embodiments, u is 0. In some embodiments, u is 1. In some embodiments, u is 2.

In some embodiments, n is 1, 2, 3, or 4. In some embodiments, n is 1, 2, or 3. In some embodiments, n is 1 or 2. In some embodiments, n is 1. In some embodiments, n is 2. In some embodiments, n is 3. In some embodiments, n is 4.

In some embodiments, s is 0, 1, 2, 3, or 4. In some embodiments, s is 0, 1, 2, or 3. In some embodiments, s is 0, 1, or 2. In some embodiments, s is 0 or 1. In some embodiments, s is 0. In some embodiments, s is 1. In some embodiments, s is 2. In some embodiments, s is 3. In some embodiments, s is 4.

In some embodiments, r is 0, 1, 2, 3, 4, 5, 6, 7, or 8. In some embodiments, r is 0, 1, 2, 3, 4, 5, 6, or 7. In some embodiments, r is 0, 1, 2, 3, 4, 5, or 6. In some embodiments, r is 0, 1, 2, 3, 4, or 5. In some embodiments, r is 0, 1, 2, 3, or 4. In some embodiments, r is 0, 1, 2, or 3. In some embodiments, r is 0, 1, or 2. In some embodiments, r is 0 or 1. In some embodiments, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8.

In some embodiments, p is 0, 1, 2, 3, 4, 5, 6, 7, or 8. In some embodiments, p is 0, 1, 2, 3, 4, 5, 6, or 7. In some embodiments, p is 0, 1, 2, 3, 4, 5, or 6. In some embodiments, p is 0, 1, 2, 3, 4, or 5. In some embodiments, p is 0, 1, 2, 3, or 4. In some embodiments, p is 0, 1, 2, or 3. In some embodiments, p is 0, 1, or 2. In some embodiments, p is 0 or 1. In some embodiments, p is 0. In some embodiments, p is 1. In some embodiments, p is 2. In some embodiments, p is 3. In some embodiments, p is 4. In some embodiments, p is 5. In some embodiments, p is 6. In some embodiments, p is 7. In some embodiments, p is 8.

In designing and making the substantially impermeable or substantially systemically non-bioavailable NHE-inhibiting compounds of the present invention that may be utilized for the treatments detailed in the instant disclosure.

Another aspect, compounds of the present invention with extended hydrocarbon functionalities may collapse upon themselves in an intramolecular fashion, causing an increased enthalpic barrier for interaction with the desired biological target. Accordingly, when designing "X" and Linkers moieties, these are designed to be resistant to hydrophobic collapse. For example, conformational constraints such as rigid monocyclic, bicyclic or polycyclic rings can be installed in a "X" and Linker moiety to increase the rigidity of the structure. Unsaturated bonds, such as alkenes and alkynes, may also or alternatively be installed. Such modifications may ensure the NHE-inhibiting compound is accessible for productive binding with its target. Furthermore, the hydrophilicity of the Linkers may be improved by adding hydrogen bond donor or acceptor motifs, or ionic motifs such as amines that are protonated in the GI, or acids that are deprotonated. Such modifications will increase the hydrophilicity of the "X" and Linker moieties and help prevent hydrophobic collapse. Furthermore, such modifications will also contribute to the impermeability of the resulting compounds by increasing tPSA.

One skilled in the art may also consider a variety of functional groups that will allow the facile and specific attachment of the rest of the molecule of the compounds of Formula I to the "X" moiety and/or Linker. These functional groups can include electrophiles, which can react with nucleophilic groups, and/or nucleophiles, which can react with electrophilic "X" and Linker moieties. NHE-inhibiting compounds of Formula I may also be similarly derivatized with, for example, boronic acid groups. The NHE-inhibiting compounds of Formula I may also contain olefins via olefin metathesis chemistry, or alkynes or azides which can then react with appropriate other "X" and Linker via [2+3] cycloaddition.

It is to be noted that one skilled in the art can envision a number of "X" and Linker moieties that may be functionalized with an appropriate electrophile or nucleophile. Shown below are a series of such compounds selected based on several design considerations, including solubility, steric effects, and their ability to confer, or be consistent with, favorable structure-activity relationships. In this regard it is to be further noted, however, that the structures provided below, and above, are for illustration purposes only, and therefore should not be viewed in a limiting sense.

Exemplary electrophilic and nucleophilic Linker moieties include, but are not limited to, the Linker moieties illustrated in the Examples and the following:

Nucleophilic Linkers

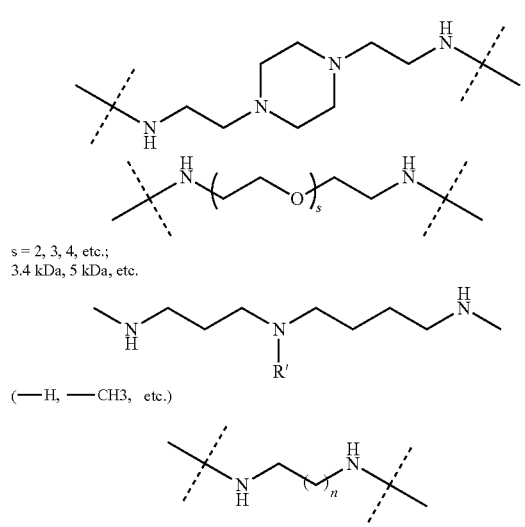

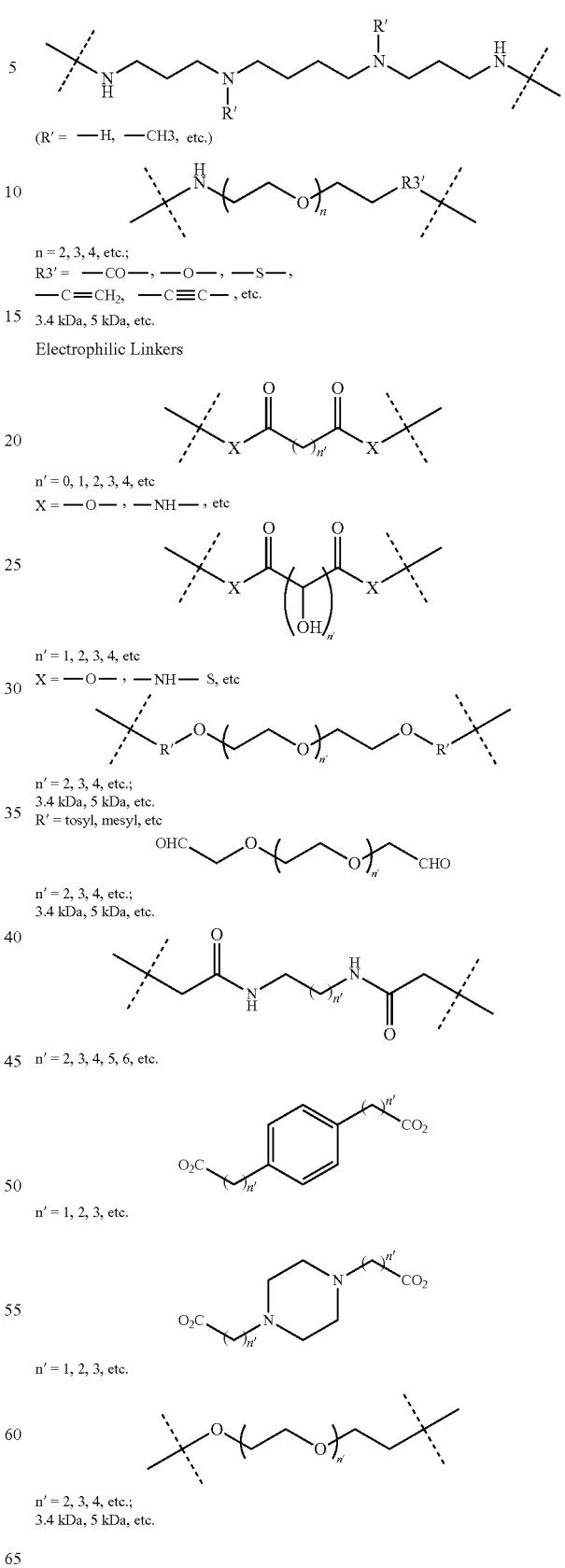

The linking moiety, Linker, in each of the described embodiments can also be a chemical bond or other moiety, for example that can be hydrophilic and/or hydrophobic. In one embodiment, the linking moiety can be a polymer moiety grafted onto a polymer backbone, for example, using living free radical polymerization approaches known in the art.

In another embodiment, "X" moieties illustrated in the compounds of Formula I may also include, but are not limited to, ether moieties, ester moieties, sulfide moieties, disulfide moieties, amine moieties, aryl moieties, alkoxyl moieties, etc., such as, for example, the following:

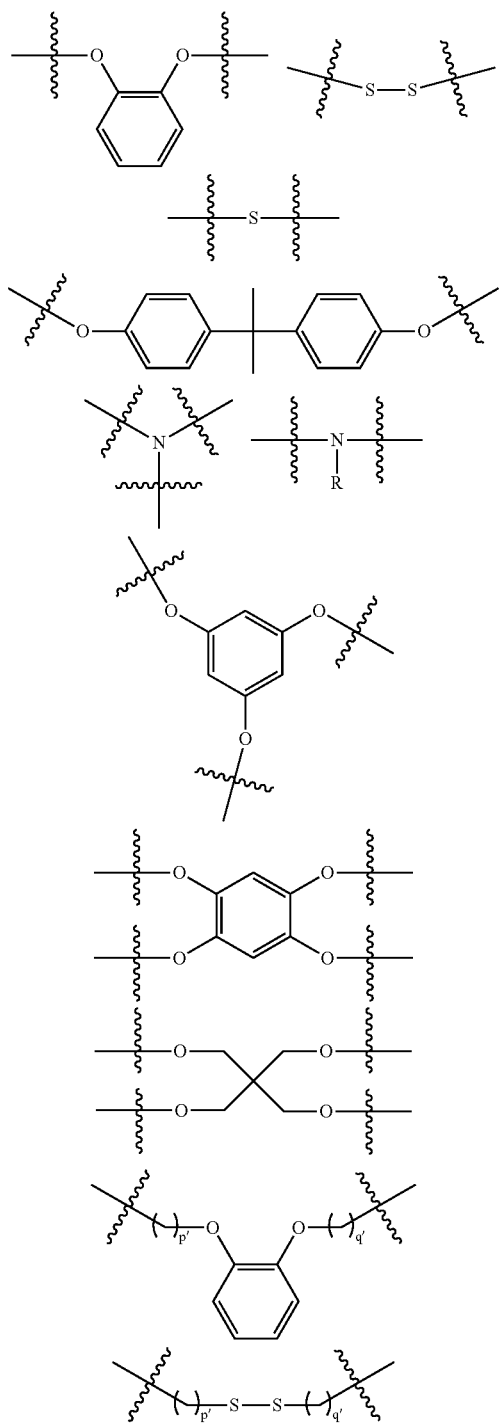

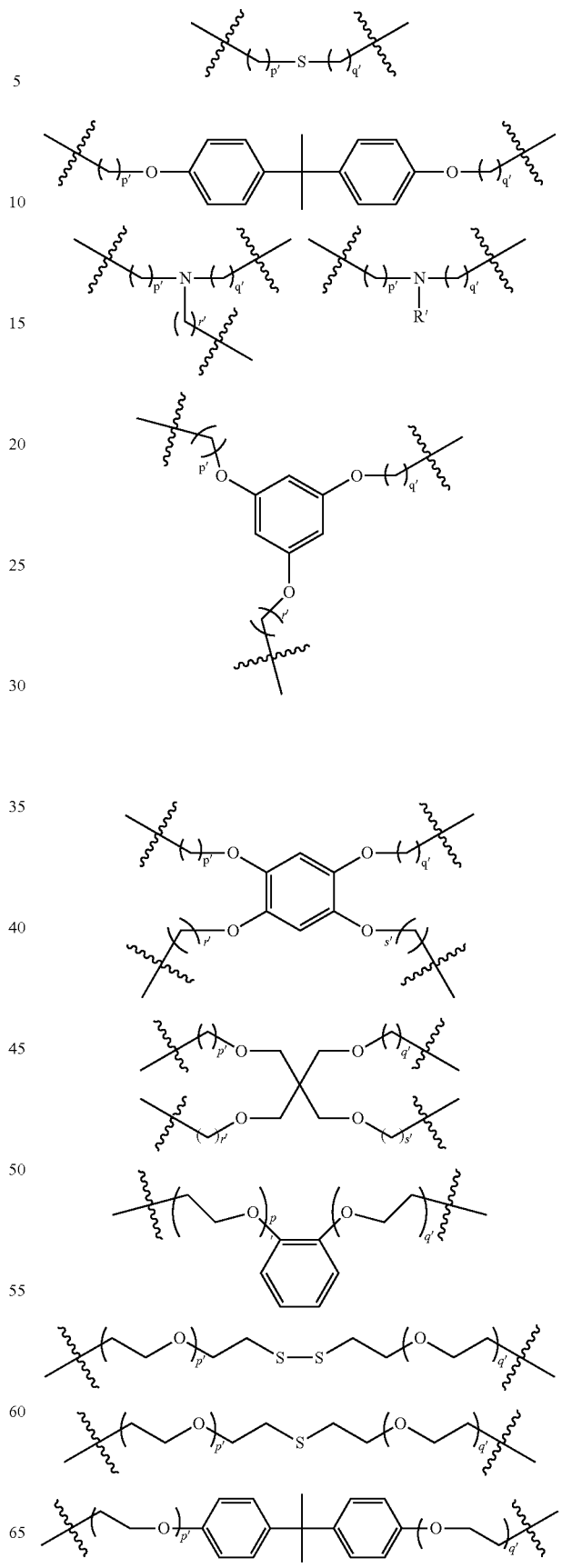

-continued
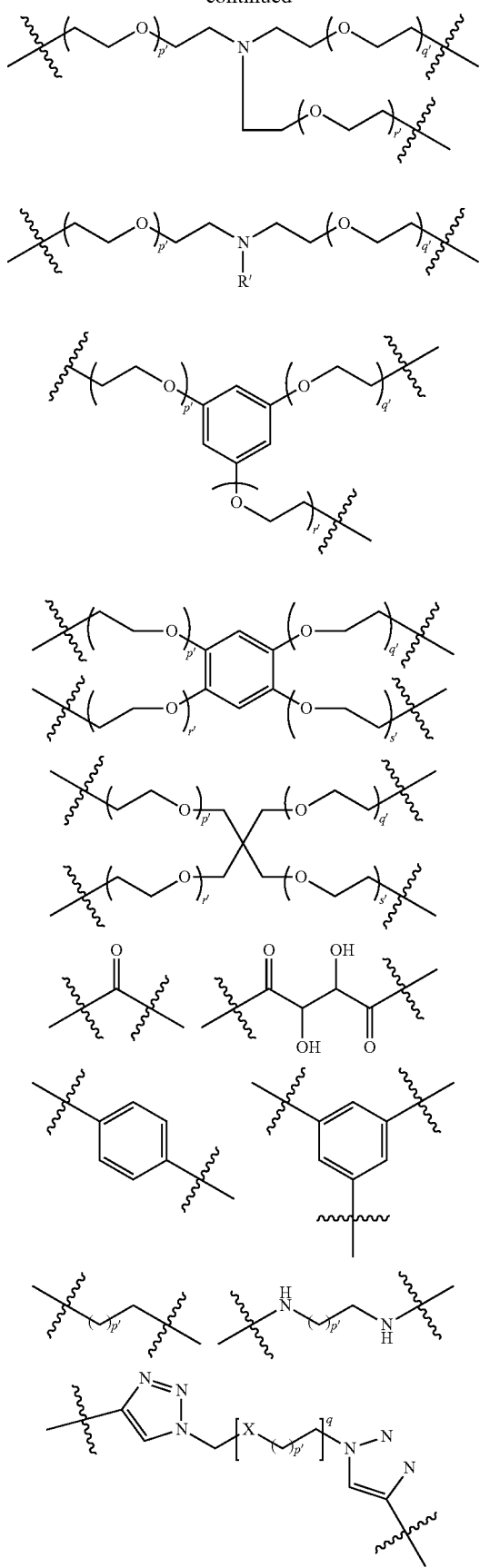
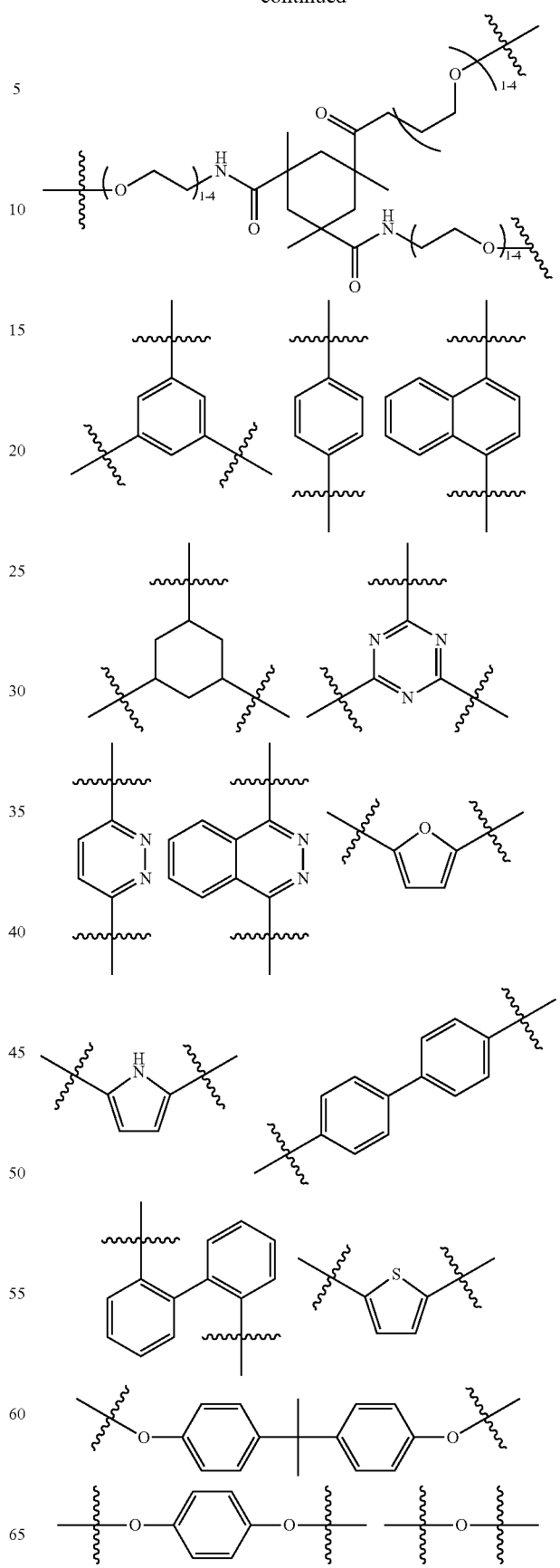

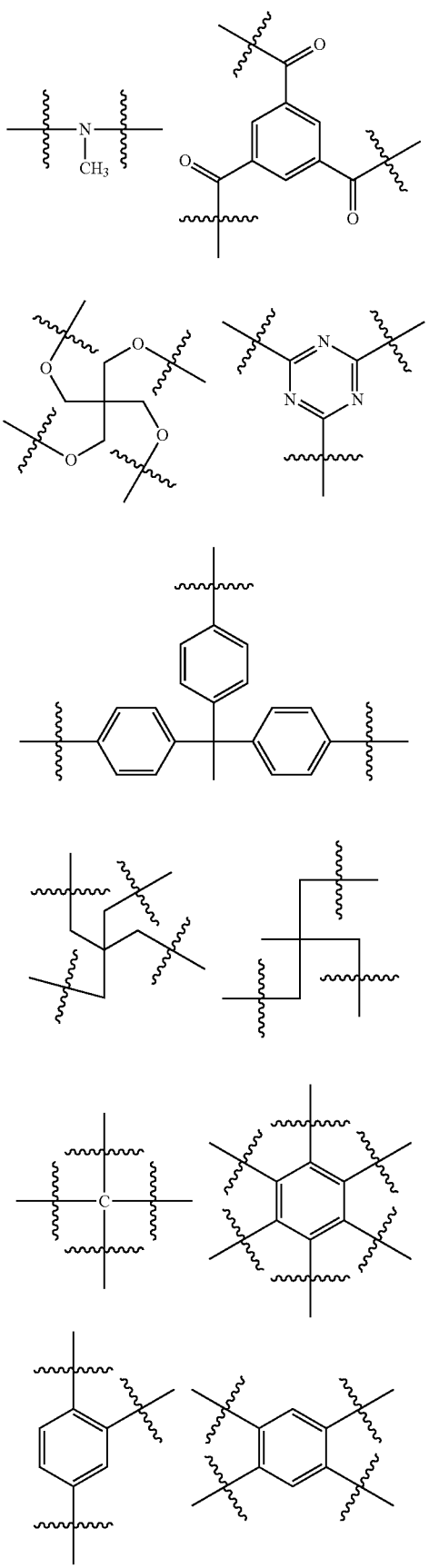
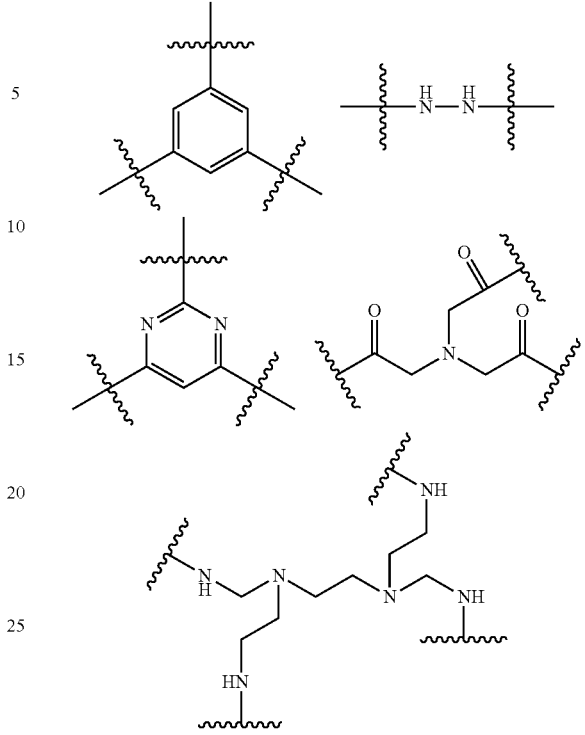

wherein the broken bonds (i.e., those having a wavy bond, ⸗, through them) are points of connection to the rest of the molecule of Formula I when n>1, where said points of connection can be made using chemistries and functional groups known to the art of medicinal chemistry, and further wherein each p', q', r' and s' is an independently selected integer ranging from about 0 to about 48, from about 0 to about 36, or from about 0 to about 24, or from about 0 to about 16. In some instances, each p, q, r and s can be an independently selected integer ranging from about 0 to 12. Additionally, R' can be a substituent moiety generally selected from halide, hydroxyl, amine, thiol, ether, carbonyl, carboxyl, ester, amide, carbocyclic, heterocyclic, and moieties comprising combinations thereof.

In another approach, the "X" moiety of formula I may be a dendrimer, defined as a repeatedly branched molecule (see, e.g., J. M. J. Fréchet, D. A. Tomalia, Dendrimers and Other Dendritic Polymers, John Wiley & Sons, Ltd. NY, NY, 2001).

In this approach, the rest of the NHE-inhibiting molecule is attached through Linker to one, several or optionally all termini located at the periphery of the dendrimer. In another approach, a dendrimer building block named dendron, and illustrated above, is used as "X" moiety, wherein the rest of NHE-inhibiting molecule is attached to one, several or optionally all termini located at the periphery of the dendron. The number of generations herein is typically between about 0 and about 6, and between about 0 and about 3. (Generation is defined in, for example, J. M. J. Fréchet, D. A. Tomalia, *Dendrimers and Other Dendritic Polymers*, John Wiley & Sons, Ltd. NY, N.Y.) Dendrimer and/or dendron structures are well known in the art and include, for example, those shown in or illustrated by: (i) J. M. J. Fréchet, D. A. Tomalia *Dendrimers and Other Dendritic Polymers*, John Wiley & Sons, Ltd. NY, N.Y.; (ii) George R Newkome, Charles N. Moorefield and Fritz Vogtle, *Dendrimers and Dendrons:*

*Concepts, Syntheses, Applications*, VCH Verlagsgesellschaft Mbh; and, (iii) Boas, U., Christensen, J. B., Heegaard, P. M. H., *Dendrimers in Medicine and Biotechnology: New Molecular Tools*, Springer, 2006.

In yet another approach, the "X" moiety may be a polymer moiety or an oligomer moiety. The polymer or oligomer may, in each case, be independently considered and comprise repeat units consisting of a repeat moiety selected from alkyl (e.g., —$CH_2$—), substituted alkyl (e.g., —CHR—, wherein, for example, R is hydroxy), alkenyl, substituted alkenyl, alkynyl, substituted alkynyl, phenyl, aryl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, as well as moieties comprising combinations thereof. In still another approach, the "X" moiety comprises repeat units resulting from the polymerization of ethylenic monomers (e.g., such as those ethylenic monomers listed elsewhere herein below).

Preferred polymers for polymeric moieties useful in constructing substantially impermeable or substantially systemically non-bioavailable NHE-inhibiting compounds that are multivalent, for use in the treatment various treatment methods disclosed herein, can be prepared by any suitable technique, such as by free radical polymerization, condensation polymerization, addition polymerization, ring-opening polymerization, and/or can be derived from naturally occurring polymers, such as saccharide polymers. Further, in some embodiments, any of these polymer moieties may be functionalized.

Examples of polysaccharides useful in preparation of such compounds include but are not limited to materials from vegetable or animal origin, including cellulose materials, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin, and/or chitosan. More preferred, in at least some instances, are polymer moieties that do not degrade, or that do not degrade significantly, under the physiological conditions of the GI tract (such as, for example, carboxymethylcellulose, chitosan, and sulfoethylcellulose).

When free radical polymerization is used, the polymer moiety can be prepared from various classes of monomers including, for example, acrylic, methacrylic, styrenic, vinylic, and dienic, whose typical examples are given thereafter: styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, and combinations thereof. Functionalized versions of these monomers may also be used and any of these monomers may be used with other monomers as comonomers. For example, specific monomers or comonomers that may be used in this disclosure include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N—N-butylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino α-methylstyrene (all isomers), p-vinylbenzene sulfonic acid, p-vinylbenzene sulfonic sodium salt, alkoxy and alkyl silane functional monomers, maleic anhydride, N-phenylmaleimide, N-butylmaleimide, butadiene, isoprene, chloroprene, ethylene, vinyl acetate, vinylformamide, allylamine, vinylpyridines (all isomers), fluorinated acrylate, methacrylates, and combinations thereof. Main chain heteroatom polymer moieties can also be used, including polyethyleneimine and polyethers such as polyethylene oxide and polypropylene oxide, as well as copolymers thereof.

In one particular embodiment, the polymer to which the NHE-inhibiting molecule is attached, or otherwise a part of, is a polyol (e.g., a polymer having a repeat unit of, for example, a hydroxyl-substituted alkyl, such as —CH(OH)—). Polyols, such as mono- and disaccharides, with or without reducing or reducible end groups thereon, may be good candidates, for example, for installing additional functionality that could render the compound substantially impermeable.

In one particular embodiment, the NHE-inhibiting molecule is attached at one or both ends of the polymer chain. More specifically, in yet another alternative approach to the polyvalent embodiment of the present disclosure, a macromolecule (e.g., a polymer or oligomer) having the generic following exemplary structures

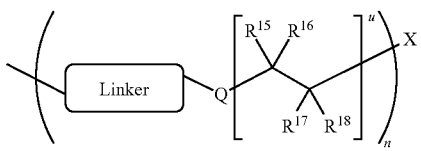

which may be exemplified, designed, and/or constructed as described for the moieties:

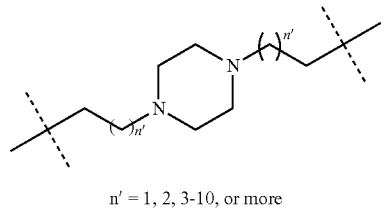

n' = 1, 2, 3-10, or more

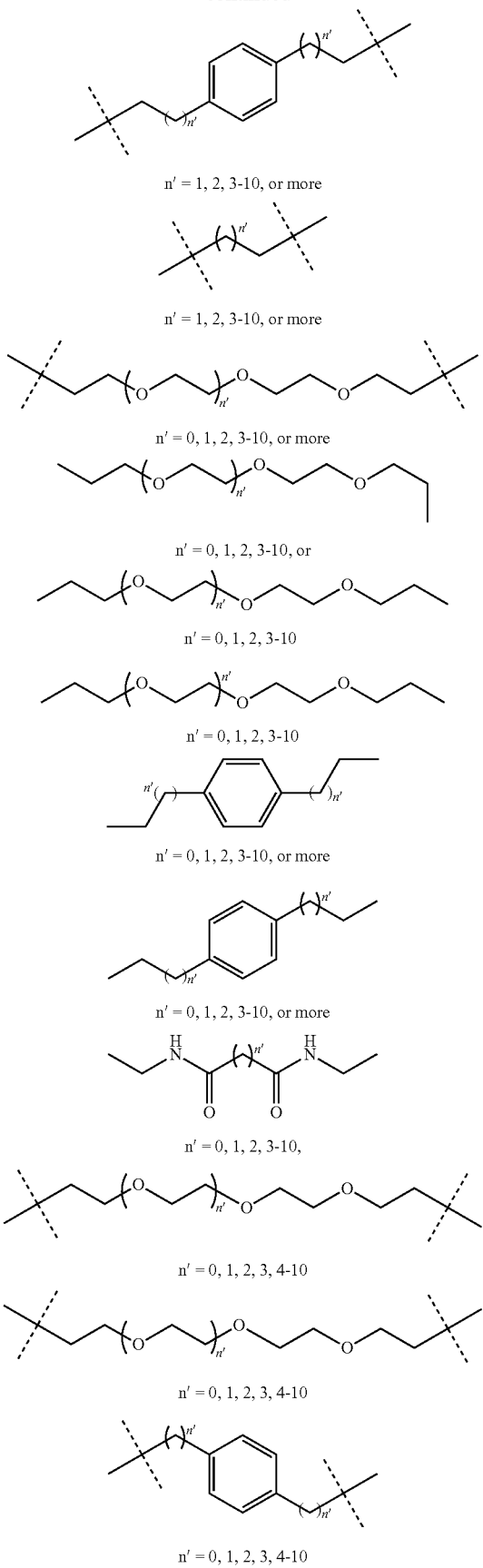
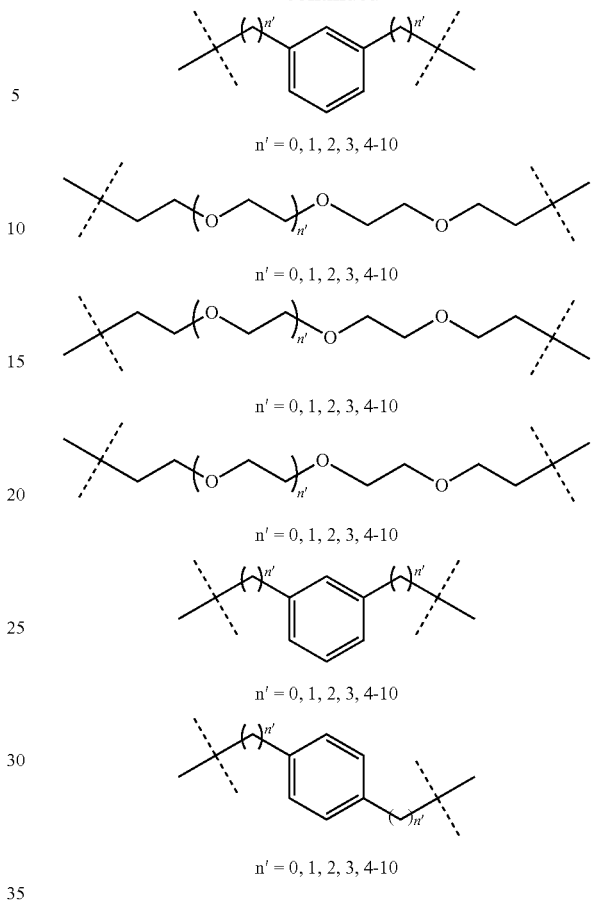

It is understood that any embodiment of the compounds of the present invention, as set forth above, and any specific substituent set forth herein in such compounds, as set forth above, may be independently combined with other embodiments and/or substituents of such compounds to form embodiments of the inventions not specifically set forth above. In addition, in the event that a list of substituents is listed for any particular substituent in a particular embodiment and/or claim, it is understood that each individual substituent may be deleted from the particular embodiment and/or claim and that the remaining list of substituents will be considered to be within the scope of the invention. Furthermore, it is understood that in the present description, combinations of substituents and/or variables of the depicted formulae are permissible only if such contributions result in stable compounds.

B. Permeability

In this regard it is to be noted that, in various embodiments, the ability of a compound to be substantially systemically non-bioavailable is based on the compound charge, size, and/or other physicochemical parameters (e.g., polar surface area, number of hydrogen bond donors and/or acceptors therein, number of freely rotatable bonds, etc.). More specifically, it is to be noted that the absorption character of a compound can be selected by applying principles of pharmacodynamics, for example, by applying Lipinski's rule, also known as "the rule of five." Although not a rule, but rather a set of guidelines, Lipinski shows that small molecule drugs with (i) a molecular weight, (ii) a number of hydrogen bond donors, (iii) a number of hydrogen bond acceptors, and/or (iv) a water/octanol partition coefficient (Moriguchi Log P), greater than a certain threshold value, generally do not show significant systemic concentration (i.e., are generally not absorbed to any significant degree). (See, e.g., Lipinski et al., *Advanced Drug Delivery Reviews*, 46, 2001 3-26, incorporated herein by reference.) Accordingly, substantially systemically non-bioavailable compounds (e.g., substantially systemically non-bioavailable NHE-inhibiting compounds) can be designed to have molecular structures exceeding one or more of Lipinski's threshold values. (See also Lipinski et al., *Experimental and Computational Approaches to Estimate Solubility and Permeability in Drug Discovery and Development Settings*, Adv. Drug Delivery Reviews, 46:3-26 (2001); and Lipinski, *Drug-like Properties and the Causes of Poor Solubility and Poor Permeability*, J. Pharm. & Toxicol. Methods, 44:235-249 (2000), incorporated herein by reference.) In some embodiments, for example, a substantially impermeable or substantially systemically non-bioavailable NHE-inhibiting compound of the present disclosure can be constructed to feature one or more of the following characteristics: (i) a MW greater than about 500 Da, about 1000 Da, about 2500 Da, about 5000 Da, about 10,000 Da or more (in the non-salt form of the compound): (ii) a total number of NH and/or OH and/or other potential hydrogen bond donors greater than about 5, about 10, about 15 or more: (iii) a total number of O atoms and/or N atoms and/or other potential hydrogen bond acceptors greater than about 5, about 10, about 15 or more; and/or (iv) a Moriguchi partition coefficient greater than about $10^5$ (i.e., Log P greater than about 5, about 6, about 7, etc.), or alternatively less than about 10 (i.e., a Log P of less than 1, or even 0).

In addition to the parameters noted above, the molecular polar surface area (i.e., "PSA"), which may be characterized as the surface belonging to polar atoms, is a descriptor that has also been shown to correlate well with passive transport through membranes and, therefore, allows prediction of transport properties of drugs. It has been successfully applied for the prediction of intestinal absorption and Caco2 cell monolayer penetration. (For Caco2 cell monolayer penetration test details, see for example the description of the Caco2 Model provided in Example 31 of U.S. Pat. No. 6,737,423, the entire contents of which are incorporated herein by reference for all relevant and consistent purposes, and the text of Example 31 in particular, which may be applied for example to the evaluation or testing of the compounds of the present disclosure.) PSA is expressed in $Å^2$ (squared angstroms) and is computed from a three-dimensional molecular representation. A fast calculation method is now available (see. e.g., Ertl et al., *Journal of Medicinal Chemistry*, 2000, 43, 3714-3717, the entire contents of which are incorporated herein by reference for all relevant and consistent purposes) using a desktop computer and commercially available chemical graphic tools packages, such as ChemDraw. The term "topological PSA" (tPSA) has been coined for this fast-calculation method. tPSA is well correlated with human absorption data with common drugs (see, e.g., Table 1, below):

TABLE 1

| name | $ FA[a] | TPSA[b] |
|---|---|---|
| metoprolol | 102 | 50.7 |
| nordiazepam | 99 | 41.5 |
| diazepam | 97 | 32.7 |
| oxyprenolol | 97 | 50.7 |
| phenazone | 97 | 26.9 |

TABLE 1-continued

| name | $ FA[a] | TPSA[b] |
|---|---|---|
| oxazepam | 97 | 61.7 |
| alprenolol | 96 | 41.9 |
| practolol | 95 | 70.6 |
| pindolol | 92 | 57.3 |
| ciprofloxacin | 69 | 74.6 |
| metolazone | 64 | 92.5 |
| tranexamic acid | 55 | 63.3 |
| atenolol | 54 | 84.6 |
| sulpiride | 36 | 101.7 |
| mannitol | 26 | 121.4 |
| foscarnet | 17 | 94.8 |
| sulfasalazine | 12 | 141.3 |
| olsalazine | 2.3 | 139.8 |
| lactulose | 0.6 | 197.4 |
| raffinose | 0.3 | 268.7 |

(from Ertl et al., *J. Med. Chem.*, 2000, 43:3714-3717). Accordingly, in some preferred embodiments, the compounds of the present disclosure may be constructed to exhibit a tPSA value greater than about 100 $Å^2$, about 120 $Å^2$, about 130 $Å^2$, or about 140 $Å^2$, and in some instances about 150 $Å^2$, about 200 $Å^2$, about 250 $Å^2$, about 270 $Å^2$, about 300 $Å^2$, about 400 $Å^2$, or even about 500 $Å^2$, such that the compounds are substantially impermeable or substantially systemically non-bioavailable (as defined elsewhere herein).

Because there are exceptions to Lipinski's "rule," or the tPSA model, the permeability properties of the compounds of the present disclosure may be screened experimentally. The permeability coefficient can be determined by methods known to those of skill in the art, including for example by Caco-2 cell permeability assay and/or using an artificial membrane as a model of a gastrointestinal epithelial cell. (As previously noted above, see for example U.S. Pat. No. 6,737,423, Example 31 for a description of the Caco-2 Model, which is incorporated herein by reference). A synthetic membrane impregnated with, for example, lecithin and/or dodecane to mimic the net permeability characteristics of a gastrointestinal mucosa, may be utilized as a model of a gastrointestinal mucosa. The membrane can be used to separate a compartment containing the compound of the present disclosure from a compartment where the rate of permeation will be monitored. Also, parallel artificial membrane permeability assays (PAMPA) can be performed. Such in vitro measurements can reasonably indicate actual permeability in vivo. (See, for example, Wohnsland et al., *J. Med. Chem.*, 2001, 44:923-930; Schmidt et al., Millipore Corp. Application Note, 2002, n° AN1725EN00, and n° AN1728EN00, incorporated herein by reference.)

Accordingly, in some embodiments, the compounds utilized in the methods of the present disclosure may have a permeability coefficient, $P_{app}$, of less than about $100 \times 10^{-6}$ cm/s, or less than about $10 \times 10^{-6}$ cm/s, or less than about $1 \times 10^{-6}$ cm/s, or less than about $0.1 \times 10^{-6}$ cm/s, when measured using means known in the art (such as for example the permeability experiment described in Wohnsland et al., *J. Med. Chem.*, 2001, 44, 923-930, the contents of which is incorporated herein by reference).

As previously noted, in accordance with the present disclosure, a NHE-inhibiting compound is modified as described above to hinder the net absorption through a layer of gut epithelial cells, rendering the resulting compound substantially systemically non-bioavailable. In various embodiments, the compounds of the present disclosure are substantially impermeable or substantially systemically non-bioavailable. More specifically, the NHE-inhibiting can be a dimer, multimer or polymer moiety, such that the resulting compound is substantially impermeable or substantially systemically non-bioavailable. The dimer, multimer or polymer may be of a molecular weight greater than about 500 Daltons (Da), about 1000 Da, about 2500 Da, about 5000 Da, about 10,000 Da or more, and in particular may have a molecular weight in the range of about 1000 Daltons (Da) to about 500,000 Da, or in the range of about 5000 to about 200,000 Da, and may have a molecular weight that is sufficiently high to essentially preclude any net absorption through a layer of gut epithelial cells of the compound.

C. Persistent Inhibitory Effect

In other embodiments, the substantially impermeable or substantially systemically non-bioavailable NHE-inhibiting compounds utilized in the treatment methods of the present disclosure may additionally exhibit a persistent inhibitor effect. This effect manifests itself when the inhibitory action of a compound at a certain concentration in equilibrium with the epithelial cell (e.g., at or above its inhibitory concentration, IC) does not revert to baseline (i.e., sodium transport without inhibitor) after the compound is depleted by simple washing of the luminal content.

This effect can be interpreted as a result of the tight binding of the NHE-inhibiting compounds to the NHE protein at the intestinal apical side of the gut epithelial cell. The binding can be considered as quasi-irreversible to the extent that, after the compound has been contacted with the gut epithelial cell and subsequently washed off said gut epithelial cell, the flux of sodium transport is still significantly lower than in the control without the compound. This persistent inhibitory effect has the clear advantage of maintaining drug activity within the GI tract even though the residence time of the active in the upper GI tract is short, and when no entero-biliary recycling process is effective to replenish the compound concentration near its site of action.

Such a persistent inhibitory effect has an obvious advantage in terms of patient compliance, but also in limiting drug exposure within the GI tract.

The persistence effect can be determined using in vitro methods, in one instance, cell lines expressing NHE transporters are split in different vials and treated with a NHE-inhibiting compound and sodium solution to measure the rate of sodium uptake. The cells in one set of vials are washed for different periods of time to remove the inhibitor, and sodium uptake measurement is repeated after the washing. Compounds that maintain their inhibitory effect after multiple/lengthy washing steps (compared to the inhibitory effect measured in the vials where washing does not occur) are persistent inhibitors. Persistence effect can also be characterized ex vivo by using the everted sac technique, whereby transport of Na is monitored using an excised segment of GI perfused with a solution containing the inhibitor and shortly after flushing the bathing solution with a buffer solution free from inhibitor. A persistence effect can also be characterized in vivo by observing the time needed for sodium balance to return to normal when the inhibitor treatment is discontinued. The limit of the method resides in the fact that apical cells (and therefore apical NHE transporters) are sloughed off after a period of 3 to 4 days, the typical turnover time of gut epithelial cells. A persistence effect can be achieved by increasing the residence time of the active compound at the apical surface of the gut epithelial cells; this can be obtained by designing NHE antiport inhibitors with several NHE-inhibiting molecule or oligomer (wherein "several" as used herein typically means at least about 2, about 4, about 6 or more). Examples of such structures in the context of analogs of the antibiotic vancomycin are given in Griffin, et al., J. Am. Chem. Soc., 2003, 125, 6517-6531. Alternatively, the compound comprises groups that contribute to increase the affinity towards the gut epithelial cell so as to increase the time of contact with the gut epithelial cell surface. Such groups are referred to as being "mucoadhesive." More specifically, the "X" and Linker moieties can be substituted by such mucoadhesive groups, such as polyacrylates, partially deacetylated chitosan or polyalkylene glycol. (See also Patil, S. B. et al., Curr. Drug. Deliv., 2008, October 5(4), pp. 312-8.)

D. GI Enzyme Resistance

Because the compounds utilized in the treatment methods of the present disclosure are substantially systemically non-bioavailable, and/or exhibit a persistent inhibitory effect, it is also desirable that, during their prolonged residence time in the gut, these compounds sustain the hydrolytic conditions prevailing in the upper GI tract. In such embodiments, compounds of the present disclosure are resistant to enzymatic metabolism. For example, administered compounds are resistant to the activity of P450 enzymes, glucurosyl transferases, sulfotransferases, glutathione S-transferases, and the like, in the intestinal mucosa, as well as gastric (e.g., gastric lipase, and pepsine), pancreatic (e.g., trypsin, triglyceride pancreatic lipase, phospholipase A2, endonucleases, nucleotidases, and alpha-amylase), and brush-border enzymes (e.g., alkaline phosphatase, glycosidases, and proteases) generally known in the art.

The compounds that are utilized in methods of the present disclosure are also resistant to metabolism by the bacterial flora of the gut; that is, the compounds are not substrates for enzymes produced by bacterial flora. In addition, the compounds administered in accordance with the methods of the present disclosure may be substantially inactive towards the gastrointestinal flora, and do not disrupt bacterial growth or survival. As a result, in various embodiments herein, the minimal inhibitory concentration (or "MIC") against GI flora is desirably greater than about 15 µg/ml, about 30 µg/ml, about 60 µg/ml, about 120 µg/ml, or even about 240 µg/ml, the MIC in various embodiments being for example between about 16 and about 32 µg/ml, or between about 64 and about 128 µg/ml, or greater than about 256 µg/ml.

To one skilled in the art of medicinal chemistry, metabolic stability can be achieved in a number of ways. Functionality susceptible to P450-mediated oxidation can be protected by, for example, blocking the point of metabolism with a halogen or other functional group. Alternatively, electron withdrawing groups can be added to a conjugated system to generally provide protection to oxidation by reducing the electrophilicity of the compound. Proteolytic stability can be achieved by avoiding secondary amide bonds, or by incorporating changes in stereochemistry or other modifications that prevent the drug from otherwise being recognized as a substrate by the metabolizing enzyme.

E. Sodium and/or Fluid Output

It is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof, may act to increase the patient's daily fecal output of sodium by at least about 20, about 30 mmol, about 40 mmol, about 50 mmol, about 60 mmol, about 70 mmol, about 80 mmol, about 90 mmol, about 100 mmol, about 125 mmol, about 150 mmol or more, the increase being for example within the range of from about 20 to about 150 mmol/day, or from about 25 to about 100 mmol/day, or from about 30 to about 60 mmol/day Additionally, or alternatively, it is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patent in need thereof, may act to increase the patient's daily fluid output by at least about 100 ml, about 200 ml, about 300 ml, about 400 ml, about 500 ml, about 600 ml, about 700 ml, about 800 ml, about 900 ml, about 1000 ml or more, the increase being for example within the range of from about 100 to about 1000 ml/day, or from about 150 to about 750 ml/day, or from about 200 to about 500 ml/day (assuming isotonic fluid).

F. $C_{max}$ and $IC_{50}$

It is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof at a dose resulting in at least a 10% increase in fecal water content, has a $C_{max}$ that is less than the $IC_{50}$ for NHE-3, more specifically, less than about 10× (10 times) the $IC_{50}$, and, more specifically still, less than about 100× (100 times) the $IC_{50}$.

Additionally, or alternatively, it is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof, may have a $C_{max}$ of less than about 10 ng/ml, about 7.5 ng/ml, about 5 ng/ml, about 2.5 ng/ml, about 1 ng/ml, or about 0.5 ng/ml, the $C_{max}$ being for example within the range of about 1 ng/ml to about 10 ng/ml, or about 2.5 ng/ml to about 7.5 ng/ml.

Additionally, or alternatively, it is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof, may have a $IC_{50}$ of less than about 10 µM, about 7.5 µM, about 5 µM, about 2.5 µM, about 1 µM, or about 0.5 µM, the $IC_{50}$ being for example within the range of about 1 µM to about 10 µM, or about 2.5 µM to about 7.5 µM.

Additionally, or alternatively, it is also to be noted that, in various embodiments of the present disclosure, one or more of the NHE-inhibiting compounds detailed herein, when administered to a patient in need thereof, may have a ratio of $IC_{50}:C_{max}$, wherein $IC_{50}$ and $C_{max}$ are expressed in terms of the same units, of at least about 10, about 50, about 100, about 250, about 500, about 750, or about 1000.

Additionally, or alternatively, it is also to be noted that, in various embodiments of the present disclosure, wherein one or more of the NHE-inhibiting compounds as detailed herein is orally administered to a patent in need thereof, within the therapeutic range or concentration, the maximum compound concentration detected in the serum, defined as $C_{max}$, is lower than the NHE inhibitory concentration $IC_{50}$ of said compound. As previously noted, as used herein, $IC_{50}$ is defined as the quantitative measure indicating the concentration of the compound required to inhibit 50% of the NHE-mediated Na/H antiport activity in a cell based assay.

III. Pharmaceutical Compositions and Methods of Treatment

A. Compositions and Methods

1. Fluid Retention and/or Salt Overload Disorders

Another aspect of the invention is directed to method for inhibiting NHE-mediated antiport of sodium and hydrogen ions. The method comprises administering to a mammal in need thereof a pharmaceutically effective amount of a compound or pharmaceutical composition of Formula I. In one embodiment, the method comprises administering to a mammal in need thereof a pharmaceutically effective amount of a compound Ia, Ib, Ic, Id, Ie, If, or Ig, or a combination thereof.

Another aspect of the invention is directed to method for treating a disorder associated with fluid retention or salt overload. The method comprises administering to a mammal in need thereof a pharmaceutically effective amount of a compound or pharmaceutical composition of Formula I. In one embodiment, the method of treating a disorder associated with fluid retention or salt overload comprises administering to a mammal in need thereof a pharmaceutically effective amount of a compound Ia, Ib, Ic, Id, Ie, If, Ig, Ih, or Ii or a combination thereof.

In one embodiment, a method for treating a disorder selected from the group consisting of heart failure (such as congestive heart failure), chronic kidney disease, end-stage renal disease, liver disease, and peroxisome proliferator-activated receptor (PPAR) gamma agonist-induced fluid retention is provided, the method comprising administering to a mammal in need thereof a pharmaceutically effective amount of a compound or pharmaceutical composition as set forth above. In another embodiment, the disorder is, but not limited to, a gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, gastric ulcers, infectious diarrhea, cancer (colorectal). "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, non-alcoholic fatty acid liver disease, Steatosis, primary sclerosing cholangitis, primary biliary cholangitis, portal hypertension, autoimmune disease (e.g., Type 1 diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestine bacterial overgrowth, chronic alcoholism, and the like.

In another embodiment, a method for treating hypertension is provided, the method comprising administering to a mammal in need thereof a pharmaceutically effective amount of a compound or pharmaceutical composition as set forth above.

In further embodiments, the method comprises administering a pharmaceutically effective amount of the compound to the mammal in order to increase the mammal's daily fecal output of sodium and/or fluid. In further embodiments, the method comprises administering a pharmaceutically effective amount of the compound to the mammal in order to increase the mammal's daily fecal output of sodium by at least about 30 mmol, and/or fluid by at least about 200 ml. In further embodiments, the mammal's fecal output of sodium and/or fluid is increased without introducing another type of cation in a stoichiometric or near stoichiometric fashion via an ion exchange process. In further embodiments, the method further comprises administering to the mammal a fluid-absorbing polymer to absorb fecal fluid resulting from the use of the compound that is substantially active in the gastrointestinal tract to inhibit NHE-mediated antiport of sodium ions and hydrogen ions therein.

In further embodiments, the compound or composition is administered to treat hypertension. In further embodiments, the compound or composition is administered to treat hypertension associated with dietary salt intake. In further embodiments, administration of the compound or composition allows the mammal to intake a more palatable diet. In further embodiments, the compound or composition is administered to treat fluid overload. In further embodiments, the fluid overload is associated with congestive heart failure. In further embodiments, the fluid overload is associated with end stage renal disease. In further embodiments, the fluid overload is associated with peroxisome proliferator-activated receptor (PPAR) gamma agonist therapy. In further embodiments, the compound or composition is administered to treat sodium overload. In further embodiments, the compound or composition is administered to reduce interdialytic weight gain in ESRD patients. In further embodiments, the compound or composition is administered to treat edema. In further embodiments, the edema is caused by chemotherapy, pre-menstrual fluid overload or preeclampsia.

In further embodiments, the compound or composition is administered to treat gastric ulcers. In further embodiments, the compound or composition is administered to treat infectious diarrhea. In further embodiments, the compound or composition is administered to treat cancer (colorectal). In further embodiments, the compound or composition is administered to treat "leaky gut syndrome". In further embodiments, the compound or composition is administered to treat cystic fibrosis gastrointestinal disease. In further embodiments, the compound or composition is administered to treat multi-organ failure. In further embodiments, the compound or composition is administered to treat microscopic colitis. In further embodiments, the compound or composition is administered to treat necrotizing enterocolitis. In further embodiments, the compound or composition is administered to treat atopy. In further embodiments, the compound or composition is administered to treat food allergy. In further embodiments, the compound or composition is administered to treat respiratory infections. In further embodiments, the compound or composition is administered to treat acute inflammation (e.g., sepsis, systemic inflammatory response syndrome). In further embodiments, the compound or composition is administered to treat chronic inflammation (e.g., arthritis). In further embodiments, the compound or composition is administered to treat obesity-induced metabolic diseases (e.g., nonalcoholic steatohepatitis, Type I diabetes, Type II diabetes, cardiovascular disease). In further embodiments, the compound or composition is administered to treat kidney disease. In further embodiments, the compound or composition is administered to treat diabetic kidney disease. In further embodiments, the compound or composition is administered to treat cirrhosis. In further embodiments, the compound or composition is administered to treat steatohepatitis. In further embodiments, the compound or composition is administered to treat nonalcoholic fatty acid liver disease. In further embodiments, the compound or composition is administered to treat steatosis. In further embodiments, the compound or composition is administered to treat primary sclerosing cholangitis. In further embodiments, the compound or composition is administered to treat primary biliary cholangitis. In further embodiments, the compound or composition is administered to treat portal hypertension. In further embodiments, the compound or composition is administered to treat autoimmune disease (e.g., Type 1 diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), or Raynaud's syndrome). In further embodiments, the compound or composition is administered to treat Schizophrenia. In further embodiments, the compound or composition is administered to treat autism spectrum disorders. In further embodiments, the compound or composition is administered to treat hepatic encephlopathy. In further embodiments, the compound or composition is administered to treat chronic alcoholism.

In further embodiments, the compound or composition is administered orally, by rectal suppository, or enema.

In further embodiments, the method comprises administering a pharmaceutically effective amount of the compound or composition in combination with one or more additional pharmaceutically active compounds or agents. In further embodiments, the one or more additional pharmaceutically active compounds or agents is selected from the group consisting of a diuretic, cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent, lipid-lowering agent, and peroxisome proliferator-activated receptor (PPAR) gamma agonist agent. In further embodiments, the diuretic is selected from the group consisting of a high ceiling loop diuretic, a benzothiadiazide diuretic, a potassium sparing diuretic, and a osmotic diuretic. In further embodiments, the pharmaceutically effective amount of the compound or composition, and the one or more additional pharmaceutically active compounds or agents, are administered as part of a single pharmaceutical preparation. In further embodiments, the pharmaceutically effective amount of the compound or composition, and the one or more additional pharmaceutically active compounds or agents, are administered as individual pharmaceutical preparations. In further embodiments, the individual pharmaceutical preparation is administered sequentially. In further embodiments, the individual pharmaceutical preparation is administered simultaneously.

In another embodiment, a method for treating a gastrointestinal tract disorder is provided, the method comprising administering to a mammal in need thereof a pharmaceutically effective amount of a compound or pharmaceutical composition as set forth above.

In further embodiments, the gastrointestinal tract disorder is a gastrointestinal motility disorder. In further embodiments, the gastrointestinal tract disorder is irritable bowel syndrome. In further embodiments, the gastrointestinal tract disorder is chronic constipation. In further embodiments, the gastrointestinal tract disorder is chronic idiopathic constipation. In further embodiments, the gastrointestinal tract disorder is chronic constipation occurring in cystic fibrosis patients. In further embodiments, the gastrointestinal tract disorder is opioid-induced constipation. In further embodiments, the gastrointestinal tract disorder is a functional gastrointestinal tract disorder. In further embodiments, the gastrointestinal tract disorder is selected from the group consisting of chronic intestinal pseudo-obstruction and colonic pseudo-obstruction. In further embodiments, the gastrointestinal tract disorder is Crohn's disease. In further embodiments, the gastrointestinal tract disorder is ulcerative colitis. In further embodiments, the gastrointestinal tract disorder is a disease referred to as inflammatory bowel disease. In further embodiments, the gastrointestinal tract disorder is associated with chronic kidney disease (stage 4 or 5). In further embodiments, the gastrointestinal tract disorder is constipation induced by calcium supplement. In further embodiments, the gastrointestinal tract disorder is constipation, and the constipation to be treated is associated with the use of a therapeutic agent. In further embodiments, the gastrointestinal tract disorder is constipation, and the constipation to be treated is associated with a neuropathic disorder. In further embodiments, the gastrointestinal tract disorder is constipation, and the constipation to be treated is post-surgical constipation (postoperative ileus). In further embodiments, the gastrointestinal tract disorder is constipation, and the constipation to be treated is idiopathic (functional constipation or slow transit constipation). In further embodiments, the gastrointestinal tract disorder is constipation, and the constipation to be treated is associated with neuropathic, metabolic or an endocrine disorder (e.g., diabetes mellitus, renal failure, hypothyroidism, hyperthyroidism, hypocalcaemia, Multiple Sclerosis, Parkinson's disease, spinal cord lesions, neurofibromatosis, autonomic neuropathy, Chagas disease, Hirschsprung's disease or cystic fibrosis, and the like). In further embodiments, the gastrointestinal tract disorder is constipation, and the constipation to be treated is due the use of drugs selected from analgesics (e.g., opioids), antihypertensives, anticonvulsants, antidepressants, antispasmodics and antipsychotics.

In other embodiments, the gastrointestinal tract disorder is associated with gastric ulcers, infectious diarrhea, cancer (colorectal), "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (e.g., arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune (e.g., Type 1 diabetes, ankylosing spondylitis, lupus, alopecia areata, rheumatoid arthritis, polymyalgia rheumatica, fibromyalgia, chronic fatigue syndrome. Sjogren's syndrome, vitiligo, thyroiditis, vasculitis, urticarial (hives), or Raynaud's syndrome), Schizophrenia, autism spectrum disorders, hepatic encephalopathy, small intestine bacterial overgrowth, or chronic alcoholism.

In another embodiment, a method for treating irritable bowel syndrome is provided, the method comprising administering to a mammal in need thereof a pharmaceutically effective amount of a compound or pharmaceutical composition as set forth above.

In further embodiments of the above embodiments, the compound or composition is administered to treat or reduce pain associated with a gastrointestinal tract disorder. In further embodiments, the compound or composition is administered to treat or reduce visceral hypersensitivity associated with a gastrointestinal tract disorder. In further embodiments, the compound or composition is administered to treat or reduce inflammation of the gastrointestinal tract. In further embodiments, the compound or composition is administered to reduce gastrointestinal transit time.

In further embodiments, the compound or composition is administered either orally or by rectal suppository.

In further embodiments, the method comprises administering a pharmaceutically effective amount of the compound or composition, in combination with one or more additional pharmaceutically active compounds or agents. In further embodiments, the one or more additional pharmaceutically active agents or compounds are an analgesic peptide or agent. In further embodiments, the one or more additional pharmaceutically active agents or compounds are selected from the group consisting of a laxative agent selected from a bulk-producing agent (e.g. psyllium husk (Metamucil)), methylcellulose (Citrucel), polycarbophil, dietary fiber, apples, stool softeners/surfactant (e.g., docusate, Colace, Diocto), a hydrating or osmotic agent (e.g., dibasic sodium phosphate, magnesium citrate, magnesium hydroxide (Milk of magnesia), magnesium sulfate (which is Epsom salt), monobasic sodium phosphate, sodium biphosphate), and a hyperosmotic agent (e.g., glycerin suppositories, sorbitol, lactulose, and polyethylene glycol (PEG)). In further embodiments, the pharmaceutically effective amount of the compound or composition, and the one or more additional pharmaceutically active compounds or agents, are administered as part of a single pharmaceutical preparation. In further embodiments, the pharmaceutically effective amount of the compound or composition, and the one or more additional pharmaceutically active compounds or agents, are administered as individual pharmaceutical preparations. In further embodiments, the individual pharmaceutical preparation is administered sequentially. In further embodiments, the individual pharmaceutical preparation is administered simultaneously.

Another aspect of the invention is directed to pharmaceutical compositions comprising a compound of Formula I and a pharmaceutically acceptable carrier. In one embodiment, the pharmaceutical composition comprising a compound of Formula Ia, Ib, Ic, Id, Ie, If, Ig, Ih, or Ii and a pharmaceutically acceptable carrier. In another embodiment, the pharmaceutical composition described herein may be used to inhibit NHE-mediated antiport of sodium and hydrogen ions. In another embodiment, the pharmaceutical composition described herein may be used to treat disorders associated with fluid retention or salt overload A pharmaceutical composition or preparation that may be used in accordance with the present disclosure for the treatment of various disorders associated with fluid retention and/or salt overload in the gastrointestinal tract (e.g., hypertension, heart failure (in particular, congestive heart failure), chronic kidney disease, end-stage renal disease, liver disease and/or peroxisome proliferator-activated receptor (PPAR) gamma agonist-induced fluid retention) comprises, in general, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein). In some particular embodiments, the NHE-inhibiting compound, including any pharmaceutical composition comprising the compound, is administered with a fluid-absorbing polymer (as more fully described below).

Subjects "in need of treatment" with a compound of the present disclosure, or subjects "in need of NHE inhibition" include subjects with diseases and/or conditions that can be treated with substantially impermeable or substantially systemically non-bioavailable NHE-inhibiting compounds, with or without a fluid-absorbing polymer, to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment may be suffering from hypertension: from salt-sensitive hypertension which may result from dietary salt intake; from a risk of a cardiovascular disorder (e.g., myocardial infarction, congestive heart failure and the like) resulting from hypertension; from heart failure (e.g., congestive heart failure) resulting in fluid or salt overload; from chronic kidney disease resulting in fluid or salt overload, from end stage renal disease resulting in fluid or salt overload: from liver disease resulting in fluid or salt overload: from peroxisome proliferator-activated receptor (PPAR) gamma agonist-induced fluid retention; or from edema resulting from congestive heart failure or end stage renal disease. In various embodiments, a subject in need of treatment typically shows signs of hypervolemia resulting from salt and fluid retention that are common features of congestive heart failure, renal failure or liver alopeccia. Fluid retention and salt retention manifest themselves by the occurrence of shortness of breath, edema, ascites or interdialytic weight gain. Other examples of subjects that would benefit from the treatment are those suffering from congestive heart failure and hypertensive patients and, particularly, those who are resistant to treatment with diuretics, i.e., patients for whom very few therapeutic options are available. A subject "in need of treatment" also includes a subject with hypertension, salt-sensitive blood pressure and subjects with systolic/diastolic blood pressure greater than about 130-139/85-89 mm Hg.

Administration of NHE-inhibiting compounds, with or without administration of fluid-absorbing polymers, may be beneficial for patients put on "non-added salt" dietary regimen (i.e., 60-100 mmol of Na per day), to liberalize their diet while keeping a neutral or slightly negative sodium balance (i.e., the overall uptake of salt would be equal of less than the secreted salt). In that context, "liberalize their diet" means that patients treated may add salt to their meals to make the meals more palatable, or/and diversify their diet with salt-containing foods, thus maintaining a good nutritional status while improving their quality of life.

The treatment methods described herein may also help patients with edema associated with chemotherapy, premenstrual fluid overload and preeclampsia (pregnancy-induced hypertension).

Accordingly, it is to be noted that the present disclosure is further directed to methods of treatment involving the administration of the compound of the present disclosure, or a pharmaceutical composition comprising such a compound.

Such methods may include, for example, a method for treating hypertension, the method comprising administering to the patient a substantially impermeable or substantially systemically non-bioavailable NHE-inhibiting compound, or a pharmaceutical composition comprising it. The method may be for reducing fluid overload associated with heart failure (in particular, congestive heart failure), the method comprising administering to the patient a substantially impermeable or substantially systemically non-bioavailable NHE-inhibiting compound or pharmaceutical composition comprising it. The method may be for reducing fluid overload associated with end stage renal disease, the method comprising administering to the patient a substantially impermeable or substantially systemically non-bioavailable NHE-inhibiting compound or composition comprising it. The method may be for reducing fluid overload associated with peroxisome proliferator-activated receptor (PPAR) gamma agonist therapy, the method comprising administering to the patient a substantially impermeable or substantially systemically non-bioavailable NHE-inhibiting compound or composition comprising it. Additionally, or alternatively, the method may be for decreasing the activity of an intestinal NHE transporter in a patient, the method comprising: administering to the patient a substantially impermeable or substantially systemically non-bioavailable NHE-inhibiting compound, or a composition comprising it. In another embodiment, the disease to be treated, includes, but is not limited to, heart failure (such as congestive heart failure), chronic kidney disease, end-stage renal disease, liver disease, and peroxisome proliferator-activated receptor (PPAR) gamma agonist-induced fluid retention is provided, gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, gastric ulcers, infectious diarrhea, cancer (colorectal). "leaky gut syndrome", cystic fibrosis gastrointestinal disease, multi-organ failure, microscopic colitis, necrotizing enterocolitis, allergy-atopy, food allergy, infections (respiratory), acute inflammation (e.g., sepsis, systemic inflammatory response syndrome), chronic inflammation (arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type 1 diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestine bacterial overgrowth, chronic alcoholism, and the like.

2. Gastrointestinal Tract Disorders

Another aspect of the invention is directed to method for treating a disorder associated with gastrointestinal tract. The method comprises administering to a mammal in need thereof a pharmaceutically effective amount of a compound or pharmaceutical composition of Formula I. In one embodiment, the method of treating a disorder associated with gastrointestinal tract comprises administering to a mammal in need thereof a pharmaceutically effective amount of a compound Ia, Ib, Ic, Id, Ie, If, Ig, Ih, or Ii or a combination thereof.

A pharmaceutical composition or preparation that may be used in accordance with the present disclosure for the treatment of various gastrointestinal tract disorders, including the treatment or reduction of pain associated with gastrointestinal tract disorders, comprises, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein). In some particular embodiments, the NHE-inhibiting compound, including any pharmaceutical composition comprising the compound, is administered with a fluid-absorbing polymer (as more fully described below).

Subjects "in need of treatment" with a compound of the present disclosure, or subjects "in need of NHE inhibition" include subjects with diseases and/or conditions that can be treated with substantially impermeable or substantially systemically non-bioavailable NHE-inhibiting compounds, with or without a fluid-absorbing polymer, to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment is suffering from a gastrointestinal tract disorder; the patient is suffering from a disorder selected from the group consisting of: a gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, gastric ulcers, infectious diarrhea, cancer (colorectal), "leaky gut syndrome", cystic fibrosis gastrointestinal disease, multi-organ failure, microscopic colitis, necrotizing enterocolitis, atopy, food allergy, infections (respiratory), acute inflammation (e.g., sepsis, systemic inflammatory response syndrome), chronic inflammation (e.g., arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type 1 diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestine bacterial overgrowth, chronic alcoholism, and the like.

In various preferred embodiments, the constipation to be treated is: associated with the use of a therapeutic agent; associated with a neuropathic disorder: post-surgical constipation (postoperative ileus); associated with a gastrointestinal tract disorder; idiopathic (functional constipation or slow transit constipation); associated with neuropathic, metabolic or endocrine disorder (e.g., diabetes mellitus, renal failure, hypothyroidism, hyperthyroidism, hypocalcaemia, Multiple Sclerosis, Parkinson's disease, spinal cord lesions, neurofibromatosis, autonomic neuropathy, Chagas disease, Hirschsprung's disease or cystic fibrosis, and the like). Constipation may also be the result of surgery (post-operative ileus) or due the use of drugs such as analgesics (e.g., opioids), antihypertensives, anticonvulsants, antidepressants, antispasmodics and antipsychotics.

In yet other embodiments, the constipation is associated with gastric ulcers, infectious diarrhea, cancer (colorectal), "leaky gut syndrome", cystic fibrosis gastrointestinal disease, multi-organ failure, microscopic colitis, necrotizing enterocolitis, atopy, food allergy, infections (respiratory), acute inflammation (e.g., sepsis, systemic inflammatory response syndrome), chronic inflammation (e.g., arthritis), obesity-induced metabolic diseases (e.g., nonalcoholic steatohepatitis, Type I diabetes, Type II diabetes, cardiovascular disease), kidney disease, diabetic kidney disease, cirrhosis, nonalcoholic steatohepatitis, nonalcoholic fatty acid liver disease, Steatosis, primary sclerosing cholangitis, primary biliary cholangitis, portal hypertension, autoimmune disease (e.g., Type 1 diabetes, ankylosing spondylitis, lupus, alopecia areata, rheumatoid arthritis, polymyalgia rheumatica, fibromyalgia, chronic fatigue syndrome, Sjogren's syndrome, vitiligo, thyroiditis, vasculitis, urticarial (hives), Raynaud's syndrome), Schizophrenia, autism spectrum disorders, hepatic encephlopathy, small intestine bacterial overgrowth, chronic alcoholism, and the like.

Accordingly, it is to be noted that the present disclosure is further directed to methods of treatment involving the administration of the compound of the present disclosure, or a pharmaceutical composition comprising such a compound. Such methods may include, for example, a method for increasing gastrointestinal motility in a patient, the method comprising administering to the patient a substantially non-permeable or substantially non-bioavailable NHE-inhibiting compound, or a pharmaceutical composition comprising it. Additionally, or alternatively, the method may be for decreasing the activity of an intestinal NHE transporter in a patient, the method comprising administering to the patient a substantially non-permeable or substantially non-bioavailable NHE-inhibiting compound, or a pharmaceutical composition comprising it. Additionally, or alternatively, the method may be for treating a gastrointestinal tract disorder, a gastrointestinal motility disorder, irritable bowel syndrome, chronic calcium-induced constipation in osteoporotic patients, chronic constipation occurring in cystic fibrosis patients, chronic constipation occurring in chronic kidney disease patients, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, colonic pseudo-obstruction, Crohn's disease, ulcerative colitis, inflammatory bowel disease, the method comprising administering an antagonist of the intestinal NHE, and more specifically, a substantially non-permeable or substantially non-bioavailable NHE-inhibiting compound, or a pharmaceutical composition comprising it, either orally or by rectal suppository. Additionally, or alternatively, the method may be for treating or reducing pain, including visceral pain, pain associated with a gastrointestinal tract disorder or pain associated with some other disorder, the method comprising administering to a patient a substantially non-permeable or substantially non-bioavailable NHE-inhibiting compound, or a pharmaceutical composition comprising it. Additionally, or alternatively, the method may be for treating inflammation, including inflammation of the gastrointestinal tract, e.g., inflammation associated with a gastrointestinal tract disorder or infection or some other disorder, the method comprising administering to a patient a substantially non-permeable or substantially non-bioavailable NHE-inhibiting compound, or a pharmaceutical composition comprising it.

3. Metabolic Disorders

A pharmaceutical composition or preparation that may be used in accordance with the present disclosure for the treatment of various metabolic disorders including the treatment or reduction of type II diabetes mellitus (T2DM), metabolic syndrome, and/or symptoms associated with such disorders comprises, in general, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein). In another embodiment, the pharmaceutical composition can be used to treat other metabolic diseases such as nonalcoholic steatohepatitis, diabetes Type I and II, and cardiovascular diseases.

Obesity is becoming a worldwide epidemic. In the United States, approximately ⅔rds of the population is either overweight (body mass index [BMI] 25 to 29.9) or obese (BMI≥30) (Ogden, C L et al, "Prevalence of overweight and obesity in the united states, 1999-2004" JAMA 2006, 295, 1549-1555). Obesity is a major risk factor for the development of diabetes and related complications, including cardiovascular disease and chronic kidney disease (CKD). The prevalence of T2DM has increased alarmingly in the United States. The American Diabetes Associated (ADA) estimates that more than 23 million U.S. adults aged 20 years or older have diabetes, with T2DM accounting for approximately 95% of these cases. The World Health Organization (WHO) has put the number of persons with diabetes worldwide at approximately 170 million (Campbell, R. K. "Type 2 diabetes: where we are today: an overview of disease burden, current treatments, and treatment strategies" Journal of the American Pharmacists Association 2009, 49(5), S3-S9).

Obesity is also a major risk factor for the development of metabolic syndrome, and subsequently the development of CKD. Metabolic syndrome, previously known as Syndrome X, the plurimetabolic syndrome, the dysmetabolic syndrome, and other names, consists of a clustering of metabolic abnormalities including abdominal obesity, hypertriglyceridemia, low levels of high-density lipoprotein (HDL) cholesterol, elevated blood pressure (BP), and elevations in fasting glucose or diabetes (Townsend, R. R. et al "Metabolic Syndrome, Components, and Cardiovascular Disease Prevalence in Chronic Kidney Disease: Findings from the Chronic Renal Insufficiency Cohort (CRIC) Study" American Journal of Nephrology 2011, 33, 477-484). Metabolic syndrome is common in patients with CKD and an important risk factor for the development and progression of CKD.

Hemodynamic factors appear to play a significant role in obesity-induced renal dysfunction. Hypertension, which is closely linked to obesity, appears to be a major cause of renal dysfunction in obese patients (Wahba, M. et al "Obesity and obesity-initiated metabolic syndrome: mechanistic links to chronic kidney disease" Clinical Journal of the American Society of Nephrology 2007, 2, 550-562). Studies in animals and in humans have shown that obesity is associated with elevated glomerular filtration rate (GFR) and increased renal blood flow. This likely occurs because of afferent arteriolar dilation as a result of proximal salt reabsorption, coupled with efferent renal arteriolar vasoconstriction as a result of elevated angiotensin II levels. These effects may contribute to hyperfiltration, glomerulomegaly, and later focal glomerulosclerosis. Even though GFR is increased in obesity, urinary sodium excretion in response to a saline load is often delayed, and individuals exhibit an abnormal pressure natriuresis, indicating avid proximal tubular sodium reabsorption. In addition, increased fat distribution can cause increased intra-abdominal pressure, leading to renal vein compression, thus raising renal venous pressure and diminishing renal perfusion. In creased fat, through a variety of mechanisms, can cause elevated renal interstitial fluid hydrostatic fluid and may stimulate renal sodium retention the thereby contribute to hypertension (Wahba_2007).

In view of the above, there exists a need in the art for agents that can divert sodium and fluid from a subject via mechanisms that either avoid the kidney, or do not depend upon normal kidney function. A subject with metabolic disease, including T2DM, metabolic syndrome, and the like, is a human, but can also be an animal in need of treatment with a compound of the disclosure, e.g., companion animals (e.g., dogs, cats, and the like), farm animals (e.g., cows, pigs, horses and the like) and laboratory animals (e.g., rats, mice, guinea pigs and the like).

The compounds utilized in the treatment methods of the present disclosure, as well as the pharmaceutical compositions comprising them, may accordingly be administered alone, or as part of a combination therapy or regimen that includes the administration or use of other therapeutic compounds related to the treatment of metabolic disorders such as T2DM and metabolic syndrome. In some particular embodiments, the NHE-inhibiting compound, including any pharmaceutical composition comprising the compound, is administered with a fluid absorbing polymer.

B. Combination Therapies

1. Fluid Retention and/or Salt Overload Disorders

As previously noted, the compounds described herein can be used alone or in combination with other agents. For example, the compounds can be administered together with a diuretic (i.e., High Ceiling Loop Diuretics, Benzothiadiazide Diuretics, Potassium Sparing Diuretics, Osmotic Diuretics), cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent, lipid-lowering agent, peroxisome proliferator-activated receptor (PPAR) gamma agonist agent or compound or with a fluid-absorbing polymer as more fully described below. The agent can be covalently attached to a compound described herein or it can be a separate agent that is administered together with or sequentially with a compound described herein in a combination therapy.

Combination therapy can be achieved by administering two or more agents, e.g., a substantially non-permeable or substantially systemically non-bioavailable NHE-inhibiting compound described herein and a diuretic, cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases, even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X—Y—X, X—X—Y, Y—X—Y, Y—Y—X, X—X—Y—Y, etc.

The compounds described herein can be used in combination therapy with a diuretic. Among the useful diuretic agents are, for example: High Ceiling Loop Diuretics [Furosemide (Lasix), Ethacrynic Acid (Edecrin), Bumetanide (Bumex)], Benzothiadiazide Diuretics [Hydrochlorothiazide (Hydrodiuril), Chlorothiazide (Diuril), Clorthalidone (Hygroton), Benzthiazide (Aguapres), Bendroflumethiazide (Naturetin), Methyclothiazide (Aguatensen), Polythiazide (Renese), Indapamide (Lozol), Cyclothiazide (Anhydron), Hydroflumethiazide (Diucardin), Metolazone (Diulo), Quinethazone (Hydromox), Trichlormethiazide (Naqua)], Potassium Sparing Diuretics [Spironolactone (Aldactone), Triamterene (Dyrenium), Amiloride (Midamor)], and Osmotic Diuretics [Mannitol (Osmitrol)]. Diuretic agents in the various classes are known and described in the literature.

Cardiac glycosides (cardenolides) or other digitalis preparations can be administered with the compounds of the disclosure in co-therapy. Among the useful cardiac glycosides are, for example: Digitoxin (Crystodigin), Digoxin (Lanoxin) or Deslanoside (Cedilanid-D). Cardiac glycosides in the various classes are described in the literature.

Angiotensin Converting Enzyme Inhibitors (ACE Inhibitors) can be administered with the compounds of the disclosure in co-therapy. Among the useful ACE inhibitors are, for example: Captopril (Capoten), Enalapril (Vasotec), Lisinopril (Prinivil). ACE inhibitors in the various classes are described in the literature.

Angiotensin-2 Receptor Antagonists (also referred to as $AT_1$-antagonists or angiotensin receptor blockers, or ARB's) can be administered with the compounds of the disclosure in co-therapy. Among the useful Angiotensin-2 Receptor Antagonists are, for example: Candesartan (Atacand), Eprosartan (Teveten), Irbesartan (Avapro), Losartan (Cozaar), Telmisartan (Micardis), Valsartan (Diovan). Angiotensin-2 Receptor Antagonists in the various classes are described in the literature.

Calcium channel blockers such as Amlodipine (Norvasc, Lotrel), Bepridil (Vascor), Diltiazem (Cardizem, Tiazac), Felodipine (Plendil), Nifedipine (Adalat, Procardia), Nimodipine (Nimotop), Nisoldipine (Sular), Verapamil (Calan, Isoptin, Verelan) and related compounds described in, for example, EP 625162B1, U.S. Pat. Nos. 5,364,842, 5,587,454, 5,824,645, 5,859,186, 5,994,305, 6,087,091, 6,136,786, WO 93/13128 A1, EP 1336409 A1, EP 835126 A1, EP 835126 B1, U.S. Pat. Nos. 5,795,864, 5,891,849, 6,054,429, WO 97/01351 A1, the entire contents of which are incorporated herein by reference for all relevant and consistent purposes, can be used with the compounds of the disclosure.

Beta blockers can be administered with the compounds of the disclosure in co-therapy. Among the useful beta blockers are, for example: Acebutolol (Sectral), Atenolol (Tenormin), Betaxolol (Kerlone), Bisoprolol/hydrochlorothiazide (Ziac), Bisoprolol (Zebeta), Carteolol (Cartrol), Metoprolol (Lopressor, Toprol XL), Nadolol (Corgard), Propranolol (Inderal), Sotalol (Betapace), Timolol (Blocadren). Beta blockers in the various classes are described in the literature.

PPAR gamma agonists such as thiazolidinediones (also called glitazones) can be administered with the compounds of the disclosure in co-therapy. Among the useful PPAR agonists are, for example: rosiglitazone (Avandia), pioglitazone (Actos) and rivoglitazone.

Aldosterone antagonists can be administered with the compounds of the disclosure in co-therapy. Among the useful Aldosterone antagonists are, for example: eplerenone, spironolactone, and canrenone.

Renin inhibitor can be administered with the compounds of the disclosure in co-therapy. Among the useful Renin inhibitors is, for example: aliskiren.

Alpha blockers can be administered with the compounds of the disclosure in co-therapy. Among the useful Alpha blockers are, for example: Doxazosin mesylate (Cardura), Prazosin hydrochloride (Minipress). Prazosin and polythiazide (Minizide), Terazosin hydrochloride (Hytrin). Alpha blockers in the various classes are described in the literature.

Central alpha agonists can be administered with the compounds of the disclosure in co-therapy. Among the useful Central alpha agonists are, for example: Clonidine hydrochloride (Catapres), Clonidine hydrochloride and chlorthalidone (Clorpres, Combipres), Guanabenz Acetate (Wytensin), Guanfacine hydrochloride (Tenex), Methyldopa (Aldomet), Methyldopa and chlorothiazide (Aldochlor), Methyldopa and hydrochlorothiazide (Aldoril). Central alpha agonists in the various classes are described in the literature.

Vasodilators can be administered with the compounds of the disclosure in co-therapy. Among the useful vasodilators are, for example: Isosorbide dinitrate (Isordil), Nesiritide (Natrecor), Hydralazine (Apresoline), Nitrates/nitroglycerin, Minoxidil (Loniten). Vasodilators in the various classes are described in the literature.

Blood thinners can be administered with the compounds of the disclosure in co-therapy. Among the useful blood thinners are, for example: Warfarin (Coumadin) and Heparin. Blood thinners in the various classes are described in the literature.

Anti-platelet agents can be administered with the compounds of the disclosure in co-therapy. Among the useful anti-platelet agents are, for example: Cyclooxygenase inhibitors (Aspirin), Adenosine diphosphate (ADP) receptor inhibitors [Clopidogrel (Plavix), Ticlopidine (Ticlid)]. Phosphodiesterase inhibitors [Cilostazol (Pletal)], Glycoprotein IIB/IIIA inhibitors [Abciximab (ReoPro), Eptifibatide (Integrilin), Tirofiban (Aggrastat), Defibrotide], Adenosine reuptake inhibitors [Dipyridamole (Persantine)]. Anti-platelet agents in the various classes are described in the literature.

Lipid-lowering agents can be administered with the compounds of the disclosure in co-therapy. Among the useful lipid-lowering agents are, for example: Statins (HMG CoA reductase inhibitors), [Atorvastatin (Lipitor), Fluvastatin (Lescol), Lovastatin (Mevacor, Altoprev), Pravastatin (Pravachol), Rosuvastatin Calcium (Crestor), Simvastatin (Zocor)], Selective cholesterol absorption inhibitors [ezetimibe (Zetia)], Resins (bile acid sequestrant or bile acid-binding drugs) [Cholestyramine (Questran, Questran Light, Prevalite, Locholest, Locholest Light). Colestipol (Colestid), Colesevelam Hcl (WelChol)], Fibrates (Fibric acid derivatives) [Gemfibrozil (Lopid), Fenofibrate (Antara, Lofibra, Tricor, and Triglide), Clofibrate (Atromid-S)], Niacin (Nicotinic acid). Lipid-lowering agents in the various classes are described in the literature.

The compounds of the disclosure can be used in combination with peptides or peptide analogs that activate the Guanylate Cyclase-receptor in the intestine and results in elevation of the intracellular second messenger, or cyclic guanosine monophosphate (cGMP), with increased chloride and bicarbonate secretion into the intestinal lumen and concomitant fluid secretion. Example of such peptides are Linaclotide (MD-1100 Acetate), endogenous hormones guanylin and uroguanylin and enteric bacterial peptides of the heat stable enterotoxin family (ST peptides) and those described in U.S. Pat. Nos. 5,140,102, 5,489,670, 5,969,097, WO 2006/001931A2, WO 2008/002971A2, WO 2008/106429A2, US 2008/0227685A1 and U.S. Pat. No. 7,041,786, the entire contents of which are incorporated herein by reference for all relevant and consistent purposes.

The compounds of the disclosure can be used in combination with type-2 chloride channel agonists, such as Amitiza (Lubiprostone) and other related compounds described in U.S. Pat. No. 6,414,016, the entire contents of which are incorporated herein by reference for all relevant and consistent purposes.

The compounds described herein can be used in combination therapy with agents used for the treatment of obesity, T2DM, metabolic syndrome and the like. Among the useful agents include: insulin; insulin secretagogues, such as sulphonylureas; glucose-lowering effectors, such as metformin; activators of the peroxisome proliferator-activated receptor γ (PPARγ), such as the thiazolidinediones; incretin-based agents including dipeptidyl peptidase-4 inhibitors such as sitagliptin, and synthetic incretin mimetics such as liraglutide and exenatide; alpha-glucosidase inhibitors, such as acarbose; glinides, such as repaglinide and nateglinide, and the like.

The compounds of the disclosure can be used in combination with P2Y2 receptor agonists, such as those described in EP 1196396B1 and U.S. Pat. No. 6,624,150, the entire contents of which are incorporated herein by reference for all relevant and consistent purposes.

Other agents include natriuretic peptides such as nesiritide, a recombinant form of brain-natriuretic peptide (BNP) and an atrial-natriuretic peptide (ANP). Vasopressin receptor antagonists such as tolvaptan and conivaptan may be co-administered as well as phosphate binders such as renagel, renleva, phoslo and fosrenol. Other agents include phosphate transport inhibitors (as described in U.S. Pat. Nos. 4,806,532; 6,355,823; 6,787,528; 7,119,120; 7,109,184; U.S. Pat. Pub. No. 2007/021509; 2006/0280719; 2006/0217426; International Pat. Pubs. WO 2001/005398, WO 2001/087294, WO 2001/082924, WO 2002/028353, WO 2003/048134, WO 2003/057225, WO2003/080630, WO 2004/085448. WO 2004/085382; European Pat. Nos. 1465638 and 1485391: and JP Patent No. 2007131532, or phosphate transport antagonists such as Nicotinamide.

2. Gastrointestinal Tract Disorders

As previously noted, the compounds described herein can be used alone or in combination with other agents. For example, the compounds can be administered together with an analgesic peptide or compound. The analgesic peptide or compound can be covalently attached to a compound described herein or it can be a separate agent that is administered together with or sequentially with a compound described herein in a combination therapy.

Combination therapy can be achieved by administering two or more agents, e.g., a substantially non-permeable or substantially non-bioavailable NHE-inhibiting compound described herein and an analgesic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X—Y—X, X—X—Y, Y—X—Y, Y—Y—X, X—X—Y—Y, etc.

The compounds described herein can be used in combination therapy with an analgesic agent, e.g., an analgesic compound or an analgesic peptide. The analgesic agent can optionally be covalently attached to a compound described herein. Among the useful analgesic agents are, for example: Ca channel blockers, 5HT3 agonists (e.g., MCK-733). 5HT4 agonists (e.g., tegaserod, prucalopride), and 5HT1 receptor antagonists, opioid receptor agonists (loperamide, fedotozine, and fentanyl), NK1 receptor antagonists, CCK receptor agonists (e.g., loxiglumide), NK1 receptor antagonists, NK3 receptor antagonists, norepinephrine-serotonin reuptake inhibitors (NSR1), vanilloid and cannabanoid receptor agonists, and sialorphin. Analgesics agents in the various classes are described in the literature.

Opioid receptor antagonists and agonists can be administered with the compounds of the disclosure in co-therapy or linked to the compound of the disclosure, e.g., by a covalent bond. For example, opioid receptor antagonists such as naloxone, naltrexone, methyl nalozone, nalmefene, cypridine, beta funaltrexamine, naloxonazine, naltrindole, and nor-binaltorphimine are thought to be useful in the treatment of opioid-induced constipaption (OIC). It can be useful to formulate opioid antagonists of this type in a delayed or sustained release formulation, such that initial release of the antagonist is in the mid to distal small intestine and/or ascending colon. Such antagonists are described in U.S. Pat. No. 6,734,188 (WO 01/32180 A2), the entire contents of which are incorporated herein by reference for all relevant and consistent purposes. Enkephalin pentapeptide (HOE825; Tyr-D-Lys-Gly-Phe-L-homoserine) is an agonist of the µ- and γ-opioid receptors and is thought to be useful for increasing intestinal motility (Eur. J. Pharm., 219:445, 1992), and this peptide can be used in conjunction with the compounds of the disclosure. Also useful is trimebutine which is thought to bind to mu/delta/kappa opioid receptors and activate release of motilin and modulate the release of gastrin, vasoactive intestinal peptide, gastrin and glucagons. K-opioid receptor agonists such as fedotozine, ketocyclazocine, and compounds described in US 2005/0176746 (WO 03/097051 A2), the entire contents of which are incorporated herein by reference for all relevant and consistent purposes, can be used with or linked to the compounds of the disclosure. In addition, µ-opioid receptor agonists, such as morphine, diphenyloxylate, frakefamide (H-Tyr-D-Ala-Phe(F)-Phe-NH$_2$; disclosed in WO 01/019849 A1, the entire contents of which are incorporated herein by reference for all relevant and consistent purposes) and loperamide can be used.

Tyr-Arg (kyotorphin) is a dipeptide that acts by stimulating the release of met-enkephalins to elicit an analgesic effect (J. Biol. Chem. 262:8165, 1987). Kyotorphin can be used with or linked to the compounds of the disclosure. CCK receptor agonists such as caerulein from amphibians and other species are useful analgesic agents that can be used with or linked to the compounds of the disclosure.

Conotoxin peptides represent a large class of analgesic peptides that act at voltage gated Ca channels, NMDA receptors or nicotinic receptors. These peptides can be used with or linked to the compounds of the disclosure.

Peptide analogs of thymulin (U.S. Pat. No. 7,309,690 or FR 2830451, the entire contents of which are incorporated herein by reference for all relevant and consistent purposes) can have analgesic activity and can be used with or linked to the compounds of the disclosure.

CCK (CCKa or CCKb) receptor antagonists, including loxiglumide and dexloxiglumide (the R-isomer of loxiglumide) (U.S. Pat. No. 5,130,474 or WO 88/05774, the entire contents of which are incorporated herein by reference for all relevant and consistent purposes) can have analgesic activity and can be used with or linked to the compounds of the disclosure.

Other useful analgesic agents include 5-HT4 agonists such as tegaserod/zelnorm and lirexapride. Such agonists are described in: EP1321142 A1, WO 03/053432A1, EP 505322 A1, EP 505322 B1, EP 507672 A1, EP 507672 B1, U.S. Pat. Nos. 5,510,353 and 5,273,983, the entire contents of which are incorporated herein by reference for all relevant and consistent purposes.

Calcium channel blockers such as ziconotide and related compounds described in, for example, EP 625162B1, U.S. Pat. Nos. 5,364,842, 5,587,454, 5,824,645, 5,859,186, 5,994,305, 6,087,091, 6,136,786, WO 93/13128 A1, EP 1336409 A1, EP 835126 A1, EP 835126 B1, U.S. Pat. Nos. 5,795,864, 5,891,849, 6,054,429, WO 97/01351 A1, the entire contents of which are incorporated herein by reference for all relevant and consistent purposes, can be used with or linked to the compounds of the disclosure.

Various antagonists of the NK-1, NK-2, and NK-3 receptors (for a review see Giardina et al. 2003 Drugs 6:758) can be can be used with or linked to the compounds of the disclosure.

NK1 receptor antagonists such as: aprepitant (Merck & Co Inc), vofopitant, ezlopitant (Pfizer, Inc.). R-673 (Hoffmann-La Roche Ltd), SR-14033 and related compounds described in, for example, EP 873753 A1, U.S. 20010006972 A1, U.S. 20030109417 A1, WO 01/52844 A1, the entire contents of which are incorporated herein by reference for all relevant and consistent purposes, can be used with or linked to the compounds of the disclosure.

NK-2 receptor antagonists such as nepadutant (Menarini Ricerche SpA), saredutant (Sanofi-Synthelabo), SR-144190 (Sanofi-Synthelabo) and UK-290795 (Pfizer Inc) can be used with or linked to the compounds of the disclosure.

NK3 receptor antagonists such as osanetant (Sanofi-Synthelabo), talnetant and related compounds described in, for example, WO 02/094187 A2, EP 876347 A1, WO 97/21680 A1, U.S. Pat. No. 6,277,862, WO 98/11090, WO 95/28418, WO 97/19927, and Boden et al. (J Med. Chem. 39:1664-75, 1996), the entire contents of which are incorporated herein by reference for all relevant and consistent purposes, can be used with or linked to the compounds of the disclosure.

Norepinephrine-serotonin reuptake inhibitors such as milnacipran and related compounds described in WO 03/077897 A1, the entire contents of which are incorporated herein by reference for all relevant and consistent purposes, can be used with or linked to the compounds of the disclosure.

Vanilloid receptor antagonists such as arvanil and related compounds described in WO 01/64212 A1, the entire contents of which are incorporated herein by reference for all relevant and consistent purposes, can be used with or linked to the compounds of the disclosure.

The compounds can be used in combination therapy with a phosphodiesterase inhibitor (examples of such inhibitors can be found in U.S. Pat. No. 6,333,354, the entire contents of which are incorporated herein by reference for all relevant and consistent purposes).

The compounds can be used alone or in combination therapy to treat disorders associated with chloride or bicarbonate secretion that may lead to constipation, e.g., Cystic Fibrosis.

The compounds can also or alternatively be used alone or in combination therapy to treat calcium-induced constipation effects. Constipation is commonly found in the geriatric population, particularly patients with osteoporosis who have to take calcium supplements. Calcium supplements have shown to be beneficial in ostoporotic patients to restore bone density but compliance is poor because of constipation effects associated therewith.

The compounds of the current disclosure have can be used in combination with an opioid. Opioid use is mainly directed to pain relief, with a notable side-effect being GI disorder, e.g. constipation. These agents work by binding to opioid receptors, which are found principally in the central nervous system and the gastrointestinal tract. The receptors in these two organ systems mediate both the beneficial effects, and the undesirable side effects (e.g. decrease of gut motility and ensuing constipation). Opioids suitable for use typically belong to one of the following exemplary classes: natural opiates, alkaloids contained in the resin of the opium poppy including morphine, codeine and thebaine; semi-synthetic opiates, created from the natural opioids, such as hydromorphone, hydrocodone, oxycodone, oxymorphone, desomorphine, diacetylmorphine (Heroin), nicomorphine, dipropanoylmorphine, benzylmorphine and ethylmorphine; fully synthetic opioids, such as fentanyl, pethidine, methadone, tramadol and propoxyphene; endogenous opioid peptides, produced naturally in the body, such as endorphins, enkephalins, dynorphins, and endomorphins.

The compound of the disclosure can be used alone or in combination therapy to alleviate GI disorders encountered with patients with renal failure (stage 3-5). Constipation is the second most reported symptom in that category of patients (Murtagh et al., 2006; Murtagh et al., 2007a: Murtagh et al., 2007b). Without being held by theory, it is believed that kidney failure is accompanied by a stimulation of intestinal Na re-absorption (Hatch and Freel, 2008). A total or partial inhibition of such transport by administration of the compounds of the disclosure can have a therapeutic benefit to improve GI transit and relieve abdominal pain. In that context, the compounds of the disclosure can be used in combination with Angiotensin-modulating agents: Angiotensin Converting Enzyme (ACE) inhibitors (e.g. captopril, enalopril, lisinopril, ramipril) and Angiotensin II receptor antagonist therapy (also referred to as $AT_1$-antagonists or angiotensin receptor blockers, or ARB's); diuretics such as loop diuretics (e.g. furosemide, bumetanide), Thiazide diuretics (e.g. hydrochlorothiazide, chlorthalidone, chlorthiazide) and potassium-sparing diuretics; amiloride; beta blockers: bisoprolol, carvedilol, nebivolol and extended-release metoprolol; positive inotropes: Digoxin, dobutamine; phosphodiesterase inhibitors such as milrinone; alternative vasodilators: combination of isosorbide dinitrate/hydralazine; aldosterone receptor antagonists: spironolactone, eplerenone: natriuretic peptides: Nesiritide, a recombinant form of brain-natriuretic peptide (BNP), atrial-natriuretic peptide (ANP); vasopressin receptor antagonists: Tolvaptan and conivaptan: phosphate binder (Renagel, Renleva, Phoslo, Fosrenol); phosphate transport inhibitor such as those described in U.S. Pat. Nos. 4,806, 532, 6,355,823, 6,787,528, WO 2001/005398, WO 2001/087294, WO 2001/082924, WO 2002/028353, WO 2003/048134, WO 2003/057225, U.S. Pat. No. 7,119,120, EP 1465638, US Appl. 2007/021509, WO 2003/080630, U.S. Pat. No. 7,109,184, US Appl. 2006/0280719, EP 1485391, WO 2004/085448, WO 2004/085382, US Appl. 2006/0217426, JP 2007/131532, the entire contents of which are incorporated herein by reference for all relevant and consistent purposes, or phosphate transport antagonist (Nicotinamide).

The compounds of the disclosure can be used in combination with peptides or peptide analogs that activate the Guanylate Cyclase-receptor in the intestine and results in elevation of the intracellular second messenger, or cyclic guanosine monophosphate (cGMP), with increased chloride and bicarbonate secretion into the intestinal lumen and concomitant fluid secretion. Example of such peptides are Linaclotide (MD-1100 Acetate), endogenous hormones guanylin and uroguanylin and enteric bacterial peptides of the heat stable enterotoxin family (ST peptides) and those described in U.S. Pat. Nos. 5,140,102, 5,489,670, 5,969,097, WO 2006/001931A2, WO 2008/002971A2, WO 2008/106429A2, US 2008/0227685A1 and U.S. Pat. No. 7,041,786, the entire contents of which are incorporated herein by reference for all relevant and consistent purposes.

The compounds of the disclosure can be used in combination with type-2 chloride channel agonists, such as Amitiza (Lubiprostone) and other related compounds described in U.S. Pat. No. 6,414,016, the entire contents of which are incorporated herein by reference for all relevant and consistent purposes.

The compounds of the disclosure can be used in combination with P2Y2 receptor agonists, such as those described in EP 1196396B1 and U.S. Pat. No. 6,624,150, the entire contents of which are incorporated herein by reference for all relevant and consistent purposes.

The compounds of the disclosure can be used in combination with laxative agents such as bulk-producing agents, e.g. psyllium husk (Metamucil), methylcellulose (Citrucel), polycarbophil, dietary fiber, apples, stool softeners/surfactant such as docusate (Colace, Diocto); hydrating agents (osmotics), such as dibasic sodium phosphate, magnesium citrate, magnesium hydroxide (Milk of magnesia), magnesium sulfate (which is Epsom salt), monobasic sodium phosphate, sodium biphosphate; hyperosmotic agents: glycerin suppositories, sorbitol, lactulose, and polyethylene glycol (PEG). The compounds of the disclosure can be also be used in combination with agents that stimulate gut peristalsis, such as Bisacodyl tablets (Dulcolax), Casanthranol, Senna and Aloin, from Aloe Vera.

In one embodiment, the compounds of the disclosure accelerate gastrointestinal transit, and more specifically in the colon, without substantially affecting the residence time in the stomach, i.e. with no significant effect on the gastric emptying time. Even more specifically the compounds of the invention restore colonic transit without the side-effects associated with delayed gastric emptying time, such as nausea. The GI and colonic transit are measured in patients using methods reported in, for example: Burton D D, Camilleri M, Mullan B P, et al., *J. Nucl. Med.,* 1997; 38:1807-1810; Cremonini F, Mullan B P, Camilleri M, et al., *Aliment. Pharmacol. Ther.,* 2002; 16:1781-1790; Camilleri M. Zinsmeister A R, *Gastroenterology,* 1992; 103:36-42; Bouras E P, Camilleri M, Burton D D, et al., *Gastroenterology,* 2000; 120:354-360; Coulie B, Szarka L A, Camilleri M, et al., *Gastroenterology,* 2000; 119:41-50: Prather C M, Camilleri M, Zinsmeister A R, et al., *Gastroenterology,* 2000; 118:463-468; and, Camilleri M. McKinzie S, Fox J. et al., *Clin. Gastroenterol. Hepatol.,* 2004; 2:895-904.

C. Polymer Combination Therapy

The NHE-inhibiting compounds described therein may be administered to patients in need thereof in combination with a fluid-absorbing polymer ("FAP"). The intestinal fluid-absorbing polymers useful for administration in accordance with embodiments of the present disclosure may be administered orally in combination with non-absorbable NHE-inhibiting compounds (e.g., a NHE-3 inhibitor) to absorb the intestinal fluid resulting from the action of the sodium transport inhibitors. Such polymers swell in the colon and bind fluid to impart a consistency to stools that is acceptable for patients. The fluid-absorbing polymers described herein may be selected from polymers with laxative properties, also referred to as bulking agents (i.e., polymers that retain some of the intestinal fluid in the stools and impart a higher degree of hydration in the stools and facilitate transit). The fluid-absorbing polymers may also be optionally selected from pharmaceutical polymers with anti-diarrhea function, i.e., agents that maintain some consistency to the stools to avoid watery stools and potential incontinence.

The ability of the polymer to maintain a certain consistency in stools with a high content of fluid can be characterized by its "water holding power." Wenzl et al. (in *Determinants of decreased fecal consistency in patients with diarrhea*; Gastroenterology, v. 108, no. 6. p. 1729-1738 (1995)) studied the determinants that control the consistency of stools of patients with diarrhea and found that they were narrowly correlated with the water holding power of the feces. The water holding power is determined as the water content of given stools to achieve a certain level of consistency (corresponding to "formed stool" consistency) after the reconstituted fecal matter has been centrifuged at a certain g number. Without being held to any particular theory, has been found that the water holding power of the feces is increased by ingestion of certain polymers with a given fluid absorbing profile. More specifically, it has been found that the water-holding power of said polymers is correlated with their fluid absorbancy under load (AUL): even more specifically the AUL of said polymers is greater than 15 g of isotonic fluid/g of polymer under a static pressure of 5 kPa, or under a static pressure of 10 kPa.

The FAP utilized in the treatment method of the present disclosure also has a AUL of at least about 10 g, about 15 g, about 20 g, about 25 g or more of isotonic fluid/g of polymer under a static pressure of about 5 kPa, or about 10 kPA, and may have a fluid absorbency of about 20 g, about 25 g or more, as determined using means generally known in the art. Additionally, or alternatively, the FAP may impart a minimum consistency to fecal matter and, in some embodiments, a consistency graded as "soft" in the scale described in the test method below, when fecal non water-soluble solid fraction is from 10% to 20%, and the polymer concentration is from 1% to 5% of the weight of stool. The determination of the fecal non water-soluble solid fraction of stools is described in Wenz et al. The polymer may be uncharged or may have a low charge density (e.g., 1-2 meq/gr). Alternatively or in addition, the polymer may be delivered directly to the colon using known delivery methods to avoid premature swelling in the esophagus.

In one embodiment of the present disclosure, the FAP is a "superabsorbent" polymer (i.e., a lightly crosslinked, partially neutralized polyelectrolyte hydrogel similar to those used in baby diapers, feminine hygiene products, agriculture additives, etc.). Superabsorbent polymers may be made of a lightly crosslinked polyacrylate hydrogel. The swelling of the polymer is driven essentially by two effects: (i) the hydration of the polymer backbone and entropy of mixing and (ii) the osmotic pressure arising from the counter-ions (e.g., Na ions) within the gel. The gel swelling ratio at equilibrium is controlled by the elastic resistance inherent to the polymer network and by the chemical potential of the bathing fluid, i.e., the gel will de-swell at higher salt concentration because the background electrolyte will reduce the apparent charge density on the polymer and will reduce the difference of free ion concentrations inside and outside the gel that drives osmotic pressure. The swelling ratio SR (g of fluid per g of dry polymer and synonymously "fluid absorbency") may vary from 1000 in pure water down to 30 in 0.9% NaCl solution representative of physiological saline (i.e., isotonic). SR may increase with the degree of neutralization and may decrease with the crosslinking density. SR generally decreases with an applied load with the extent of reduction dependent on the strength of the gel, i.e., the crosslinking density. The salt concentration within the gel, as compared with the external solution, may be lower as a result of the Donnan effect due to the internal electrical potential.

The fluid-absorbing polymer may include crosslinked polyacrylates which are fluid absorbent such as those prepared from α,β-ethylenically unsaturated monomers, such as monocarboxylic acids, polycarboxylic acids, acrylamide and their derivatives. These polymers may have repeating units of acrylic acid, methacrylic acid, metal salts of acrylic acid, acrylamide, and acrylamide derivatives (such as 2-acrylamido-2-methylpropanesulfonic acid) along with various combinations of such repeating units as copolymers. Such derivatives include acrylic polymers which include hydrophilic grafts of polymers such as polyvinyl alcohol. Examples of suitable polymers and processes, including gel polymerization processes, for preparing such polymers are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; 4,190,562; 4,286,082; 4,857,610; 4,985,518; 5,145,906; 5,629,377 and 6,908,609 which are incorporated herein by reference for all relevant and consistent purposes (in addition, see Buchholz, F. L. and Graham, A. T., "Modern Superabsorbent Polymer Technology," John Wiley & Sons (1998), which is also incorporated herein by reference for all relevant and consistent purposes). A class of preferred polymers for treatment in combination with NHE-inhibitors is polyelectrolytes.

The degree of crosslinking can vary greatly depending upon the specific polymer material; however, in most applications the subject superabsorbent polymers are only lightly crosslinked, that is, the degree of crosslinking is such that the polymer can still absorb over 10 times its weight in physiological saline (i.e., 0.9% saline). For example, such polymers typically include less than about 0.2 mole % crosslinking agent.

In some embodiments, the FAP's utilized for treatment are Calcium Carbophil (Registry Number: 9003-97-8, also referred as Carbopol EX-83), and Carpopol 934P.

In some embodiments, the fluid-absorbing polymer is prepared by high internal phase emulsion ("HIPE") processes. The HIPE process leads to polymeric foam slabs with a very large porous fraction of interconnected large voids (about 100 microns) (i.e., open-cell structures). This technique produces flexible and collapsible foam materials with exceptional suction pressure and fluid absorbency (see U.S. Pat. Nos. 5,650,222; 5,763,499 and 6,107,356, which are incorporated herein for all relevant and consistent purposes). The polymer is hydrophobic and, therefore, the surface should be modified so as to be wetted by the aqueous fluid. This is accomplished by post-treating the foam material by a surfactant in order to reduce the interfacial tension. These materials are claimed to be less compliant to loads, i.e., less prone to de-swelling under static pressure.

In some embodiments, fluid-absorbing gels are prepared by aqueous free radical polymerization of acrylamide or a derivative thereof, a crosslinker (e.g., methylene-bis-acrylamide) and a free radical initiator redox system in water. The material is obtained as a slab. Typically, the swelling ratio of crosslinked polyacrylamide at low crosslinking density (e.g., 2%-4° % expressed as weight % of methylene-bis-acrylamide) is between 25 and 40 (F. Horkay, *Macromolecules*, 22, pp. 2007-09 (1989)). The swelling properties of these polymers have been extensively studied and are essentially the same of those of crosslinked polyacrylic acids at high salt concentration. Under those conditions, the osmotic pressure is null due to the presence of counter-ions and the swelling is controlled by the free energy of mixing and the network elastic energy. Stated differently, a crosslinked polyacrylamide gel of same crosslink density as a neutralized polyacrylic acid will exhibit the same swelling ratio (i.e., fluid absorbing properties) and it is believed the same degree of deswelling under pressure, as the crosslinked polyelectrolyte at high salt content (e.g., 1 M). The properties (e.g., swelling) of neutral hydrogels will not be sensitive to the salt environment as long as the polymer remains in good solvent conditions. Without being held to any particular theory, it is believed that the fluid contained within the gel has the same salt composition than the surrounding fluid (i.e., there is no salt partitioning due to Donnan effect).

Another subclass of fluid-absorbing polymers that may be utilized is hydrogel materials that include N-alkyl acrylamide polymers (e.g., N-isopropylacrylamide (NIPAM)). The corresponding aqueous polyNIPAM hydrogel shows a temperature transition at about 35° C. Above this temperature the hydrogel may collapse. The mechanism is generally reversible and the gel re-swells to its original swelling ratio when the temperature reverts to room temperature. This allows production of nanoparticles by emulsion polymerization (R. Pelton, *Advances in Colloid and Interface Science*, 85. pp. 1-33, (2000)). The swelling characteristics of poly-NIPAM nanoparticles below the transition temperature have been reported and are similar to those reported for bulk gel of polyNIPAM and equivalent to those found for poly-acrylamide (i.e. 30-50 g/g) (W. McPhee, *Journal of Colloid and Interface Science*, 156, pp. 24-30 (1993); and, K. Oh, *Journal of Applied Polymer Science*, 69, pp. 109-114 (1997)).

In some embodiments, the FAP utilized for treatment in combination with a NHE-inhibitor is a superporous gel that may delay the emptying of the stomach for the treatment of obesity (J. Chen, *Journal of Controlled Release*, 65, pp. 73-82 (2000), or to deliver proteins. Polyacrylate-based SAP's with a macroporous structure may also be used. Macroporous SAP and superporous gels differ in that the porous structure remains almost intact in the dry state for superporous gels, but disappears upon drying for macroporous SAP's. The method of preparation is different although both methods use a foaming agent (e.g., carbonate salt that generates $CO_2$ bubbles during polymerization). Typical swelling ratios, SR, of superporous materials are around 10. Superporous gels keep a large internal pore volume in the dry state.

Macroporous hydrogels may also be formed using a method whereby polymer phase separation in induced by a non-solvent. The polymer may be poly-NIPAM and the non-solvent utilized may be glucose (see, e.g., Z. Zhang, *J. Org. Chem.*, 69, 23 (2004)) or NaCl (see, e.g., Cheng et al., *Journal of Biomedical Materials Research—Part A*, Vol. 67, Issue 1, 1 Oct. 2003, Pages 96-103). The phase separation induced by the presence of NaCl leads to an increase in swelling ratio. These materials are preferred if the swelling ratio of the material, SR, is maintained in salt isotonic solution and if the gels do not collapse under load. The temperature of "service" should be shifted beyond body temperature, e.g. by diluting NIPAM in the polymer with monomer devoid of transition temperature phenomenon.

In some embodiments, the fluid-absorbing polymer may be selected from certain naturally-occurring polymers such as those containing carbohydrate moieties. In a preferred embodiment, such carbohydrate-containing hydrogels are non-digestible, have a low fraction of soluble material and a high fraction of gel-forming materials. In some embodiments, the fluid-absorbing polymer is selected from xanthan, guar, wellan, hemicelluloses, alkyl-cellulose, hydro-alkyl-cellulose, carboxy-alkyl-cellulose, carrageenan, dextran, hyaluronic acid and agarose. In a preferred embodiment, the gel forming polymer is psyllium. Psyllium (or "ispaghula") is the common name used for several members of the plant genus *Plantago* whose seeds are used commercially for the production of mucilage. The fluid-absorbing polymer is also in the gel-forming fraction of psyllium, i.e., a neutral saccharide copolymer of arabinose (25%) and xylose (75%) as characterized in (J. Marlett, *Proceedings of the Nutrition Society*, 62, pp. 2-7-209 (2003); and, M. Fischer, *Carbohydrate Research*, 339, 2009-2012 (2004)), and further described in U.S. Pat. Nos. 6,287,609; 7,026,303; 5,126, 150; 5,445,831; 7,014,862; 4,766,004; 4,999,200, each of which is incorporated herein for all relevant and consistent purposes, and over-the-counter psillium-containing agents such as those marketed under the name Metamucil (The Procter and Gamble company). A psyllium-containing dosage form is also suitable for chewing, where the chewing action disintegrates the tablet into smaller, discrete particles prior to swallowing but which undergoes minimal gelling in the mouth, and has acceptable mouthfeel and good aesthetics as perceived by the patient.

The psyllium-containing dosage form includes physically discrete unit suitable as a unitary dosage for human subjects and other mammals, each containing a predetermined quantity of active material (e.g. the gel-forming polysaccharide) calculated to produce the desired therapeutic effect. Solid oral dosage forms that are suitable for the present compositions include tablets, pills, capsules, lozenges, chewable tablets, troches, cachets, pellets, wafer and the like.

In some embodiments, the FAP is a polysaccharide particle wherein the polysaccharide component includes xylose and arabinose. The ratio of the xylose to the arabinose may be at least about 3:1 by weight, as described in U.S. Pat. Nos. 6,287,609; 7,026,303 and 7,014,862, each of which is incorporated herein for all relevant and consistent purposes.

The fluid-absorbing polymers described herein may be used in combination with the NHE-inhibiting compound or a pharmaceutical composition containing it. The NHE-inhibiting compound and the FAP may also be administered with other agents including those described under the heading "Combination Therapies" without departing from the scope of the present disclosure. As described above, the NHE-inhibiting compound may be administered alone without use of a fluid-absorbing polymer to resolve symptoms without eliciting significant diarrhea or fecal fluid secretion that would require the co-administration of a fluid-absorbing polymer.

The fluid-absorbing polymers described herein may be selected so as to not induce any substantial interaction with the NHE-inhibiting compound or a pharmaceutical composition containing it. As used herein, "no substantial interaction" generally means that the co-administration of the FAP polymer would not substantially alter (i.e., neither substantially decrease nor substantially increase) the pharmacological property of the NHE-inhibiting compounds administered alone. For example, FAPs containing negatively charged functionality, such as carboxylates, sulfonates, and the like, may potentially interact ionically with positively charged NHE-inhibiting compounds, preventing the inhibitor from reaching its pharmacological target. In addition, it may be possible that the shape and arrangement of functionality in a FAP could act as a molecular recognition element, and sequestor NHE-inhibiting compounds via "host-guest" interactions via the recognition of specific hydrogen bonds and/or hydrophobic regions of a given inhibitor. Accordingly, in various embodiments of the present disclosure, the FAP polymer may be selected, for co-administration or use with a compound of the present disclosure, to ensure that (i) it does not ionically interact with or bind with the compound of the present disclosure (by means of, for example, a moiety present therein possessing a charge opposite that of a moiety in the compound itself), and/or (ii) it does not possess a charge and/or structural conformation (or shape or arrangement) that enables it to establish a "host-guest" interaction with the compound of the present disclosure (by means of, for example, a moiety present therein that may act as a molecular recognition element and sequester the NHE inhibitor or inhibiting moiety of the compound).

D. Dosage

It is to be noted that, as used herein, an "effective amount" (or "pharmaceutically effective amount") of a compound disclosed herein, is a quantity that results in a beneficial clinical outcome of the condition being treated with the compound compared with the absence of treatment. The amount of the compound or compounds administered will depend on the degree, severity, and type of the disease or condition, the amount of therapy desired, and the release characteristics of the pharmaceutical formulation. It will also depend on the subject's health, size, weight, age, sex and tolerance to drugs. Typically, the compound is administered for a sufficient period of time to achieve the desired therapeutic effect.

In embodiments wherein both an NHE-inhibitor compound and a fluid-absorbing polymer are used in the treatment protocol, the NHE-inhibiting compound and FAP may be administered together or in a "dual-regimen" wherein the two therapeutics are dosed and administered separately. When the NHE-inhibiting compound and the fluid-absorbing polymer are dosed separately, the typical dosage administered to the subject in need of the NHE-inhibiting compound is typically from about 5 mg per day and about 5000 mg per day and, in other embodiments, from about 50 mg per day and about 1000 mg per day. Such dosages may induce fecal excretion of sodium (and its accompanying anions), from about 10 mmol up to about 250 mmol per day, from about 20 mmol to about 70 mmol per day or even from about 30 mmol to about 60 mmol per day.

The typical dose of the fluid-absorbing polymer is a function of the extent of fecal secretion induced by the non-absorbable NHE-inhibiting compound. Typically, the dose is adjusted according to the frequency of bowel movements and consistency of the stools. More specifically the dose is adjusted so as to avoid liquid stools and maintain stool consistency as "soft" or semi-formed, or formed. To achieve the desired stool consistency and provide abdominal relief to patients, typical dosage ranges of the fluid-absorbing polymer to be administered in combination with the NHE-inhibiting compound, are from about 2 g to about 50 g per day, from about 5 g to about 25 g per day or even from about 10 g to about 20 g per day. When the NHE-inhibiting compound and the FAP are administered as a single dosage regimen, the daily uptake may be from about 2 g to about 50 g per day, from about 5 g to about 25 g per day, or from about 10 g to about 20 g per day, with a weight ratio of NHE-inhibiting compound to fluid-absorbing polymer being from about 1:1000 to 1:10 or even from about 1:500 to 1:5 or about 1:100 to 1:5.

A typical dosage of the substantially impermeable or substantially systemically non-bioavailable, NHE-inhibiting compound when used alone without a FAP may be between about 0.2 mg per day and about 2 g per day, or between about 1 mg and about 1 g per day, or between about 5 mg and about 500 mg, or between about 10 mg and about 250 mg per day, which is administered to a subject in need of treatment.

The frequency of administration of therapeutics described herein may vary from once-a-day (QD) to twice-a-day (BID) or thrice-a-day (TID), etc., the precise frequency of administration varying with, for example, the patient's condition, the dosage, etc. For example, in the case of a dual-regimen, the NHE-inhibiting compound could be taken once-a-day while the fluid-absorbing polymer could be taken at each meal (TID). Furthermore, as disclosed in U.S. Application No. 61/584,753 filed Jan. 9, 2012, the NHE-inhibiting compound is administered twice-a-day (BID), or thrice-a-day (TID), and in a more specific embodiment, the NHE-inhibiting compound is administered in an amount ranging from 2-200 mg per dose BID, or 2-100 mg per dose TID. In more specific embodiments, the NHE-inhibiting compound is administered in an amount of about 15 mg per dose, about 30 mg per dose, or about 45 mg per dose, and in a more specific embodiment, in an amount of 15 mg per dose, 30 mg per dose, or 45 mg per dose.

E. Modes of Administration

The substantially impermeable or substantially systemically non-bioavailable NHE-inhibiting compounds of the present disclosure with or without the fluid-absorbing polymers described herein may be administered by any suitable route. The compound is administrated orally (e.g., dietary) in capsules, suspensions, tablets, pills, dragees, liquids, gels, syrups, slurries, and the like. Methods for encapsulating compositions (such as in a coating of hard gelatin or cyclodextran) are known in the art (Baker, et al., "Controlled Release of Biological Active Agents". John Wiley and Sons, 1986). The compounds can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers are biocompatible, i.e., non-toxic, non-inflammatory, non-immunogenic and devoid of other undesired reactions at the administration site. Examples of pharmaceutically acceptable carriers include, for example, saline, commercially available inert gels, or liquids supplemented with albumin, methyl cellulose or a collagen matrix. Standard pharmaceutical formulation techniques can be employed, such as those described in Remington's Pharmaceutical Sciences, Mack Publishing Company, Easton, Pa.

In other embodiments, the NHE-3 inhibiting compounds may be systemically administered. In one embodiment, the compounds of the present invention are administered systemically to inhibit NHE-3 in the kidney. Without being held to any particular theory, the impermeable NHE-inhibiting compounds (e.g., NHE-3, -2 and/or -8 inhibitors) of the present disclosure can also be administered parenterally, by intravenous, subcutaneous or intramuscular injection or infusion to inhibit NHE3 in the kidney. NHE3 is expressed at high levels on the apical surface of the proximal tubule of the kidney and couples luminal Na reabsorption to the secretion of intracellular protons. Since NHE3 accounts for approximately 60-80% of sodium reabsorption in the kidney, it is anticipated that NHE inhibition could permit the removal of substantial quantities of systemic fluid and sodium to prevent edema and resolve congestive heart failure symptoms. This effect could be achieved by NHE inhibition in combination with other diuretics, specifically loop diuretics, like furosemide, to inhibit tubuloglomerular feedback. In addition, since sodium reabsorption via NHE3 in the proximal tubule is responsible for a large proportion of the energy requirement of the proximal tubule cell, it is anticipated that NHE inhibition in the kidney could be beneficial by reducing the energy requirement and protecting the proximal tubule cell in settings of decreased energy availability to the proximal tubule, such as those that occur as a result of kidney hypoxia such as in kidney ischemia reperfusion injury resulting in acute kidney injury.

Pharmaceutical preparations for oral use can be obtained by combining a compound of the present disclosure with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol: cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as crosslinked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of a suitable material, such as gelatin, as well as soft, sealed capsules made of a suitable material, for example, gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

It will be understood that, certain compounds of the disclosure may be obtained as different stereoisomers (e.g., diastereomers and enantiomers) or as isotopes and that the disclosure includes all isomeric forms, racemic mixtures and isotopes of the disclosed compounds and a method of treating a subject with both pure isomers and mixtures thereof, including racemic mixtures, as well as isotopes. Stereoisomers can be separated and isolated using any suitable method, such as chromatography.

F. Delayed Release

NHE proteins show considerable diversity in their patterns of tissue expression, membrane localization and functional roles. (See, e.g., *The sodium-hydrogen exchanger— From molecule To Its Role In Disease*, Karmazyn, M., Avkiran, M., and Fliegel, L., eds., Kluwer Academics (2003).)

In mammals, nine distinct NHE genes (NHE-1 through -9) have been described. Of these nine, five (NHE-1 through -5) are principally active at the plasma membrane, whereas NHE-6, -7 and -9 reside predominantly within intracellular compartments.

NHE-1 is ubiquitously expressed and is chiefly responsible for restoration of steady state intracellular pH following cytosolic acidification and for maintenance of cell volume. Recent findings show that NHE-1 is crucial for organ function and survival (e.g., NHE-1-null mice exhibit locomotor abnormalities, epileptic-like seizures and considerable mortality before weaning).

In contrast with NHE-1 expressed at the basolateral side of the nephrons and gut epithelial cells, NHE-2 through -4 are predominantly expressed on the apical side of epithelia of the kidney and the gastrointestinal tract. Several lines of evidence show that NHE-3 is the major contributor of renal bulk Na+ and fluid re-absorption by the proximal tubule. The associated secretion of H+ by NHE-3 into the lumen of renal tubules is also essential for about ⅔ of renal $HCO_3^-$ re-absorption. Complete disruption of NHE-3 function in mice causes a sharp reduction in $HCO_3^-$, Na+ and fluid re-absorption in the kidney, which is consistently associated with hypovolemia and acidosis.

In one embodiment, the compounds of the disclosure are intended to target the apical NHE antiporters (e.g. NHE-3, NHE-2 and NHE-8) without substantial permeability across the layer of gut epithelial cells, and/or without substantial activity towards NHEs that do not reside predominantly in the GI tract. This invention provides a method to selectively inhibit GI apical NHE antiporters and provide the desired effect of salt and fluid absorption inhibition to correct abnormal fluid homeostasis leading to constipations states. Because of their absence of systemic exposure, said compounds do not interfere with other key physiological roles of NHEs highlighted above. For instance, the compounds of the disclosure are expected to treat constipation in patients in need thereof, without eliciting undesired systemic effects, such as for example salt wasting or bicarbonate loss leading to hyponatriemia and acidosis among other disorders.

In another embodiment, the compounds of the disclosure are delivered to the small bowel with little or no interaction with the upper GI such as the gastric compartment and the duodenum. The applicant found that an early release of the compounds in the stomach or the duodenum can have an untoward effect on gastric secretion or bicarbonate secretion (also referred to as "bicarbonate dump"). In this embodiment the compounds are designed so as to be released in an active form past the duodenum. This can be accomplished by either a prodrug approach or by specific drug delivery systems.

As used herein, "prodrug" is to be understood to refer to a modified form of the compounds detailed herein that is inactive (or significantly less active) in the upper GI, but once administered is metabolised in vivo into an active metabolite after getting past, for example, the duodenum. Thus, in a prodrug approach, the activity of the NHE-inhibiting compound can be masked with a transient protecting group that is liberated after compound passage through the desired gastric compartment. For example, acylation or alkylation of the essential guanidinyl functionality of the NHE-inhibiting compound would render it biochemically inactive; however, cleavage of these functional groups by intestinal amidases, esterases, phosphatases, and the like, as well enzymes present in the colonic flora, would liberate the active parent compound. Prodrugs can be designed to exploit the relative expression and localization of such phase I metabolic enzymes by carefully optimizing the structure of the prodrug for recognition by specific enzymes. As an example, the anti-inflammatory agent sulfasalazine is converted to 5-aminosalicylate in the colon by reduction of the diazo bond by intestinal bacteria.

In a drug delivery approach the NHE-inhibiting compounds of the disclosure are formulated in certain pharmaceutical compositions for oral administration that release the active in the targeted areas of the GI, i.e., jejunum, ileum or colon, the distal ileum and colon, or the colon.

Methods known from the skilled-in-the-art are applicable. (See, e.g., Kumar, P. and Mishra, B., Colon Targeted Drug Delivery Systems—An Overview, *Curr. Drug Deliv.*, 2008, 5 (3), 186-198: Jain, S. K. and Jain, A., Target-specific Drug Release to the Colon., *Expert Opin. Drug Deliv.*, 2008, 5 (5), 483-498: Yang, L., Biorelevant Dissolution Testing of Colon-Specific Delivery Systems Activated by Colonic Microflora, *J. Control Release,* 2008, 125 (2), 77-86; Siepmann, F.; Siepmann, J.; Walther, M.; MacRae, R. J.; and Bodmeier, R., Polymer Blends for Controlled Release Coatings, *J. Control Release* 2008, 125 (1), 1-15: Patel, M.; Shah, T.; and Amin, A., Therapeutic Opportunities in Colon-Specific Drug-Delivery Systems, *Crit. Rev. Ther. Drug Carrier Syst.,* 2007, 24 (2), 147-202; Jain, A.; Gupta, Y.; Jain, S. K., Perspectives of Biodegradable Natural Polysaccharides for Site-specific Drug Delivery to the Colon., *J. Pharm. Sci.,* 2007, 10 (1), 86-128; Van den, M. G., Colon Drug Delivery, *Expert Opin. Drug Deliv.,* 2006, 3 (1), 111-125; Basit, A. W., Advances in Colonic Drug Delivery, *Drugs* 2005, 65 (14), 1991-2007; Chourasia, M. K.; Jain, S. K., Polysaccharides for Colon-Targeted Drug Delivery, *Drug Deliv.* 2004, 11 (2), 129-148; Shareef, M. A.; Khar. R. K.; Ahuja. A.; Ahmad, F. J.; and Raghava, S., Colonic Drug Delivery: An Updated Review, *AAPS Pharm. Sci.* 2003, 5 (2), E17: Chourasia, M. K.; Jain, S. K., Pharmaceutical Approaches to Colon Targeted Drug Delivery Systems, *J. Pharm. Sci.* 2003, 6 (1), 33-66; and, Sinha, V. R.: Kumria, R., Colonic Drug Delivery: Prodrug Approach, *Pharm. Res.* 2001, 18 (5), 557-564. Typically, the active pharmaceutical ingredient (API) is contained in a tablet/capsule designed to release said API as a function of the environment (e.g., pH, enzymatic activity, temperature, etc.), or as a function of time. One example of this approach is Eudracol™ (Pharma Polymers Business Line of Degussa's Specialty Acrylics Business Unit), where the API-containing core tablet is layered with various polymeric coatings with specific dissolution profiles. The first layer ensures that the tablet passes through the stomach intact so it can continue through the small intestine. The change from an acidic environment in the stomach to an alkaline environment in the small intestine initiates the release of the protective outer layer. As it travels through the colon, the next layer is made permeable by the alkalinity and intestinal fluid. This allows fluid to penetrate to the interior layer and release the active ingredient, which diffuses from the core to the outside, where it can be absorbed by the intestinal wall. Other methods are contemplated without departing from the scope of the present disclosure.

In another example, the pharmaceutical compositions of the invention can be used with drug carriers including pectin and galactomannan, polysaccharides that are both degradable by colonic bacterial enzymes. (See, e.g., U.S. Pat. No. 6,413,494, the entire contents of which are incorporated herein by reference for all relevant and consistent purposes.) While pectin or galactomannan, if used alone as a drug carrier, are easily dissolved in simulated gastric fluid and simulated intestinal fluid, a mixture of these two polysaccharides prepared at a pH of about 7 or above produces a strong, elastic, and insoluble gel that is not dissolved or disintegrated in the simulated gastric and intestinal fluids, thus protecting drugs coated with the mixture from being released in the upper GI tract. When the mixture of pectin and galactomannan arrives in the colon, it is rapidly degraded by the synergic action of colonic bacterial enzymes. In yet another aspect, the compositions of the invention may be used with the pharmaceutical matrix of a complex of gelatin and an anionic polysaccharide (e.g., pectinate, pectate, alginate, chondroitin sulfate, polygalacturonic acid, tragacanth gum, arabic gum, and a mixture thereof), which is degradable by colonic enzymes (U.S. Pat. No. 6,319,518).

In yet other embodiments, fluid-absorbing polymers that are administered in accordance with treatment methods of the present disclosure are formulated to provide acceptable/pleasant organoleptic properties such as mouthfeel, taste, and/or to avoid premature swelling/gelation in the mouth and in the esophagus and provoke choking or obstruction. The formulation may be designed in such a way so as to ensure the full hydration and swelling of the FAP in the GI tract and avoid the formation of lumps. The oral dosages for the FAP may take various forms including, for example, powder, granulates, tablets, wafer, cookie and the like, or are delivered to the small bowel with little or no interaction with the upper GI such as the gastric compartment and the duodenum.

The above-described approaches or methods are only some of the many methods reported to selectively deliver an active in the lower part of the intestine, and therefore should not be viewed to restrain or limit the scope of the disclosure.

IV. Preparation of Compounds

The following Reaction Schemes I-IV illustrate methods for making compounds of this invention, i.e., compounds of Formula (I). It is understood that one skilled in the art may be able to make these compounds by similar methods or by combining other methods known to one skilled in the art. It is also understood that one skilled in the art would be able to make, in a similar manner as described below, other compounds of Formula (I) not specifically illustrated below by using the appropriate starting components and modifying the parameters of the synthesis as needed. The compounds described herein may be made from commercially available starting materials or synthesized using known organic, inorganic, and/or enzymatic processes. In general, starting components may be obtained from sources such as Sigma Aldrich, Lancaster Synthesis. Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

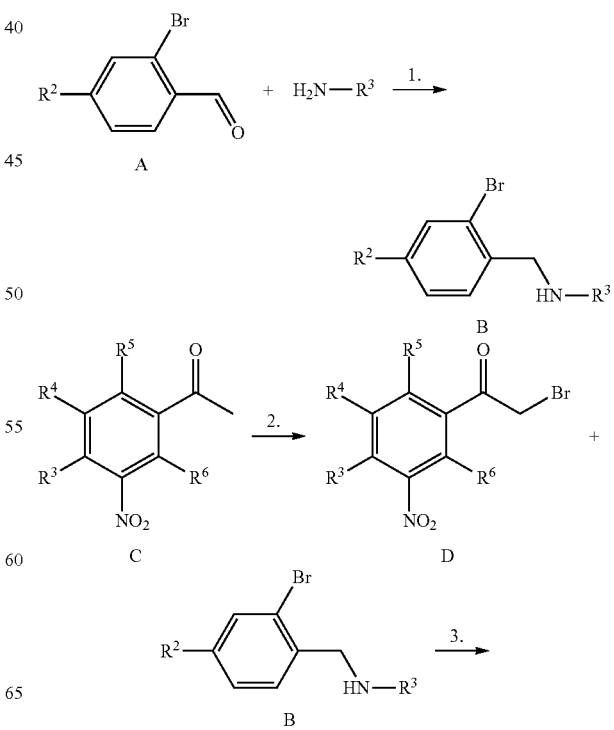

General Reaction Scheme I

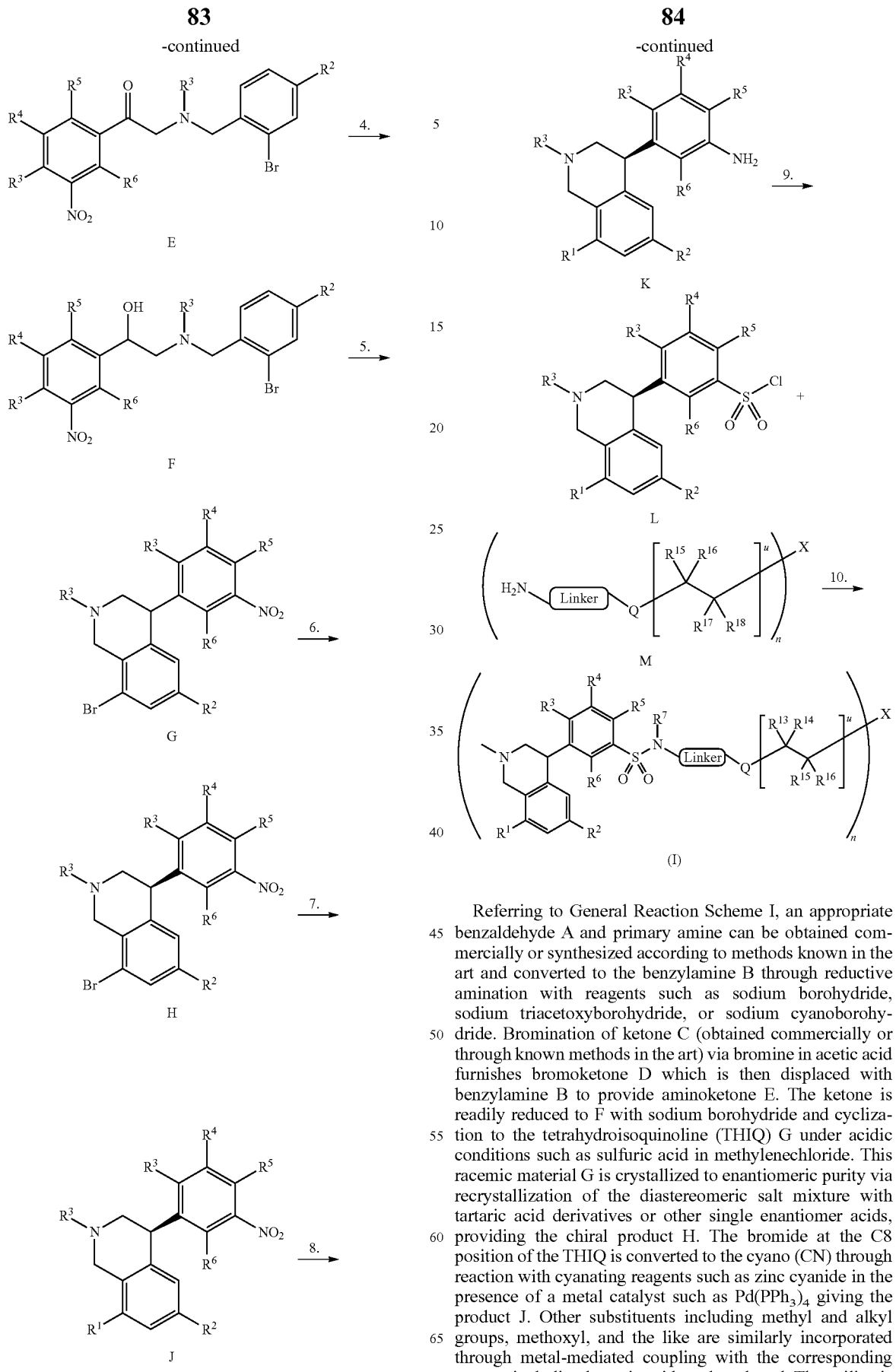

Referring to General Reaction Scheme I, an appropriate benzaldehyde A and primary amine can be obtained commercially or synthesized according to methods known in the art and converted to the benzylamine B through reductive amination with reagents such as sodium borohydride, sodium triacetoxyborohydride, or sodium cyanoborohydride. Bromination of ketone C (obtained commercially or through known methods in the art) via bromine in acetic acid furnishes bromoketone D which is then displaced with benzylamine B to provide aminoketone E. The ketone is readily reduced to F with sodium borohydride and cyclization to the tetrahydroisoquinoline (THIQ) G under acidic conditions such as sulfuric acid in methylenechloride. This racemic material G is crystallized to enantiomeric purity via recrystallization of the diastereomeric salt mixture with tartaric acid derivatives or other single enantiomer acids, providing the chiral product H. The bromide at the C8 position of the THIQ is converted to the cyano (CN) through reaction with cyanating reagents such as zinc cyanide in the presence of a metal catalyst such as $Pd(PPh_3)_4$ giving the product J. Other substituents including methyl and alkyl groups, methoxyl, and the like are similarly incorporated through metal-mediated coupling with the corresponding reagent including boronic acids and methanol. The aniline is converted to the sulfonyl chloride L via diazotization in the presence of sulfur dioxide, a copper catalyst, and hydrogen chloride. A diamine "linker" such as M is then reacted with the two equivalents of the sulfonyl chloride L in the presence of a base such as triethylamine, pyridine, sodium or potassium carbonate, or the like giving compounds of structure (I).

General Reaction Scheme II

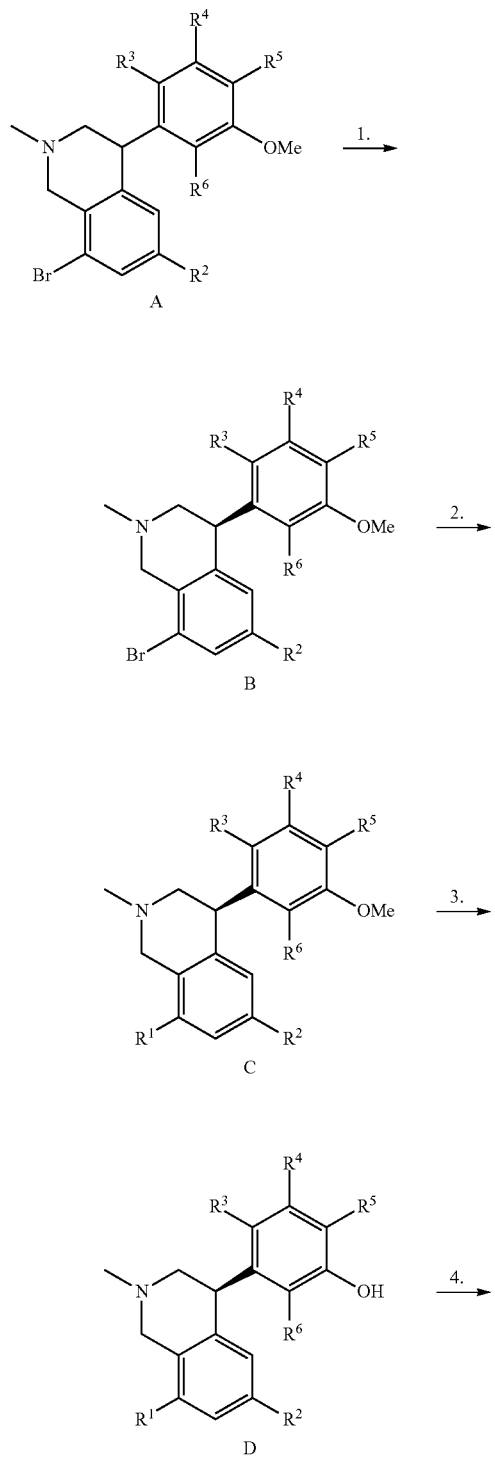

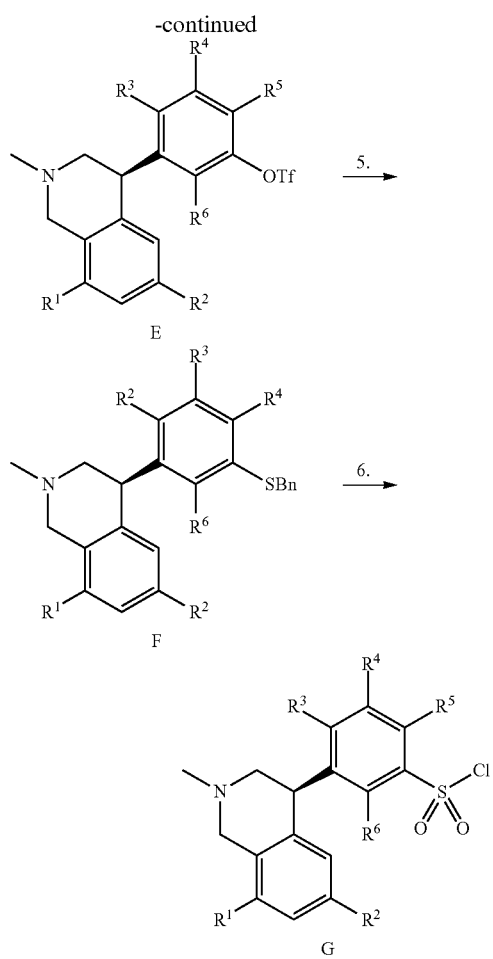

Alternatively, this sequence can be performed using the methoxy variant in place of the nitro substituent. Compound A with the methoxy substituent is prepared through analogous procedures as described in General Reaction Scheme I. Subsequently, this material may be crystallized to enantiomeric purity via recrystallization of the diastereomeric salt mixture with tartaric acid derivatives or other single enantiomer acids, providing the chiral product B. The bromide at the C8 position of the THIQ is converted to the cyano (CN) through reaction with cyanating reagents such as zinc cyanide in the presence of a metal catalyst such as $Pd(PPh_3)_4$ giving the product C. Other substituents including methyl and alkyl groups, methoxyl, and the like are similarly incorporated through metal-mediated coupling with the corresponding reagent including boronic acids and methanol. The methoxy is converted to the phenol D via Lewis acid reagents such as $BBr_3$, $AlCl_3$, etc or with acids including HBr and HCl or similar. Conversion to the reactive triflate E is facilitated by reaction with reagents that include trifluoromethane sulfonic anhydride or N,N-bis(trifluoromethylsulfonyl)aniline in the presence of a base including tertiary or heterocyclic amines such as triethylamine, pyridine, 2,6-lutidine, or the like, potassium carbonate, or sodium hydride. Reaction with benzylmercaptan in the presence of a tertiary amine base such as diisopropylethylamine or triethylamine and a catalyst including $Pd_2(dba)_3$ with a ligand such as Xantphos at elevated temperature yields the thioether F. Sulfonyl chloride G is synthesized by oxidative chlorination of thioether INT-S8 with either N-chlorosuccinimide (NCS)

in acetic acid/water or chlorine gas. These reagents can then be elaborated to compounds of structure (I) via methods described in General Reaction Scheme I.

With regard to General Reaction Schemes I and II, typical carboxylate activation reagents include DCC, EDCI, HATU, oxalyl chloride, thionyl chloride and the like. Typical bases include TEA, DIEA, pyridine, K$_2$CO$_3$, NaH and the like. Typical acylation catalysts include HOBt, HOAt, 4-dimethylaminopyridine and the like. Typical catalysts for hydrogenation include palladium on carbon, rhodium on carbon, platinum on carbon, raney nickel and the like.

One skilled in the art will recognize that variations to the order of the steps and reagents discussed in reference to the Reaction Schemes are possible. Methodologies for preparation of compounds of Formula (I) are described in more detail in the following non-limiting exemplary schemes.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, trifluoroacetyl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following non-limiting examples are provided to further illustrate the present disclosure.

EXAMPLES

General Scheme for the Synthesis of Haloacetophenones:

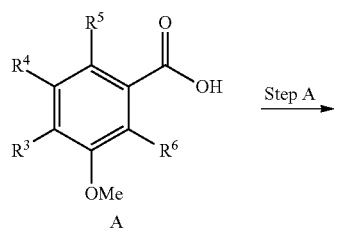

Step A:
Carboxylic acids A are converted to the Weinreb amides B through the addition of N,O-dimethylhydroxylamine to the activated form of A, mediated by acid chloride formation with oxalyl chloride or thionyl chloride or through coupling reagents such as EDC, CDI, DCC, HATU, and the like.

Step B:
Addition of nucleophiles such as organomagnesium reagents to the amides B yields the acetophenones C.

Step C:
Bromination (or chlorination) of acetophenones B with reagents such as bromine. N-bromosuccinimide (NBS), or N-chlorosuccimide (NCS) provides the desired haloacetophenone INT-KB.

This route may be used for both the methoxy and nitro analogs. Derivatives prepared through this route include:

-continued
INT-KB4
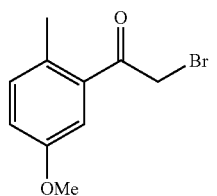
INT-KB5
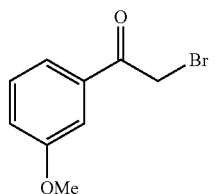
INT-KB6
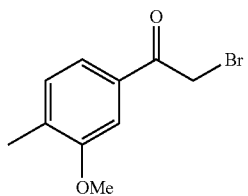
INT-KB7
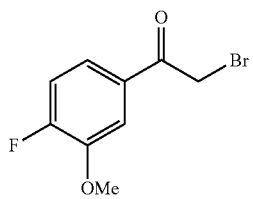
INT-KB8
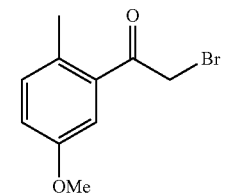
-continued
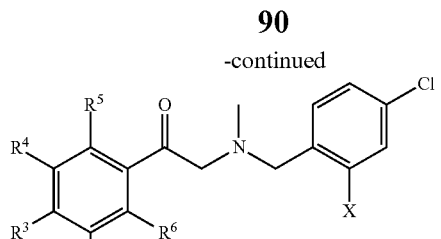 Step C
INT-S2
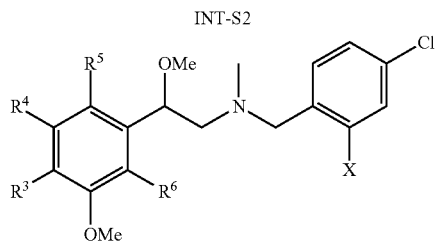 Step D
INT-S3
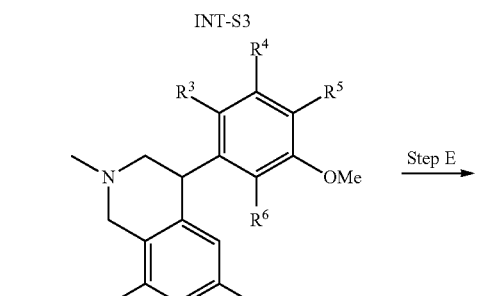 Step E
INT-S4
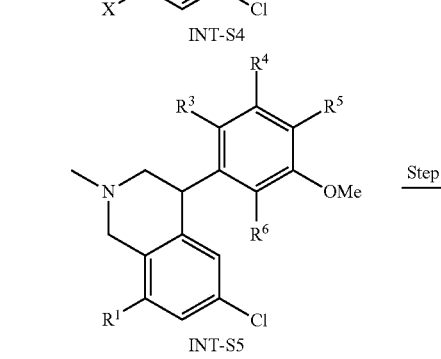 Step F
INT-S5
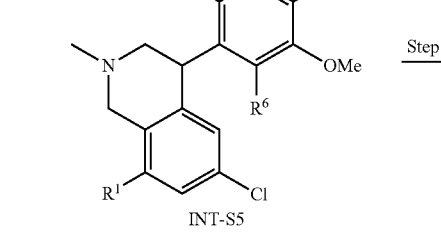 Step G
INT-S6
General Scheme for the Synthesis of Substituted Sulfonyl Chlorides:
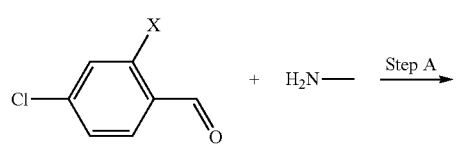 Step A
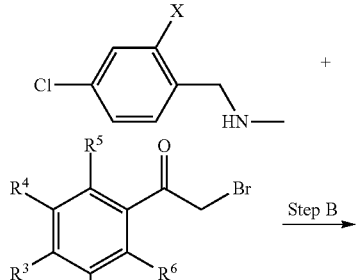 +
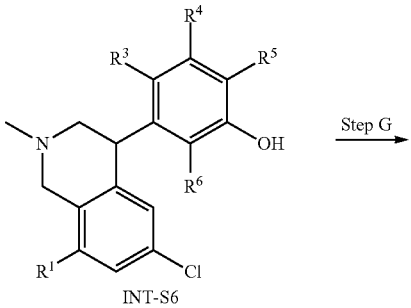 Step H
INT-S7
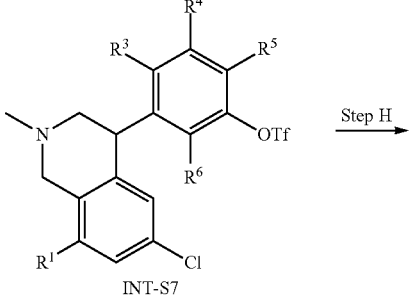 Step B
INT-KB
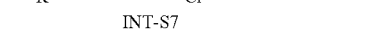

-continued

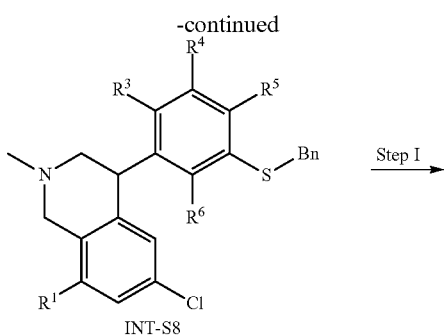

INT-S8

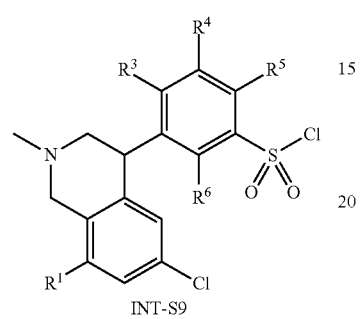

INT-S9

Step A:

An appropriate benzaldehyde where X=I, Br, or Cl and primary amine can be obtained commercially or synthesized according to methods known in the art and converted to the benzylamine INT-S1 through reductive amination with reagents such as sodium borohydride, sodium triacetoxyborohydride, or sodium cyanoborohydride.

Step B:

The ketobenzylamine INT-S2 is obtained through alkylation of benzylamine INT-S1 with ketobromide INT-KB in the presence of a base such as any trialkylamine (e.g. triethylamine, diisopropylethylamine), potassium or sodium carbonate, sodium hydride, or the like.

Step C:

The ketone of INT-S2 is readily reduced in the presence of a reducing agent such as sodium borohydride, sodium triacetoxyborohydride, or sodium cyanoborohydride to provide the benzylalcohol INT-S3.

Step D:

Intramolecular Friedel-Crafts alkylation of INT-S3 is facilitated in the presence of acid such as sulfuric acid or a Lewis Acid such as aluminum chloride, providing tetrahydroisoquinoline INT-S4.

Step E:

The bromide at the C8 position of the THIQ INT-S4 is converted to the cyano (CN) through reaction with cyanating reagents such as zinc cyanide in the presence of a metal catalyst such as $Pd(PPh_3)_4$ giving the product INT-S5. Other substituents including methyl and alkyl groups, methoxyl, and the like are similarly incorporated through metal-mediated coupling with the corresponding reagent including boronic acids and methanol.

Step F:

The methoxy moiety of INT-S5 is converted to the free phenol through treatment with boron tribromide, sodium iodide/aluminum chloride, or other similar conditions, providing the phenol INT-S6.

Step G:

Triflate INT-S7 is generated beginning with phenol INT-S6 through treatment with reagents such as triflic anhydride or N,N-bis(trifluoromethylsulfonyl)aniline in the presence of a base including tertiary or heterocyclic amines such as triethylamine, pyridine, 2,6-lutidine, or the like, potassium carbonate, or sodium hydride.

Step H:

Triflate INT-S7 is converted to the thioether INT-S8 through treatment with benzylmercaptan and a tertiary amine base such as diisopropylethylamine or triethylamine in the presence of a palladium source such as $Pd_2(dba)_3$ with a ligand such as Xantphos at elevated temperature.

Step I:

Sulfonyl chloride INT-S9 is synthesized by oxidative chlorination of thioether INT-S8 with either N-chlorosuccinimide (NCS) in acetic acid/water or chlorine gas.

Sulfonyl chlorides provided through this route include:

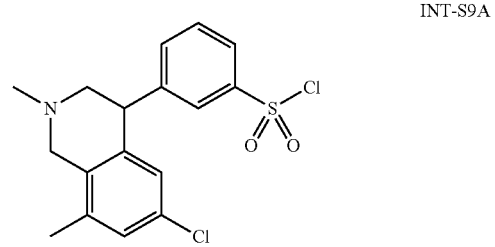

INT-S9A

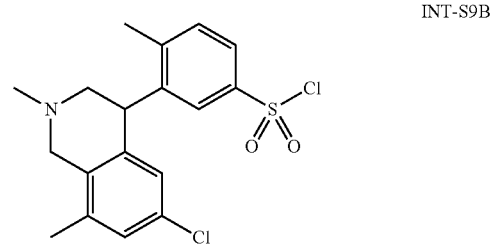

INT-S9B

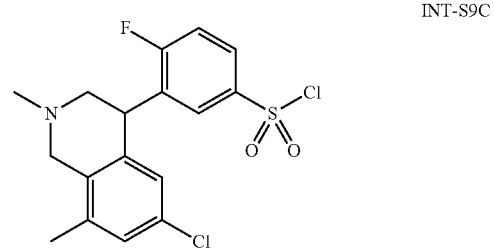

INT-S9C

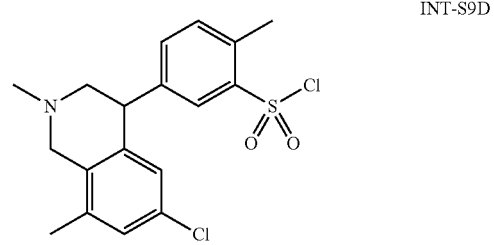

INT-S9D

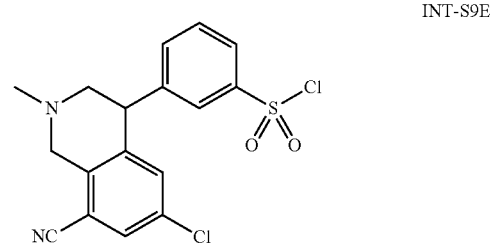

INT-S9E

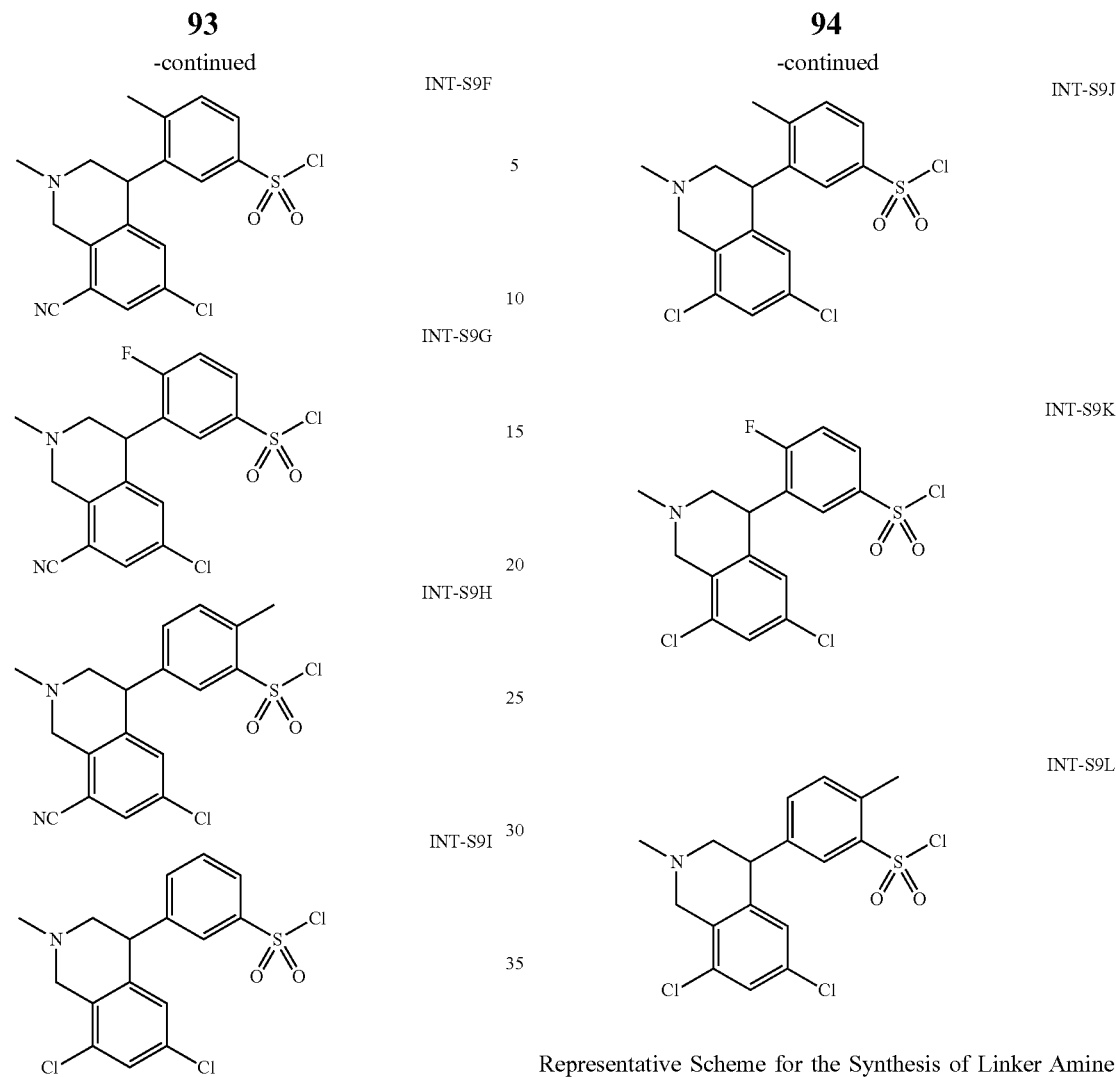
Representative Scheme for the Synthesis of Linker Amine Dimers:
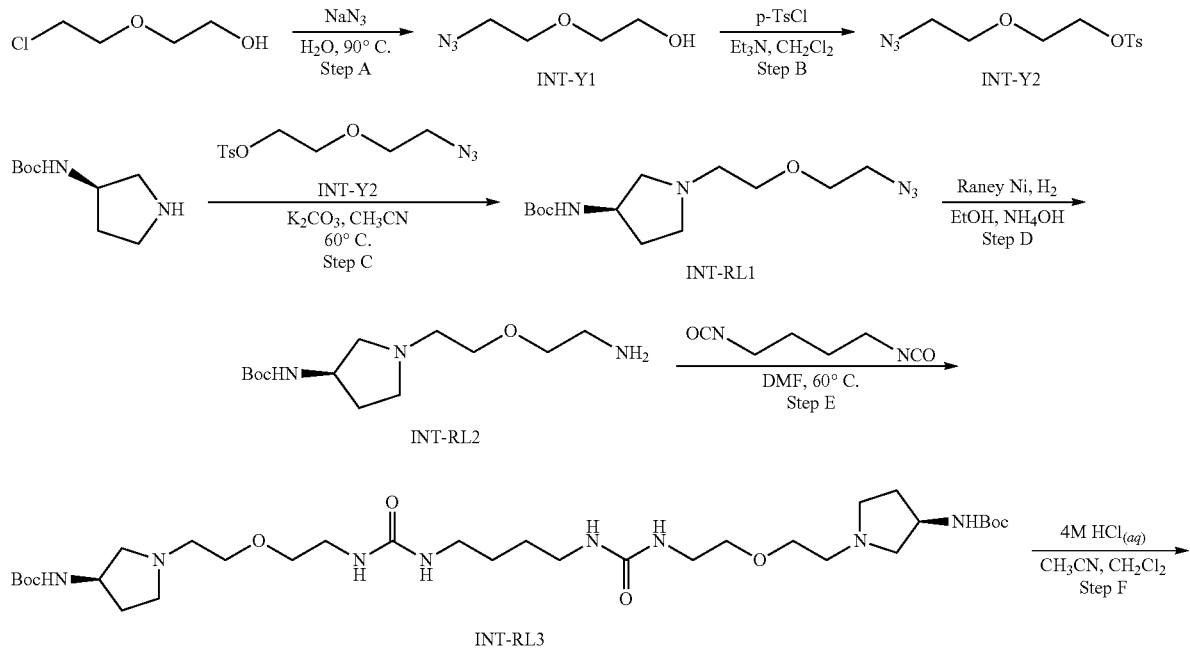

-continued

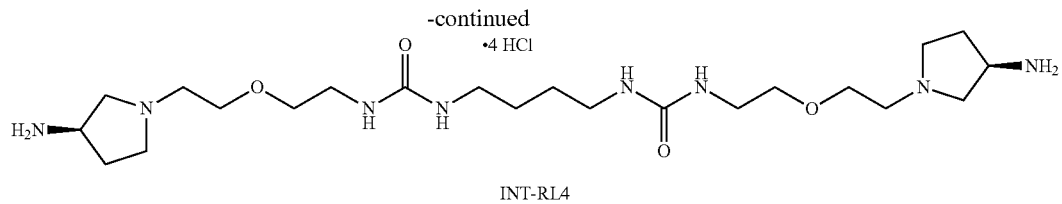

INT-RL4

Step A:

To a 250-mL round-bottom flask was placed 2-(2-chloroethoxy)ethan-1-ol (7.8 g, 62.62 mmol, 1 equiv) and water (300 mL). This was followed by the addition of a solution of sodium azide (7.7 g, 118.4 mmol, 2 equiv) in water (40 mL) dropwise with stirring. The resulting solution was stirred overnight at 80° C. The reaction mixture was cooled to 0° C. with a water/ice bath and extracted with 3×500 mL of $CH_2Cl_2$. The organic layers were combined, dried over anhydrous sodium sulfate, filtered, and concentrated under vacuum providing 10 g (crude) of 2-(2-azidoethoxy)ethan-1-ol (INT-Y1) as a colorless oil.

Step B:

To a 500-mL round-bottom flask was added azidoalcohol INT-Y1 (10 g crude from Step A, theoretical 62.6 mmol, 1 equiv), dichloromethane (300 mL), 4-methylbenzene-1-sulfonyl chloride (18 g. 94.42 mmol, 1.3 equiv), and triethylamine (10 mL, 1.15 equiv). The resulting solution was stirred for 2 h at room temperature. The reaction was then quenched by the addition of 50 mL of water and extracted with 3×300 mL of dichloromethane. The organic layers were combined, dried over anhydrous sodium sulfate, filtered, and concentrated under vacuum. The residue was applied onto a silica gel column with petroleum ether/ethyl acetate (1:3) providing 15 g (69%) of 1-[[2-(2-azidoethoxy)ethoxy]sulfonyl]-4-methylbenzene (INT-Y2) as a colorless oil.

Step C:

To a 500-mL round-bottom flask was added tert-butyl N-[(3R)-pyrrolidin-3-yl]carbamate (10 g, 53.7 mmol, 1 equiv), 1-[[2-(2-azidoethoxy)ethoxy]sulfonyl]-4-methylbenzene (16.85 g, 59.1 mmol, 1.1 equiv), $CH_3CN$ (100 mL), and potassium carbonate (22.26 g, 161 mmol, 3 equiv). The resulting solution was stirred overnight at 60° C. The solids were filtered out and the resulting mixture was concentrated under vacuum providing 13 g (81%) of tert-butyl N-[(3R)-1-[2-(2-azidoethoxy)ethyl]pyrrolidin-3-yl]carbamate (INT-RL1) as a yellow oil.

Step D:

To a 250-mL round-bottom flask purged was added ethanol (100 mL), Raney Ni (10 g), azide INT-RL1 (6 g, 20 mmol, 1 equiv), and $NH_4OH$ (10 mL). To the above $H_{2(g)}$ was introduced in followed by a purging/filling cycle, leaving the slurry under an atmosphere of $H_{2(g)}$. The resulting slurry was stirred for 2 h at room temperature. The solids were filtered out and the resulting mixture concentrated under vacuum providing 4.8 g (88%) of tert-butyl N-[(3R)-1-[2-(2-aminoethoxy)ethyl]pyrrolidin-3-yl]carbamate (INT-RL2) as a yellow oil.

Step E:

To a 500-mL round-bottom flask purged and maintained with an inert atmosphere of nitrogen was added amine INT-RL2 (10 g, 36.6 mmol, 1 equiv), DMF (250 mL), and 1,4-diisocyanatobutane (2.6 mL, 0.45 equiv). The resulting solution was stirred for 2 h at 60° C. The resulting slurry was concentrated under vacuum. The residue was applied onto a silica gel column with $CH_3CN:H_2O$ (35:65) providing 9.0 g of tert-butyl N-[(3R)-1-[2-(2-[[(4-[[(2-[2-[(3R)-3-[[(tert-butoxy)carbonyl]amino]pyrrolidin-1-yl]ethoxy]ethyl)carbamoyl]amino]butyl)carbamoyl]amino]ethoxy)ethyl]pyrrolidin-3-yl]carbamate (INT-RL3) as a white solid.

Step F:

3-(2-[2-[(3R)-3-Aminopyrrolidin-1-yl]ethoxy]ethyl)-1-(4-[[(2-[2-[(3R)-3-aminopyrrolidin-1-yl]ethoxy]ethyl)carbamoyl] amino]butyl)urea hydrochloride. To a 250-mL round-bottom flask was added Boc-diamine INT-RL3 (3.0 g, 4.37 mmol, 1 equiv), $CH_2Cl_2$ (15 mL), $CH_3CN$ (15 mL), and hydrogen chloride (4 $M_{(aq)}$, 15 mL). The resulting solution was stirred for 2 h at room temperature. The resulting mixture was concentrated under vacuum. This resulted in 2.2099 g (91%) of the title compound as a brown oil. MS (m/z): 487 [M+H]$^+$. $^1$H NMR (Methanol-d4, 300 MHz) δ 4.29-4.12 (m, 3H), 4.01-3.73 (m, 7H), 3.75-3.48 (n, 10OH), 3.40 (t, J=4.9 Hz, 6H), 3.19 (d, J=5.8 Hz, 4H), 2.70 (tt, J=24.7, 11.1 Hz, 2H), 2.30 (qd, J=8.0, 3.7 Hz, 2H), 1.60-1.49 (m, 4H).

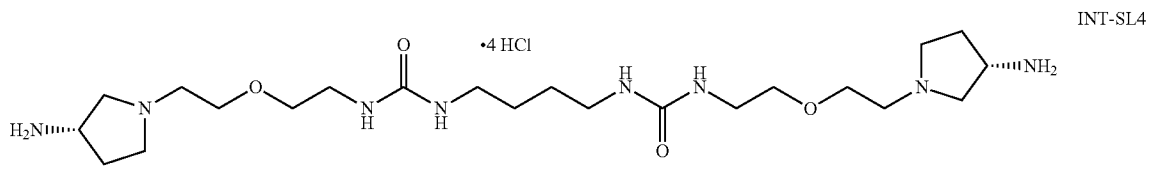 [SMILES: N[C@H]1CCN(CCOCCNC(=O)NCCCCNC(=O)NCCOCCN2CC[C@H](N)C2)C1]

INT-SL4

Through Steps A-F, 2.2449 g (92%) of 3-(2-[2-[(3S)-3-aminopyrrolidin-1-yl]ethoxy]ethyl)-1-(4-[[(2-[2-[(3S)-3-aminopyrrolidin-1-yl]ethoxy]ethyl)carbamoyl]amino]butyl) urea hydrochloride (INT-SL4) was prepared as a brown solid. MS (m/z): 487 [M+1]$^+$. $^1$H NMR (Methanol-d4, 300 MHz) δ 4.26 (s, 2H), 4.18 (s, 1H), 3.98 (d, J=12.5 Hz, 2H), 3.83 (t, J=4.5 Hz, 5H), 3.77-3.50 (m, 1 OH), 3.41 (t, J=5.2 Hz, 5H), 3.26-3.16 (m, 4H), 2.74 (s, 2H), 2.31 (ddd, J=13.8, 8.4, 5.0 Hz, 2H), 1.62-1.51 (m, 4H).

Similarly, Steps A-F beginning with 1-Boc-4-aminopiperidine provide linker INT-PL1.

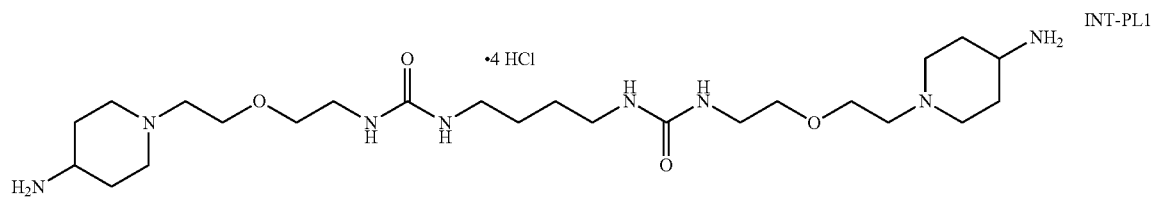 [SMILES: NC1CCN(CCOCCNC(=O)NCCCCNC(=O)NCCOCCN2CCC(N)CC2)CC1]

Representative Scheme for the Synthesis of Ethyleneglycol-Based Diamines:

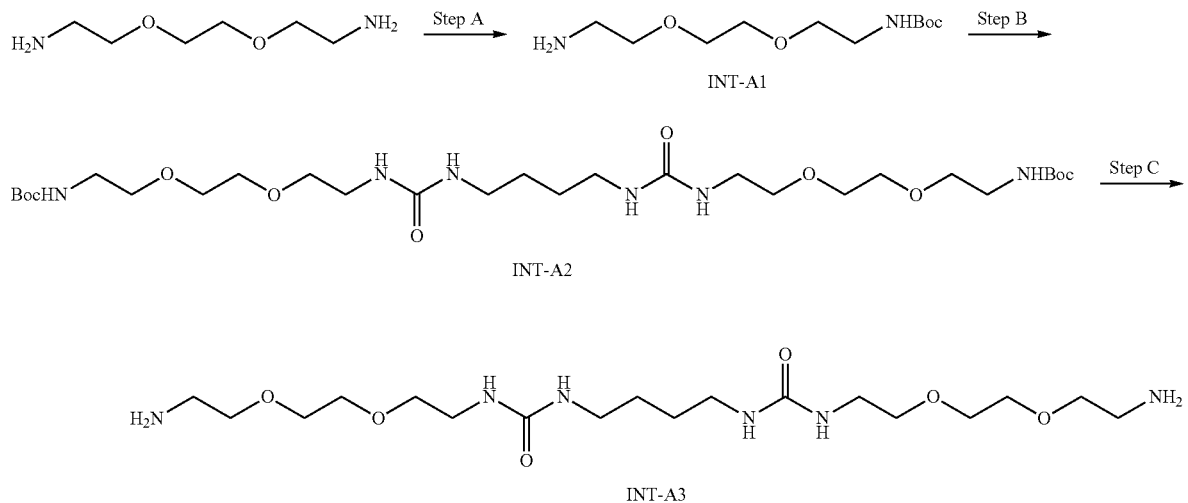

Step A:
The diamine 2,2'-(ethylenedioxy)bis(ethylamine) is mono-protected with a group such as tert-butyloxycarbamate (Boc) through reaction with the anhydride and a suitable amine such as triethylamine or pyridine, providing the desired INT-A1.

Step B:
Mono-protected INT-A1 is reacted with a limiting amount (0.4-0.45 equiv) of 1,4-diisocyanatobutane in the presence of base (if necessary, in cases of low reactivity or amine salts) to yield the dimer INT-A2.

Step C:
Removal of the Boc protecting group is facilitated by trifluoroacetic acid or other protic acid such as hydrogen chloride or sulfuric acid. The final product diamine INT-A3 can be isolated as the salt or neutralized to provide the free base.

General Scheme for the Synthesis of THIQ Dimer Products:

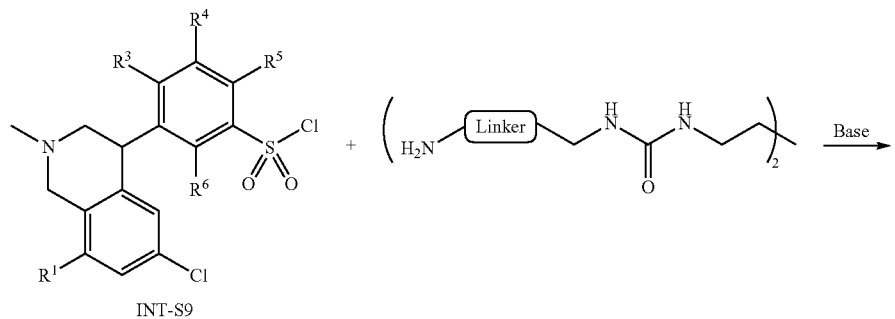

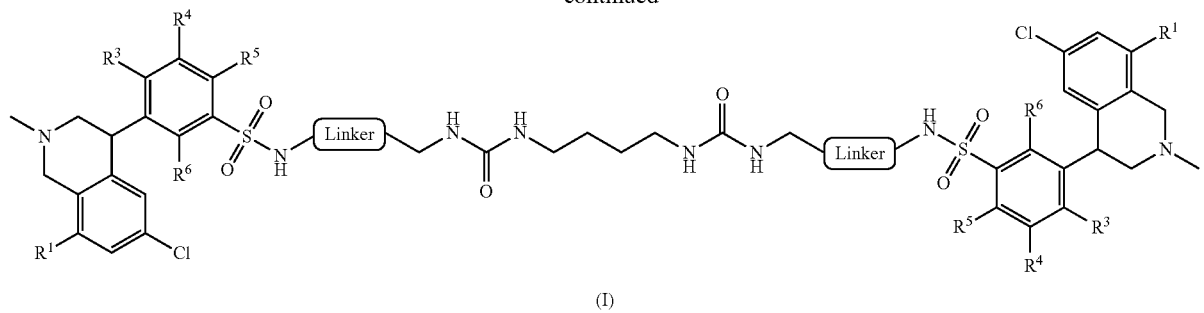

(I)

A sulfonyl chloride INT-S9 and a substoichiometric amount (0.4-0.45 equiv) of a diamine linker are reacted together in the presence of a base such as trimethylamine, pyridine, or the like to provide compounds of structure (I).

The following examples are prepared from the sulfonyl chlorides INT-S9 and the appropriate linker diamine INT-RL4, INT-SL4, INT-PL, 1, or INT-A3.

Example 1: N,N'-(10,17-Dioxo-3,6,21,24-tetraoxa-9,11,16,18-tetraazahexacosane-1,26-diyl)bis[3-(6-chloro-2,8-dimethyl-1,2,3,4-tetrahydroisoquinolin-4-yl)benzenesulfonamide]

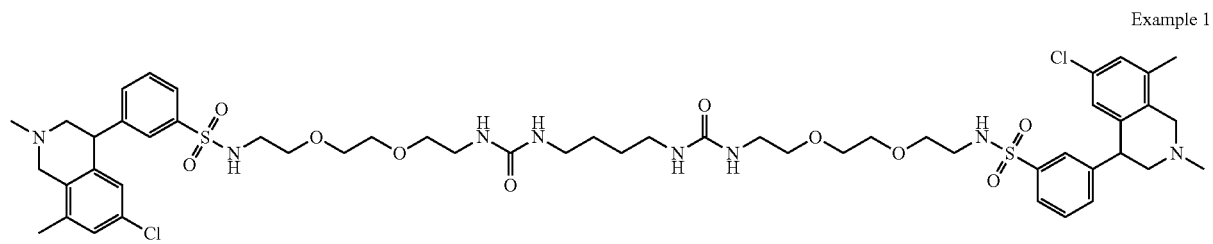

Example 1

Example 2: N,N'-(10,17-Dioxo-3,6,21,24-tetraoxa-9,1,16,18-tetraazahexacosane-1,26-diyl)]bis[3-(6-chloro-8-cyano-2-methyl-1,2,3,4-tetrahydroisoquinolin-4-yl)benzenesulfonamide

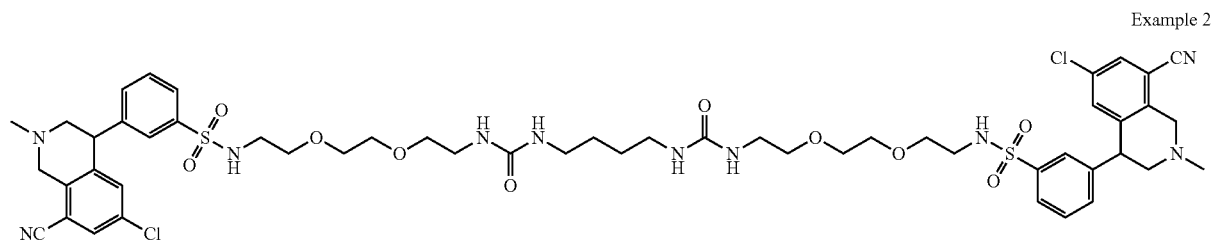

Example 2

Example 3: N,N'-(10,17-Dioxo-3,6,21,24-tetraoxa-9,11,16,18-tetraazahexacosane-1,26-diyl)]bis[3-(6,8-dichloro-2-methyl-1,2,3,4-tetrahydroisoquinolin-4-yl)-4-methylbenzenesulfonamide

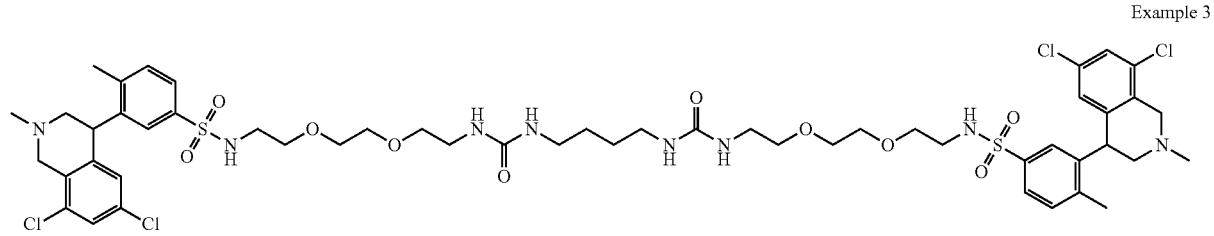

Example 3

Example 4: N,N'-(10,17-Dioxo-3,6,21,24-tetraoxa-9,11,16,18-tetraazahexacosane-1,26-diyl)]bis[3-(6-chloro-2,8-dimethyl-1,2,3,4-tetrahydroisoquinolin-4-yl)-4-methylbenzenesulfonamide

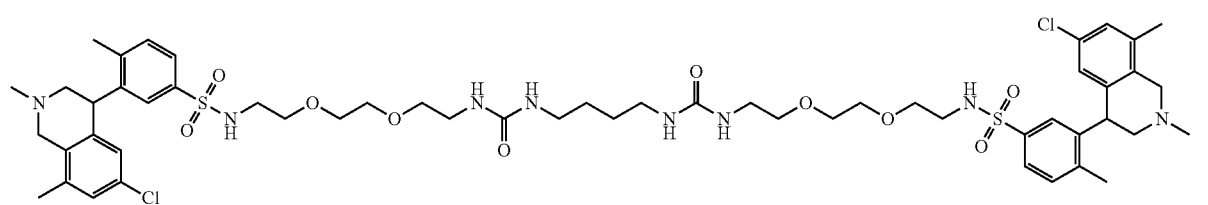

Example 4

Example 5: N,N'-(10,17-Dioxo-3,6,21,24-tetraoxa-9,11,16,18-tetraazahexacosane-1,26-diyl)]bis[3-(6-chloro-8-cyano-2-methyl-1,2,3,4-tetrahydroisoquinolin-4-yl)-4-methylbenzenesulfonamide]

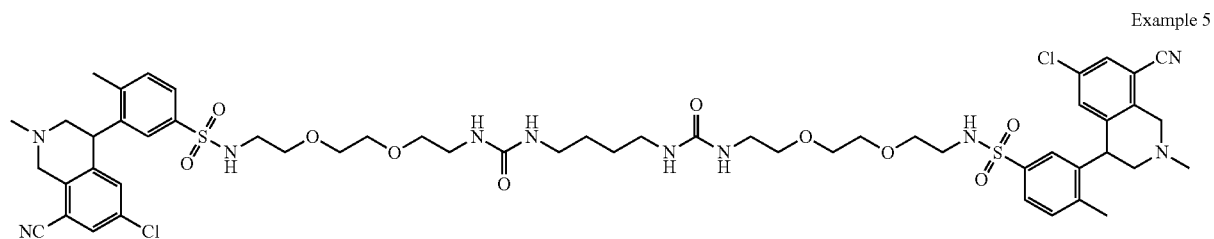

Example 5

Example 6: N,N'-(10,17-Dioxo-3,6,21,24-tetraoxa-9,11,16,18-tetraazahexacosane-1,26-diyl)]bis[5-(6,8-dichloro-2-methyl-1,2,3,4-tetrahydroisoquinolin-4-yl)-2-methylbenzenesulfonamide]

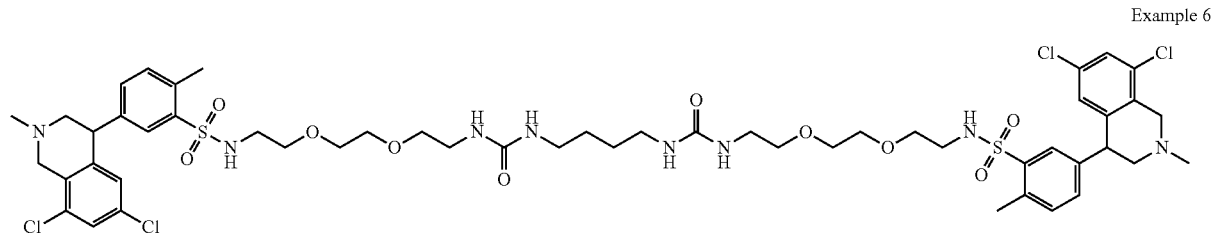

Example 6

Example 7: N,N'-(10,17-Dioxo-3,6,21,24-tetraoxa-9,11,16,18-tetraazahexacosane-1,26-diyl)]bis[5-(6-chloro-2,8-dimethyl-1,2,3,4-tetrahydroisoquinolin-4-yl)-2-methylbenzenesulfonamide]

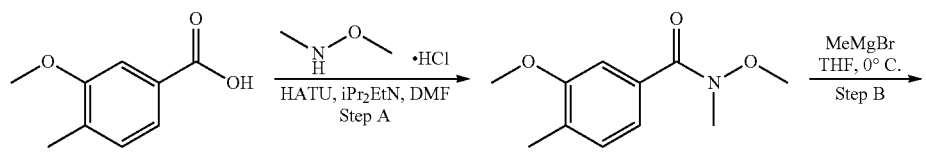

-continued
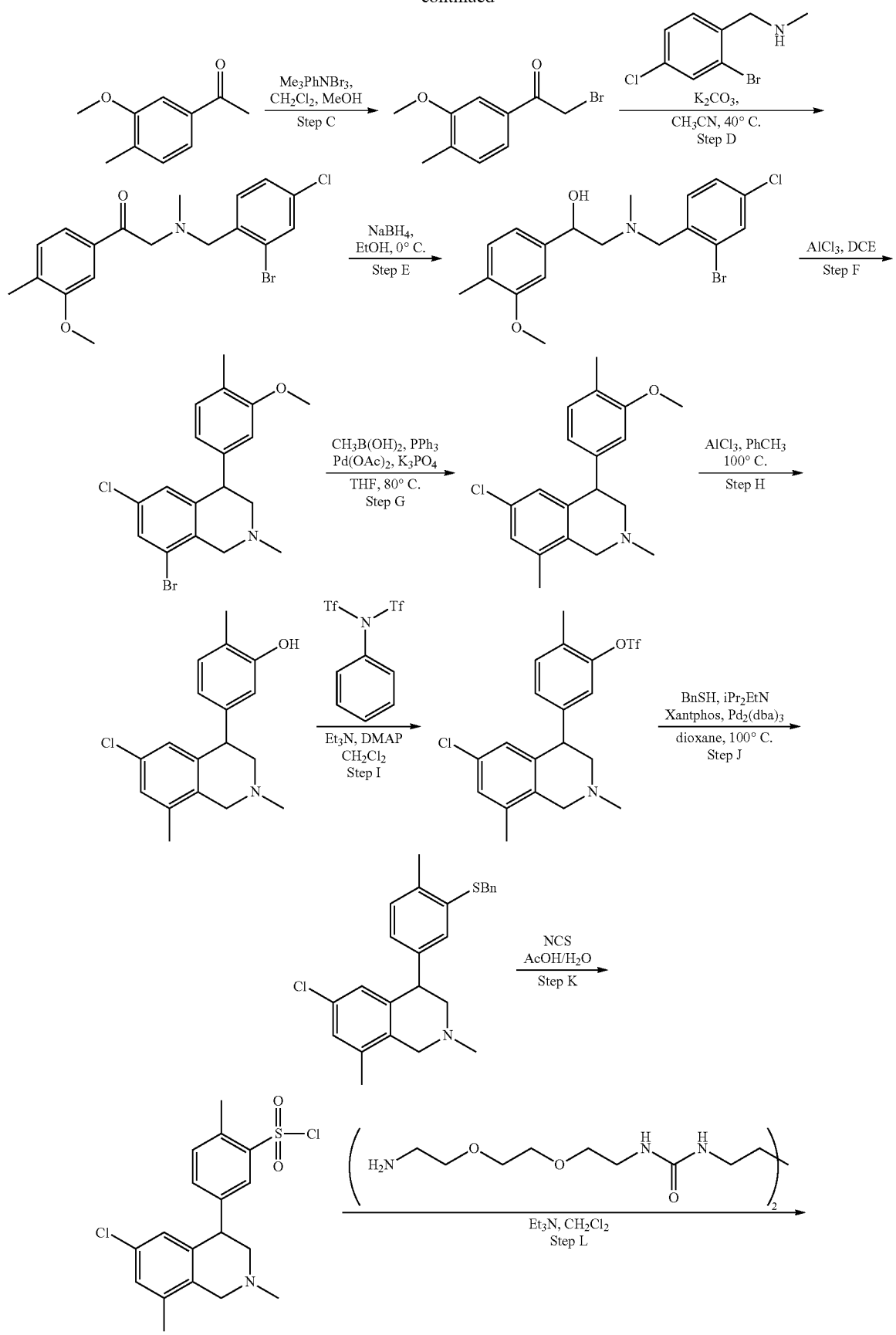

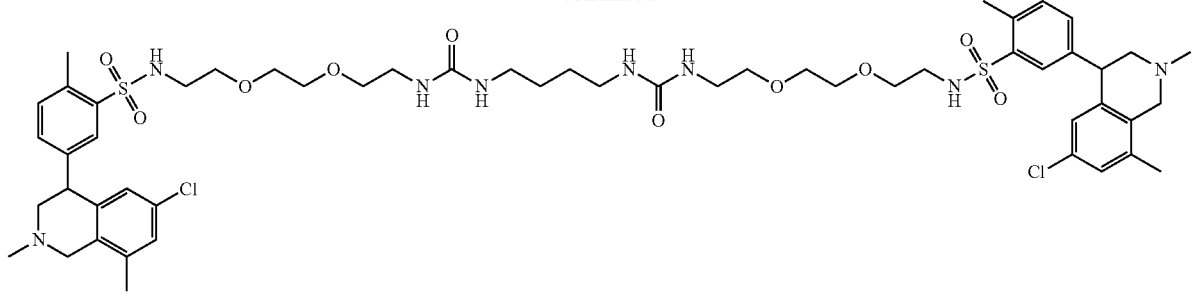

Example 7

Step A:

Into a 1000-mL round-bottom flask purged and maintained with an inert atmosphere of nitrogen was placed 3-methoxy-4-methylbenzoic acid (20 g. 120.36 mmol, 1 equiv). N,N-dimethylformamide (200 mL), N,O-dimethylhydroxylamine hydrochloride (17.6 g, 180.43 mmol, 1.50 equiv), iPr$_2$EtN (100 mL, 5.00 equiv) followed by the addition of HATU (34.3 g, 90.21 mmol, 1.50 equiv) in several batches. The resulting solution was stirred overnight at room temperature. The resulting solution was extracted with 3×200 mL of ethyl acetate and the organic layers combined, washed with 5×200 mL of brine, dried over Na$_2$SO$_4$, filtered, and concentrated. The solid was dried in an oven under reduced pressure. The residue was applied onto a silica gel column with 1:1 ethyl acetate/hexane to provide 24 g (95%) of N,3-dimethoxy-N,4-dimethylbenzamide as a colorless liquid.

Step B:

Into a 500-mL round-bottom flask purged and maintained with an inert atmosphere of nitrogen was placed N,3-dimethoxy-N,4-dimethylbenzamide (24 g. 114.70 mmnol, 1.00 equiv), THF (240 mL) followed by CH$_3$MgBr (3 M in THF, 95 mL, 2.50 equiv) dropwise with stirring at 0° C. in 1 hr. The resulting solution was stirred for 1 h at 0° C. in an ice/salt bath. The reaction was quenched by the addition of NH$_4$Cl and extracted with 3×200 mL of ethyl acetate. The organic layers were combined and washed with 1×200 mL of brine, dried over Na$_2$SO$_4$, filtered, and concentrated. The solid was dried in an oven under reduced pressure. The residue was applied onto a silica gel column with ethyl acetate/hexane (1/10) to provide 18.55 g (98%) of 1-(3-methoxy-4-methylphenyl)ethan-1-one as colorless liquid.

Step C:

Into a 1000-mL round-bottom flask purged and maintained with an inert atmosphere of nitrogen was placed 1-(3-methoxy-4-methylphenyl)ethan-1-one (18.55 g, 112.97 mmol, 1.00 equiv), dichloromethane (200 mL), methanol (200 mL), and trimethylphenylammonium tribromide (44.6 g, 1.05 equiv). The resulting solution was stirred for 2 h at room temperature. The reaction was quenched by the addition of water and extracted with 3×500 mL of ethyl acetate. The organic layers were combined, washed with 1×200 mL of brine, dried over Na$_2$SO$_4$, filtered, and concentrated. The solid was dried in an oven under reduced pressure. The residue was applied onto a silica gel column with ethyl acetate/hexane (1/9) to provide 27.46 g (100%) of 2-bromo-1-(3-methoxy-4-methylphenyl)ethan-1-one as a white solid.

Step D:

Into a 1000-mL round-bottom flask purged and maintained with an inert atmosphere of nitrogen was placed 2-bromo-1-(3-methoxy-4-methylphenyl)ethan-1-one (27.46 g, 112.96 mmol, 1.00 equiv), CH$_3$CN (300 mL), [(2-bromo-4-chlorophenyl)methyl](methyl)amine (26.75 g, 114.06 mmol, 1.01 equiv), and potassium carbonate (39 g. 282.18 mmol, 2.50 equiv). The resulting solution was stirred overnight at 40° C. in an oil bath. The resulting mixture was concentrated under vacuum and the residue applied onto a silica gel column with ethyl acetate/hexane (1/4). This resulted in 39 g (87%) of 2-[[(2-bromo-4-chlorophenyl)methyl](methyl)amino]-1-(3-methoxy-4-methylphenyl)ethan-1-one as a white solid.

Step E:

Into a 1-L round-bottom flask purged and maintained with an inert atmosphere of nitrogen was placed 2-[[(2-bromo-4-chlorophenyl)methyl](methyl)amino]-1-(3-methoxy-4-methylphenyl)ethan-1-one (39 g, 98.31 mmol. 1.00 equiv) and ethanol (400 mL) followed by NaBH$_4$ (3.7 g, 97.81 mmol, 1.00 equiv) in several batches at 0° C. over 35 min. The resulting solution was stirred for 2 h at 25° C. in an oil bath. The reaction was quenched by the addition of water the slurry concentrated under vacuum. The resulting slurry was extracted with 3×200 mL of ethyl acetate and the organic layers were combined, dried over Na$_2$SO$_4$, filtered, and concentrated under vacuum. The residue was applied onto a silica gel column with ethyl acetate/hexane (1/2) to provide 32 g (82%) of 2-[[(2-bromo-4-chlorophenyl)methyl](methyl)amino]-1-(3-methoxy-4-methylphenyl)ethan-1-ol as a white solid.

Step F:

Into a 250-mL round-bottom flask purged and maintained with an inert atmosphere of nitrogen was placed 2-[[(2-bromo-4-chlorophenyl)methyl](methyl)amino]-1-(3-methoxy-4-methylphenyl)ethan-1-ol (12 g, 30.10 mmol, 1.00 equiv) and ClCH$_2$CH$_2$C$_1$ (DCE, 250 mL) followed by AlCl$_1$(20 g, 5.00 equiv) at room temperature. After 30 min at room temperature, the resulting solution was diluted with CH$_2$Cl$_2$ and the pH of the solution adjusted to 9-10 with potassium carbonate. The resulting solution was extracted with ethyl acetate and the organic layers combined, dried over Na$_2$SO$_4$, filtered, and concentrated under vacuum. The residue was applied onto a silica gel column with ethyl acetate/hexane (1/10) to provide 10 g (87%) of 8-bromo-6-chloro-4-(3-methoxy-4-methylphenyl)-2-methyl-1,2,3,4-tetrahydroisoquinoline as yellow oil.

Step G:

Into a 25-mL round-bottom flask purged and maintained with an inert atmosphere of nitrogen was placed 5-(8-bromo-6-chloro-2-methyl-1,2,3,4-tetrahydroisoquinolin-4-yl)-2-methylphenol (700 mg, 1.91 mmol, 1.00 equiv), tetrahydrofuran (8 mL), K$_3$PO$_4$ (1.56 g, 7.35 mmol, 4.00 equiv), CH$_3$B(OH)$_2$ (166 mg, 1.50 equiv), PPh$_3$ (96.3 mg, 0.37 mmol, 0.20 equiv), and Pd(OAc)$_2$ (41.37 mg, 0.18 mmol, 0.10 equiv). The resulting solution was stirred overnight at 80° C. in an oil bath. The slurry was extracted with ethyl acetate and the organic layers were combined, washed with brine, dried over Na₂SO₄, filtered, and concentrated under vacuum. The solid was dried in an oven under reduced pressure. The residue was applied onto a silica gel column with ethyl acetate/hexane (1/1) to provide 520 mg (90%) of 5-(6-chloro-2,8-dimethyl-1,2,3,4-tetrahydroisoquinolin-4-yl)-2-methylphenol as a white solid.

Step H:

Into a 100-mL round-bottom flask purged and maintained with an inert atmosphere of nitrogen was placed 6-chloro-4-(3-methoxy-4-methylphenyl)-2,8-dimethyl-1,2,3,4-tetrahydroisoquinoline (2.6 g, 8.23 mmol, 1.00 equiv), toluene (26 mL), and AlCl₃ (3.3 g). The resulting solution was stirred for 6 h at 100° C. in an oil bath. The reaction mixture was cooled to room temperature with a water bath, diluted with 100 mL of CH₂Cl₂, and quenched by the addition of 200 mL of saturated potassium carbonate. The resulting slurry was extracted with 3×200 mL of ethyl acetate and the organic layers combined, dried over Na₂SO₄, filtered, and concentrated under vacuum. The residue was applied onto a silica gel column with ethyl acetate/petroleum ether (1:1) to provide 2.2 g (89%) of 5-(6-chloro-2,8-dimethyl-1,2,3,4-tetrahydroisoquinolin-4-yl)-2-methylphenol as a brown solid.

Step I:

Into a 100-mL round-bottom flask purged and maintained with an inert atmosphere of nitrogen was placed 5-(6-chloro-2,8-dimethyl-1,2,3,4-tetrahydroisoquinolin-4-yl)-2-methylphenol (740 mg, 2.45 mmol, 1.00 equiv), dichloromethane (25 mL), triethylamine (1.02 mL, 3.00 equiv), 4-dimethylaminopyridine (30 mg, 0.25 mmol, 0.10 equiv), and 1,1,1-trifluoro-N-phenyl-N-(trifluoromethane)sulfonylmethanesulfonamide (1.75 g, 4.90 mmol, 2.00 equiv). The resulting solution was stirred for 2 h at room temperature. The resulting mixture was concentrated under vacuum and the residue applied onto a silica gel column with ethyl acetate/petroleum ether (1/2) to provide 1.06 g (100%) of 5-(6-chloro-2,8-dimethyl-1,2,3,4-tetrahydroisoquinolin-4-yl)-2-methylphenyl trifluoromethanesulfonate as yellow oil.

Step J:

Into a 50-mL round-bottom flask purged and maintained with an inert atmosphere of nitrogen was placed 5-(6-chloro-2,8-dimethyl-1,2,3,4-tetrahydroisoquinolin-4-yl)-2-methylphenyl trifluoromethane sulfonate (1.06 g, 2.44 mmol, 1.00 equiv), BnSH (0.57 mL, 2.00 equiv), diisopropylethylamine (0.8 mL, 2.00 equiv), dioxane (10 mL), Xantphos (170 mg, 0.29 mmol, 0.06 equiv), and Pd₂(dba)₃·CHCl₃ (152 mg, 0.06 equiv). The resulting solution was stirred overnight at 100° C. in an oil bath. The reaction mixture was cooled and extracted with 3×100 mL of ethyl acetate. The organic layers were combined, washed with 1×100 mL of brine, dried over Na₂SO₄, filtered, and concentrated under vacuum. The residue was applied onto a silica gel column with ethyl acetate/petroleum ether (1/5) to provide 0.31 g (31%) of 4-[3-(benzylsulfanyl)-4-methylphenyl]-6-chloro-2,8-dimethyl-1,2,3,4-tetrahydroisoquinoline as yellow oil.

Step K:

Into a 8-mL round-bottom flask purged and maintained with an inert atmosphere of nitrogen was placed 4-[3-(benzylsulfanyl)-4-methylphenyl]-6-chloro-2,8-dimethyl-1,2,3,4-tetrahydroisoquinoline (310 mg, 0.76 mmol, 1.00 equiv), AcOH (1.55 mL), and water (0.041 mL) followed by NCS (304 mg, 2.28 mmol, 3.00 equiv) in several batches. The resulting solution was stirred for 1 h at room temperature. The slurry was diluted with 100 mL of ethyl acetate and washed with 3×100 mL of cold H₂O and 3×100 mL of cold brine. The mixture was dried over Na₂SO₄, filtered, and concentrated under vacuum. This resulted in 384 mg (crude) of 5-(6-chloro-2,8-dimethyl-1,2,3,4-tetrahydroisoquinolin-4-yl)-2-methylbenzene-1-sulfonyl chloride as yellow oil.

Step L:

Into a 8-mL round-bottom flask purged and maintained with an inert atmosphere of nitrogen was placed 3-[2-[2-(2-aminoethoxy)ethoxy]ethyl]-1-[4-[([2-[2-(2-aminoethoxy)ethoxy]ethyl]carbamoyl)amino]butyl]urea (114 mg, 0.26 mmol, 1.00 equiv), dichloromethane (1.5 mL), triethylamine (49 mg, 0.48 mmol, 1.87 equiv), and a solution of 5-(6-chloro-2,8-dimethyl-1,2,3,4-tetrahydroisoquinolin-4-yl)-2-methylbenzene-1-sulfonyl chloride (200 mg, 0.52 mmol, 2.00 equiv) in dichloromethane (1.5 mL). The resulting solution was stirred overnight at room temperature. The reaction slurry was concentrated under vacuum. The crude product was purified by Prep-HPLC with the following conditions: Column, XBridge Shield RP18 OBD Column, 5 um, 19*150 mm; mobile phase, water (0.05% NH₃H₂O) and CH₃CN (48.0% CH₃CN up to 65.0% in 10 min); Detector, UV 254 nm. This resulted in 51 mg (17%) of the title compound (Example 7) as a white solid. LC-MS (ES, m/z) [M+1]; 1132. ¹H NMR (300 MHz, Methanol-d4) δ 7.66 (s, 2H), 7.30 (d, J=1.2 Hz, 4H), 7.03 (d, J=2.1 Hz, 2H), 6.58 (d, J=1.5 Hz, 2H), 4.30 (t, J=7.1 Hz, 2H), 3.71 (d, J=15.7 Hz, 2H), 3.55-3.31 (m, 19H), 3.24 (t, J=5.4 Hz, 4H), 3.03 (dt, J=18.6, 5.3 Hz, 11H), 2.59 (s, 8H), 2.44 (s, 6H), 2.23 (s, 6H), 1.49-1.39 (m, 4H).

Example 8: N,N'-(10,17-Dioxo-3,6,21,24-tetraoxa-9,11,16,18-tetraazahexacosane-1,26-diyl)bis(5-(6-chloro-8-cyano-2-methyl-1,2,3,4-tetrahydroisoquinolin-4-yl)-2-methylbenzenesulfonamide)

Example 8

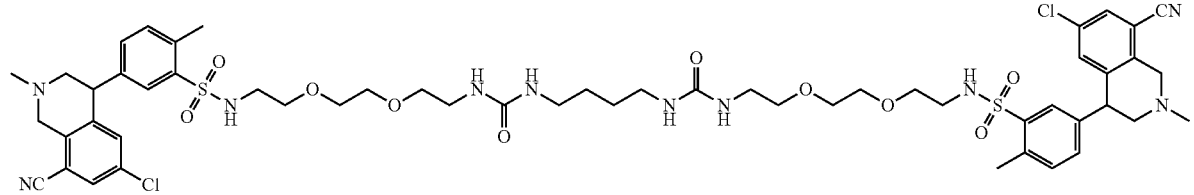

The title compound was prepared through the same route as Example 7 with the exception of the cyanation procedure below replacing the methylation (Suzuki) conditions. Cyanation procedure: Into a 50-mL round-bottom flask purged and maintained with an inert atmosphere of nitrogen was placed 5-(8-bromo-6-chloro-2-methyl-1,2,3,4-tetrahydroisoquinolin-4-yl)-2-methylphenol (700 mg, 1.91 mmol, 1.00 equiv), NMP (7 mL), Zn(CN)₂ (110 mg, 0.50 equiv), and Pd(PPh₃)₄ (450 mg, 0.39 mmol, 0.20 equiv). The resulting solution was stirred overnight at 100° C. in an oil bath. The slurry was extracted with 3×100 mL of ethyl acetate and the organic layers combined, washed with 3×100 mL of brine, dried over Na₂SO₄, filtered, and concentrated under vacuum. The residue was applied onto a silica gel column with ethyl acetate/petroleum ether (1/1) to provide 400 mg (67%) of 6-chloro-4-(3-hydroxy-4-methylphenyl)-2-methyl-1,2,3,4-tetrahydroisoquinoline-8-carbonitrile as yellow oil.

LCMS (ES, m/z) [M+1]; 1155. ¹H NMR (300 MHz, DMSO-d6) δ 7.91 (d, J=2.2 Hz, 2H), 7.75 (d, J=5.9 Hz, 2H), 7.65 (s, 2H), 7.39-7.26 (m, 4H), 7.20 (d, J=2.2 Hz, 2H), 5.89 (t, J=5.7 Hz, 2H), 5.76 (t, J=5.8 Hz, 2H), 4.37 (t, J=5.3 Hz, 2H), 3.83 (d, J=16.1 Hz, 2H), 3.64 (d, J=16.2 Hz, 2H), 3.45-3.30 (m, 8H), 3.29 (d, J=6.2 Hz, 4H), 3.10 (q, J=5.8 Hz; 4H), 2.98-2.81 (m, 11H), 2.64 (dd, J=11.7, 5.9 Hz, 2H), 2.52 (s, 6H), 2.37 (s, 5H), 2.07 (s, 3H), 1.35-1.20 (m, 4H).

Example 9: N,N'-(10,17-Dioxo-3,6,21,24-tetraoxa-9,11,16,18-tetraazahexacosane-1,26-diyl)bis[3-(6,8-dichloro-2-methyl-1,2,3,4-tetrahydroisoquinolin-4-yl)-4-fluorobenzenesulfonamide]

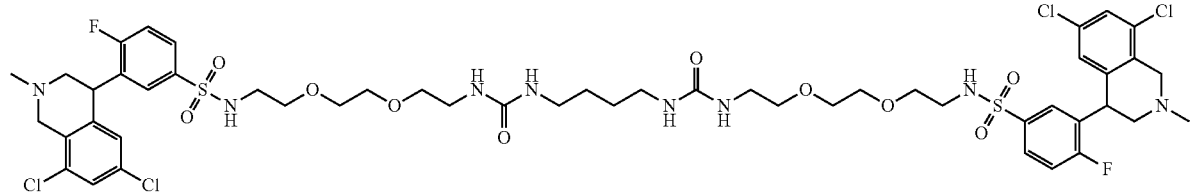

Example 9

Example 10: N,N'-(10,17-Dioxo-3,6,21,24-tetraoxa-9,11,16,18-tetraazahexacosane-1,26-diyl)bis[3-(6-dichloro-2-dimethyl-1,2,3,4-tetrahydroisoquinolin-4-yl)-4-fluorobenzenesulfonamide]

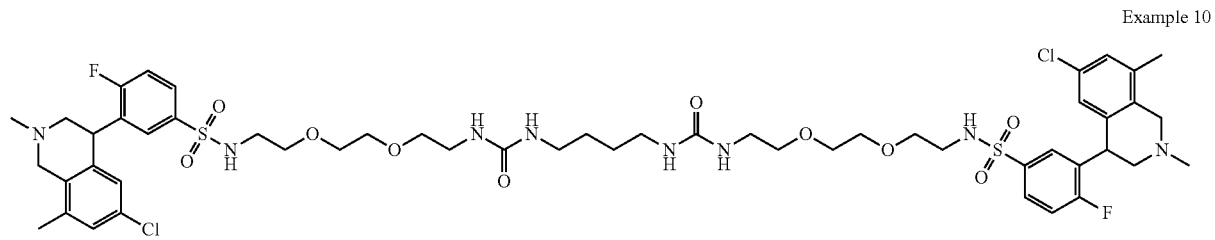

Example 10

Example 11: N,N'-(10,17-Dioxo-3,6,21,24-tetraoxa-9,11,16,18-tetraazahexacosane-1,26-diyl)bis[3-(6-dichloro-2-methyl-1,2,3,4-tetrahydroisoquinolin-4-yl)-4-fluorobenzenesulfonamide]

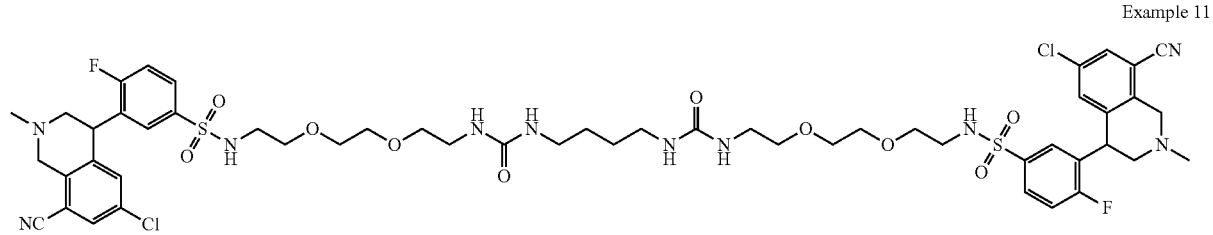

Example 11

Example 12: N,N'-((3S,3'S)-(7,14-Dioxo-3,18-di-oxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)benzenesulfonamide]

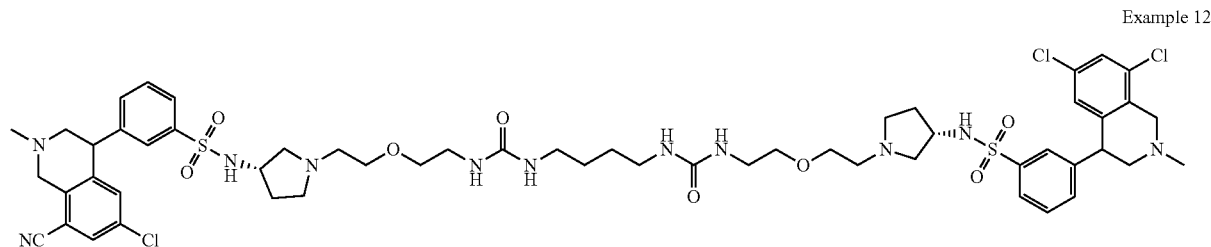

Example 12

Example 13: N,N'-[(3S,3'S)-(7,14-Dioxo-3,18-di-oxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)benzenesulfonamide]

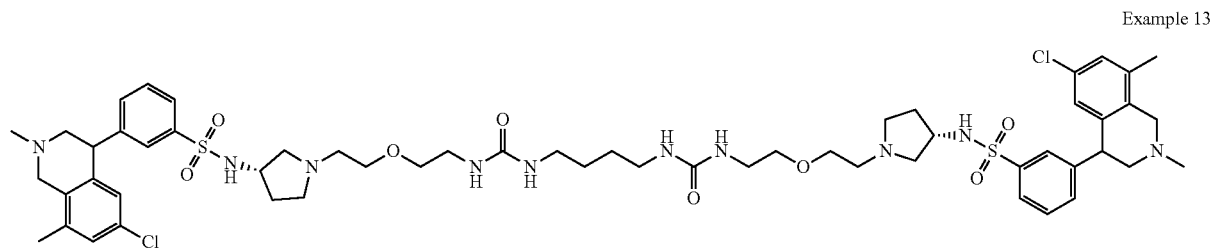

Example 13

Example 14: N,N'-[(3S,3'S)-(7,14-Dioxo-3,18-di-oxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)benzenesulfonamide]

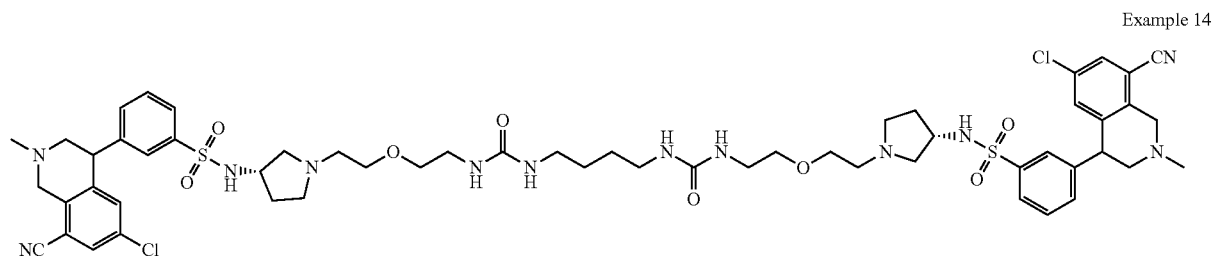

Example 14

Example 15: N,N'-[(3S,3)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-methylbenzenesulfonamide]

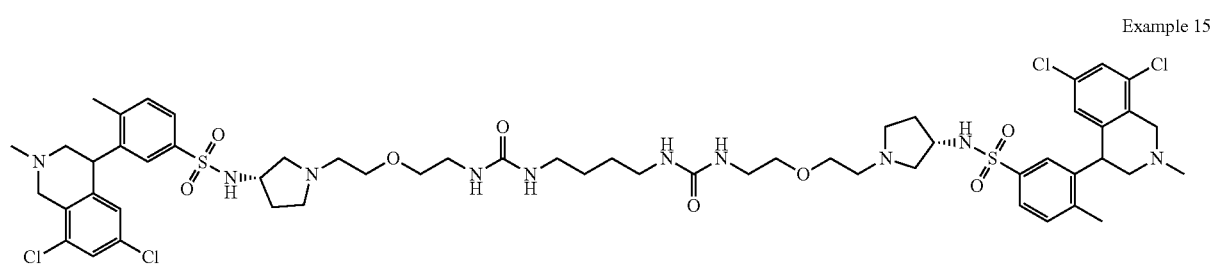

Example 15

Example 16: N,N'-[(3S,3'S)-(7,14-Dioxo-3,18-di-oxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-methylbenzenesulfonamide]

Example 16

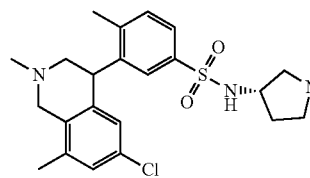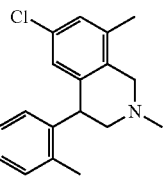

Example 17: N,N'-[(3S,3'S)-(7,14-Dioxo-3,18-di-oxa-6,8,13,15-tetraazaicosane-1,20-diyl)bis(pyrrolidine-1,3-diyl)]bis[3-(6-chloro-8-cyano-2methyl -1,2,3,4-tetrahydroisoquinolin-4-yl)-4-methylbenzenesulfonamide]

Example 17

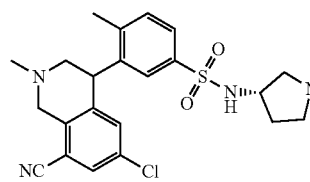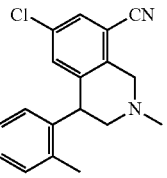

Example 18: N,N'-[(3S,3'S)-7,14-Dioxo-3,18-dioxa-6,8,13,15-tetraazaicosane-1,20-diyl)bis(pyrolidine-1,3-diyl)]bis[5-(6,8-dichloro-2-methyl-1,2,3,4-tetrahydroisoquinolin-4-yl)-2-methylbenzenesulfonamide]

Example 18

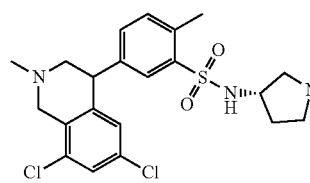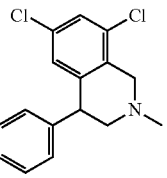

Example 19: N,N'-[(3S,3'S)-(7,14-Dioxo-3,18-di-oxa-6,8,13,15-tetraazaicosane-1,20-diyl)bis(pyrrolidine-1,3-diyl)]bis[5-(6-chloro-2,8-dimethyl-1,2,3,4-tetrahydroisoquinolin-4-yl)-2-methylbenzenesulfonamide]

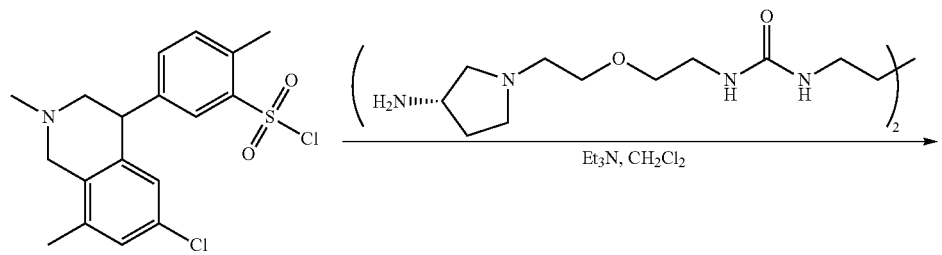

-continued

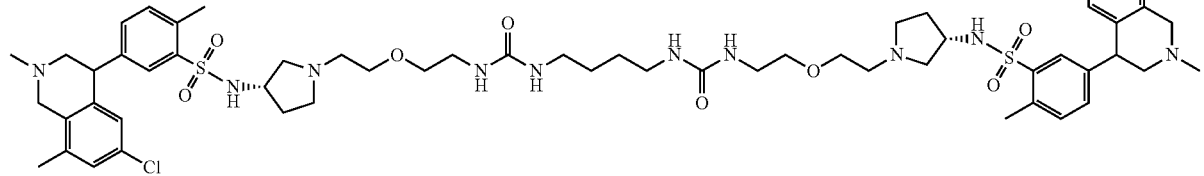

Example 19

Into a 25-mL round-bottom flask purged and maintained with an inert atmosphere of nitrogen was placed 3-(2-[2-[(3S)-3-aminopyrrolidin-1-yl]ethoxy]ethyl)-1-(4-[[(2-12-[(3S)-3-aminopyrrolidin-1-yl] ethoxy]ethyl)carbamoyl]amino]butyl)urea (150 mg, 0.31 mmol, 1.00 equiv), CH$_2$Cl$_2$ (4 mL), and triethylamine (58.32 mg, 0.58 mmol, 1.87 equiv) followed by a solution of 5-(6-chloro-2,8-dimethyl-1,2,3,4-tetrahydroisoquinolin-4-yl)-2-methylbenzene-1-sulfonyl chloride (237 mg, 0.62 mmol, 2.00 equiv) in dichloromethane (4 mL) dropwise with stirring. The resulting solution was stirred overnight at room temperature. The slurry was concentrated under vacuum. The crude product was purified by Prep-HPLC with the following conditions: Column, XBridge Shield RP18 OBD Column, 5 um, 19*150 mm; mobile phase, Water (0.05% NH$_3$H$_2$O) and CH$_3$CN (48.0% CH$_3$CN up to 66.0% in 8 min); Detector, UV 254 nm. This resulted in 28.6 mg (8%) of the title compound as a white solid. LCMS (ES, m/z) [M+1]; 1184. $^1$H NMR (400 MHz, Methanol-d$_4$) δ 1.44-1.60 (m, 6H), 1.85-2.02 (m, 2H), 2.28 (s, 6H), 2.40 (td, J=10.3, 5.3 Hz, 2H), 2.49 (d, J=1.2 Hz, 8H), 2.54-2.72 (m, 16H), 3.06 (dt, J=9.8, 4.4 Hz, 2H), 3.14 (d, J=6.5 Hz, 4H), 3.33 (p, J=1.7 Hz, 4H), 3.42-3.59 (m, 10H), 3.63-3.81 (m, 4H), 4.27-4.52 (m, 2H), 6.62 (d, J=7.0 Hz, 2H), 7.08 (d, J=2.1 Hz, 2H), 7.33-7.43 (m, 4H), 7.69 (d, J=1.7 Hz, 2H).

Example 20: N,N'-[(3S,3'S)-(7,14-Dioxo-3,18-dioxa-6,8,13,15-tetraazaicosane-1,20-diyl)bis(pyrrolidine-1,3-diyl)]bis[5-(6-chloro-8-cyano-2-methyl-1,2,3,4-tetrahydroisoquinolin-4-yl)-2-methylbenzenesulfonamide]

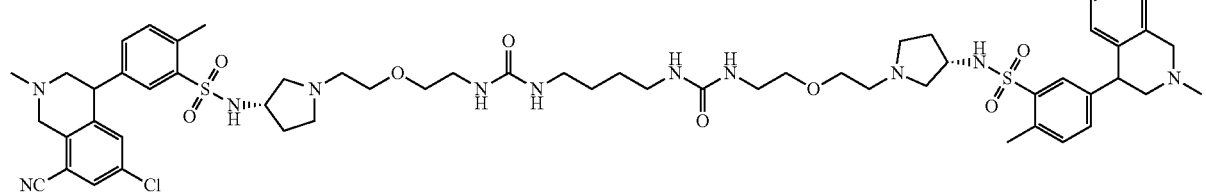

Example 20

Example 20 was prepared using the the methods and intermediates from Examples 8 and 19. LCMS (ES, m/z) [M+1]: 1205. $^1$H NMR (300 MHz, Methanol-d4) δ 7.73 (d, J=15.7 Hz, 4H), 7.40 (s, 4H), 7.16 (s, 2H), 4.40 (s, 2H), 3.87 (s, 4H), 3.72 (s, 3H), 3.51 (d, J=18.5 Hz, 10H), 3.29 (s, 3H), 3.14 (s, 2H), 2.75 (s, 1H), 2.65 (s, 9H), 2.52 (s, 7H), 2.42 (d, J=5.1 Hz, 1H), 1.97 (s, 2H), 1.51 (s, 7H), 1.32 (s, 1H).

Example 21: N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-fluorobenzenesulfonamide]

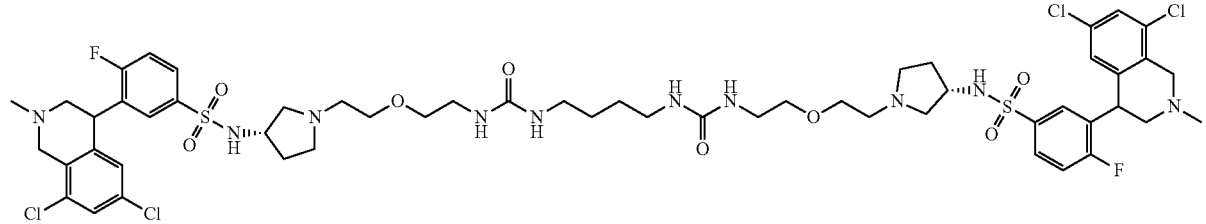

Example 21

Example 22: N,N'-[(3S,3'S)-(7,14-Dioxo-3,18-di-oxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-fluorobenzenesulfonamide]

Example 22

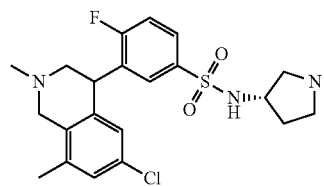
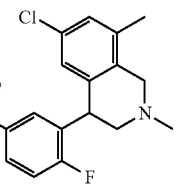

Example 23: N,N'-[(3S,3'S)-(7,14-Dioxo-3,18-di-oxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-fluorobenzenesulfonamide]

Example 23

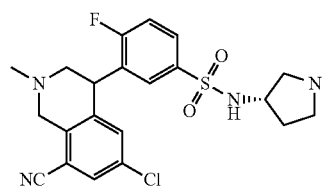
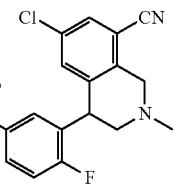

Example 24: N,N'-[(3R,3'R)-(7,14-Dioxo-3,18-di-oxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)benzenesulfonamide]

Example 24

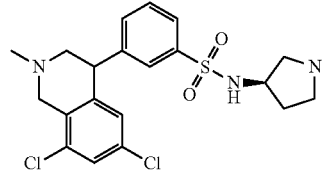
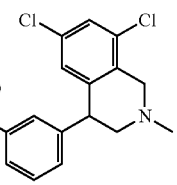

Example 25: N,N'-[(3R,3'R)-(7,14-Dioxo-3,18-di-oxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)benzenesulfonamide Example 25

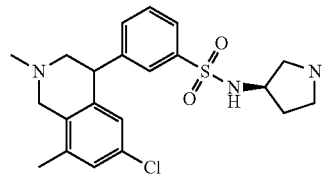
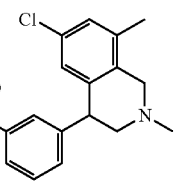

Example 26: N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)benzenesulfonamide]

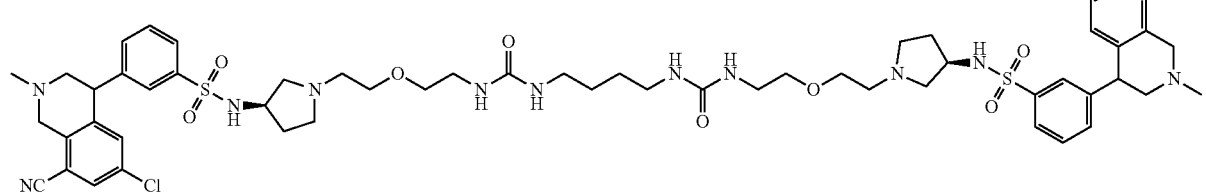

Example 26

Example 27: N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-methylbenzenesulfonamide]

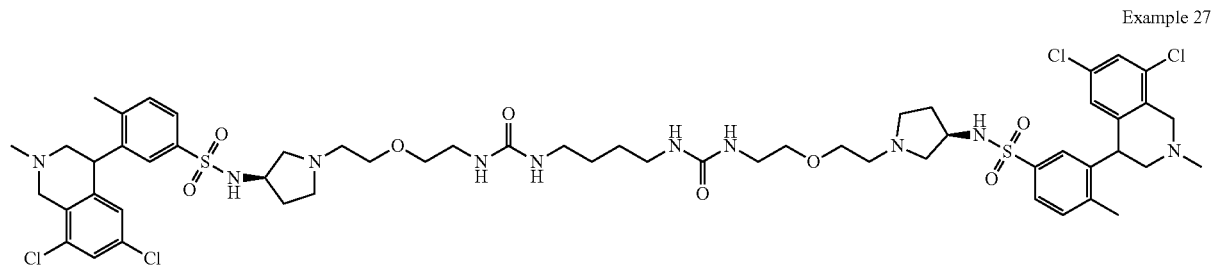

Example 27

Example 28: N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-methylbenzenesulfonamide]

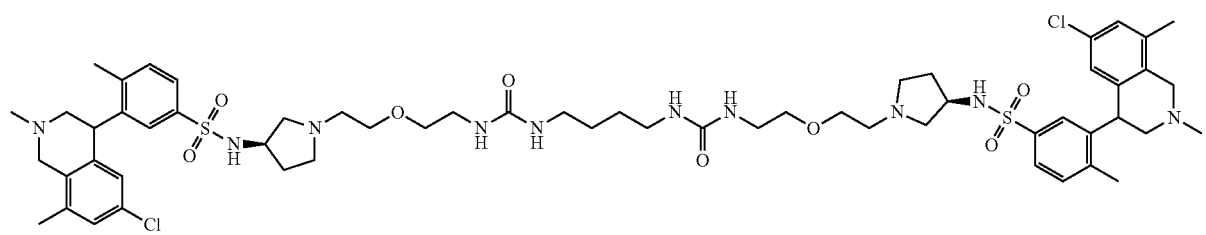

Example 28

Example 29: N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-methylbenzenesulfonamide]

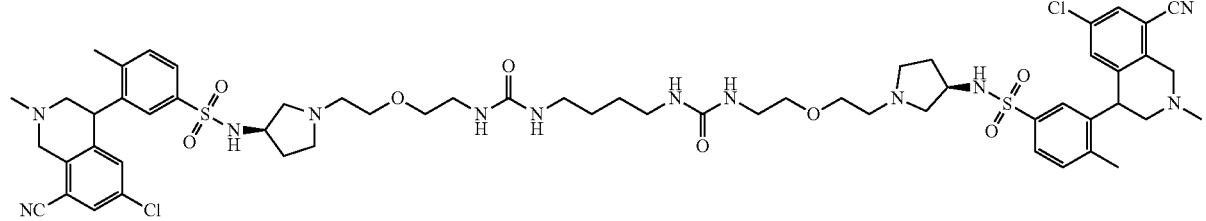

Example 29

Example 30: N,N'-[(3R,3'R)-(7,14-Dioxo-3,18-6,8,13,15-tetraazaicosane-1,20-diyl)bis(pyrrolidine-1,3-diyl)]bis[5-(6,8-dichloro-2-methy-1,2,3,4-tetrahydroisoquinolin-4-yl)-2-methylbenzenesulfonamide]

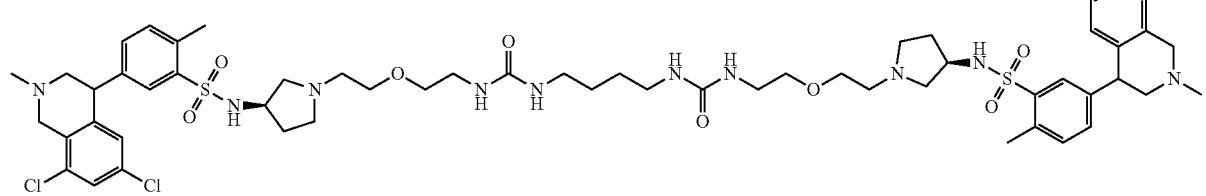

Example 30

Example 31: N,N'-[(3R,3'R)-(7,14-Dioxo-3,18-di-oxa-6,8,13,15-tetraazaicosane-1,20-diyl)bis(pyrrolidine-1,3-diyl)]bis[5-(6-chloro-2,8-dimethyl-1,2,3,4-tetrahydroisoquinolin-4-yl)-2-methylbenzenesulfonamide]

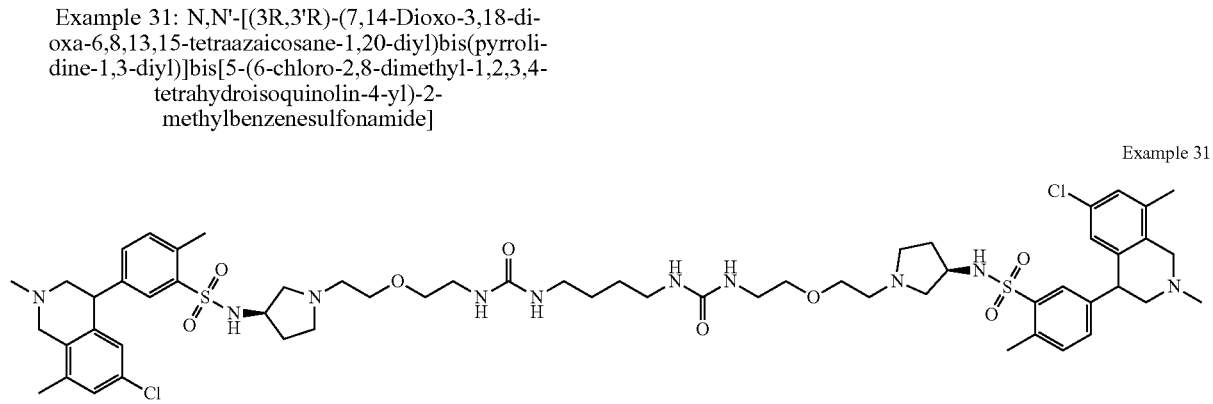

Example 31

Example 32: N,N'-[(3R,3'R)-(7,14-Dioxo-3,18-di-oxa-6,8,13,15-tetraazaicosane-1,20-diyl)bis(pyrrolidine-1,3-diyl)]bis[5-(6chloro-8-cyano-2-methyl-1,2,3,4-tetrahydroisoquinolin-4-yl)-2-methylbenzenesulfonamide]

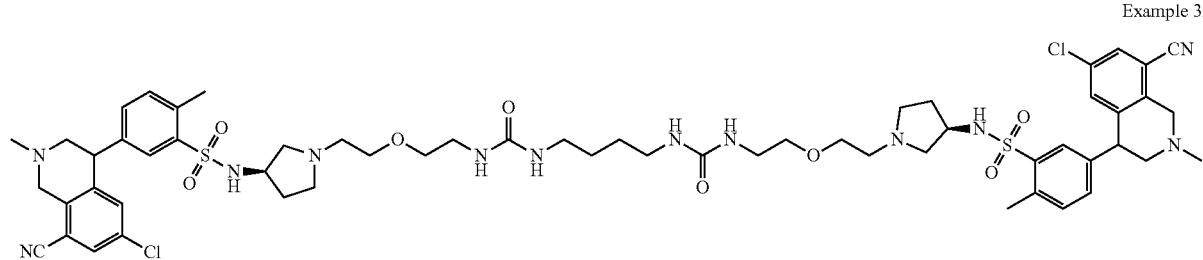

Example 32

Example 33: N,N'-[(3R,3'R)-(7,14-Dioxo-3,18-di-oxa-6,8,13,15-tetraazaicosane-1,20-diyl)bis(pyrrolidine-1,3-diyl)bis[3-(6,8-dichloro-2-methyl-1,2,3,4 tetrahydroisoquinolin-4-yl)-4-fluorobenzenesulfonamide]

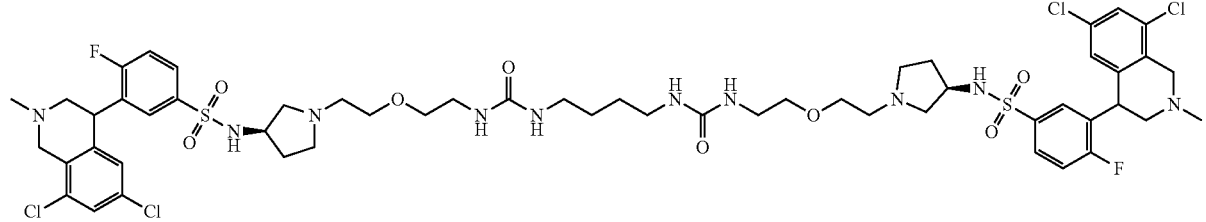

Example 33

Example 34: N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-fluorobenzenesulfonamide]

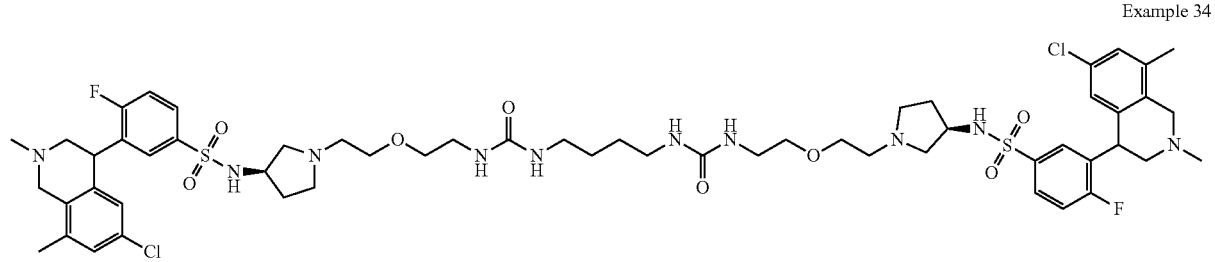

Example 34

Example 35: N,N'-[(3R,3'R)-(7,14-Dioxo-3,18-dioxa-6,8,13,15-tetraazaicosane-1,20-diyl)bis(pyrrolidine-1,3-diyl)]bis[3-(6chloro-8-cyano-2-methyl-1,2,3,4-tetrahydroisoquinolin-4-yl)-4 fluorobenzenesulfonamide]

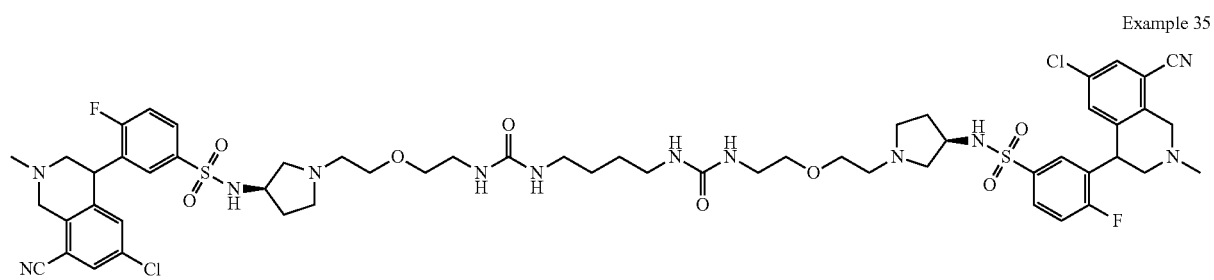

Example 35

Example 36: N,N'-[(7,14-Dioxo-3,18-dioxa-6,8,13,15-tetraazaicosane-1,20-diyl)bis(piperidine-1,4-diyl)]bis[3-(6-chloro-2,8-dimethyl-1,2,3,4-tetrahydroisoquinolin-4-yl)benzenesulfonamide]

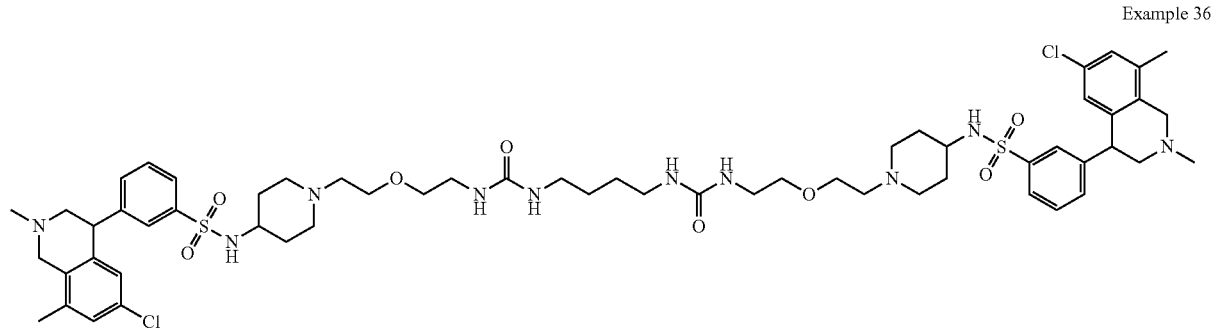

Example 36

Example 37: N,N'-[(7,14-Dioxo-3,18-dioxa-6,8,13, 15-tetraazaicosane-1,20-diyl)bis(piperidine-1,4-diyl)]bis[3-(6-chloro-8-cyano-2-methyl-1,2,3,4-tetrahydroisoquinolin-4-yl)benzenesulfonamide]
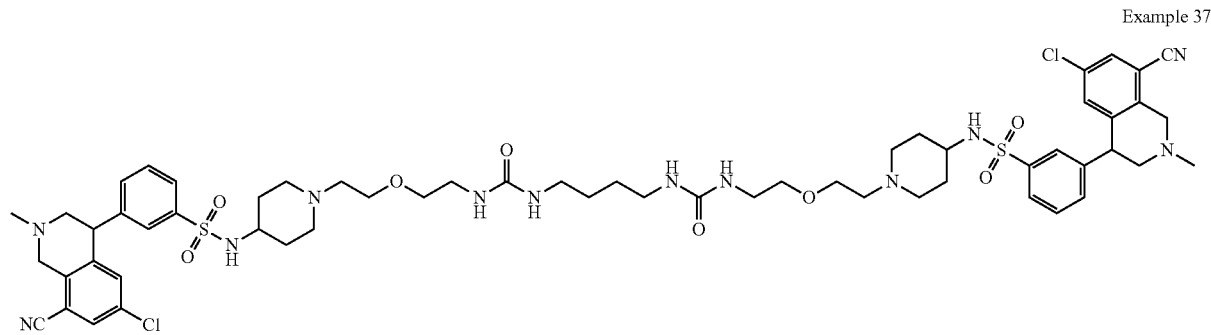
General Scheme for the Synthesis of N-Acylsulfonamide Dimer Products:
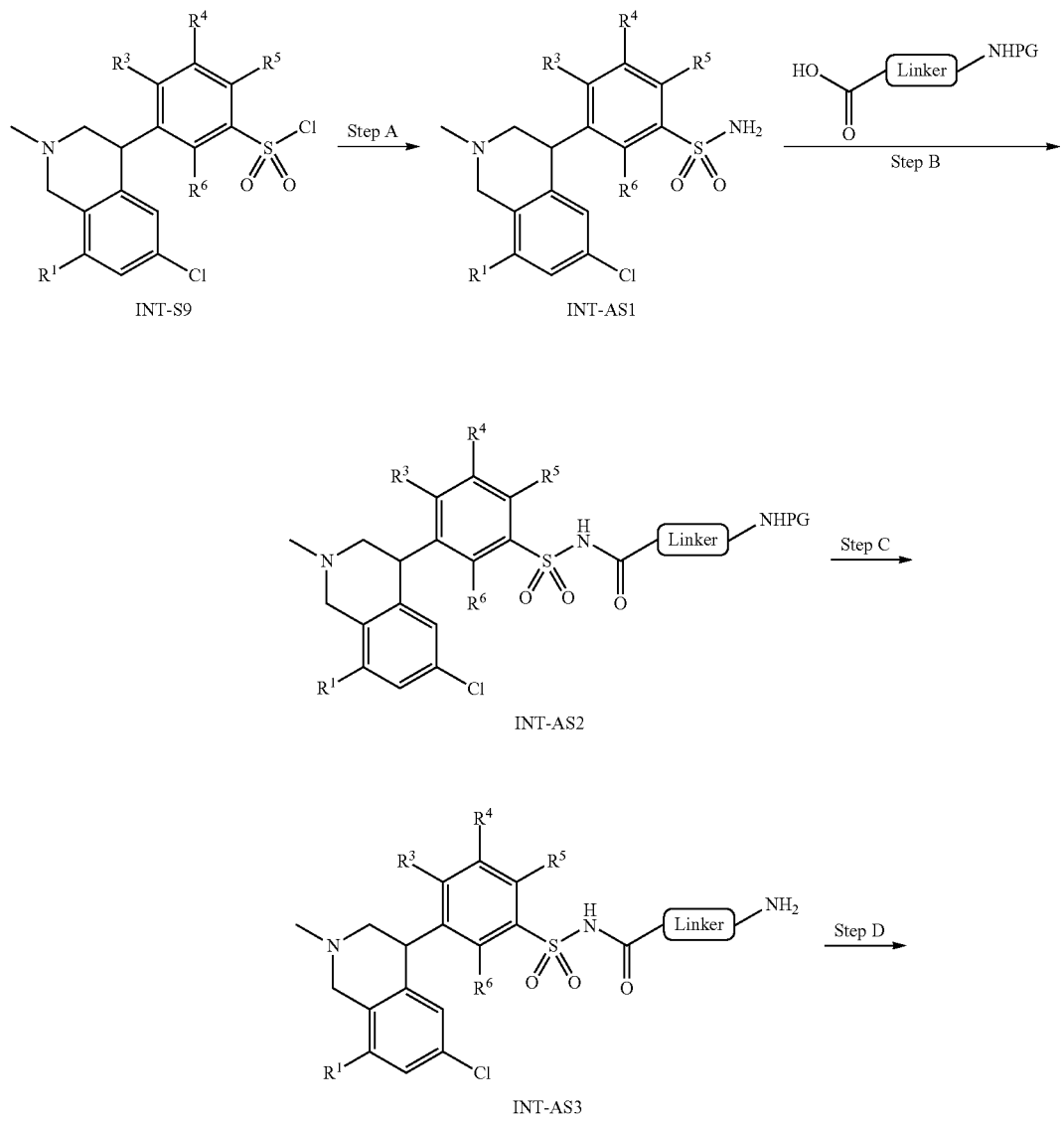

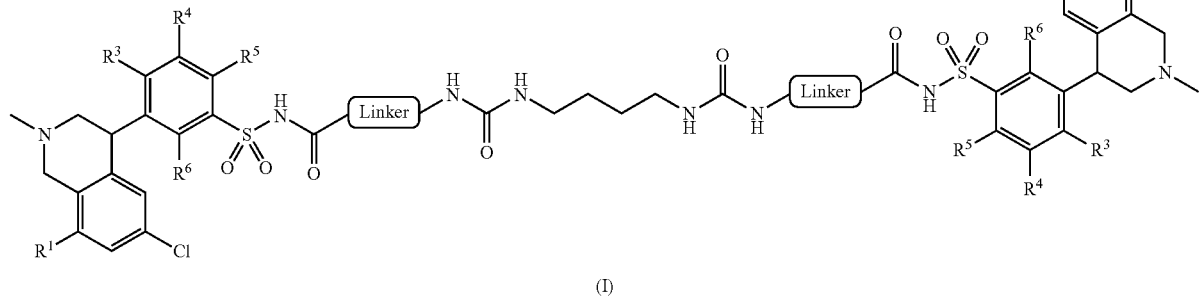

(I)

Beginning with the sulfonyl chlorides INT-S9 described earlier, the primary sulfonamides INT-AS1 are formed from reaction with an ammonia equivalent, through use of ammonium hydroxide, ammonia in methanol, or the like. Subsequently, carboxylic acid equivalents including protected amino acids, are activated through formation of the acid chlorides (using oxalyl chloride, thionyl chloride, etc) or activated esters (using coupling reagents such as CDI, HATU, EDC, DCC, DIC, etc). These activated groups are then treated with the sulfonamide INT-AS1 in Step B to provide the N-acylsulfonamide INT-AS2. The protecting group PG is removed through suitable conditions such as TFA or HCl in the case of Boc or through NaOH or $K_2CO_3$ or similar in the case of trifluoroacetamide, yielding INT-AS3 in Step C. Finally, in Step D, the dimer product is formed through treatment of the amine INT-AS3 with 1,4-diisocyanatobutane or other symmetric active reagent to provide compounds of structure (II).

The following examples are prepared according to the General Scheme for preparation of compounds of structure (II).

Example 38: 1,1'-[(3R,3'R)-(7,14-Dioxo-3,18-dioxa-6,8,13,15-tetraazaicosane-1,2-diyl)bis(pyrrolidine-1,3-diyl)]bis[N-([3-(6-chloro-2,8-dimethyl-1,2,3,4-tetrahydroisoquinolin-4-yl)phenyl]sulfonyl)formamide]

Example 38

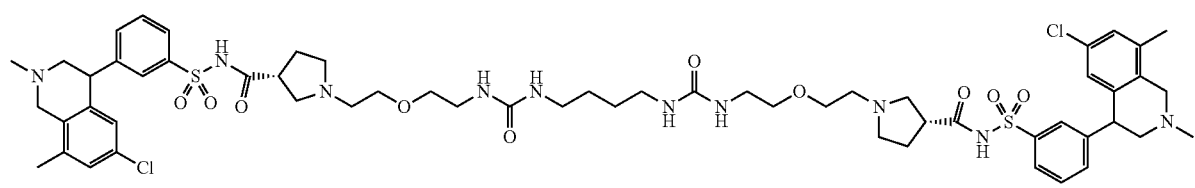

Example 39: 1,1'-[(3R,3'R)-(7,14-Dioxo-3,18-dioxa-6,8,13,15-tetraazaicosane-1,2-diyl)bis(pyrrolidine-1,3-diyl)]bis[N-([3-(6-chloro-8-cyano-2-methyl-1,2,3,4-tetrahydroisoquinolin-4-yl)phenyl]sulfonyl)formamide]

Example 39

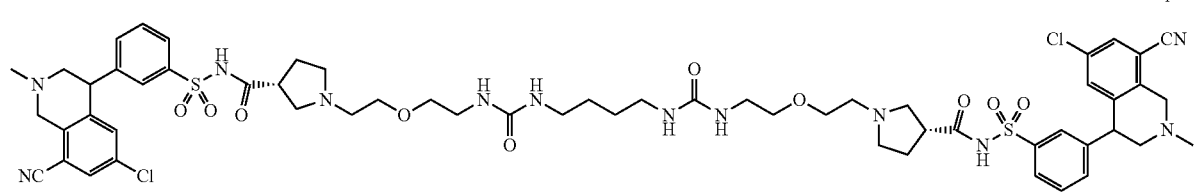

Example 40: 1,1'-(5,12-Dioxo-4,6,11,13-tetraaza-hexadecane-1,16-diyl)bis[N-([3-(6,8-dichloro-2-methyl-1,2,3,4-tetrahydroisoquinolin-4-yl)phenyl]sulfonyl)piperidine-4-carboxamide]

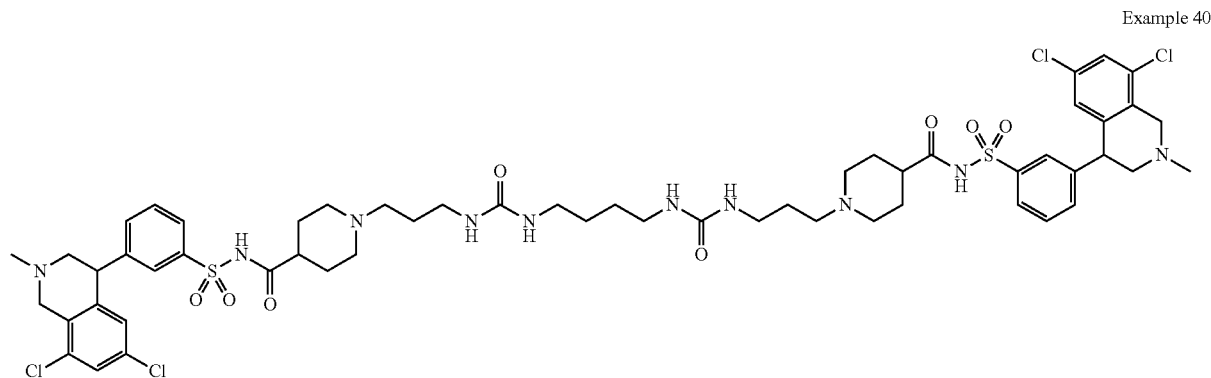

Example 40

Example 41: 1,1'-(5,12-Dioxo-4,6,11,13-tetraaza-hexadecane-1,16-diyl)bis[N-([3-(6,8-dichloro-2-methyl-1,2,3,4-tetrahydroisoquinolin-4-yl)phenyl]sulfonyl)piperidine-4-carboxamide]

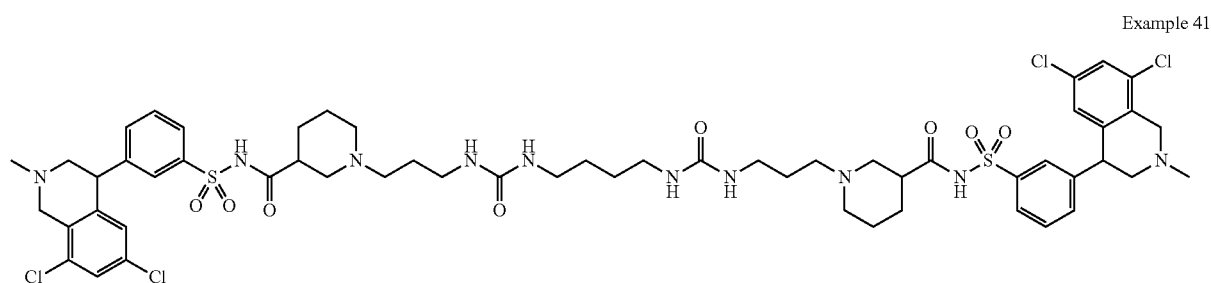

Example 41

Example 42: $N^1,N^{18}$-Bis([3-(6,8-Dichloro-2-dimethyl-1,2,3,4-tetrahydroisoquinolin-4-yl)phenyl]sulfonyl)-6,13-dioxo-5,7,12,14-tetraazaoctadecanediamide]

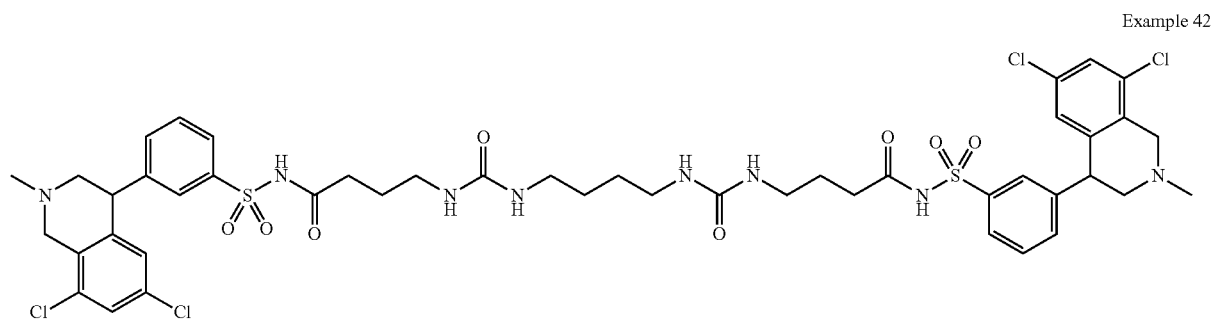

Example 42

General Scheme for Synthesis of Amide Linker Dimer Products:
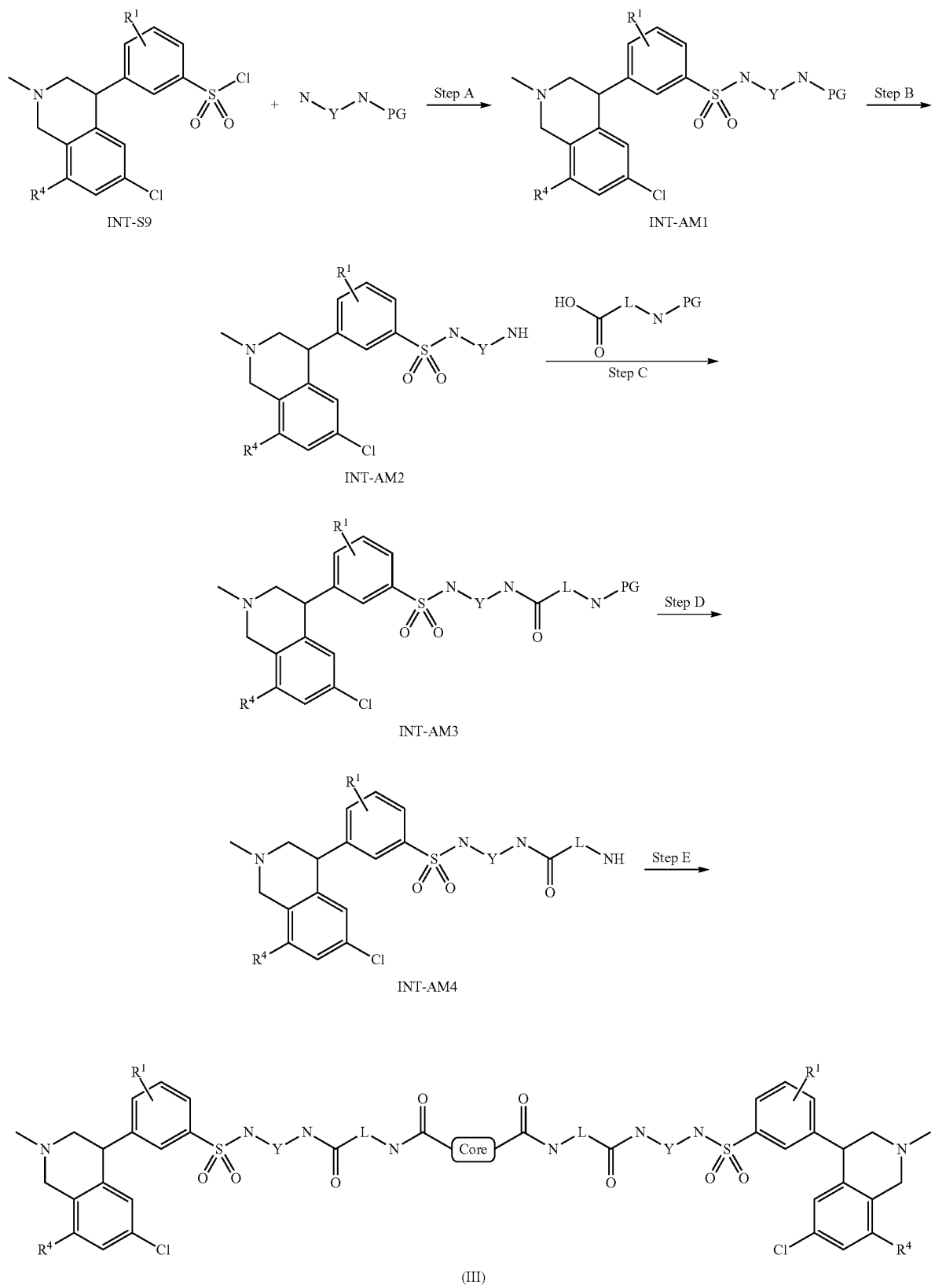
(III)

According to the General Scheme for the synthesis of compounds of structure (III), the previously described sulfonyl chloride INT-S9 is combined with a mono-protected diamine substrate (acyclic or non-cyclic) in the presence of a base such as triethylamine, pyridine, sodium or potassium carbonate, or the like to yield sulfonamide INT-AM1. The protecting group PG is removed with the appropriate conditions, such as trifluoroacetic acid or hydrogen chloride for a Boc group or sodium hydroxide or sodium carbonate in methanol for a trifluoracetamide. The amine obtained (INT-AM2) is reacted with a protected amino acid or other substrate with a masked reactive functionality through acid chloride formation with oxalyl chloride or thionyl chloride or through coupling reagents such as EDC, CDI, DCC, HATU, and the like to yield amides INT-AM3. Removal of the protecting group PG with the appropriate conditions, such as trifluoroacetic acid or hydrogen chloride for a Boc group or sodium hydroxide or sodium carbonate in methanol for a trifluoracetamide yields the desired amine INT-AM4 in Step D. Dimerization with an appropriate bisfunctional "core" molecule such as 1,1'-carbonyldiimidazole or 1,4-diisocyanatobutane in the presence of a base including amine bases like triethylamine or pyridine or carbonates as necessary provides compounds of the structure (III).

The following examples are synthesized through the General Reaction Scheme for compounds of structure (III) using the appropriate sulfonamides INT-S9, mono-protected diamines such as (R) and (S)-1-Boc-3-aminopyrrolidine or 1-Boc-4-aminopiperidine, protected amino acids, and core bisfunctional compounds.

Example 43: N,N'-[(3S,3'S)-(6,13-Dioxo-5,7,12,14-tetraazaoctadecanedioyl)bis(pyrrolidine-1,3-diyl)]bis[3-(6-chloro-2,8-dimethyl-1,2,3,4-tetrahydroisoquinolin-4-yl)benzenesulfonamide]

Example 43

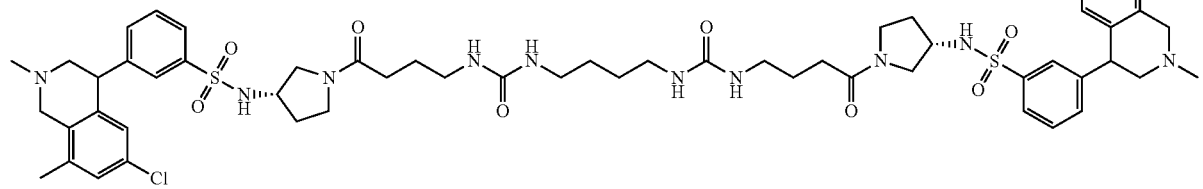

Example 44: N,N'-[(3S,3'S)-(6,13-Dioxo-5,7,12,14-tetraazaoctadecanedoyl)bis(pyrrolidine-1,3-diyl)]bis[3-(6-chloro-8-cyano-2-methyl-1,2,3,4-tetrahydroisoquinolin-4-yl)benzenesulfonamide]

Example 44

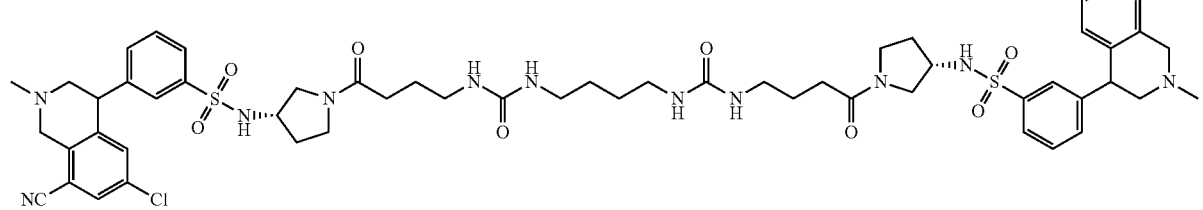

Example 45: N,N'-[(6,13-Dioxo-5,7,12,14-tetraazaoctadecanedioyl)bis(piperidine-1,4-diyl)]bis[3-(6-chloro-2,8-dimethyl-1,2,3,4-tetrahydroisoquinolin-4-yl)benzenesulfonamide]

Example 45

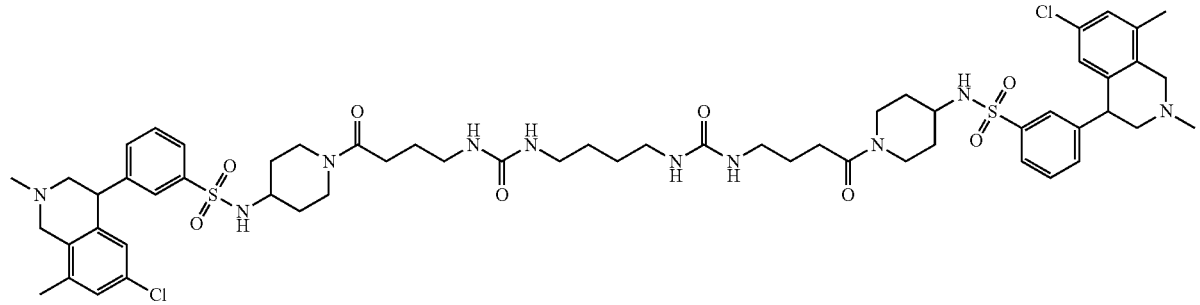

Example 46: N,N'-[(6,13-Dioxo-5,7,12,14-tetraazaoctadecanedioyl)bis(piperidine-1,4-diyl)]bis[3-(6-chloro-8-cyan-2-methyl-1,2,3,4-tetrahydroisoquinolin-4-yl)benzenesulfonamide]

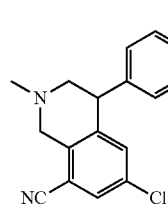
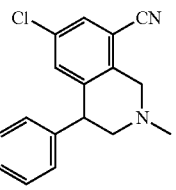

Example 46

Scheme for Synthesis of Geminal Dimethyl Linker Dimer Product:

Step A:

To a 100-mL 3-necked round-bottom flask purged and maintained with an inert atmosphere of nitrogen was added methyl 3-hydroxy-2,2-dimethylpropanoate (1.32 g, 10 mmol, 1 equiv), $CH_2Cl_2$ (40 mL), and 2,6-lutidine (1.6 g, 15 mmol, 1.5 equiv). This was followed by the dropwise addition of triflic anhydride ($Tf_2O$, 3.39 g, 12 mmol, 1.2 equiv) −78° C. The resulting solution was stirred for 15 min at −78° C. and then gradually warmed to room temperature over 3 h. The resulting solution was diluted with 100 mL of ethyl acetate and sequentially washed with 1×50 mL of water, 2×40 mL of 2 M hydrogen chloride, and 2×40 mL of brine. The mixture was dried over anhydrous sodium sulfate, filtered, and concentrated under vacuum. This resulted in 2.64 g (100% crude) of methyl 2,2-dimethyl-3-[(trifluoromethane)sulfonyloxy]propanoate INT-G as a brown oil.

Step B:

To a 100-mL round-bottom flask was added triflate INT-G1 (2.64 g, 10 mmol, 2 equiv). 2-(2-azidoethoxy)ethan-1-ol (INT-Y1, 650 mg, 5 mmol, 1 equiv), and DMF (40 mL). This was followed by the addition of sodium hydride (60% in oil, 400 mg, 10 mmol, 2 equiv) in portions at 0° C. The resulting slurry was stirred for 14 h at room temperature. The reaction was quenched by the slow addition of 100 mL of water and extracted with 3×50 mL of ethyl acetate. The combined organic layers were washed with 1×100 mL of water and 1×100 mL of brine, dried over anhydrous sodium sulfate, filtered, and concentrated under vacuum. This resulted in 1.23 g (100% crude) of methyl 3-[2-(2-azidoethoxy)ethoxy]-2,2-dimethylpropanoate (INT-G2) as a brown oil.

Step C:

To a 100-mL round-bottom flask was added ester INT-G2 (3.68 g, 15 mmol, 1 equiv), tetrahydrofuran (30 mL), and water (20 mL). This was followed by the addition of LiOH—$H_2O$ (1.26 g, 30 mmol, 2 equiv) in portions at room temperature. The resulting solution was stirred for 4 h at 50° C. The reaction mixture was cooled to room temperature and diluted with of water. The volatiles were removed under vacuum and the resulting mixture washed with 2×30 mL of petroleum ether. The pH of the aqueous layer was adjusted to 1-2 with 3 M aqueous hydrogen chloride and extracted with 3×40 mL of $CH_2Cl_2$. The combined organic layers were washed with 1×50 mL of water and 1×50 mL of brine, dried over anhydrous sodium sulfate, filtered, and concentrated under vacuum. This resulted in 2.4 g (69% crude) of 3-[2-(2-azidoethoxy)ethoxy]-2,2-dimethylpropanoic acid (INT-G3) as a light yellow oil.

Step D:

To a 100-mL round-bottom flask was added carboxylic acid INT-G3 (2.4 g, 10.4 mmol, 1 equiv), toluene (30 mL), and triethylamine (2.1 g, 20.8 mmol, 2 equiv). This was followed by the dropwise addition of DPPA (4.1 g, 14.9 mmol, 1.5 equiv) with stirring at room temperature. The resulting solution was stirred for 1 h at room temperature. Water (10 mL) was added and the resulting slurry allowed to react with stirring for an additional 14 h at reflux. The resulting solution was diluted with 40 mL of water and hydrogen chloride (3 $M_{(aq)}$, 20 mL). The resulting mixture was washed with 1×50 mL of petroleum ether. The pH value of the aqueous layer was adjusted to 13-14 with sodium hydroxide and extracted with 3×50 mL of $CH_2Cl_2$. The combined organic layers were washed with 1×50 mL of water and 1×50 mL of brine, dried over anhydrous sodium sulfate, filtered, and concentrated under vacuum. This resulted in 1.5 g (71% crude) of 1-(2-amino-2-methylpropoxy)-2-(2-azidoethoxy)ethane (INT-G4) as a light yellow oil.

Step E:

To a 50-mL round-bottom flask was added amine INT-G4 (202 mg, 1 mmol, 2 equiv), $CH_2Cl_2$ (20 mL), and triethylamine (102 mg, 1 mmol, 2 equiv). This was followed by the addition of 3-[(4S)-6,8-dichloro-2-methyl-1,2,3,4-tetrahydroisoquinolin-4-yl]benzene-1-sulfonyl chloride hydrochloride (Charmont et al, WO 2010078449, 210 mg, 0.5 mmol, 0.5 equiv), in portions at room temperature. The resulting solution was stirred overnight at room temperature. The resulting mixture was concentrated under vacuum. The residue was applied onto a silica gel column with ethyl acetate/petroleum ether (1:2-2:1) providing 180 mg (66%) of (4S)-4-[3-([1-[2-(2-azidoethoxy)ethoxy]-2-methylpropan-2-yl]sulfamoyl)phenyl]-6,8-dichloro-2-methyl-1,2,3,4-tetrahydroisoquinoline (INT-G5) as a yellow oil.

Step F:

To a 100-mL round-bottom flask was added azide INT-G5 (300 mg, 0.54 mmol, 1 equiv), methanol (50 mL), and palladium on carbon (30 mg). To the above $H_{2(g)}$ was introduced in. The resulting solution was stirred vigorously for 3 h at room temperature. The solids were removed by filtration and the filtrate concentrated under vacuum. The residue was applied onto a silica gel column with $CH_2Cl_2$/ methanol (10:1) providing 120 mg (42%) of N-[1-[2-(2-aminoethoxy)ethoxy]-2-methylpropan-2-yl]-3-[(4S)-6,8-dichloro-2-methyl-1,2,3,4-tetrahydroisoquinolin-4-yl]benzene-1-sulfonamide (INT-G6) as a white solid.

Step G:

To a 100-mL round-bottom flask was added amine INT-G6 (120 mg, 0.23 mmol, 1 equiv), DMF (4.8 mL), 1,4-diisocyanatobutane (5.8 mg, 0.04 mmol, 0.50 equiv). The resulting solution was stirred 1 overnight at 40° C. The solids were filtered out and the crude product was purified by preparative-HPLC with the following conditions: Column, XBridge Preparative C18 OBD Column, 19*150 mm; 5 μm; mobile phase, water (10 mmol/L NH$_4$HCO$_3$) and ACN (55.0% ACN up to 95.0% in 8 min); Detector. UV 254 nm.

Example 47: 3-(2-[2-[2-([3-[(4S)-6,8-dichloro-2-methyl-1,2,3,4-tetrahydroisoquinolin-4-yl]benzene]sulfonamido)-2-methylpropoxy]ethoxy]ethyl)-1-(4-[[(2-[2-[2-([3-[(4S)-6,8-dichloro-2-methyl-1,2,3,4-tetrahydroisoquinolin-4-yl]benzene]sulfonamido)-2-methylpropoxy]ethoxy]ethyl)carbamoyl]amino]butyl)urea

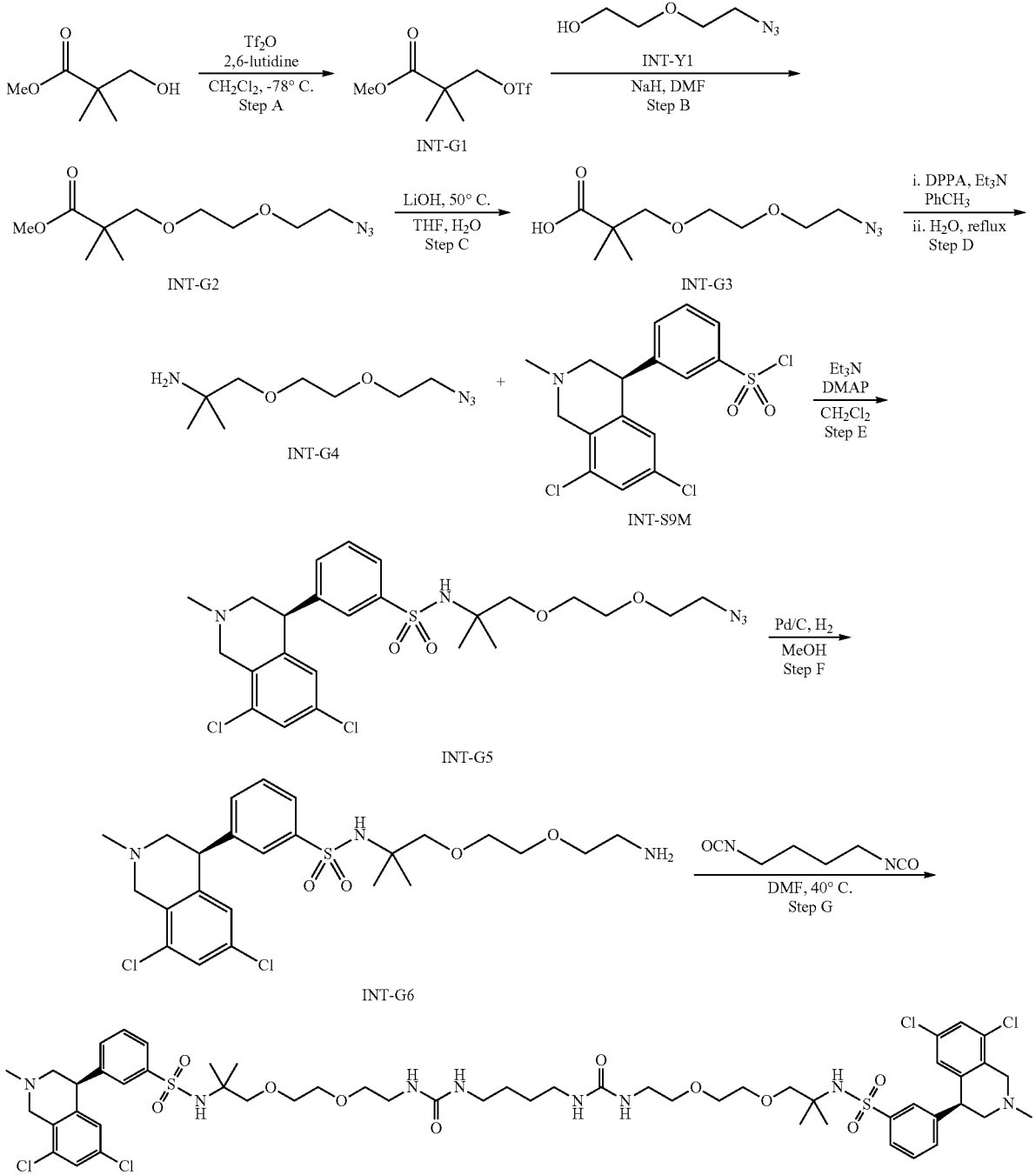

Example 47

Steps A-G resulted in 39 mg (14%) of the title compound as a white solid. MS (m z): 1201.05 [M+H]+. 1H NMR (Methanol-d4, 400 MHz) δ 7.87-7.80 (m, 2H), 7.68 (s, 2H), 7.57-7.50 (m, 4H), 7.37 (s, 2H), 6.78 (s, 2H), 4.42 (t, J=6.8 Hz, 2H), 3.73 (AB q, J=16.0 Hz, 4H), 3.60-3.48 (m, 12H), 3.32-3.28 (m, 8H), 3.14-3.04 (m, 6H), 2.67 (dd, J=11.6 Hz, 8.0 Hz, 2H), 2.53 (s, 6H), 1.47 (s, 4H), 1.11 (d, J=8.4 Hz, 12H).

Representative Scheme for the Synthesis of Aminoalcohol Linker Dimer Products:

Step A:

To a 250-mL round-bottom flask was added tert-butyl 4-hydroxypiperidine-1-carboxylate (564.2 mg, 2.80 mmol, 1 equiv), DMF (100 mL), and INT-Y2 (750 mg, 2.63 mmol, 1.1 equiv). This was followed by the addition of 60% sodium hydride (260 mg, 6.5 mmol, 2.5 equiv) in several batches at 0° C. The resulting solution was stirred for 3 h at 30° C. The reaction was then quenched by the addition of 50 mL of water and extracted with 3×100 mL of ethyl acetate. The combined organic layers were washed with 3×150 mL of brine, dried over anhydrous sodium sulfate, and concentrated under vacuum. This resulted in 800 mg (crude) of tert-butyl 4-[2-(2-azidoethoxy)ethoxy]piperidine-1-carboxylate (INT-AA1) as a colorless oil.

Step B:

To a 100-mL round-bottom flask, was added INT-AA1 (800 mg, 2.54 mmol, 1 equiv), CH2Cl2 (100 mL), and trifluoroacetic acid (10 mL). The resulting solution was stirred for 30 min at room temperature. The pH value of the solution was adjusted to 14 with saturated aqueous potassium carbonate and extracted with 3×150 mL of CH2Cl2. The combined organic layers were washed with 3×150 mL of brine, dried over anhydrous sodium sulfate, and concentrated under vacuum. This resulted in 350 mg (crude) of 4-[2-(2-azidoethoxy)ethoxy]piperidine (INT-AA2) as a colorless oil.

Step C:

To a 250-mL round-bottom flask was added amine INT-AA2 (350 mg, 1.63 mmol, 2 equiv), sulfonyl chloride INT-SM9 (700 mg, 1.79 mmol, 1 equiv), CH2Cl2 (15 mL), and triethylamine (3 mL). The resulting solution was stirred for 30 min at room temperature. The resulting mixture was concentrated under vacuum. The residue was applied onto a silica gel column with ethyl acetate/petroleum ether (1:1) providing 700 mg (69%) of (4S)-4-(3-[4-[2-(2-azidoethoxy)ethoxy]piperidine-1-sulfonyl]phenyl)-6,8-dichloro-2-methyl-1,2,3,4-tetrahydroisoquinoline (INT-AA3) as a light yellow solid.

Step D:

To a 250-mL round-bottom flask purged and maintained with an inert atmosphere of nitrogen was added azide INT-AA3 (700 mg, 1.23 mmol, 1 equiv), tetrahydrofuran (150 mL), water (30 mL), and PPh3 (645.7 mg, 2.46 mmol, 2 equiv). The resulting solution was stirred for 3 h at 60° C. The reaction was then quenched by the addition of 25 mL of water and extracted with 3×150 mL of CH2Cl2. The combined organic layers were washed with 3×250 mL of brine, dried over anhydrous sodium sulfate, and concentrated under vacuum. The residue was applied onto a silica gel column with CH2Cl2:methanol:triethylamine (10:1:0.1) providing 350 mg (52%) of 2-(2-[1-([3-[(4S)-6,8-dichloro-2-methyl-1,2,3,4-tetrahydroisoquinolin-4-yl]benzene]sulfonyl)piperidin-4-yl]oxy]ethoxy)ethan-1-amine (INT-AA4) as a yellow solid Step E:

To a 100-mL round-bottom flask was added amine INT-AA4 (100 mg, 0.18 mmol, 1 equiv), DMF (30 mL), and 1,4-diisocyanatobutane (11 mg, 0.08 mmol, 0.45 equiv). The resulting solution was stirred for 1 h at 60° C. The solids were collected by filtration. The crude product was purified by preparative-HPLC with the following conditions: Column, XBridge C18 OBD Preparative Column, 19*250 mm; 5 μm; mobile phase, waters and ACN (75.0% ACN up to 93.0% in 8 min); Detector, UV 254 nm.

Example 48: 1-[2-(2-[(1-[(3-[(S)-6,8-Dichloro-2-methyl-1,2,3,4-tetrahydroisoquinolin-4-yl]phenyl)sulfonyl]piperidin-4-yl)oxyethoxy)ethyl]-3-[4-(3-[2-(2-[(1-[(3-[(S)-6,8-Dichloro-2-methyl-1,2,3,4-tetrahydroisoquinolin-4-yl]phenyl)sulfonyl]piperidin-4-yl)oxy]ethoxy)ethyl]ureido)butyl]urea

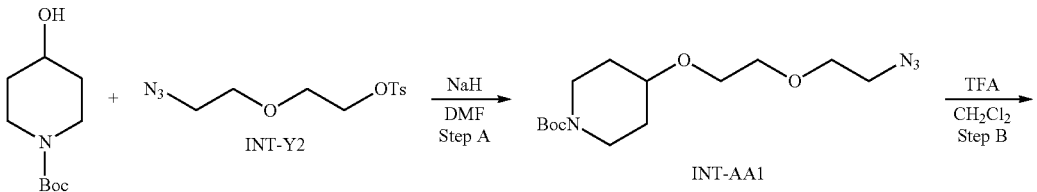

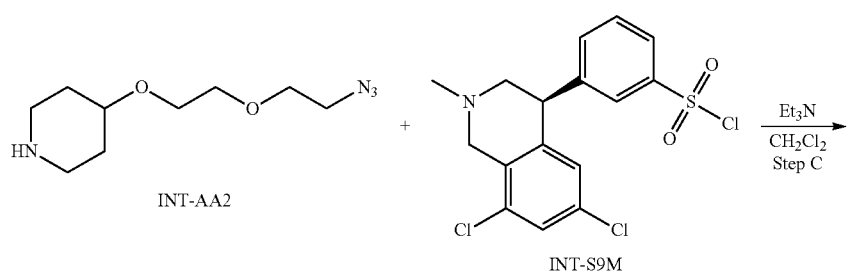

-continued

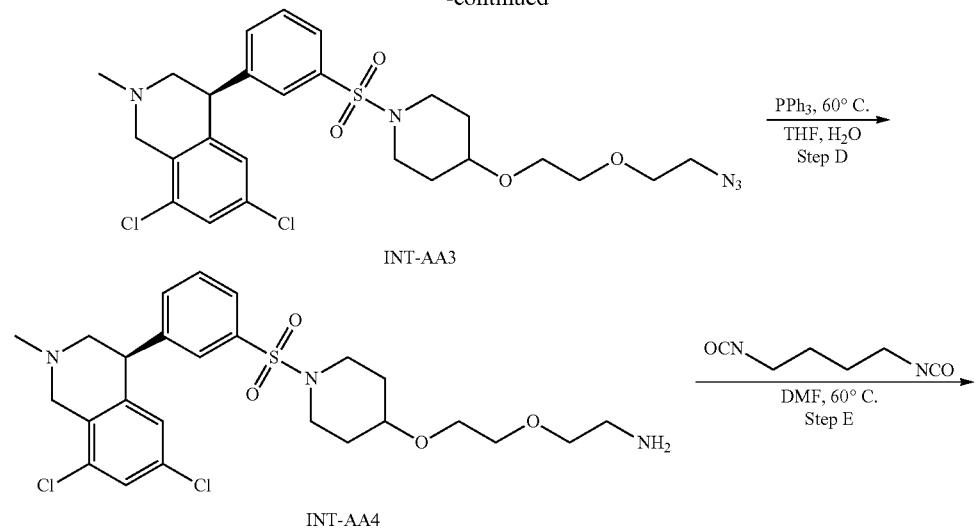

INT-AA3

INT-AA4

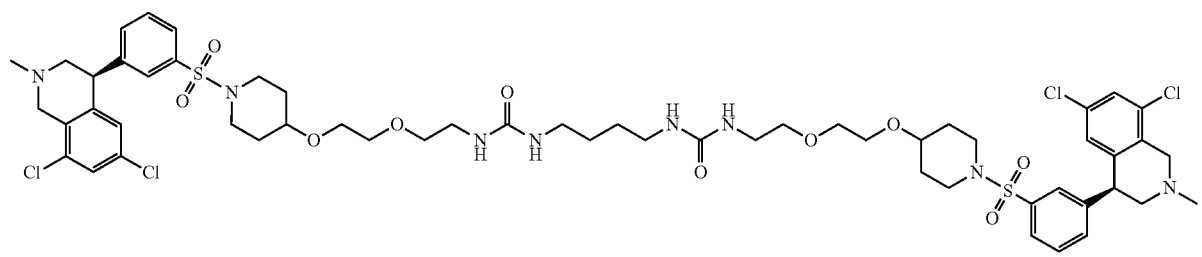

Example 48

Steps A-E provided in 45.3 mg (20%) of the title compound as a white solid. MS (m/z): 1225.55 [M+H]$^+$. $^1$H NMR (Methanol-d4, 400 MHz) δ 7.67 (t, 0.1=3.0 Hz, 2H), 7.62-7.50 (m, 6H), 7.36 (d, J=2.8 Hz, 2H), 6.81 (s, 2H), 4.41 (d, J=6.8 Hz, 2H), 3.70 (AB q, J=17.2 Hz, 4H), 3.54 (t, J=5.4 Hz, 8H), 3.49-3.36 (m, 7H), 3.30-3.20 (m, 8H), 3.10 (dd, J=5.6, 5.6 Hz, 4H), 3.10-2.98 (m, 2H), 2.85-2.70 (m, 4H), 2.66 (dd. J=6.4, 5.4 Hz, 2H), 2.47 (s, 6H), 1.86 (t, J=5.0 Hz, 4H), 1.62 (d, J=3.6 Hz, 4H), 1.48 (t, J=4.2 Hz, 4H), 1.31-1.28 (m, 1H).

Example 49: 1-(2-(2-(((R)-1-((3-((S)-6,8-dichloro-2-methyl-1,2,3,4-tetrahydroisoquinolin-4-yl)phenyl)sulfonyl)pyrrolidin-3-yl)oxy)ethoxy)ethyl)-3-(4-(3-(2-(2-(((R)-1-((3-((S)-6,8-dichloro-2-methyl-1,2,3,4-tetrahydroisoquinolin-4-yl)phenyl)sulfonyl)pyrrolidin-3-yl)oxy)ethoxy)ethyl)ureido)butyl)urea Beginning with 1-Boc-3-(R)-hydroxypyrrolidine, Steps A-E provided crude product that was purified by preparative-HPLC with the following conditions: Column, XBridge Preparative C18 OBD Column, 5 um, 19*150 mm; mobile phase, waters (10 mmol/L NH$_4$HCO$_3$) and ACN (40.0% ACN up to 65.0% in 8 min); Detector, UV 254 nm. This resulted in 25.2 mg (7%) of the title compound as a white solid. MS (m/z): 1197.4 [M+H]$^+$. $^1$H NMR (Methanol-d4, 400 MHz) δ 7.76-7.75 (m, 2H), 7.61-7.59 (m, 6H), 7.38 (d, J=2.0 Hz, 2H), 6.84 (s, 2H), 4.46-4.42 (m, 2H), 4.03-4.02 (m, 2H), 3.73 (AB q, J=6.0 Hz, 5H), 3.51-3.41 (m, 4H), 3.29-3.25 (m, 7H), 3.20-3.13 (m, 6H), 3.05-3.03 (m, 2H), 2.68-2.65 (m, 2H), 2.50 (s, 6H), 1.97-1.94 (m, 2H), 1.88-1.83 (m, 2H), 1.50-1.47 (m, 5H), 1.37-1.32 (m, 2H).

Example 49

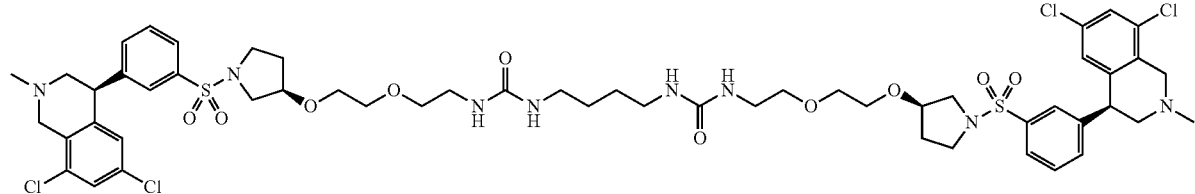

Example 50: 1-(2-[2-([(S)-1-[(3-[(S)-6,8-dichloro-2-methyl-1,2,3,4-tetrahydroisoquinolin-4-yl]phenyl)sulfonyl]pyrrolidin-3-yl]oxy)ethoxy]ethyl)-3-(4-[3-(2-[2-([(S)-1-(3-[(S)-6,8-dichloro-2-methyl-1,2,3,4-tetrahydroisoquinolin-4-yl]phenyl)sulfonyl]pyrrolidin-3-yl]oxy)ethoxy]ethyl)ureido]butyl)urea Example 50

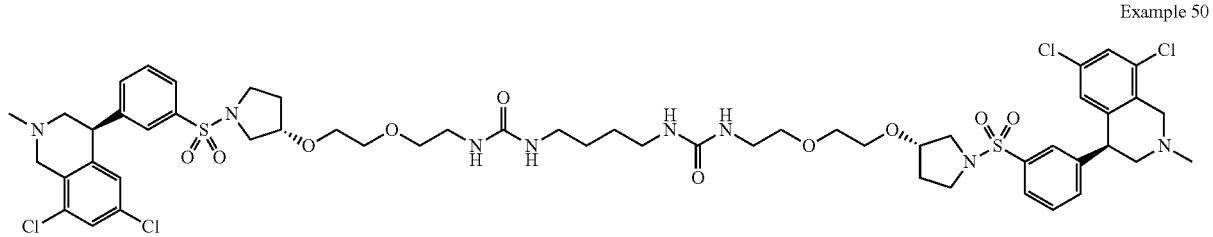

Beginning with 1-Boc-3-(S)-hydroxypyrrolidine, Steps A-E provided crude product that was purified by preparative-HPLC with the following conditions: Column, XBridge Preparative C, 18 OBD Column, 5 μm, 19*150 mm; mobile phase, water (10 mmol/L NH$_4$HCO$_3$) and ACN (60.0% ACN up to 80.0% in 8 min): Detector, UV 254 nm. This resulted in 50.4 mg (12%) of the title compound as a white solid. MS (m/z): 1197.3 [M+H]$^+$. $^1$H NMR (Methanol-d4, 400 MHz) δ 7.77-7.65 (m, 2H), 7.65 (s, 2H), 7.58 (d, J=1.6 Hz, 4H), 7.38 (d, J=2.0 Hz, 2H), 6.88 (d, J=1.6 Hz, 2H), 4.89-4.43 (m, 2H), 4.03-4.02 (m, 2H), 3.72 (AB q, J=15.2 Hz, 4H), 3.46-3.40 (m, 13H), 3.30-3.24 (m, 12H), 3.16-3.13 (m, 4H), 3.06-3.02 (m, 2H), 2.51 (s, 6H), 2.68 (q, J=6.4 Hz, 2H), 1.96-1.93 (m, 2H), 1.82-1.80 (m, 2H), 1.51-1.49 (m, 4H).

Scheme for Synthesis of α-Alkyl Linker Dimer Products:

Step A:

To a 250-mL round-bottom flask was added sulfonyl chloride INT-S9M (600 mg, 1.40 mmol, 1 equiv), (2R)-2-amino-3-methylbutan-1-ol (507 mg, 4.91 mmol, 3.5 equiv), CH$_2$Cl$_2$ (50 mL), and triethylamine (0.9 mL, 5 equiv). The resulting solution was stirred for 30 min at room temperature. The resulting mixture was concentrated under vacuum. The residue was applied onto a silica gel column with CH$_2$Cl$_2$/methanol (25:1) providing 515 mg (80%) of (2R)—S-[3-[(4S)-6,8-dichloro-2-methyl-1,2,3,4-tetrahydroisoquinolin-4-yl]phenyl]-1-hydroxy-3-methylbutane-2-sulfonamido (INT-AA5) as a white solid.

Step B:

To a 100-mL round-bottom flask purged and maintained with an inert atmosphere of nitrogen was added alcohol INT-AA5 (510 mg, 1.11 mmol, 1 equiv), tosylate INT-Y2 (477 mg, 1.67 mmol, 1.5 equiv), DMF (20 mL), and 95% sodium hydride (178 mg, 7.42 mmol, 4 equiv). The resulting slurry was stirred overnight at 30° C. The reaction was then quenched by the addition of 50 mL of water and extracted with 3×100 mL of ethyl acetate. The combined organic layers were washed with 2×50 mL of brine, concentrated under vacuum, and dried in an oven under reduced pressure. The residue was applied onto a silica gel column with CH$_2$Cl$_2$/methanol (20:1) providing 283 mg (44%) of (4S)-4-(3-[[(2R)-1-[2-(2-azidoethoxy)ethoxy]-3-methylbutan-2-yl]sulfamoyl]phenyl)-6,8-dichloro-2-methyl-1,2,3,4-tetrahydroisoquinoline (INT-AA6) as a yellow oil.

Step C:

To a 250-mL round-bottom flask was added azide INT-AA6 (270 mg, 0.47 mmol, 1 equiv), tetrahydrofuran (54 mL), water (7 mL), and triphenylphosphine (372 mg, 1.42 mmol, 3 equiv). The resulting solution was stirred for 2 h at 60° C. in an oil bath. The resulting solution was diluted with water and extracted with 3×50 mL of CH$_2$Cl$_2$. The combined organic layers were washed with 1×50 mL of brine, dried over anhydrous sodium sulfate, and concentrated under vacuum. The residue was applied onto a silica gel column with CH$_2$Cl$_2$/methanol (10:1) providing 156 mg (61%) of N-[(2R)-1-[2-(2-aminoethoxy)ethoxy]-3-methylbutan-2-yl]-3-[(4S)-6,8-dichloro-2-methyl-1,2,3,4-tetrahydroisoquinolin-4-yl]benzene-1-sulfonamide (INT-AA7) as a yellow oil.

Step D:

To a 50-mL round-bottom flask was added amine INT-AA7 (156 mg, 0.29 mmol, 1 equiv), DMF (7 mL), and 1,4-diisocyanatobutane (20 mg, 0.14 mmol, 0.5 equiv). The resulting solution was stirred for 1 h at 60° C. in an oil bath. The reaction mixture was concentrated under vacuum.

Example 51: 3-[(S)-6,8-Dichloro-2-methyl-1,2,3,4-tetrahydroisoquinolin-4-yl]-N-[(3R,28R)-28-[(3-(S)-6,8-dichloro-2-methyl-1,2,3,4-tetrahydroisoquinolin-4-yl]phenyl)sulfonamido]-2,29-dimethyl-12,19-dioxo-5,8,23,26-tetraoxa-11,13,18,20-tetraazariacontan-3-yl]benzenesulfonamide

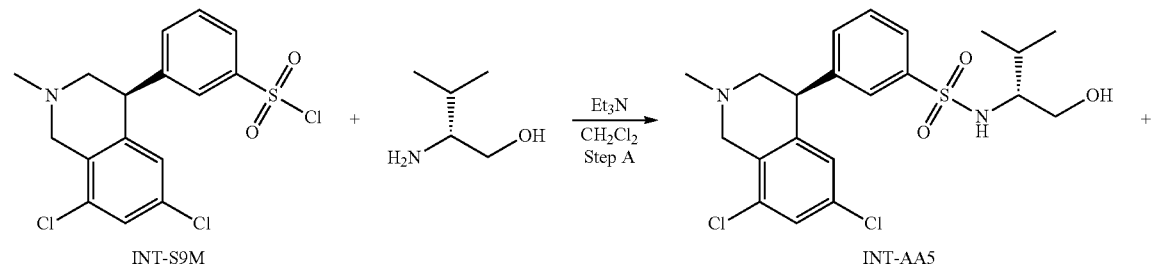

INT-S9M                                    INT-AA5

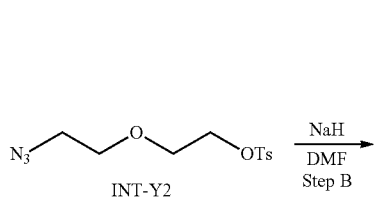

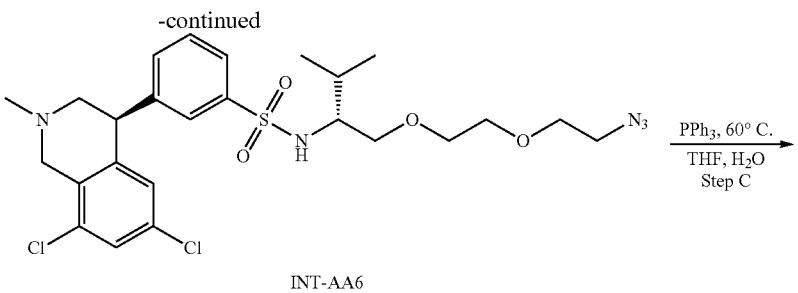

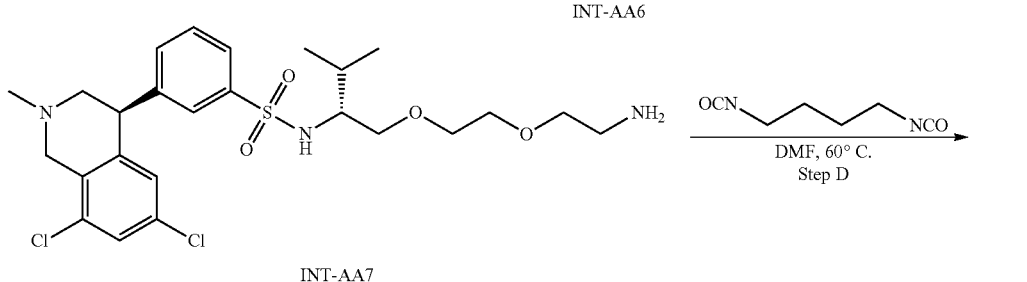

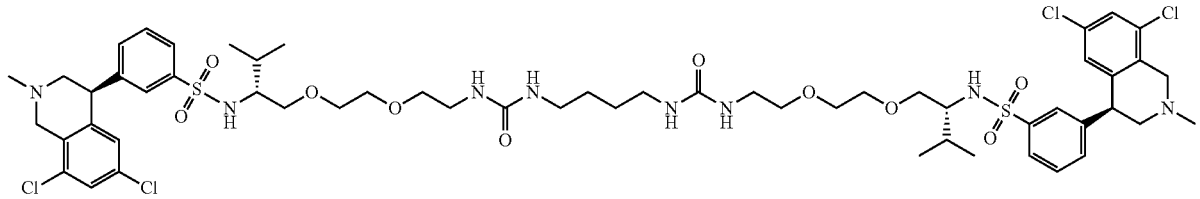

Example 51

The crude product was purified by preparative-HPLC with the following conditions: Column, XBridge C18 OBD Preparative Column, 19*250 mm; mobile phase, water (10 mmolL/L NH$_4$HCO$_3$) and ACN (75.0% ACN up to 90.0% in 9 min); Detector, UV 254 nm. This resulted in 31.6 g (18%) of the title compound as a white solid. MS (m/z): 1229.55 [M+H]+. $^1$H NMR (CDCl$_3$, 400 MHz) δ 7.82-7.67 (m, 4H), 7.50-7.40 (m, 4H), 7.25 (q, J=3.4 Hz, 2H), 6.70 (q, J=3.4 Hz, 2H), 5.95 (d, J=3.4 Hz, 2H), 5.40 (q, J=5.6 Hz, 2H), 5.02 (s, 2H), 4.30 (s, 2H), 3.82-3.48 (m, 15H) 3.45-3.30 (m, 6H), 3.25-3.10 (m, 7H), 3.05-2.95 (m, 4H), 2.72-2.60 (m, 2H), 2.48 (s, 6H), 1.90-1.80 (m, 2H), 1.46 (s, 4H), 1.25 (s, 1H), 0.81 (q, J=3.8 Hz, 12H).

General Scheme for Synthesis of Urea Dimer Products:

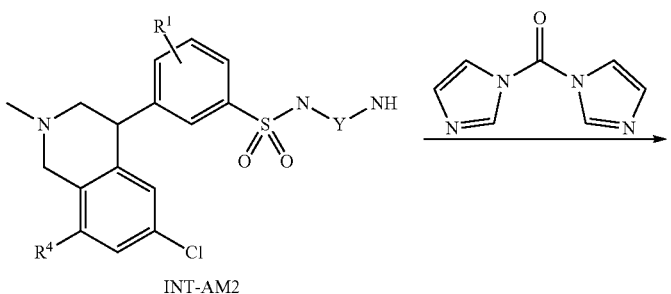

INT-AM2

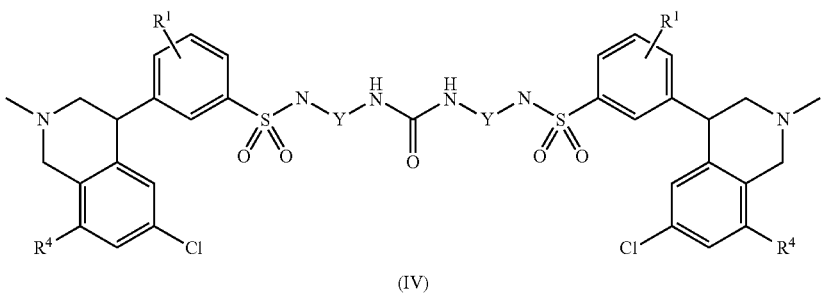

(IV)

According to the General Scheme for the synthesis of compounds of structure (IV), the elaborated structures such as INT-AM2, "monomers", are dimerized to the symmetric urea (IV) through reaction with 1,1'-carbonyldiimidazole or p-nitrophenylchloroformate or the like. Through this step, compounds such as Example 52 and 53 are prepared.

Example 52: N,N'-(10-Oxo-3,6,14,17-tetraoxa-9,11-diazanonadecane-1,19-diyl)bis[3-(6,8-dichloro-2-methyl-1,2,3,4-tetrahydroisoquinolin-4-yl)benzenesulfonamide

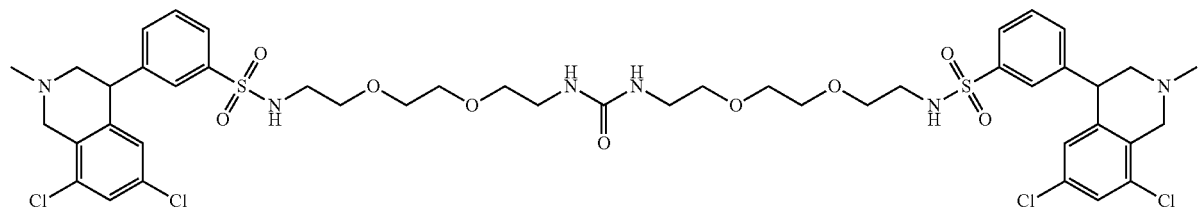

Example 52

Example 53: N,N'-[(3S,3'S)-(7-Oxo-3,11-dioxa-6,8-diazatridecane-1,13-diyl]bis[pyrrolidine-1,3-diyl))bis(3-(6,8-dichloro-2-methyl-1,2,3,4-tetrahydroisoquinolin-4-yl)benzenesulfonamide

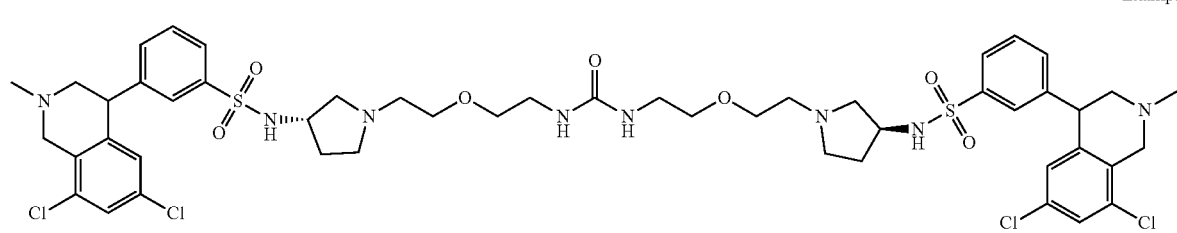

Example 53

Example 54: Cell-Based Assay of NHE-3 Activity (Pre-Incubation Inhibition)

Rat and human NHE-3-mediated $Na^+$-dependent $H^+$ antiport was measured using a modification of the pH sensitive dye method originally reported by Paradiso (*Proc. Natl. Acad. Sci. USA*. (1984) 81(23): 7436-7440). PS120 fibroblasts stably expressing human NHE3 and NHERF2 were obtained from Mark Donowitz (Baltimore, Md.). Opossum kidney (OK) cells were obtained from the ATCC and propagated per their instructions. The rat NHE-3 gene (GenBank M85300) was introduced into OK cells via electroporation, and cells were seeded into 96 well plates and grown overnight. Medium was aspirated from the wells then incubated for 30 min at 37° C. with $NH_4Cl$-HEPES buffer (20 mM $NH_4Cl_2$, 80 mM NaCl, 50 mM HEPES, 5 mM KCl, 2 mM $CaCl_2$, 1 mM $MgCl_2$, pH 7.4) containing 5 μM BCECF-AM. Cells were washed once with Ammonium free, $Na^+$-free HEPES (100 mM choline, 50 mM HEPES, 10 mM glucose, 5 mM KCl, 2 mM $CaCl_2$), 1 mM $MgCl_2$, pH 7.4) and incubated in the same buffer for 10 minutes at room temperature to lower intracellular pH with 0-30 μM test compound. After incubation, NHE-3-mediated recovery of neutral intracellular pH was initiated by addition of Na-HEPES buffer containing 0.4 uM ethyl isopropyl amiloride (EIPA, a selective antagonist of NHE-1 activity that does not inhibit NHE-3). Changes in intracellular pH were monitored using a FLIPR Tetra®® (Molecular Devices, Sunnyvale, Calif.) by excitation at $\lambda_{ex}$ 439 to 505 nm, and measuring BCECF fluorescence at $\lambda_{em}$ 538 nm. The initial rate of the fluorescence ratio change was used as a measure of NHE-mediated $Na^+/H^+$ activity, and reported as the change in fluorescence ratio per minute. Initial rates were plotted as the average of 2 or more replicates, and $pIC_{50}$ values were estimated using GraphPad Prism.

TABLE 2

Data for example in human Preincuba assay:

| Result | $pIC_{50}$ Range | % inhibition range |
|---|---|---|
| A | NHE3 $pIC_{50}$ <6 | NHE3 <40% |
| B | NHE3 $pIC_{50}$ 6-7 | 40-70% |
| C | NHE3 $pIC_{50}$ >7 | >70% |

| Example | $pIC_{50}$ | % inhibition |
|---|---|---|
| 12 | C | C |
| 24 | C | C |
| 47 | C | C |
| 48 | C | C |
| 49 | C | C |
| 50 | C | C |
| 51 | A | A |

Example 55: Cell-Based Assay of NHE-3 Activity (Persistent Inhibition)

The ability of compounds to inhibit human and rat NHE-3-mediated Na$^+$-dependent H$^+$ antiport after application and washout was measured using a modification of the pH sensitive dye method described above. PS120 fibroblasts stably expressing human NHE3 and NHERF2 were obtained from Mark Donowitz (Baltimore, Md.). Opossum kidney (OK) cells were obtained from the ATCC and propagated per their instructions. The rat NHE-3 gene was introduced into OK cells via electroporation, and cells were seeded into 96 well plates and grown overnight. Medium was aspirated from the wells, cells were washed once with NaCl-HEPES buffer (100 mM NaCl, 50 mM HEPES, 10 mM glucose, 5 mM KCl, 2 mM CaCl$_2$, 1 mM MgCl$_2$, pH 7.4), then overlayed with NaCl-HEPES buffer containing 0-30 µM test compound. After a 60 min incubation at room temperature, the test drug containing buffer was aspirated from the cells. Following aspiration, cells were washed once with NaCl-HEPES buffer without drug, then incubated for 30 min at 37° C. with NH$_4$Cl-HEPES buffer (20 mM NH$_4$Cl, 80 mM NaCl, 50 mM HEPES. 5 mM KCl, 2 mM CaCl$_2$), 1 mM MgCl$_2$, pH 7.4) containing 5 µM BCECF-AM. Cells were washed once with Ammonium free, Na$^+$-free HEPES (100 mM choline, 50 mM HEPES, 10 mM glucose. 5 mM KCl, 2 mM CaCl$_2$), 1 mM MgCl$_2$, pH 7.4) and incubated in the same buffer for 10 minutes at room temperature to lower intracellular pH. NHE-3-mediated recovery of neutral intracellular pH was initiated (10 min after compound washout) by addition of Na-HEPES buffer. For the rat NHE3 assay, the Na-HEPES buffer contained 0.4 µM ethyl isopropyl amiloride (EIPA, a selective antagonist of NHE-1 activity that does not inhibit NHE-3). Changes in intracellular pH were monitored using a FLIPR Tetra® (Molecular Devices, Sunnyvale, Calif.) by excitation at $\lambda_{ex}$ 439 to 505 nm, and measuring BCECF fluorescence at $\lambda_{em}$ 538 nm. The initial rate of the fluorescence ratio change was used as a measure of NHE-mediated Na$^+$/H$^+$ activity, and reported as the change in fluorescence ratio per minute. Initial rates were plotted as the average of 2 or more replicates, and pIC$_{50}$ values were estimated using GraphPad Prism.

TABLE 3

Data for example in human Persistence assay:

| Result | pIC$_{50}$ Range | % inhibition range |
|---|---|---|
| A | NHE3 pIC$_{50}$ <6 | NHE3 <40% |
| B | NHE3 pIC$_{50}$ 6-7 | 40-70% |
| C | NHE3 pIC$_{50}$ >7 | >70% |

| Example | pIC50 | % inhibition |
|---|---|---|
| 12 | C | C |
| 24 | C | C |
| 47 | B | C |
| 48 | B | C |
| 49 | B | C |
| 50 | B | C |
| 51 | A | A |

Example 56: Sustained Inhibition of Apical Acid Secretion in Human Organoid Monolayer Cell Cultures Basal media (BM) consists of advanced DMEM/F, 12 containing 10 mM HEPES (Invitrogen, 15630-080), 1:100 Glutamax (Invitrogen, 35050-061), and 1:100 penicillin/streptomycin (Invitrogen, 15140-122). Supplemented basal media (SBM) contains 1:100 N2 (Invitrogen, 17502-048), 1:50 B27 (Invitrogen, 12587-010), 1 mM N-acetylcysteine (Sigma, A9165), and 10 nM [Leu15]-gastrin I (Sigma, G9145). Growth factors used include 50 ng per mL mouse EGF (Peprotech. 315-09), 100 ng per mL mouse noggin (Peprotech, 250-38). 500 ng per mL human R-spondin 1 (R&D, 4645-RS), 100 ng per mL mouse Wnt-3a (R&D, 1324-WN), 20 µM Y-27632 (Tocris, 1254), 10 mM nicotinamide (Sigma, N0636), 500 nM A83-01 (Tocris, 2939), 10 µM SB202190 (Tocris, 1264). Transwells are 0.4 µm pore polyester membrane 24-well Transwell inserts (Corning). Cultures are incubated at 37° C. in 5% CO$_2$.

Human ileum organoids are cultured in WENRNAS (Wnt, EGF, noggin, R-spondin1, nicotinamide, A83-01, SB202190) and typically grown for 7-12 days before being used to plate monolayer cultures. On day 0, organoid cultures embedded in Matrigel are treated with TrypLE Express to break organoids into small pieces and/or single cells. The cells are resuspended to 0.5×10$^6$ cells/mL in SBM containing WENRAY (Wnt, EGF, noggin, R-spondin1, A83-01, Y-27632). Following this step, 200 µL of cell suspension is plated into the apical side of a 24-well Transwell (100,000 cells/well) and 600 µL of SBM with WENRAY is added to the basolateral side. Ileum cells are differentiated with ENRA (EGF, noggin, R-spondin 1, A83-01) on day 3. The color of apical compartment turns from pink or orange to yellow due to the increase in NHE3 expression after differentiation.

Each human ileum monolayer culture well is washed twice with fresh SBM on the apical side on day 6 before compound dosing. All compound stocks are 10 mM dissolved in DMSO. Each compound stock is individually mixed with fresh SBM to reach final compound concentration 1 µM and dosed only on the apical side of the monolayer (total volume 200 µl). DMSO at the equivalent concentration i used as the vehicle control. Duplicate wells are dosed for each compound. On day 8, apical media pH is measured by pH electrode, to determine the ability of example compounds to produce sustained inhibition of NHE3 activity in a human monolayer culture system by preventing proton secretion into the apical compartment. Each of the duplicate apical pH values for each example compound is compared to the average of the DMSO wells and expressed as a percent inhibition of apical acid secretion.

Example 57: Increased Trans-Epithelial Resistance in Human Organoid Monolayer Cell Cultures Basal media (BM) consists of advanced DMEM/F, 12 containing 10 mM HEPES (Invitrogen, 15630-080), 1:100 Glutamax (Invitrogen, 35050-061), and 1:100 penicillin/streptomycin (Invitrogen, 15140-122). Supplemented basal media (SBM) contains 1:100 N2 (Invitrogen, 17502-048), 1:50 B27 (Invitrogen, 12587-010), 1 mM N-acetylcysteine (Sigma, A9165), and 10 nM [Leu15]-gastrin I (Sigma, G9145). Growth factors used include 50 ng per mL mouse EGF (Peprotech, 315-09), 100 ng per mL mouse noggin (Peprotech, 250-38). 500 ng per mL human R-spondin 1 (R&D, 4645-RS), 100 ng per mL mouse Wnt-3a (R&D, 1324-WN), 20 µM Y-27632 (Tocris, 1254), 10 mM nicotinamide (Sigma, N0636), 500 nM A83-01 (Tocris, 2939), 10 µM SB202190 (Tocris, 1264). Transwells are 0.4 µm pore polyester membrane 24-well Transwell inserts (Corning). Cultures are incubated at 37° C. in 5% CO$_2$.

Human duodenum organoids are cultured in WENRNAS (Wnt, EGF, noggin, R-spondin1, nicotinamide, A83-01, SB202190) and typically grown for 7-12 days before being used to plate monolayer cultures. On day 0, organoid cultures embedded in Matrigel are treated with TrypLE Express to break organoids into small pieces and/or single cells. The cells are resuspended to $0.5 \times 10^6$ cells/mL in SBM containing WENRAY (Wnt, EGF, noggin, R-spondin1, A83-01, Y-27632). Following this step, 200 µL of cell suspension is plated into the apical side of a 24-well Transwell (100,000 cells/well) and 600 µL of SBM with WENRAY is added to the basolateral side. Duodenum cells are differentiated with ENA (EGF, noggin, A83-01) on day 3. The color of apical compartment turns from pink or orange to yellow due to the increase in NHE3 expression after differentiation.

Each human duodenum monolayer culture well is washed twice with fresh SBM on the apical side on day 6 or day 7 before dosing. All compound stocks are 10 mM dissolved in DMSO. Each compound stock is individually mixed with fresh SBM to reach final compound concentration 1 µM and dosed only on the apical side of the monolayer (total volume 200 µl). DMSO at the equivalent concentration is used as the vehicle control. Duplicate wells are dosed for each compound. Transepithelial electrical resistance (TEER) is used as a quantitative technique to measure of tight junction permeability. TEER values are recorded (MERS00002, Millipore) before dosing and 30 mins and 1 hr after dosing for all wells. Each of the duplicate TEER values following treatment is corrected for the individual well baseline TEER. Baseline corrected TEER for each example compound is compared to the average of the DMSO wells and expressed as a percent TEER of vehicle control.

Example 58: Inhibition of Intestinal Sodium Absorption in Mice

Urinary and fecal sodium excretion are measured to assess the ability of selected example compounds to inhibit the absorption of sodium from the intestinal lumen. In addition, an assessment of the absence or presence of diarrhea in response to compound treatment is made. Approximately eight-week old, male. CD-1 mice are purchased from Envigo (Livermore, Calif.), are housed 6 per cage and acclimated for at least 48 hours before study initiation. Animals are fed Harlan Teklad Global TD. 160470 rodent chow (Maddison, Wis.), standard laboratory rodent chow Harlan Teklad Global 2018 with the addition of 0.4% inorganic phosphorous. Animals have ad libitum access to food and water for the duration of the study and are maintained in a temperature and humidity controlled room on a standard light/dark cycle of 6 AM to 6 PM. To initiate the study, mice are weighed and then individually placed in metabolic cages. Following a 3-day acclimation period to the metabolic cage, a 24-hr baseline collection of urine and feces is performed. Mice (n=8/group) are then dosed by oral gavage with test compound (0.01 to 15 mg/kg) or vehicle (3 mM HCl, 0.01% Tween80) at a dose volume of 5 mL/kg, twice daily at 6 AM and 3 PM for 3 consecutive days. Each day, measurements of body weight. 24-hour food intake, water intake, urine volume and wet fecal weight are recorded, along with any observation of diarrhea. Fecal samples are dried using a lyophilizer for at least 3 days, following which dry weight is recorded and fecal fluid content is calculated based on the difference between the wet and dry stool weights. Fecal fluid content on day 3 of compound treatment is calculated as a change from the vehicle group mean. For urine samples, the volumes are determined gravimetrically. Feces and urine are analyzed for sodium content by microwave plasma-atomic emission spectroscopy or ion chromatography, respectively. Urine samples are analyzed on an ion chromatography system (Thermo Fisher ICS-3000 or ICS-5000+) coupled with conductivity detectors. Chromatographic separation of cations is performed using an IonPac CS12A (Thermo Fisher) 2×250 mm analytical column with an isocratic elution using 25 mM methanesulfonic acid. Concentrations interpolated from a standard curve (prepared in 10 mM HCl) for sodium ion based on retention time and peak area. Fecal sample analysis is performed by Microwave Plasma Atomic Emission Spectrometry (MP-AES). Dry fecal samples are ground into a fine powder on a homogenizer and the ground samples (400-600 mg aliquots weighed) are digested with nitric acid by microwave method (Mars 6). These digested samples are diluted with 1% nitric acid and analyzed on Agilent 4100 MP-AES. Concentrations are calculated relative to a standard curve (prepared in 1% nitric acid) for sodium based on the signal intensity. Sodium is detected at a wavelength of 588.995 nm. Twenty-four-hour urinary sodium excretion (mg/24-hours) is calculated by multiplying urinary sodium concentration by 24-hour urine volume. Twenty-four-hour fecal sodium excretion (mg/24-hours) is calculated by multiplying fecal sodium concentration by 24-hour dry fecal weight. The urinary and fecal sodium excretion on day 3 of compound treatment are normalized to dietary sodium intake and expressed as a percentage of the vehicle mean.

Example 59: Inhibition of Intestinal Sodium Absorption in Rats

Urinary sodium excretion and fecal form were measured to assess the ability of selected example compounds to inhibit the absorption of sodium and phosphorous from the intestinal lumen. Eight-week old, male, Sprague Dawley rats were purchased from Envigo (Livermore, Calif.), were housed 2 per cage and acclimated for at least 48 hours before study initiation. Animals were fed Harlan Teklad Global TD. 160470 rodent chow (Maddison, Wis.), standard laboratory rodent chow Harlan Teklad Global 2018 with the addition of 0.4% inorganic phosphorous. Animals had ad libitum access to food and water for the duration of the study and were maintained in a temperature and humidity controlled room on a standard light/dark cycle of 6 AM to 6 PM. On the day of study initiation, rats (n=5/group) were dosed by oral gavage with test compound or vehicle (3 mM HCl, 0.01% Tween80) at a dose volume of 5 mL/kg. Immediately after dose administration animals were placed in individual metabolic cages. At 13-hours post-dose, urine samples were collected and fecal form was assessed. In addition, the weight of food consumed over the 13-hour period was measured and recorded. Fecal forms were scored according to a common scale associated with increasing fecal water to the wettest observation in the cage's collection funnel (1, normal pellet; 2, pellet adhering to sides of collection funnel due to moisture; 3, loss of normal pellet shape; 4, complete loss of shape with a blotting pattern; 5, liquid fecal streams evident). Fecal form score (FFS) was calculated for each group as the median of each individual rat's FFS within the group and reported in Table 4. Fecal samples were dried using a lyophilizer for at least 3 days, following which dry weight was recorded and fecal fluid content was calculated based on the difference between the wet and dry stool weights. Fecal fluid content was calculated as a change from the vehicle group mean. For urine samples, the volumes were determined gravimetrically. Urine samples were analyzed on an ion chromatography system (Thermo Fisher ICS-3000 or ICS-5000+) coupled with conductivity detectors. Chromatographic separation of cations was performed using an IonPac CS12A (Thermo Fisher) 2×250 mm analytical column with an isocratic elution using 25 mM methanesulfonic acid. Concentrations were interpolated from a standard curve (prepared in 10 mM HCl) for sodium based on retention time and peak area. Thirteen-hour urinary sodium excretion (mg/13-hours) was calculated by multiplying urinary sodium concentration by 13-hour urine volume. The urinary sodium and phosphorous excretion of compound treatment was normalized to dietary sodium intake and expressed as a percentage of the vehicle mean.

TABLE 4

| Result | Urinary Na (% of Vehicle, out/in) | |
|---|---|---|
| A | >70% | |
| B | 40-70% | |
| C | <40% | |

| Example | Dose (mg/kg) | Urinary Na (% of Vehicle, out/in) | FFS (1-5) |
|---|---|---|---|
| 12 | 0.01 | A | 3 |
| 12 | 0.03 | A | 2 |
| 12 | 0.1 | C | 3 |

Example 60: Inhibition of Intestinal Sodium and Phosphorous Absorption in the Rat Balance Model Urinary and fecal sodium excretion, along with urinary phosphorous excretion are measured to assess the ability of selected example compounds to inhibit the absorption of sodium and phosphorous from the intestinal lumen. In addition, an assessment of fecal form in response to compound treatment is made. Approximately eight-week old, male, Sprague Dawley rats are purchased from Envigo (Livermore, Calif.), housed 2 per cage and acclimated for at least 48 hours before study initiation. Animals are fed Harlan Teklad Global TD. 160470 rodent chow (Maddison, Wis.), standard laboratory rodent chow Harlan Teklad Global 2018 with the addition of 0.4% inorganic phosphorous. Animals have ad libitum access to food and water for the duration of the study and are maintained in a temperature and humidity controlled room on a reversed light/dark cycle of 6 PM to 6 AM. To initiate the study, rats are weighed and individually placed in metabolic cages. Following a 2-day acclimation period to the metabolic cage, a 24-hr baseline collection of urine and feces is performed. Rats (n=6/group) are then dosed by oral gavage with test compound or vehicle (3 mM HCl, 0.01% Tween80) at a dose volume of 5 mL/kg, twice daily at 6 AM and 3 PM for 3 consecutive days. Each day, measurements of body weight, 24-hour food intake, water intake, urine volume and wet fecal weight are recorded, along with any observation of diarrhea. Fecal samples are dried using a lyophilizer for at least 3 days, following which dry weight is recorded and fecal fluid content is calculated based on the difference between the wet and dry stool weights. Fecal fluid content on day 3 of compound treatment is calculated as a change from the vehicle group mean. For urine samples, the volumes are determined gravimetrically. Feces and urine are analyzed for sodium and phosphorous content by microwave plasma-atomic emission spectroscopy or ion chromatography, respectively. Urine samples are analyzed on an ion chromatography system (Thermo Fisher ICS-300 or ICS-5000+) coupled with conductivity detectors. Chromatographic separation of cations is performed using an IonPac CS12A (Thermo Fisher) 2×250 mm analytical column with an isocratic elution using 25 mM methanesulfonic acid. Chromatographic separation of anions is performed using an IonPac AS18 (Thermo Fisher) 2×250 mm analytical column with an isocratic elution using 35 mM potassium hydroxide. Concentrations are interpolated from a standard curve (prepared in 10 mM HCl) for each ion based on retention time and peak area. Fecal sample analysis by Microwave Plasma Atomic Emission Spectrometry (MP-AES). Dry fecal samples are ground into a fine powder on a homogenizer and the ground samples (400-600 mg aliquots weighed) are digested with nitric acid by microwave method (Mars 6). These digested samples are diluted with 1% Nitric acid and analyzed on Agilent 4100 MP-AES. Concentrations are interpolated from a standard curve (prepared in 1% Nitric acid) for sodium based on the signal intensity. Sodium is detected at a wavelength of 588.995 nm. Twenty-four-hour urinary sodium and phosphorous excretion (mg/24-hours) is calculated by multiplying urinary sodium or phosphorous concentration, respectively, by 24-hour urine volume. Twenty-four-hour fecal sodium excretion (mg/24-hours) is calculated by multiplying fecal sodium concentration by 24-hour dry fecal weight. The urinary and fecal sodium excretion and urinary phosphorous excretion on day 3 of compound treatment are normalized to dietary sodium or phosphorous intake, respectively, and expressed as a percentage of the vehicle mean.

Example 61: Restoration of Gastrointestinal Motility in Opioid Induced Constipation Gastrointestinal transit is measured in mice treated with the peripherally acting μ-opioid agonist loperamide to assess the ability of selected example compounds to restore gastrointestinal motility in a model of opioid induced constipation. Approximately eight-week old, female, CD 1 rats are purchased from Envigo (Livermore, Calif.), are housed 4 per cage and acclimated for at least 48 hours before study initiation. Animals are fed standard laboratory rodent chow Harlan Teklad Global 2018 (Maddison, Wis.). Animals have ad libitum access to food and water for the duration of the acclimation period and are maintained in a temperature and humidity controlled room on a standard light/dark cycle of 6 AM to 6 PM. Following an overnight fast, with free access to water, animals are dosed by oral gavage with varying doses of test compound or vehicle (3 mM HCl, 0.01% Tween80), at a dose volume of 5 mL/kg. Approximately fifteen minutes following oral dosing of test compound or vehicle, animals are dosed by subcutaneous injection with loperamide (0.3 to 6 mg/kg) or vehicle (30:70 PG:0.9% NaCl) at a dose volume of 5 mL/kg. Fifteen minutes later, animals are dosed orally with Evans Blue Dye (6%) at a dose volume of 100 μL. 30 minutes later, animals are euthanized by carbon dioxide inhalation, and the length from the pylorus to cecum (whole length of the small intestine) and the length from the pylorus to the Evans Blue dye front are measured and recorded. For an individual animal, the length travelled by the Evans Blue dye front is divided by the length of the whole small intestine, measured from the pylorus to the cecum, and multiplied by 100, to provide the distance of the small intestine travelled by the dye as a percentage. In animals dosed orally with vehicle and injected subcutaneously with vehicle (vehicle/vehicle), the Evans Blue dye front travels approximately 70% of the length of the small intestine in the 30-minute period. In animals dosed orally with vehicle and injected subcutaneously with loperamide (vehicle/loperamide), the Evans Blue dye front travels approximately only 25% of the length of the small intestine in the 30-minute period, indicating decreased gastrointestinal motility in response to loperamide. The effect of example compounds on GIT motility in the presence of loperamide is calculated as the ability to restore vehicle/vehicle transit distance from the vehicle/loperamide transit, expressed as a percentage.

Example 62: Restoration of Gastrointestinal Motility in Multiple Sclerosis

Gastrointestinal transit time is measured to assess the ability of selected example compounds to restore gastrointestinal motility in a model of multiple sclerosis. Multiple sclerosis (MS) patients often experience constipation and other gastrointestinal manifestations related to disturbed gastrointestinal motility. The Experimental Autoimmune Encephalomyelitis (EAE) mouse model is one of the most frequently used animal models for studying multiple sclerosis (MS), in which immunization against CNS-specific antigen results in central nervous system inflammation. This model results in a spectrum of acute, chronic, and relapsing disease that results in varying degrees of progressive paralysis and gastrointestinal dysmotility.

Animals are 8-16 weeks of age at study initiation, and are fed standard laboratory rodent chow Harlan Teklad Global 2018 (Maddison, Wis.). Animals have ad libitum access to food and water for the duration of the study and are maintained in a temperature and humidity controlled room on a standard light/dark cycle of 6 AM to 6 PM. EAE is induced in female mice by injection of a combination of antigen (MOG35-55, S.C.) in complete Freund's adjuvant (CFA), and pertussis toxin (PTX, IP). After somatic motor symptoms develop, generally 10 or more days' post immunization, EAE mice are dosed by oral gavage with test compound at varying doses (0.01 to 30 mg/kg) or vehicle (3 mM HCl, 0.01% Tween80) at a dose volume of 5 mL/kg. Test compound is administered for a single dose or twice daily for multiple doses. Fecal output is monitored for a standardized period of time (1-24 hours) and recorded as fecal pellet number, fecal mass and fecal dr weight. Whole gastrointestinal transit time is determined by oral gavage of carmine red or Evans Blue and calculating the latency for dye to appear in the feces. Small intestinal transit is measured by dosing carmine red or Evans Blue by oral gavage and measuring the distance of the leading edge of the dye from compared to the whole length of the small intestine 15 minutes to two hours following oral dosing of the dye. Colonic motility is assessed by measuring time to extrusion of a single glass bead inserted a standardized distance into the distal colon. The effect of example compounds on GIT motility in EAE mice is calculated as the ability to restore transit distance to those observed in control mice from those observed in EAE treated with vehicle, expressed as a percentage.

Example 63: Restoration of Gastrointestinal Motility in Parkinson's Disease

Gastrointestinal transit time is measured to assess the ability of selected example compounds to restore gastrointestinal motility in a model of Parkinson's Disease. Parkinson's Disease (PD) is a neurodegenerative disorder characterized by chronic and progressive motor impairment. PD patients also experience significant non-motor symptoms including constipation and other gastrointestinal manifestations related to disturbed gastrointestinal motility. The toxin, 1-methyl-4-phenyl-1,2,3,6-tetrahydropyridine (MPTP) has been widely used to develop animal models for testing new therapies in the PD. This model results in motor changes and pathology that resemble PD and has also been reported to manifest gastrointestinal dysmotility (Scientific Reports, 2016 6:30269)

Animals are 8-16 weeks of age at study initiation, and fed standard laboratory rodent chow Harlan Teklad Global 2018 (Maddison, Wis.). Animals have ad libitum access to food and water for the duration of the study and are maintained in a temperature and humidity controlled room on a standard light/dark cycle of 6 AM to 6 PM. PD is induced in mice by multiple, generally four, intraperitoneal injections of MPTP. After MPTP is injected, generally 4 to 20 days' post injection, PD mice are dosed by oral gavage with test compound at varying doses (0.01 to 30 mg/kg) or vehicle (3 mM HCl, 0.01% Tween80) at a dose volume of 5 mL/kg. Test compound is administered for a single dose or twice daily for multiple doses. Fecal output is monitored for a standardized period of time (1-24 hours) and recorded as fecal pellet number, fecal mass and fecal dry weight. Whole gastrointestinal transit time is determined by oral gavage of carmine red or Evans Blue and calculating the latency for dye to appear in the feces. Small intestinal transit is measured by dosing carmine red or Evans Blue by oral gavage and measuring the distance of the leading edge of the dye from compared to the whole length of the small intestine 15 minutes to two hours following oral dosing of the dye. Colonic motility is assessed by measuring time to extrusion of a single glass bead inserted a standardized distance into the distal colon. The effect of example compounds on GIT motility in PD mice is calculated as the ability to restore transit distance to those observed in control mice from those observed in PD mice treated with vehicle, expressed as a percentage.

Example 64: Effect on Blood Pressure in a Models of Salt-Sensitive Hypertension

Arterial blood pressure is measured to assess the ability of selected example compounds to attenuate hypertension in a model of salt-sensitive hypertension. Dahl Salt Sensitive (DSS) rats are a well characterized model of salt-sensitive hypertension and end-organ injury. Salt-sensitive hypertension is established in DSS rats by increasing the NaCl content of the diet from 0.49% up to 4% NaCl for a period of 1 to 4-weeks. DSS rats maintained on 0.49% NaCl are used as a control group. Animals are 6-10 weeks of age at study initiation, and have ad libitum access to food and water for the duration of the study and are maintained in a temperature and humidity controlled room on a 12-hr light/dark cycle. Rats (n=6-8/group) are dosed by oral gavage with test compound (0.01-30 mg/kg) or vehicle (3 mM HCl, 0.01% Tween80) at a dose volume of 5 mL/kg, twice daily for 1 to 3 weeks, while maintained on a 4% NaCl diet. Arterial blood pressure is measured weekly by tail cuff plethysmography. A 24-hr urine collection is also collected weekly by placing animals individually in metabolic cages.

Example 65: Effect on Cardiac Function in Models of Heart Failure

Serial echocardiography is used to measure cardiac function and morphology to assess the ability of selected example compounds to improve cardiac function, structure and neuro-humoral activation in a rat model of heart failure. Male Dahl Salt Sensitive (DSS) rats or male Lewis rats are used to induce heart failure by permanent left main coronary arterial ligation. Animals are 6-10 weeks of age at study initiation, and have ad libitum access to food and water for the duration of the study and are maintained in a temperature and humidity controlled room on a 12-hr light/dark cycle. Rats (n=6-10/group) are dosed by oral gavage with test compound (0.01-30 mg/kg) or vehicle (3 mM HCl, 0.01% Tween80) at a dose volume of 5 mL/kg, twice daily for 1 to 8 weeks. Serial echocardiography is performed weekly to assess time-dependent cardiac remodeling (HWI, LVI, chamber size), time-dependent cardiac performance (EF, dP/dt, LVEDP) changes and time-dependent cardiac morphometry (HWI, LVI, LVEDV, LVESV) indices. Terminal assessment of load-dependent and load-independent left ventricular function are made using pressure-volume loop analysis. Extracellular volume expansion is assessed by measuring volume sensitive hormones ANP and BNP.

Example 66: Effect of Intracellular pH on TEER in Human Organoid Monolayer Cell Cultures Basal media (BM) consisted of advanced DMEM/F, 12 containing 10 mM HEPES (Invitrogen, 15630-080), 1:100 Glutamax (Invitrogen, 35050-061), and 1:100 penicillin/streptomycin (Invitrogen, 15140-122). Supplemented basal media (SBM) contained 1:100 N2 (Invitrogen, 17502-048). 1:50 B27 (Invitrogen, 12587-010), 1 mM N-acetylcysteine (Sigma, A9165), and 10 nM [Leu15]-gastrin I (Sigma, G9145). Growth factors used included 50 ng per mL mouse EGF (Peprotech, 315-09). 100 ng per mL mouse noggin (Peprotech, 250-38), 500 ng per mL human R-spondin 1 (R&D, 4645-RS), 100 ng per mL mouse Wnt-3a (R&D, 1324-WN), 20 µM Y-27632 (Tocris, 1254), 10 mM nicotinamide (Sigma, N0636), 500 nM A83-01 (Tocris, 2939), 10 µM SB202190 (Tocris, 1264). Transwells were 0.4 µm pore polyester membrane 24-well Transwell inserts (Corning). Cultures were incubated at 37° C. in 5% $CO_2$.

Human ileum organoids were cultured in WENRNAS (Wnt, EGF, noggin, R-spondin1, Nicotinamide, A83-01, SB202190) and grown for 7-12 days before being used to plate monolayer cultures. On day 0, organoid cultures embedded in Matrigel were treated with TrypLE Express to break organoids into small pieces and/or single cells. The cells were resuspended to 0.5×106 cells/mL in SBM containing WENRAY (Wnt, EGF, noggin, R-spondin1, A83-01, Y-27632). Following this step, 200 µL of cell suspension was plated into the apical side of a 24-well Transwell (100,000 cells/well) and 600 µL of SBM with WENRAY was added to the basolateral side. Ileum cells were differentiated with ENRA (EGF, noggin, R-spondin 1, A83-01) on day 3. The color of apical compartment turns from pink or orange to yellow due to the increase in NHE3 expression after differentiation.

Each human ileum monolayer culture well was washed twice with fresh SBM on the apical side on day 6 before compound dosing. All compound stocks were 10 mM dissolved in DMSO. Each compound stock was individually mixed with fresh SBM to reach final compound concentration and dosed only on the apical side of the monolayer (total volume 200 µl). DMSO at the equivalent concentration was used as the vehicle control. Duplicate wells were dosed for each compound. Transepithelial electrical resistance (TEER) was used as a quantitative technique to measure of tight junction permeability. TEER values were recorded using a volt/ohm meter (MERS00002, Millipore) before and after dosing for all wells. Each of the duplicate TEER values following treatment were corrected for the individual well baseline TEER. Baseline corrected TEER for each example compound was compared to the average of the DMSO wells and expressed as a percent TEER of vehicle control. Intracellular pH was measured in human ileum stem cells grown as monolayers on 96 well Transwell plates cells incubated with 10 µM of pH sensitive dye BCECF-AM (Life Technologies, cat# B1150) for 30 min at 37° C., 5% CO2 in Na-containing buffer (120 mM NaCl, 10 mM HEPES, 10 mM glucose, 5 mM KCl, 2 mM $CaCl_2$, 1 mM $MgCl_2$, pH 7.4). After 30 min the dye was aspirated and cells were washed twice with Na-containing buffer.

Known NHE3 inhibitor Tenapanor, as well as non NHE3 inhibitors nigericin, BAM15, FCCP, or DMSO control, were diluted into Na-containing buffer and added to the apical compartment of the Transwell. Fluorescent readings were acquired every 5 minutes for a period of 30 minutes on a Flexstation microplate reader at dual excitation wavelengths of 495 nm and 439 nm and emission wavelength of 538 nm (Molecular Devices). The fluorescent ratio for pH indication was calculated from ratio of the two excitation wavelengths (495/439 nm). The ionophore nigericin reduced intracellular pH compared with control (FIG. 1A), and showed a similar increase in TEER relative to control, as was observed with tenapanor (FIG. 1B). Similarly, the compounds BAM15 and FCCP, which decrease intracellular pH by uncoupling oxidative phosphorylation in the mitochondria (FIG. 1C), increased TEER compared with control (FIG. 1D). Moreover, neither nigericin, BAM15 nor FCCP inhibited NHE3 activity in enterocytes, as assessed by intracellular pH recovery following acid loading. These results show that intracellular pH is a direct regulator of TEER, independent of NHE3 activity.

Example 67: Pain Relief in IBS-C-Reduction of Visceral Hypersensitivity in Rats

The ability of selected example compounds to reduce the hypersensitivity of the colon to balloon distension (CRD) in a rat model of visceral hypersensitivity is measured by grading the rat's abdominal withdrawal reflex (AWR) and by measuring electromyographic (EMG) responses. Visceral hypersensitivity is induced by injecting 10-day old male Sprague Dawley rat pups with a 0.2 mL infusion of 0.5% acetic acid solution in saline into the colon 2 cm from the anus. Control rats receive an equal volume of saline. Visceral hypersensitivity is then assessed in these rats as adults, between 8 and 12 weeks of age. Rats (n=4-10/group) are dosed by oral gavage with test compound (0.01 to 30 mg/kg) or vehicle (3 mM HCl, 0.01% Tween80) at a dose volume of 5 mL/kg, twice daily for up to 2 weeks prior to the assessment of visceral hypersensitivity. Visceral hypersensitivity is measured by grading the response to CRD. Under mild sedation with 1% methohexital sodium, a flexible balloon attached to Tygon tubing is inserted 8 cm into the descending colon and rectum via the anus and secured in place by taping the tube to the tail. Approximately 30 minutes later, CRD is performed by rapidly inflating the balloon to varying pressures (10 to 80 mmHg) measured by a sphygmomanometer connected to a pressure transducer for a 20 second period followed by a 2-minute rest period. Behavioral responses to CRD are measured by grading the AWR by blinded observer and assigning an AWR score as follows: 1, normal behavior without response; 2, contraction of abdominal muscles; 3, lifting of abdominal wall; 4, body arching and lifting of pelvic structures. EMG responses are measured continuously in response to CRD via two electrodes implanted at least one-week prior to in the external oblique muscle and calculated as the area under the curve of the EMG in response to CRD.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

The invention claimed is:
1. A compound of Formula I':

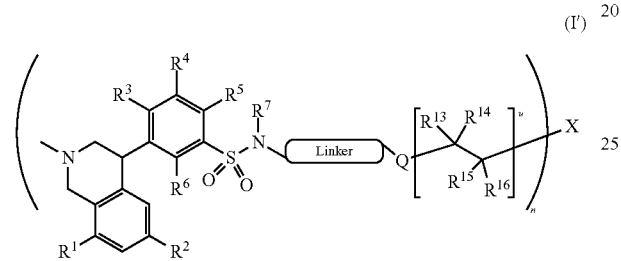

or a pharmaceutically acceptable salt, prodrug, solvate, hydrate, isomer, or tautomer thereof,
wherein:
Linker is selected the group consisting of:

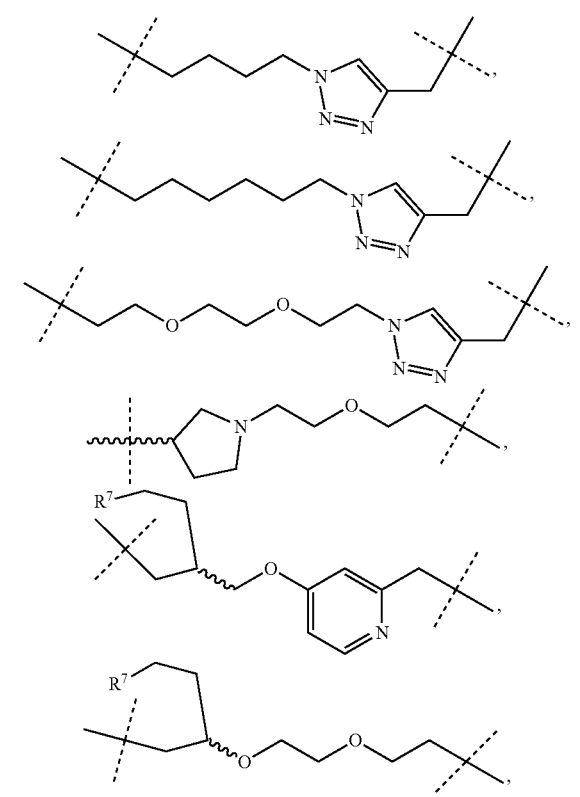

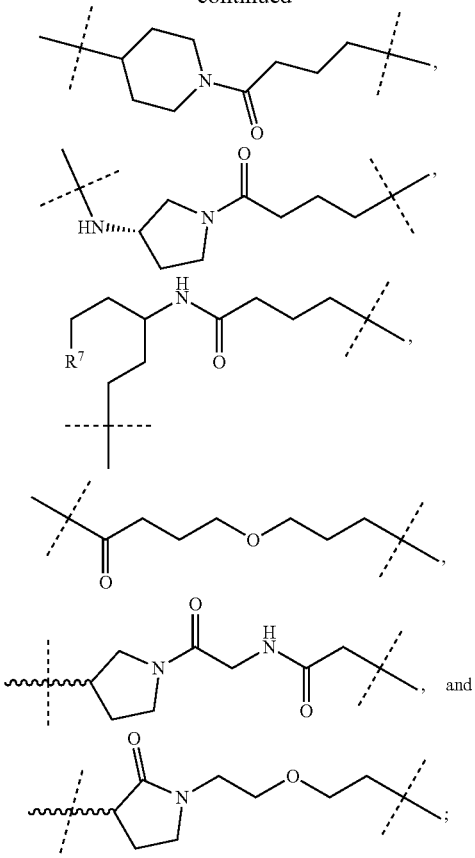

Q is a bond or —NHC(O)NH—;
X is a bond, NH, O, $CR^{11}R^{12}$, $CR^{11}$, C, or —NHC(O)NH—;
n is an integer from 2 to 4;
u is an integer from 0 to 2;
$R^1$ and $R^2$ are independently halogen, OH, CN, $C_1$-$C_6$alkyl, $C_1$-$C_6$alkoxy, $C_1$-$C_6$haloalkyl, $C_1$-$C_6$haloalkoxy, or —C(O)$NR^9R^{10}$;
$R^3$, $R^4$, $R^5$, and $R^6$ are independently H, halogen, OH, CN, —$NO_2$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl containing 1-5 heteroatoms selected from the group consisting of N, S, P and O, —$SR^9$, —$OR^9$, —$NHR^9$, —$NR^9R^{10}$, —$S(O)_2N(R^9)_2$—, —$S(O)_2R^9$, —$C(O)R^9$, —$C(O)OR^9$, —$NR^9S(O)_2R^{10}$, —$S(O)R^9$, —$S(O)NR^9R^{10}$, —$NR^8S(O)R^9$;
$R^7$ is independently, at each occurrence, H, $C_1$-$C_6$alkyl, or $C_1$-$C_6$haloalkyl;
$R^8$ is independently, at each occurrence, a bond, H, $C_1$-$C_6$alkyl, $C_4$-$C_8$cycloalkenyl, $C_3$-$C_8$cycloalkyl, heterocyclyl, aryl, or heteroaryl, wherein each cycloalkenyl, cycloalkyl, heterocyclyl, aryl, or heteroaryl is optionally substituted with one or more $R^{17}$; or
$R^7$ and $R^8$ together with the atoms to which they are attached may combine to form independently, at each occurrence, heterocyclyl or heteroaryl containing 1-5 heteroatoms selected from the group consisting of N, S, P and O, wherein each heterocyclyl or heteroaryl is optionally substituted with one or more $R^{17}$;
$R^9$ and $R^{10}$ are independently H, $C_1$-$C_6$alkyl, $C_2$-$C_6$alkenyl, $C_4$-$C_8$cycloalkenyl, $C_2$-$C_6$alkynyl, C$_3$-C$_8$cycloalkyl, heterocyclyl, aryl, or heteroaryl containing 1-5 heteroatoms selected from the group consisting of N, S, P and O;

R$^{11}$ and R$^{12}$ are independently H, C$_1$-C$_6$alkyl, OH, NH$_2$, CN, or NO$_2$;

R$^{13}$, R$^{14}$, R$^{15}$ and R$^{16}$ are independently, at each occurrence, H, OH, NH$_2$, or C$_1$-C$_3$ alkyl, wherein the alkyl is optionally substituted with one or more R$^{17}$; and R$^{17}$ is independently, at each occurrence, H, OH, NH$_2$, oxo, C$_1$-C$_6$alkyl, C$_1$-C$_6$haloalkyl, or C$_1$-C$_6$alkoxy;

provided that:

(1) when X is a bond, O, or CR$^{11}$R$^{12}$, n is 2;

(2) when n is 3, X is CR$^{11}$;

(3) when n is 4 X is C; and (4) only one of Q and X is —NHC(O)NH—.

2. The compound of claim 1, wherein Linker is selected from the group consisting of

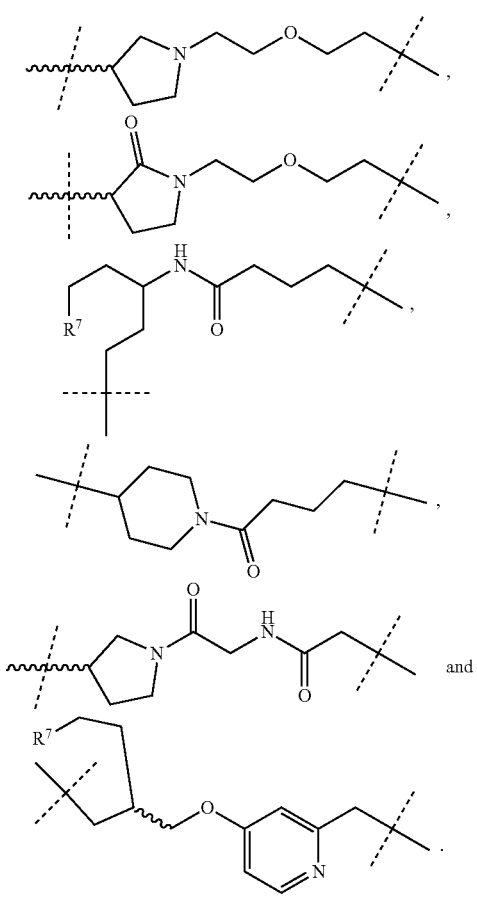

3. The compound of claim 1, wherein Q is —NHC(O)NH—.

4. The compound of claim 1, wherein Q is a bond and X is —NHC(O)NH—.

5. The compound of claim 1, wherein R$^{13}$ and R$^{15}$ are H and R$^{14}$ and R$^{16}$ are OH.

6. The compound of claim 1, wherein n is 2.

7. The compound of claim 1, wherein n is 3 or 4.

8. The compound of claim 1 having the formula Ia:

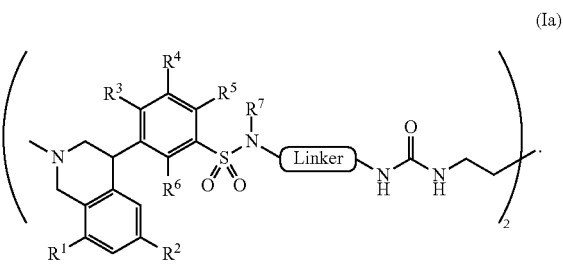

9. The compound of claim 1 having the formula Ig:

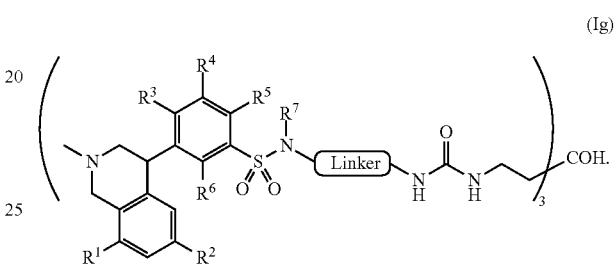

10. A compound selected from:

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)benzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6,8-dichloro-2-methyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6-chloro-2,8-dimethyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[5-(6-chloro-8-cyano-2-methyl-1,2,3,4-tetrahydroisoquinolin-4-yl)-2-methylbenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-

(6,8-dichloro-2-methyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-fluorobenzenesulfonamide];

N,N'-[(3S,3'S)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)benzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6,8-dichloro-2-methyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6-chloro-2,8-dimethyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[5-(6-chloro-8-cyano-2-methyl-1,2,3,4-tetrahydroisoquinolin-4-yl)-2-methylbenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6,8-dichloro-2-methyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-2,8-dimethyl-1,2,3,4-tetrahydroisoquinolin-4-yl)-4-fluorobenzenesulfonamide];

N,N'-[(3R,3'R)-(7,14-Dioxo-3,18-dioxa-6,8,13,15-tetraazaicosane-1,20-diyl)bis(pyrrolidine-1,3-diyl)]bis[3-(6-chloro-8-cyano-2-methyl-1,2,3,4-tetrahydroisoquinolin-4-yl)-4-fluorobenzenesulfonamide];

N,N'-[(7,14-Dioxo-3,18-dioxa-6,8,13,15-tetraazaicosane-1,20-diyl)bis(piperidine-1,4-diyl)]bis[3-(6-chloro-2,8-dimethyl-1,2,3,4-tetrahydroisoquinolin-4-yl)benzenesulfonamide];

N,N'-[(7,14-Dioxo-3,18-dioxa-6,8,13,15-tetraazaicosane-1,20-diyl)bis(piperidine-1,4-diyl)]bis[3-(6-chloro-8-cyano-2-methyl-1,2,3,4-tetrahydroisoquinolin-4-yl)benzenesulfonamide];

1,1'-[(3R,3'R)-(7,14-Dioxo-3,18-dioxa-6,8,13,15-tetraazaicosane-1,20-diyl)bis(pyrrolidine-1,3-diyl)]bis[N-([3-(6-chloro-2,8-dimethyl-1,2,3,4-tetrahydroisoquinolin-4-yl)phenyl]sulfonyl)formamide];

1,1'-[(3R,3'R)-(7,14-Dioxo-3,18-dioxa-6,8,13,15-tetraazaicosane-1,20-diyl)bis(pyrrolidine-1,3-diyl)]bis[N-([3-(6-chloro-8-cyano-2-methyl-1,2,3,4-tetrahydroisoquinolin-4-yl)phenyl]sulfonyl)formamide];

1,1'-(5,12-Dioxo-4,6,11,13-tetraazahexadecane-1,16-diyl)bis[N-([3-(6,8-dichloro-2-methyl-1,2,3,4-tetrahydroisoquinolin-4-yl)phenyl]sulfonyl)piperidine-4-carboxamide];

1,1'-(5,12-Dioxo-4,6,11,13-tetraazahexadecane-1,16-diyl)bis[N-([3-(6,8-dichloro-2-methyl-1,2,3,4-tetrahydroisoquinolin-4-yl)phenyl]sulfonyl)piperidine-3-carboxamide];

$N^1,N^{18}$-Bis([3-(6,8-Dichloro-2-dimethyl-1,2,3,4-tetrahydroisoquinolin-4-yl)phenyl]sulfonyl)-6,13-dioxo-5,7,12,14-tetraazaoctadecanediamide;

N,N'-[(3S,3'S)-(6,13-Dioxo-5,7,12,14-tetraazaoctadecanedioyl)bis(pyrrolidine-1,3-diyl)]bis[3-(6-chloro-2,8-dimethyl-1,2,3,4-tetrahydroisoquinolin-4-yl)benzenesulfonamide];

N,N'-[(3S,3'S)-(6,13-Dioxo-5,7,12,14-tetraazaoctadecanedioyl)bis(pyrrolidine-1,3-diyl)]bis[3-(6-chloro-8-cyano-2-methyl-1,2,3,4-tetrahydroisoquinolin-4-yl)benzenesulfonamide];

1-[2-(2-[(1-[(3-[(5)-6,8-Dichloro-2-methyl-1,2,3,4-tetrahydroisoquinolin-4-yl]phenyl)sulfonyl]piperidin-4-yl)oxy]ethoxy)ethyl]-3-[4-(3-[2-(2-[(1-[(3-[(5)-6,8-dichloro-2-methyl-1,2,3,4-tetrahydroisoquinolin-4-yl]phenyl)sulfonyl]piperidin-4-yl)oxy]ethoxy)ethyl]ureido)butyl]urea;

1-(2-(2-(((R)-1-((34(5)-6, 8-dichloro-2-methyl-1,2,3,4-tetrahydroisoquinolin-4-yl)phenyl)sulfonyl)pyrrolidin-3-yl)oxy)ethoxy)ethyl)-3-(4-(3-(2-(2-(((R)-1-((3 chloro-2-methyl-1,2,3,4-tetrahydroisoquinolin-4-yl)phenyl)sulfonyl)pyrrolidin-3-yl)oxy)ethoxy)ethyl)ureido)butyl)urea;

1-(2-[2-([(5)-1-[(3-[(5)-6,8-dichloro-2-methyl-1,2,3,4-tetrahydroisoquinolin-4-yl]phenyl]sulfonyl]pyrrolidin-3-yl] oxy)ethoxy]ethyl)-3-(4-[3-(2-[2-([(5)-1-[(3-[(5)-6,8-dichloro-2-methyl-1,2,3,4-tetrahydroisoquinolin-4-yl]phenyl)sulfonyl]pyrrolidin-3-yl] oxy)ethoxy]ethyl]ureido]butyl)urea;

N,N'-[(3S,3'S)-(7-Oxo-3,11-dioxa-6,8-diazatridecane-1,13-diyl]bis[pyrrolidine-1,3-diyl))bis(3-(6,8-dichloro-2-methyl-1,2,3,4-tetrahydroisoquinolin-4-yl)benzenesulfonamide];

$N^1,N^{18}$-Bis(1-[(3-[(S)-6,8-dichloro-2-methyl-1,2,3,4-tetrahydroisoquinolin-4-yl]phenyl)sulfonyl]piperidin-4-yl)-6,13-dioxo-5,7,12,14-tetraazaoctadecanediamide;

$N^1,N^{18}$-Bis(1-[(3-[(S)-6-chloro-8-cyano-2-methyl-1,2,3,4-tetrahydroisoquinolin-4-yl]phenyl)sulfonyl]piperidin-4-yl)-6,13-dioxo-5,7,12,14-tetraazaoctadecanediamide;

$N^1,N^{18}$-Bis(1-[(3-[(S)-6-chloro-2,8-dimethyl-1,2,3,4-tetrahydroisoquinolin-4-yl]phenyl)sulfonyl]piperidin-4-yl)-6,13-dioxo-5,7,12,14-tetraazaoctadecanediamide;

3-[2-(2-{245-(6-chloro-8-cyano-2-methyl-1,2,3,4-tetrahydroisoquinolin-4-yl)-2-methylbenzenesulfonamido]ethoxy}ethoxy)ethyl]-1-[4-({[2-(2-{2-[5-(6-chloro-8-cyano-2-methyl-1,2,3,4-tetrahydroisoquinolin-4-yl)-2-methylbenzenesulfonamido]ethoxy}ethoxy)ethyl] carbamoyl amino}butyl]urea;

3-[2-(3 S)-3-[5-(6-chloro-8-cyano-2-methyl-1,2,3,4-tetrahydroisoquinolin-4-yl)-2-methylbenzenesulfonamido]

pyrrolidin-1-yl] ethoxy ethyl)-1-(4-{[(2-{2-[(3 S)-3-[5-(6-chloro-8-cyano-2-methyl-1,2,3,4-tetrahydroisoquinolin-4-yl)-2-methylbenzenesulfonamido]pyrrolidin-1-yl] ethoxy I ethyl)carbamoyl] amino}butyl)urea;

3-[2-(2-{245-(6-chloro-2,8-dimethyl-1,2,3,4-tetrahydroisoquinolin-4-yl)-2-methylbenzenesulfonamido] ethoxy}ethoxy)ethyl]-1-[4-({[2-(2-{2-[5-(6-chloro-2, 8-dimethyl-1,2,3,4-tetrahydroisoquinolin-4-yl)-2-methylbenzenesulfonamido]ethoxy}ethoxy)ethyl] carbamoyl amino)butyl]urea;

3-(2-{2-[(3 S)-3-[5-(6-chloro-2,8-dimethyl-1,2,3,4-tetrahydroisoquinolin-4-yl)-2-methylbenzenesulfonamido] pyrrolidin-1-yl] ethoxy ethyl)-1-(4-{[(2-{2-[(3 S)-3-[5-(6-chloro-2, 8-dimethyl-1,2,3,4-tetrahydroisoquinolin-4-yl)-2-methylbenzenesulfonamido]pyrrolidin-1-yl] ethoxy}ethyl)carbamoyl] amino}butyl)urea; and 3-(2-{2-[(3R)-3-[3-(6-chloro-2, 8-dimethyl-1,2,3,4-tetrahydroisoquinolin-4-yl)benzenesulfonamido]pyrrolidin-1-yl] ethoxy ethyl)-1-(4-{[(2-{2-[(3R)-3-[3-(6-chloro-2,8-dimethyl-1,2,3,4-tetrahydroisoquinolin-4-yl)benzenesulfonamido]pyrrolidin-1-yl] ethoxy}ethyl) carbamoyl] amino}butyl)urea;

or a pharmaceutically acceptable salt thereof.

11. A pharmaceutical composition comprising a compound or pharmaceutically acceptable salt of claim 1, and a pharmaceutically acceptable carrier.

12. A method for inhibiting NHE-mediated antiport of sodium and hydrogen ions, the method comprising administering to a mammal in need thereof a pharmaceutically effective amount of a compound or pharmaceutically acceptable salt of claim 1.

13. A method for treating a disorder associated with fluid retention or salt overload, the method comprising administering to a mammal in need thereof a pharmaceutically effective amount of a compound or pharmaceutically acceptable salt of claim 1.

* * * * *

UNITED STATES PATENT AND TRADEMARK OFFICE
CERTIFICATE OF CORRECTION

PATENT NO. : 11,147,884 B2
APPLICATION NO. : 16/476835
DATED : October 19, 2021
INVENTOR(S) : Irina Dotsenko, Dean Dragoli and Jason Lewis It is certified that error appears in the above-identified patent and that said Letters Patent is hereby corrected as shown below:

In the Claims

Column 161, Line 7, Claim 1, delete "$C_1$-$C_3$ alkyl" and insert -- $C_1$-$C_3$alkyl --;

Column 164, Line 24, Claim 10, delete "(3S,3'5)" and insert -- (3S,3'S) --;

Column 164, Line 28, Claim 10, delete "(3-[(5)" and insert -- (3-[(S) --;

Column 164, Line 30, Claim 10, delete "(3-[(5)" and insert -- (3-[(S) --;

Column 164, Line 34, Claim 10, delete "((34(5)-6, 8-" and insert -- ((3-((S)-6,8- --;

Column 164, Lines 36-37, Claim 10, delete "1-((3 chloro-2" and insert -- 1-((3-((S)-6,8-dichloro-2 --;

Column 164, Line 40, Claim 10, delete "[2-[(5)-1-[(3-[(5)-6,8" and insert -- [2-([(S)-1-[(3-[(S)-6,8 --;

Column 164, Line 42, Claim 10, delete "[2-[(5)-1-[(3-[(5)-6,8" and insert -- [2-([(S)-1-[(3-[(S)-6,8 --;

Column 164, Line 44, Claim 10, delete "3-yl] oxy)" and insert -- 3-yl]oxy) --;

Column 164, Line 46, Claim 10, delete "(3S,3'5)" and insert -- (3S,3'S) --;

Column 164, Line 60, Claim 10, delete "(2-{245-(6-chloro" and insert -- (2-{2-[5-(6-chloro --;

Column 164, Line 65, Claim 10, delete "carbamoyl amino" and insert -- carbamoyl}amino --;

Column 164, Line 66, Claim 10, delete "3-[2-(3S)-" and insert -- 3-(2-{2-[(3S)- --;

Column 165, Line 1, Claim 10, delete "-yl] ethoxy ethyl)-" and insert -- -yl]ethoxy}ethyl)- --;

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,147,884 B2

Column 165, Lines 4-5, Claim 10, delete "-yl] ethoxy I ethyl)-" and insert -- -yl]ethoxy}ethyl)- --;

Column 165, Line 5, Claim 10, delete "carbamoyl] amino" and insert -- carbamoyl]amino --;

Column 165, Line 6, Claim 10, delete "3-[2-(2-{245-(6-chloro" and insert
-- 3-[2-(2-{2-[5-(6-chloro --;

Column 165, Line 11, Claim 10, delete "carbamoyl amino" and insert -- carbamoyl}amino --;

Column 165, Line 12, Claim 10, delete "3-(2-{2-[(3 S)" and insert -- 3-(2-{2-[(3S) --;

Column 165, Line 14, Claim 10, delete "-yl] ethoxy ethyl)-" and insert -- -yl]ethoxy}ethyl)- --;

Column 165, Line 15, Claim 10, delete "(6-chloro-2, 8-dimethyl" and insert
-- (6-chloro-2,8-dimethyl --;

Column 165, Line 17, Claim 10, delete "carbamoyl] amino" and insert -- carbamoyl]amino --;

Column 165, Line 18, Claim 10, delete "(6-chloro-2, 8-dimethyl" and insert
-- (6-chloro-2,8-dimethyl --;

Column 166, Line 1, Claim 10, delete "-yl] ethoxy ethyl)-" and insert -- -yl]ethoxy}ethyl)- --;

Column 166, Line 3, Claim 10, delete "yl] ethoxy}" and insert -- yl]ethoxy} --; and Column 166, Line 4, Claim 10, delete "carbamoyl] amino" and insert -- carbamoyl]amino -- therefor.